United States Patent
Kato et al.

(10) Patent No.: US 8,057,919 B2
(45) Date of Patent: Nov. 15, 2011

(54) MATERIAL FOR ORGANIC ELECTROLUMINESCENCE DEVICE AND ORGANIC ELECTROLUMINESCENCE DEVICE USING THE SAME

(75) Inventors: Tomoki Kato, Chiba (JP); Masaki Numata, Chiba (JP); Kazuki Nishimura, Chiba (JP); Toshihiro Iwakuma, Chiba (JP); Chishio Hosokawa, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 282 days.

(21) Appl. No.: 12/253,627

(22) Filed: Oct. 17, 2008

(65) Prior Publication Data

US 2009/0302743 A1     Dec. 10, 2009

(30) Foreign Application Priority Data

Jun. 5, 2008   (JP) .................. 2008-148515

(51) Int. Cl.
*H01J 1/63* (2006.01)
*C07D 307/77* (2006.01)

(52) U.S. Cl. ........ 428/690; 428/917; 313/504; 548/418; 549/456

(58) Field of Classification Search .................. None
See application file for complete search history.

(56) References Cited

U.S. PATENT DOCUMENTS 5,942,340 A * 8/1999 Hu et al. .............. 428/690
2006/0063033 A1 * 3/2006 Sohn et al. .............. 428/690
2007/0224446 A1 * 9/2007 Nakano et al. ............ 428/690
2008/0220285 A1 * 9/2008 Vestweber et al. ......... 428/690
2009/0302742 A1 * 12/2009 Komori et al. ............ 313/504

FOREIGN PATENT DOCUMENTS

| JP | 2007088016 A | * | 4/2007 |
| WO | WO 2006122630 A1 | * | 11/2006 |
| WO | WO 2007063754 A1 | * | 6/2007 |

OTHER PUBLICATIONS

Machine translation of JP2007-088016. Date of publication: May 4, 2007.*
Hadizad et al. Organic Letters 2005, 7, 795-797. Date of online publication: Feb. 9, 2005.*
U.S. Appl. No. 12/253,586, filed Oct. 17, 2008, Kato, et al.

* cited by examiner

*Primary Examiner* — Dawn L Garrett
*Assistant Examiner* — Andrew K Bohaty
(74) *Attorney, Agent, or Firm* — Oblon, Spivak, McClelland, Maier & Neustadt, L.L.P.

(57) ABSTRACT

Provided are an organic electroluminescence device, which: shows high luminous efficiency; is free of any pixel defect; and has a long lifetime, and a material for an organic electroluminescence device for realizing the device. The material for an organic electroluminescence device is a compound of a specific structure having a n-conjugated heteroacene skeleton crosslinked with a carbon atom, nitrogen atom, or oxygen atom. The organic electroluminescence device has one or more organic thin film layers including a light emitting layer between a cathode and an anode, and at least one layer of the organic thin film layers contains the material for an organic electroluminescence device.

15 Claims, No Drawings

MATERIAL FOR ORGANIC ELECTROLUMINESCENCE DEVICE AND ORGANIC ELECTROLUMINESCENCE DEVICE USING THE SAME

TECHNICAL FIELD

The present invention relates to a material for an organic electroluminescence device and an organic electroluminescence device using the material, in particular, an organic electroluminescence device, which: shows high luminous efficiency; is free of any pixel defect; and has a long lifetime, and a material for an organic electroluminescence device for realizing the device.

BACKGROUND ART

An organic electroluminescence device (hereinafter, "electroluminescence" may be abbreviated as "EL") is a spontaneous light emitting device which utilizes the principle that a fluorescent substance emits light by energy of recombination of holes injected from an anode and electrons injected from a cathode when an electric field is applied. Since an organic EL device of the laminate type driven under a low electric voltage was reported, many studies have been conducted on organic EL devices using organic materials as the constituent materials. The devices of the laminate type use tris(8-quinolinolato) aluminum for a light emitting layer and a triphenyldiamine derivative for a hole transporting layer. Advantages of the laminate structure are that the efficiency of hole injection into the light emitting layer can be increased, that the efficiency of forming exciton which are formed by blocking and recombining electrons injected from the cathode can be increased, and that exciton formed within the light emitting layer can be enclosed. As described above, for the structure of the organic EL device, a two-layered structure having a hole transporting (injecting) layer and an electron transporting light emitting layer and a three-layered structure having a hole transporting (injecting) layer, a light emitting layer, and an electron transporting (injecting) layer are well known. To increase the efficiency of recombination of injected holes and electrons in the devices of the laminate type, the structure of the device and the process for forming the device have been studied.

As the light emitting material of the organic EL device, chelate complexes such as tris(8-quinolinolato) aluminum complexes, coumarine derivatives, tetraphenylbutadiene derivatives, distyrylarylene derivatives, and oxadiazole derivatives are known. It is reported that light in the visible region ranging from blue light to red light can be obtained by using these light emitting materials, and development of a device exhibiting color images is expected.

In addition, it has been recently proposed that a phosphorescent material as well as a fluorescent material be utilized in the light emitting layer of an organic EL device. High luminous efficiency is achieved by utilizing the singlet and triplet states of an excited state of an organic phosphorescent material in the light emitting layer of an organic EL device. Upon recombination of an electron and a hole in an organic EL device, singlet excitons and triplet excitons may be produced at a ratio of 1:3 owing to a difference in spin multiplicity between the singlet and triplet excitons, so the use of a phosphorescent material may achieve luminous efficiency three to four times as high as that of a device using fluorescence alone.

Patent Documents 1 to 7 are exemplary inventions each describing such materials for an organic EL device.

Patent Document 1 describes a compound using a structure obtained by crosslinking a terphenylene skeleton with, for example, a carbon atom, nitrogen atom, or oxygen atom as a mother skeleton. The document, which mainly discloses data indicative of the potential of the compound to serve as a hole transporting material, describes that the compound is used as a host material for a phosphorescent material in a light emitting layer. However, the description is limited to a red phosphorescent device, and the luminous efficiency of the device is not high enough for the device to be put into practical use.

Patent Document 2 describes an indolocarbazole compound having a substituent on a nitrogen atom or on an aromatic ring. The document recommends that the compound be used as a hole transporting material, and describes that a thermally and morphologically stable, thin hole transporting layer can be prepared from the compound. However, the document does not describe data indicative of the usefulness of the compound as a host material or electron transporting material to be used together with a phosphorescent material.

Patent Document 3 describes indolocarbazole compounds each having a substituent on a nitrogen atom or on an aromatic ring. The document discloses data on a green light emitting device using any one of those compounds as a host material for a phosphorescent material in its light emitting layer. However, a high voltage must be applied to the device to drive the device, and the device shows low luminous efficiency, so the device cannot be sufficiently put into practical use.

Patent Document 4 describes indolocarbazole compounds each having a substituent. The document describes that each of the compounds functions as a host material for a phosphorescent material in a light emitting layer. However, each of those compounds is characterized in that the compound has a dimer or trimer structure through a linking group, and each of the compounds tends to have a large molecular weight. The document discloses data on a green phosphorescent device using any one of those compounds, but all the compounds used each have a large molecular weight of 800 or more. The efficiency with which a material having a large molecular weight is deposited in a vacuum is poor, and the material may decompose owing to heating for a long time period, so the material may be insufficient in terms of practical use.

Patent Documents 5 and 6 describe indenofluorene compounds each having a substituent on an aromatic ring, and describe that each of the compounds functions as a fluorescent material in a light emitting layer. However, none of the documents describes data indicative of the usefulness of each of the compounds as a host material or electron transporting material to be used together with a phosphorescent material.

Patent Document 7 describes compounds each using a structure obtained by crosslinking a terphenylene skeleton with a sulfur atom, boron atom, or phosphorus atom as a mother skeleton. The document describes that each of those compounds has excellent oxidation resistance, and allows the formation of an organic semiconductor active layer by an application method. However, the document does not describe data indicative of the usefulness of each of the compounds as a host material or electron transporting material to be used together with a fluorescent material or phosphorescent material.

Patent Document 1: WO 2006/122630
Patent Document 2: EP 0908787
Patent Document 3: WO 2007/063754
Patent Document 4: WO 2007/063754
Patent Document 5: US 2002/0132134
Patent Document 6: US 2003/0044646
Patent Document 7: JP 2008-81494

DISCLOSURE OF THE INVENTION

Problems to be Solved by the Invention

The present invention has been made with a view to solving the above problems, and an object of the present invention is to provide an organic EL device which: shows high luminous efficiency; is free of any pixel defect; and has a long lifetime, and a material for an organic EL device for realizing the device.

Means for Solving the Problems

The inventors of the present invention have made extensive studies with a view to achieving the above object. As a result, the inventors have found that the above object can be achieved by using a compound having a π-conjugated heteroacene skeleton crosslinked with a carbon atom, nitrogen atom, oxygen atom, or sulfur atom as a material for an organic EL device. Thus, the inventors have completed the present invention.

According to one aspect of the present invention, there is provided a material for an organic EL device represented by one of the following formulae (1) and (2).

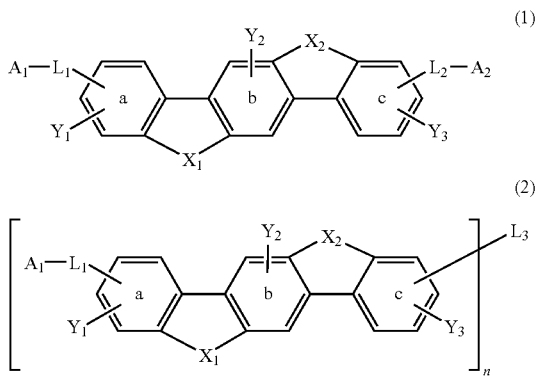

[In the formulae (1) and (2), $X_1$ and $X_2$ each independently represent O, N—$R_1$, or $CR_2R_3$, provided that a case where both $X_1$ and $X_2$ represent $CR_2R_3$ is excluded.

In the formulae (1) and (2), $R_1$, $R_2$, and $R_3$ each independently represent an alkyl group having 1 to 20 carbon atoms, a substituted or unsubstituted cycloalkyl group having a ring formed of 3 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group having a ring formed of 3 to 24 atoms, provided that, when both $X_1$ and $X_2$ represent N—$R_1$, at least one $R_1$ represents a substituted or unsubstituted, monovalent fused aromatic heterocyclic group having a ring formed of 8 to 24 atoms.

In the formula (2), n represents 2, 3, or 4, and the material represented by the formula (2) includes a dimer using $L_3$ as a linking group for n=2, a trimer using $L_3$ as a linking group for n=3, or a tetramer using $L_3$ as a linking group for n=4.

In the formulae (1) and (2), $L_1$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring a through a carbon-carbon bond.

In the formula (1), $L_2$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring c through a carbon-carbon bond.

In the formula (2), when n represents 2, $L_3$ represents a single bond, an alkylene group having 1 to 20 carbon atoms, a substituted or unsubstituted cycloalkylene group having a ring formed of 3 to 20 carbon atoms, a divalent silyl group having 2 to 20 carbon atoms, a substituted or unsubstituted, divalent aromatic hydrocarbon group having a ring formed of 6 to 24 carbon atoms, or a substituted or unsubstituted, divalent aromatic heterocyclic group which has a ring formed of 3 to 24 atoms and which is linked with the benzene ring c through a carbon-carbon bond, when n represents 3, $L_3$ represents a trivalent alkane having 1 to 20 carbon atoms, a substituted or unsubstituted, trivalent cycloalkane having a ring formed of 3 to 20 carbon atoms, a trivalent silyl group having 1 to 20 carbon atoms, a substituted or unsubstituted, trivalent aromatic hydrocarbon group having a ring formed of 6 to 24 carbon atoms, or a substituted or unsubstituted, trivalent aromatic heterocyclic group which has 3 to 24 atoms and which is linked with the benzene ring c through a carbon-carbon bond, or when n represents 4, $L_3$ represents a tetravalent alkane having 1 to 20 carbon atoms, a substituted or unsubstituted, tetravalent cycloalkane having a ring formed of 3 to 20 carbon atoms, a silicon atom, a substituted or unsubstituted, tetravalent aromatic hydrocarbon group having a ring formed of 6 to 24 carbon atoms, or a substituted or unsubstituted, tetravalent aromatic heterocyclic group which has a ring formed of 3 to 24 atoms and which is linked with the benzene ring c through a carbon-carbon bond.

In the formulae (1) and (2), $A_1$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_1$ through a carbon-carbon bond, provided that, when $L_1$ represents an alkyl or alkylene group having 1 to 20 carbon atoms, a case where $A_1$ represents a hydrogen atom is excluded.

In the formula (1), $A_2$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_2$ through a carbon-carbon bond, provided that, when $L_2$ represents an alkyl or alkylene group having 1 to 20 carbon atoms, a case where $A_2$ represents a hydrogen atom is excluded, and, when $X_1$ and $X_2$ each represent O or $CR_2R_3$ and both $L_1$ and $L_2$ represent single bonds, a case where $A_1$ and $A_2$ simultaneously represent hydrogen atoms is excluded.

In the formulae (1) and (2), $Y_1$, $Y_2$, and $Y_3$ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with the benzene ring a, b, or c through a carbon-carbon bond, the number of each of $Y_1$ and $Y_3$ is 0, 1, 2, or 3, and the number of $Y_2$ is 0, 1, or 2.

In the formulae (1) and (2), $A_1$, $A_2$, $L_1$, $L_2$, and $L_3$ are each free of any carbonyl group.]

According to another aspect of the present invention, there is provided an organic EL device having one or more organic thin film layers including a light emitting layer between a cathode and an anode in which at least one layer of the organic thin film layers contains a material for an organic EL device as a compound having a π-conjugated heteroacene skeleton crosslinked with a carbon atom, nitrogen atom, oxygen atom, or sulfur atom. A material for an organic EL device represented by the above formula (1) or (2) is preferably used as the material for an organic EL device of the present invention.

Further, the material for an organic EL device is effective also as a material for an organic electron device such as an organic solar cell, organic semiconductor laser, a sensor using organic matter, or an organic TFT.

Effects of the Invention

According to the present invention, there can be provided an organic EL device which: shows high luminous efficiency; is free of any pixel defect; and has a long lifetime, and a material for an organic EL device for realizing the device.

BEST MODE FOR CARRYING OUT THE INVENTION

A material for an organic EL device of the present invention is represented by one of the following general formulae (1) and (2).

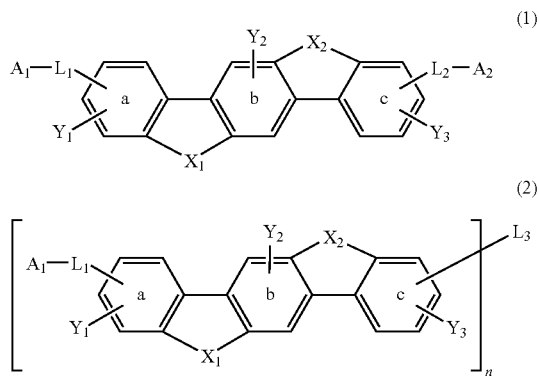

[In the formulae (1) and (2), $X_1$ and $X_2$ each independently represent O, N—$R_1$, or $CR_2R_3$, provided that a case where both $X_1$ and represent $CR_2R_3$ is excluded.

In the formulae (1) and (2), $R_1$, $R_2$, and $R_3$ each independently represent an alkyl group having 1 to 20 carbon atoms, a substituted or unsubstituted cycloalkyl group having a ring formed of 3 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group having a ring formed of 3 to 24 atoms, provided that, when both and $X_2$ represent N—$R_1$, at least one $R_1$ represents a substituted or unsubstituted, monovalent fused aromatic heterocyclic group having a ring formed of 8 to 24 atoms.

In the formula (2), n represents 2, 3, or 4, and the material represented by the formula (2) includes a dimer using $L_3$ as a linking group for n=2, a trimer using $L_3$ as a linking group for n=3, or a tetramer using $L_3$ as a linking group for n=4.

In the formulae (1) and (2), $L_1$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring a through a carbon-carbon bond.

In the formula (1), $L_2$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring c through a carbon-carbon bond.

In the formula (2), when n represents 2, $L_3$ represents a single bond, an alkylene group having 1 to 20 carbon atoms, a substituted or unsubstituted cycloalkylene group having a ring formed of 3 to 20 carbon atoms, a divalent silyl group having 2 to 20 carbon atoms, a substituted or unsubstituted, divalent aromatic hydrocarbon group having a ring formed of 6 to 24 carbon atoms, or a substituted or unsubstituted, divalent aromatic heterocyclic group which has a ring formed of 3 to 24 atoms and which is linked with the benzene ring c through a carbon-carbon bond, when n represents 3, $L_3$ represents a trivalent alkane having 1 to 20 carbon atoms, a substituted or unsubstituted, trivalent cycloalkane having a ring formed of 3 to 20 carbon atoms, a trivalent silyl group having 1 to 20 carbon atoms, a substituted or unsubstituted, trivalent aromatic hydrocarbon group having a ring formed of 6 to 24 carbon atoms, or a substituted or unsubstituted, trivalent aromatic heterocyclic group which has 3 to 24 atoms and which is linked with the benzene ring c through a carbon-carbon bond, or when n represents 4, $L_3$ represents a tetravalent alkane having 1 to 20 carbon atoms, a substituted or unsubstituted, tetravalent cycloalkane having a ring formed of 3 to 20 carbon atoms, a silicon atom, a substituted or unsubstituted, tetravalent aromatic hydrocarbon group having a ring formed of 6 to 24 carbon atoms, or a substituted or unsubstituted, tetravalent aromatic heterocyclic group which has a ring formed of 3 to 24 atoms and which is linked with the benzene ring c through a carbon-carbon bond.

In the formulae (1) and (2), $A_1$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_1$ through a carbon-carbon bond, provided that, when $L_1$ represents an alkyl or alkylene group having 1 to 20 carbon atoms, a case where $A_1$ represents a hydrogen atom is excluded.

In the formula (2), $A_2$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_2$ through a carbon-carbon bond, provided that, when $L_2$ represents an alkyl or alkylene group having 1 to 20 carbon atoms, a case where $A_2$ represents a hydrogen atom is excluded, and, when $X_1$ and $X_2$ each represent O or $CR_2R_3$ and both $L_1$ and $L_2$ represent single bonds, a case where $A_1$ and $A_2$ simultaneously represent hydrogen atoms is excluded.

In the formulae (1) and (2), $Y_1$, $Y_2$, and $Y_3$ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with the benzene ring a, b, or c through a carbon-carbon bond, the number of each of $Y_1$ and $Y_3$ is 0, 1, 2, or 3, and the number of $Y_2$ is 0, 1, or 2.

When the benzene ring a is substituted by multiple $Y_1$s, the benzene ring b is substituted by multiple $Y_2$s, or the benzene ring c is substituted by multiple $Y_3$s in the formulae (1) and (2), each of the rings is represented as shown below.

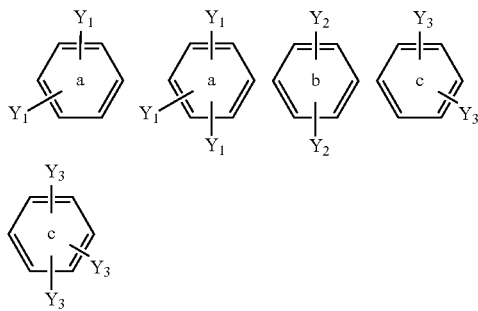

In the formulae (1) and (2), $A_1$, $A_2$, $L_1$, $L_2$, and $L_3$ are each free of any carbonyl group.]

The material for an organic EL device represented by the general formula (1) is preferably a material for an organic EL device represented by any one of the following general formulae (3) to (6) and (11), and the material for an organic EL device represented by the general formula (2) is preferably a material for an organic EL device represented by any one of the following general formulae (7) to (10) and (12).

(3)

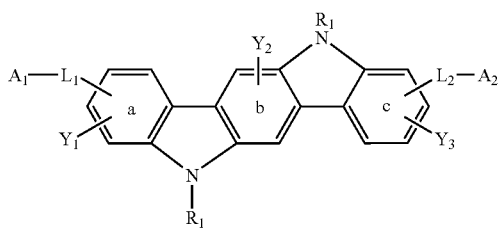

(4)

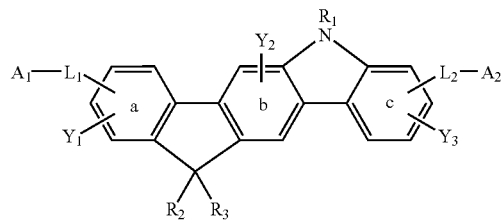

(5)

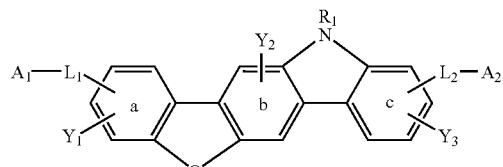

(6)

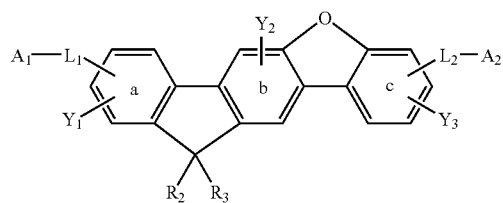

(7)

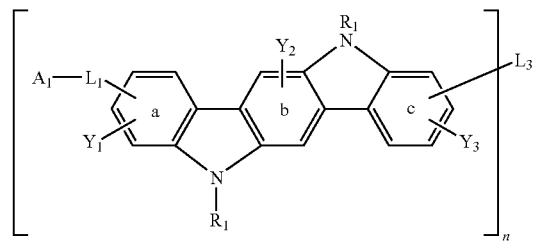

(8)

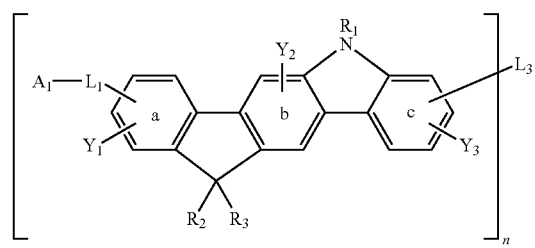

(9)

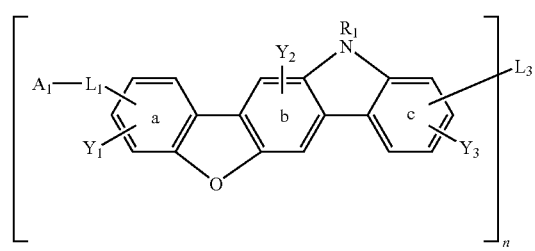

(10)

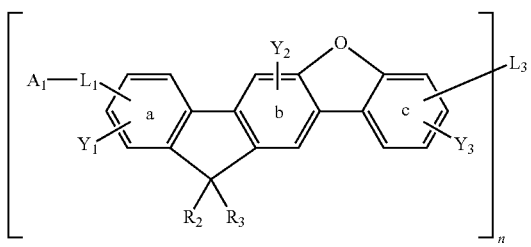

[In the formulae (3) to (10), $R_1$, $R_2$, and $R_3$ each independently represent an alkyl group having 1 to 20 carbon atoms, a substituted or unsubstituted cycloalkyl group having a ring formed of 3 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group having a ring formed of 3 to 24 atoms, provided that at least one $R_1$ in each of the formulae (3) and (7) represents a substituted or unsubstituted, monovalent fused aromatic heterocyclic group having a ring formed of 8 to 24 atoms.

In the formulae (7) to (10), n represents 2, 3, or 4, and the material represented by any one of the formulae (7) to (10) includes a dimer using $L_3$ as a linking group for n=2, a trimer using $L_3$ as a linking group for n=3, or a tetramer using $L_3$ as a linking group for n=4.

In the formulae (3) to (10), $L_1$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with the benzene ring a through a carbon-carbon bond.

In the formulae (3) to (6), $L_2$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with the benzene ring c through a carbon-carbon bond.

In the formulae (7) to (10), when n represents 2, $L_3$ represents a single bond, an alkylene group having 1 to 20 carbon atoms, a substituted or unsubstituted cycloalkylene group having a ring formed of 3 to 20 carbon atoms, a divalent silyl group having 2 to 20 carbon atoms, a substituted or unsubstituted, divalent aromatic hydrocarbon group having a ring formed of 6 to 24 carbon atoms, or a substituted or unsubstituted, divalent aromatic heterocyclic group which has a ring formed of 3 to 24 atoms and which is linked with the benzene ring c through a carbon-carbon bond, when n represents 3, $L_3$ represents a trivalent alkane having 1 to 20 carbon atoms, a substituted or unsubstituted, trivalent cycloalkane having a ring formed of 3 to 20 carbon atoms, a trivalent silyl group having 1 to 20 carbon atoms, a substituted or unsubstituted, trivalent aromatic hydrocarbon group having a ring formed of 6 to 24 carbon atoms, or a substituted or unsubstituted, trivalent aromatic heterocyclic group which has 3 to 24 atoms and which is linked with the benzene ring c through a carbon-carbon bond, or when n represents 4, $L_3$ represents a tetravalent alkane having 1 to 20 carbon atoms, a substituted or unsubstituted, tetravalent cycloalkane having a ring formed of 3 to 20 carbon atoms, a silicon atom, a substituted or unsubstituted, tetravalent aromatic hydrocarbon group having a ring formed of 6 to 24 carbon atoms, or a substituted or unsubstituted, tetravalent aromatic heterocyclic group which has a ring formed of 3 to 24 atoms and which is linked with the benzene ring c through a carbon-carbon bond.

In the formulae (3) to (10), $A_1$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_1$ through a carbon-carbon bond, provided that, when $L_1$ represents an alkyl or alkylene group having 1 to 20 carbon atoms, a case where $A_1$ represents a hydrogen atom is excluded.

In the formulae (3) to (6), $A_2$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_2$ through a carbon-carbon bond, provided that, when $L_2$ represents an alkyl or alkylene group having 1 to 20 carbon atoms, a case where $A_2$ represents a hydrogen atom is excluded, and, when both $L_1$ and $L_2$ represent single bonds, a case where $A_1$ and $A_2$ simultaneously represent hydrogen atoms is excluded.

In the formulae (3) to (10), $Y_1$, $Y_2$, and $Y_3$ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with the benzene ring a, b, or c through a carbon-carbon bond, the number of each of $Y_1$ and $Y_3$ is 0, 1, 2, or 3, and the number of $Y_2$ is 0, 1, or 2.

In the formulae (3) to (10), $A_1$, $A_2$, $L_1$, $L_2$, and $L_3$ are each free of any carbonyl group.]

(11)

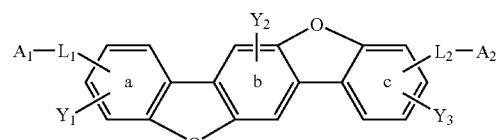

(12)

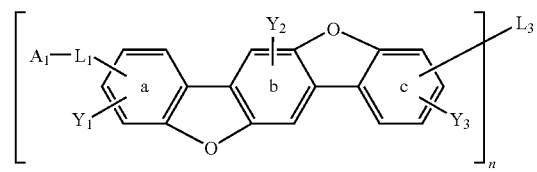

In addition, the general formulae (11) and (12) is preferably the following general formulae (13) and (14).

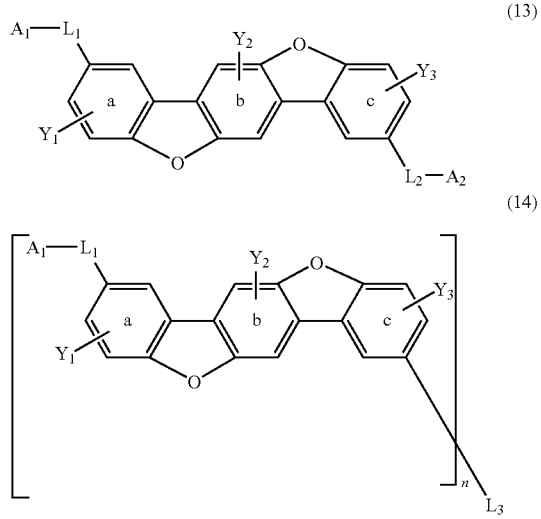

[In the formulae (12) and (14), n represents 2, 3, or 4, and the material represented by one of the formulae (12) and (14) includes a dimer using $L_3$ as a linking group for n=2, a trimer using $L_3$ as a linking group for n=3, or a tetramer using $L_3$ as a linking group for n=4.

In the formulae (11) to (14), $L_1$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with the benzene ring a through a carbon-carbon bond.

In the formulae (11) and (13), $L_2$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring c through a carbon-carbon bond.

In the formulae (12) and (14), when n represents 2, $L_3$ represents a single bond, an alkylene group having 1 to 20 carbon atoms, a substituted or unsubstituted cycloalkylene group having a ring formed of 3 to 20 carbon atoms, a divalent silyl group having 2 to 20 carbon atoms, a substituted or unsubstituted, divalent aromatic hydrocarbon group having a ring formed of 6 to 24 carbon atoms, or a substituted or unsubstituted, divalent aromatic heterocyclic group which has a ring formed of 3 to 24 atoms and which is linked with the benzene ring c through a carbon-carbon bond, when n represents 3, $L_3$ represents a trivalent alkane having 1 to 20 carbon atoms, a substituted or unsubstituted, trivalent cycloalkane having a ring formed of 3 to 20 carbon atoms, a trivalent silyl group having 1 to 20 carbon atoms, a substituted or unsubstituted, trivalent aromatic hydrocarbon group having a ring formed of 6 to 24 carbon atoms, or a substituted or unsubstituted, trivalent aromatic heterocyclic group which has 3 to 24 atoms and which is linked with the benzene ring c through a carbon-carbon bond, or when n represents 4, $L_3$ represents a tetravalent alkane having 1 to 20 carbon atoms, a substituted or unsubstituted, tetravalent cycloalkane having a ring formed of 3 to 20 carbon atoms, a silicon atom, a substituted or unsubstituted, tetravalent aromatic hydrocarbon group having a ring formed of 6 to 24 carbon atoms, or a substituted or unsubstituted, tetravalent aromatic heterocyclic group which has a ring formed of 3 to 24 atoms and which is linked with the benzene ring c through a carbon-carbon bond.

In the formulae (11) to (14), $A_1$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_1$ through a carbon-carbon bond, provided that, when $L_1$ represents an alkyl or alkylene group having 1 to 20 carbon atoms, a case where $A_1$ represents a hydrogen atom is excluded.

In the formulae (12) and (13), $A_2$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_2$ through a carbon-carbon bond, provided that, when $L_2$ represents an alkyl or alkylene group having 1 to 20 carbon atoms, a case where $A_2$ represents a hydrogen atom is excluded, and, when both $L_1$ and $L_2$ represent single bonds, a case where $A_1$ and $A_2$ simultaneously represent hydrogen atoms is excluded.

In the formulae (11) to (14), $Y_1$, $Y_2$, and $Y_3$ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with the benzene ring a, b, or c through a carbon-carbon bond, the number of each of $Y_1$ and $Y_3$ is 0, 1, 2, or 3, and the number of $Y_2$ is 0, 1, or 2.

In the formulae (11) to (14), $A_1$, $A_2$, $L_1$, $L_2$, and $L_3$ are each free of any carbonyl group.]

In the general formulae (11) to (14), $A_1$ preferably represents a silyl group having 3 to 20 carbon atoms, or an aromatic heterocyclic group which has a ring formed of 3 to 24 atoms and which is linked with $L_1$ through a carbon-carbon bond.

Further, in the general formulae (11) to (14), $A_1$ preferably represents an aromatic heterocyclic group which is linked with $L_1$ through a carbon-carbon bond and which is selected from pyridazine, pyrimidine, pyrazine, 1,3,5-triazine, carbazole, dibenzofuran, dibenzothiophene, phenoxazine, phenothiazine, and dihydroacridine.

In the general formulae (1) to (14), specific examples of each group are described below.

Examples of the substituted or unsubstituted aromatic hydrocarbon group having a ring formed of 6 to 24 carbon atoms represented by $Y_1$ to $Y_3$, $R_1$ to $R_3$, $L_1$ to $L_3$, and $A_1$ and $A_2$ include residues having corresponding valencies such as substituted or unsubstituted benzene, naphthalene, biphenyl, terphenyl, fluorene, phenanthrene, triphenylene, perylene, chrysene, fluoranthene, benzofluorene, bnezotriphenylene, benzochrysene, and anthracene. Preferred are benzene, naphthalene, biphenyl, terphenyl, fluorene, and phenanthrene.

Examples of the substituted or unsubstituted aromatic hydrocarbon group having a ring formed of 3 to 24 atoms represented by $Y_1$ to $Y_3$, $R_1$ to $R_3$, $L_1$ to $L_3$, and $A_1$ and $A_2$ include residues having corresponding valencies such as pyridine, pyridazine, pyrimidine, pyrazine, 1,3,5-triazine, carbazole, dibenzofuran, dibenzothiophene, phenoxazine, phenothiazine, and dihydroacridine. Preferred are pyridine, pyridazine, pyrimidine, pyrazine, carbazole, dibenzofuran, dibenzothiophene, phenoxazine, and dihydroacridine. In addition, examples of at least one substituted or unsubstituted, monovalent fused aromatic heterocyclic group having a ring formed of 8 to 24 atoms represented by $R_1$ include aromatic heterocyclic groups each having a fused structure in examples of the aromatic heterocyclic groups.

Examples of the alkyl group, alkylene group, and trivalent or tetravalent alkane, each of which has 1 to 20 carbon atoms represented by Y, $Y_1$ to $Y_3$, $L_1$ to $L_3$, and $R_1$ to $R_3$ include a methyl group, an ethyl group, a propyl group, an isopropyl group, an n-butyl group, an s-butyl group, a t-butyl group, an isobutyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 2-methylpentyl group, a 1-pentylhexyl group, a 1-butylpentyl group, a 1-heptyloctyl group, and a 3-methylpentyl group or groups obtained by allowing those groups to have two to four valencies. Preferred are a methyl group, an ethyl group, a propyl group, an isopropyl group, an n-butyl group, an s-butyl group, an isobutyl group, a t-butyl group, n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 1-pentylhexyl group, a 1-butylpentyl group, and a 1-heptyloctyl group.

Examples of the substituted or unsubstituted cycloalkyl group, cycloalkylene group, and trivalent or tetravalent cycloalkane, each of which has a ring formed of 3 to 20 carbon atoms, represented by $Y_1$ to $Y_3$, $L_1$ to $L_3$, $R_1$ to $R_3$, and $A_1$ and $A_2$ include a cyclopropyl group, a cyclobutyl group, a cyclopentyl group, a cyclohexyl group, and groups obtained by allowing those group to have two to four valencies. Preferred are a cyclobutyl group, a cyclopentyl group, and a cyclohexyl group.

Examples of the alkoxy group having 1 to 20 carbon atoms and represented by $Y_1$ to $Y_3$ include a methoxy group, an ethoxy group, a methoxy group, an i-propoxy group, an n-propoxy group, an n-butoxy group, an s-butoxy group, and a t-butoxy group. Preferred are a methoxy group, an ethoxy group, a methoxy group, an i-propoxy group, and an n-propoxy group.

Examples of the silyl group having 1 to 20 carbon atoms represented by $Y_1$ to $Y_3$, $L_1$ to $L_3$, $R_1$ to $R_3$, and $A_1$ and $A_2$ include a trimethyl silyl group, a triethyl silyl group, a tributyl silyl group, a trioctyl silyl group, a triisobutyl silyl group, a dimethylethyl silyl group, a dimethylisopropyl silyl group, a dimethylpropyl silyl group, a dimethylbutyl silyl group, a dimethyltertiary butyl silyl group, a diethylisopropyl silyl group, a phenyldimethyl silyl group, a diphenylmethyl silyl group, a diphenyl tertiary butyl group, a triphenyl silyl group, and groups obtained by allowing those groups to have two or three valencies. Preferred are a trimethyl silyl group, a triethyl silyl group, and a tributyl silyl group.

Examples of the aralkyl group having 7 to 24 carbon atoms represented by $Y_1$ to $Y_3$, and $R_1$ to $R_3$ include a benzyl group, a phenethyl group, and a phenylpropyl group.

Examples of the substituent that can be substituted for the each group in the general formulae (1) to (14) include alkyl groups each having 1 to 10 carbon atoms (such as a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, a iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and a 1,2,3-trinitropropyl group), cycloalkyl groups each having a ring formed of 3 to 40 carbon atoms (such as a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group), alkoxy groups each having 1 to 6 carbon atoms (such as an ethoxy group, a methoxy group, an i-propoxy group, an n-propoxy group, an s-butoxy group, a t-butoxy group, a pentoxy group, and a hexyloxy group), cycloalkoxy groups each having a ring formed of 3 to 10 carbon atoms (such as a cyclopentoxy group and a cyclohexyloxy group), aromatic hydrocarbon groups each having a ring formed of 6 to 40 carbon atoms, aromatic heterocyclic groups having a ring formed of 3 to 40 atoms, amino groups substituted with aromatic hydrocarbon groups having a ring formed of 6 to 40 carbon atoms, ester groups having aromatic hydrocarbon groups having a ring formed of 6 to 40 carbon atoms, an ester group, cyano group, nitro group, and halogen atom, each of which has an alkyl group having 1 to 6 carbon atoms.

Of those, alkyl groups each having 1 to 6 carbon atoms, a phenyl group, a pyridyl group, a carbazolyl group, and a dibenzofuranyl group are preferred and the number of substituents is preferably 1 or 2.

In the material for an organic EL device represented by the general formula (2), (7) to (10), (12), or (14), n preferably represents 2.

In the general formula (1), (3) to (6), (11), or (13), the total number of the substituents represented by $Y_1$, $Y_2$, and $Y_2$ is preferably 3 or less, and the total number of the substituents represented by $Y_1$, $Y_2$, and $Y_3$ in the structure of [ ]$_n$ in the general formula (2), (7) to (10), (12), or (14) is preferably 3 or less.

In the general formula (1) or (2), $X_1$ and $X_2$ are each represented by N—$R_1$. N—$R_1$ of $X_1$ and N—$R_1$ of $X_2$ may be preferably different from each other.

Specific examples of the material for an organic EL device represented by any one of the general formulae (1) to (14) of the present invention are shown below. However, the present invention is not limited to these exemplified compounds.

No. 1

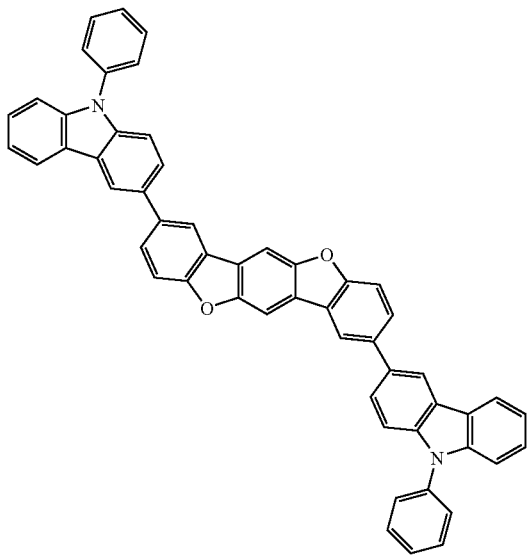

No. 2

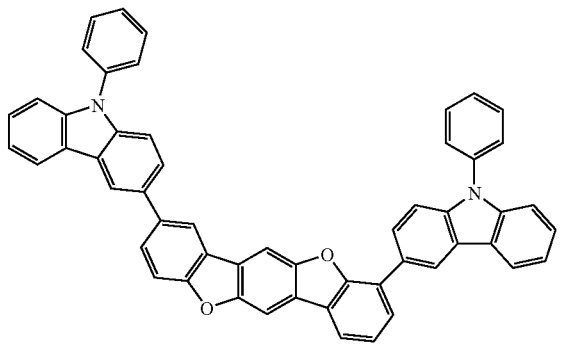

No. 3

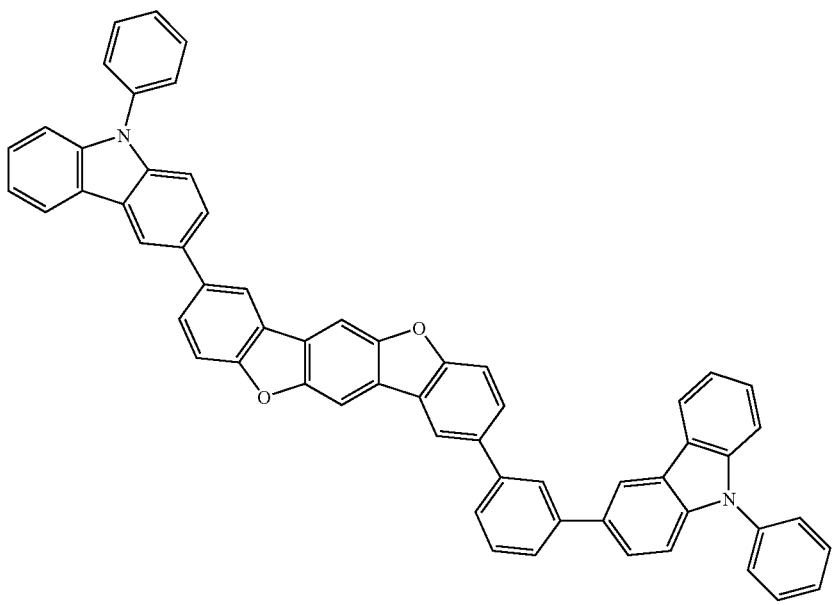

-continued
No. 4
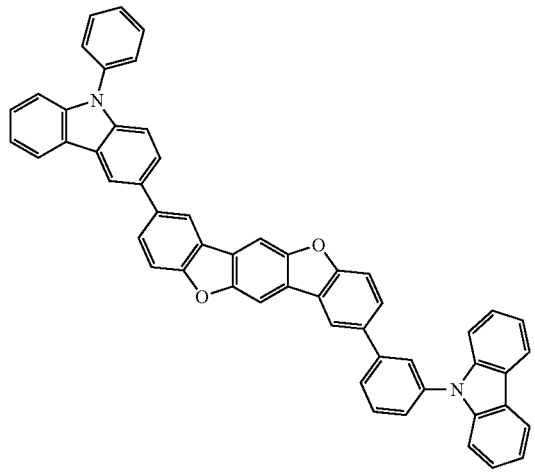
No. 5
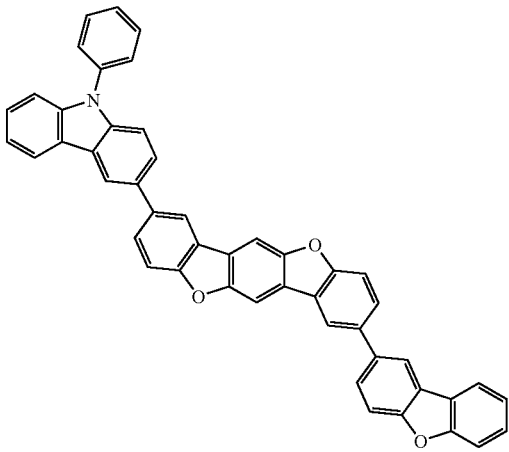
No. 6
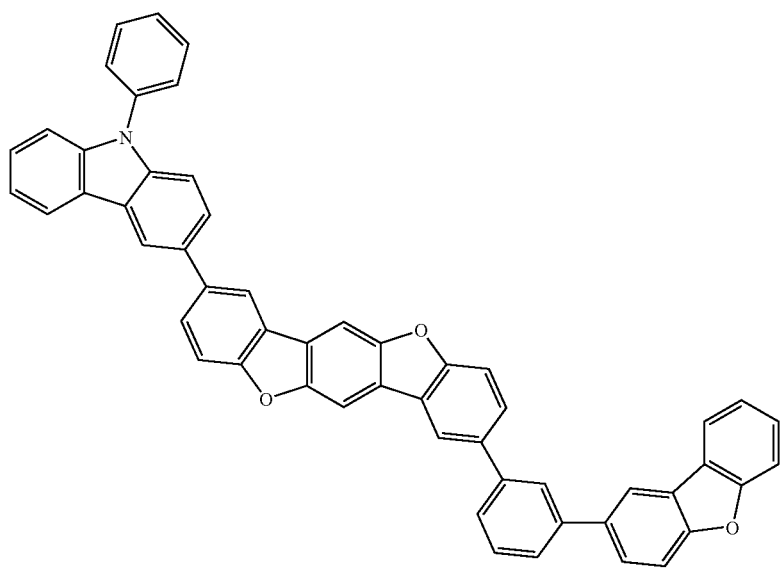
No. 7
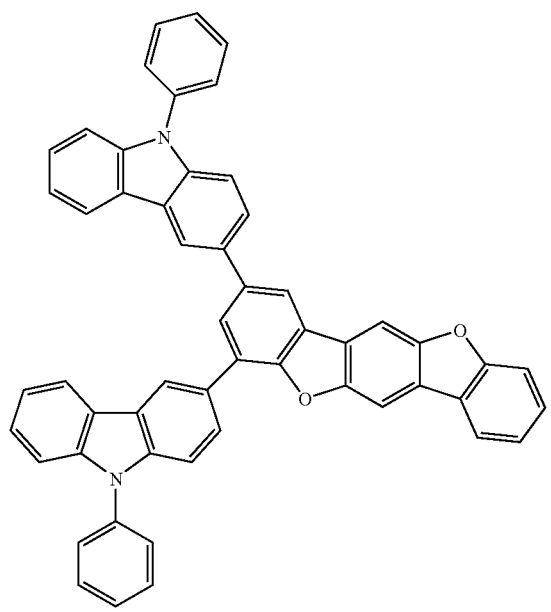
No. 8

-continued
No. 9
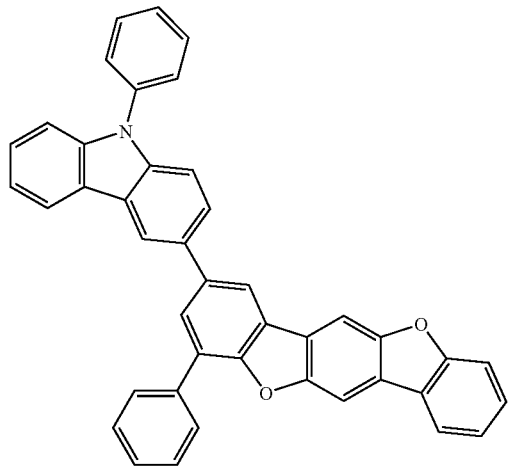
No. 10
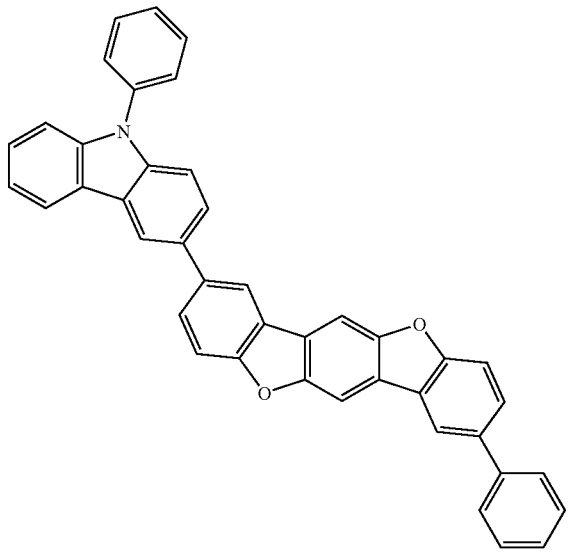
No. 11
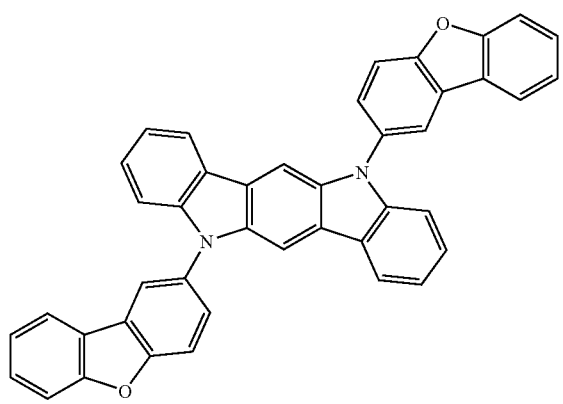
No. 12
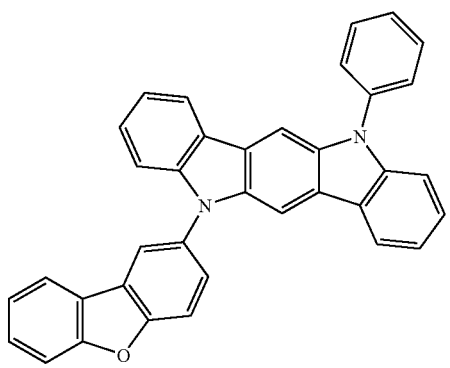
No. 13
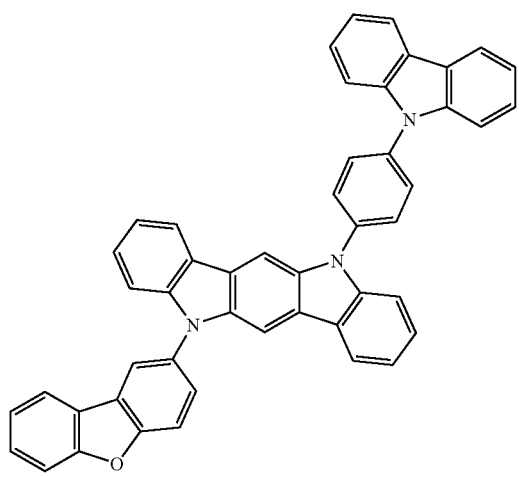
No. 14
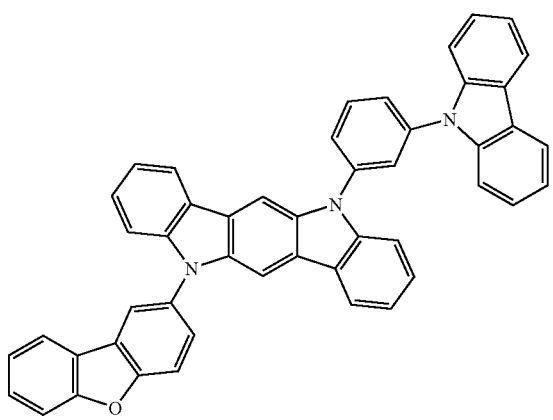

-continued
No. 15
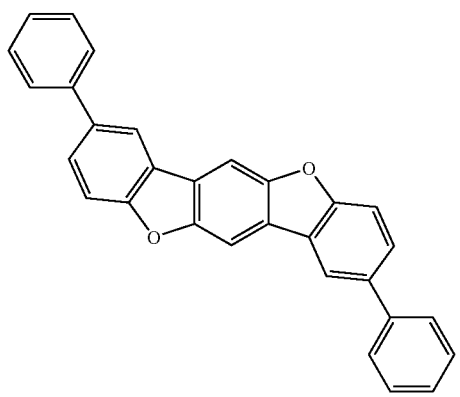
No. 16
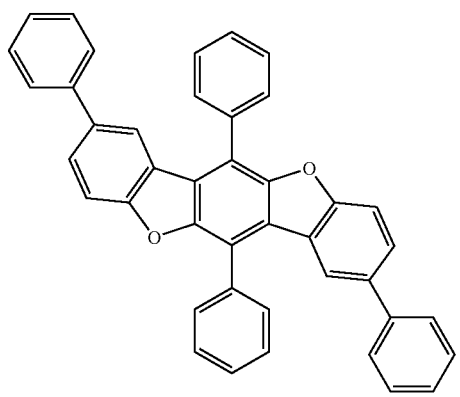
No. 17
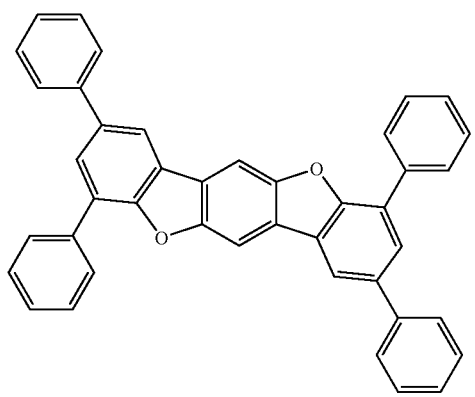
No. 18
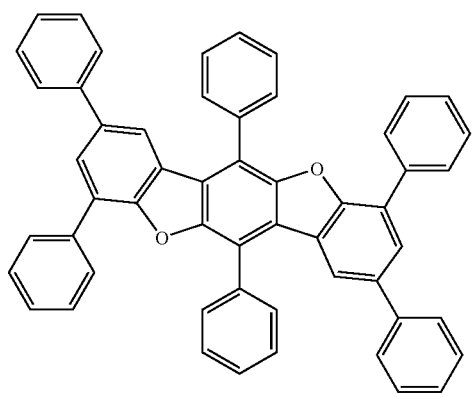
No. 19
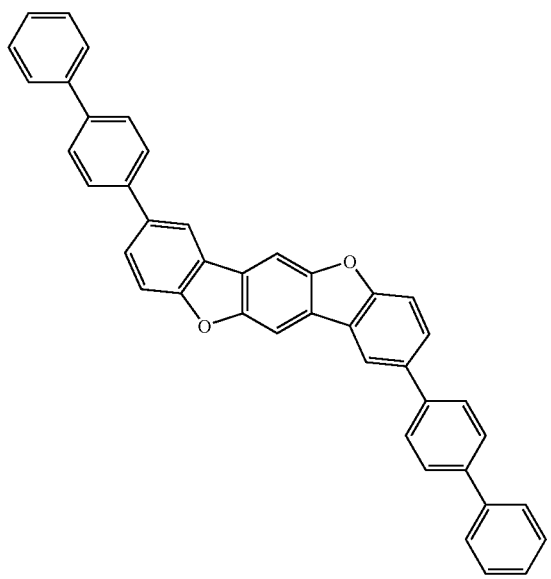
No. 20
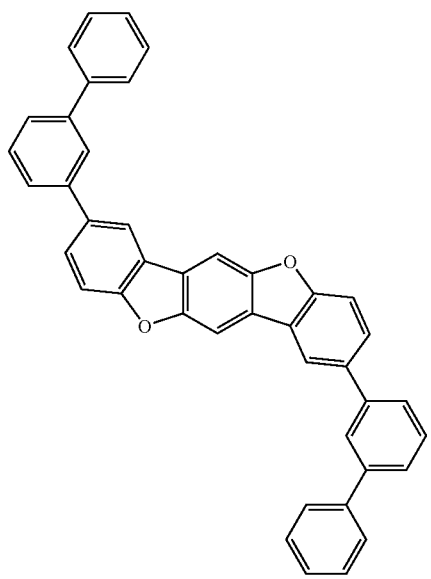

-continued
No. 21
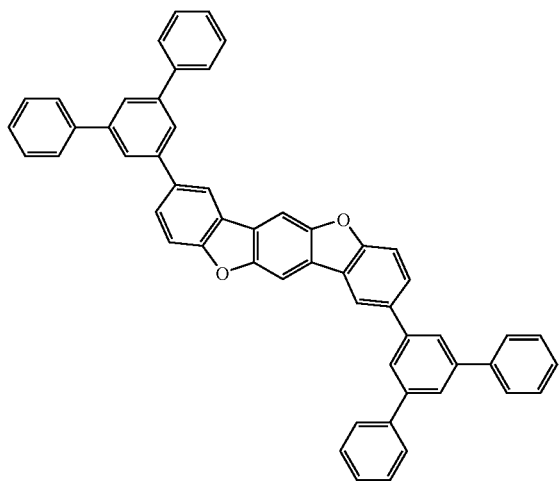
No. 22
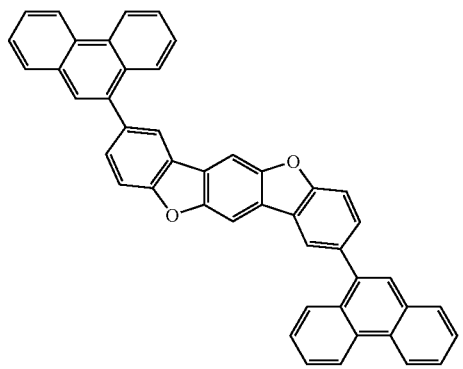
No. 23
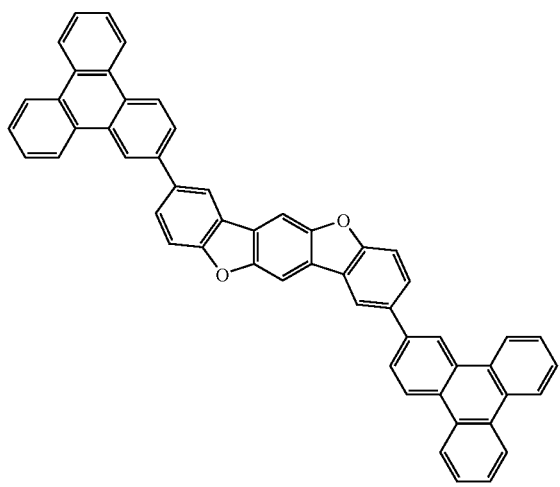
No. 24
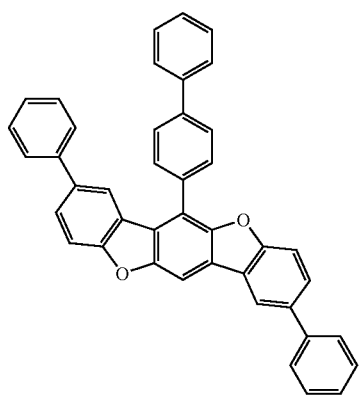
No. 25
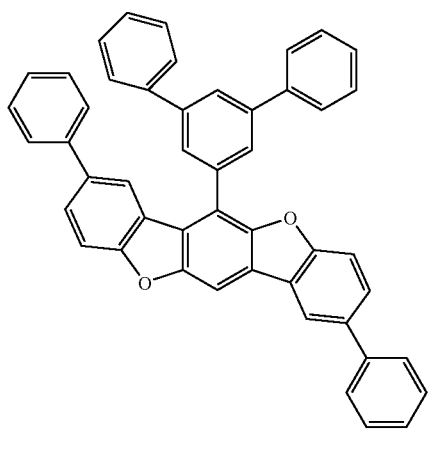
No. 26
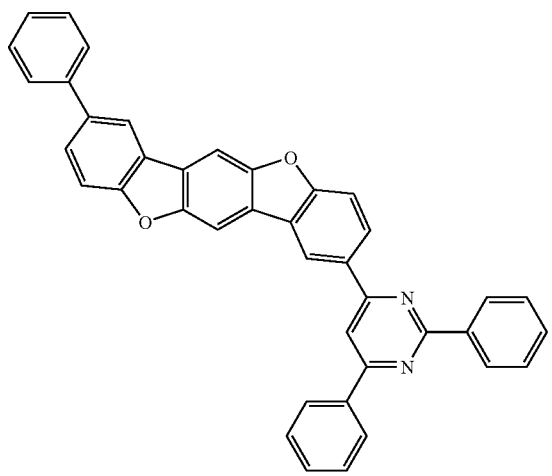

No. 27
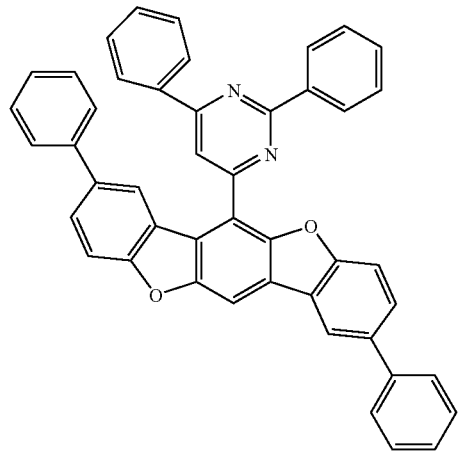
No. 28
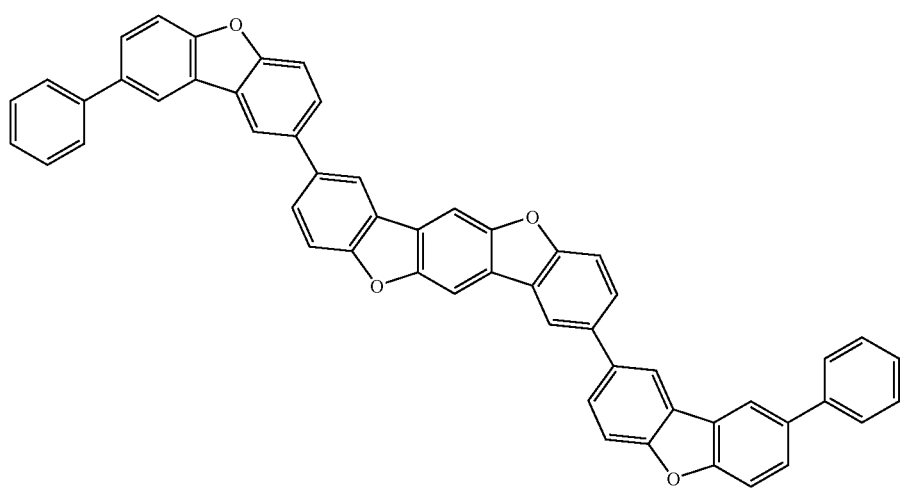
No. 29
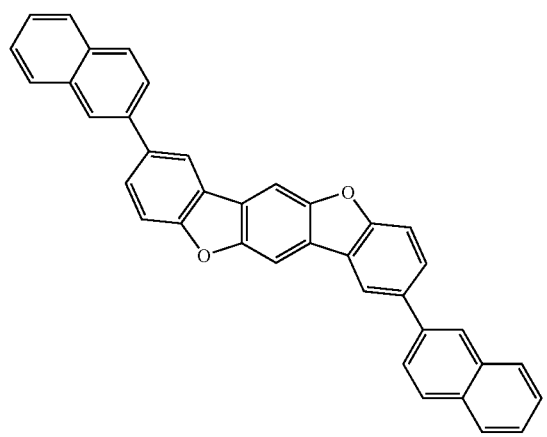
No. 30
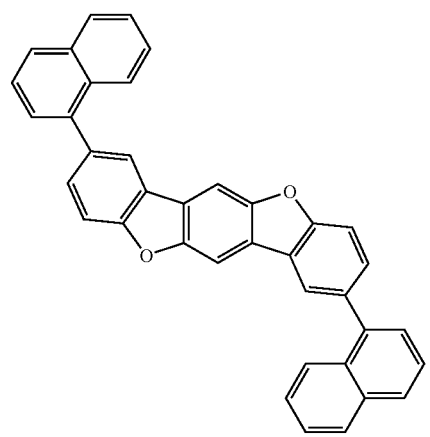

-continued
No. 31
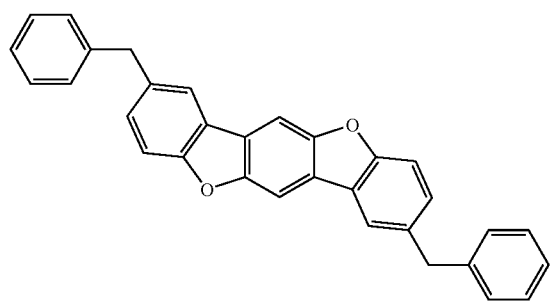
No. 32
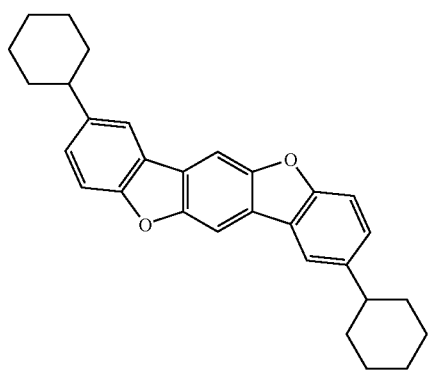
No. 33
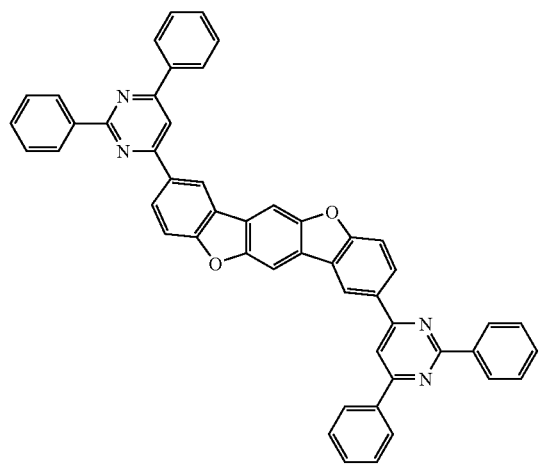
No. 34
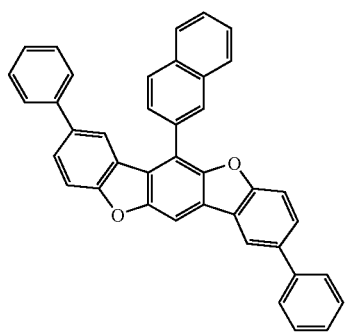
No. 35
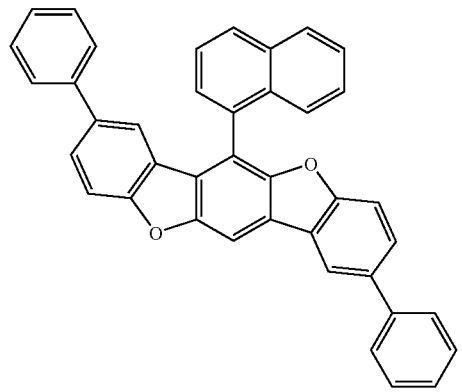
No. 36
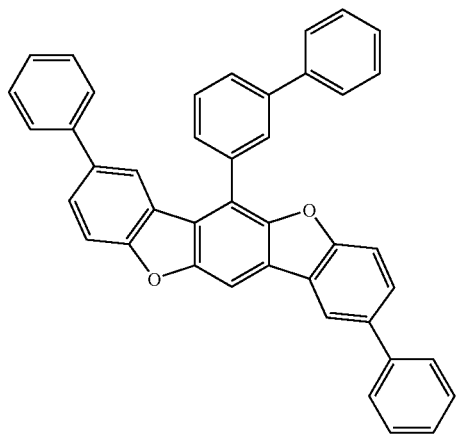

-continued
No. 37
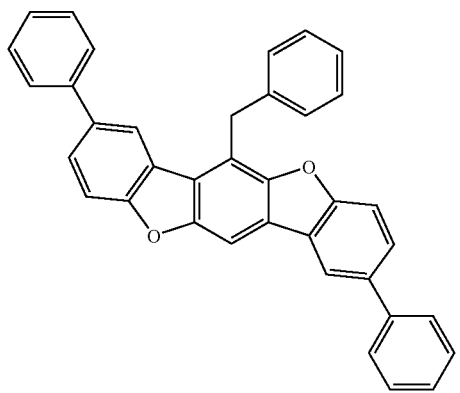
No. 38
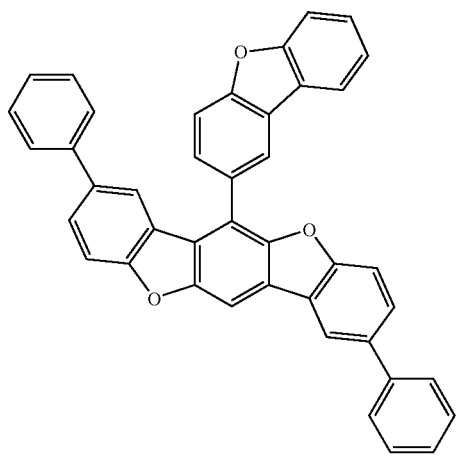
No. 39
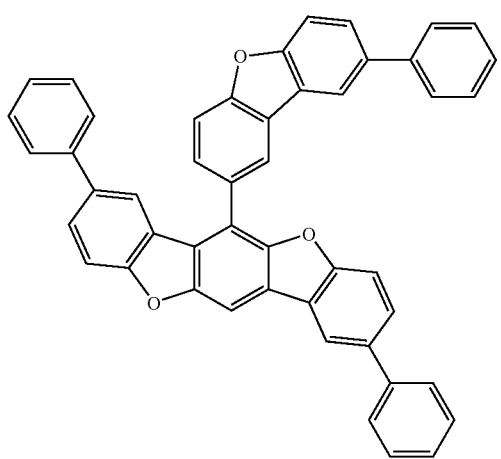
No. 40
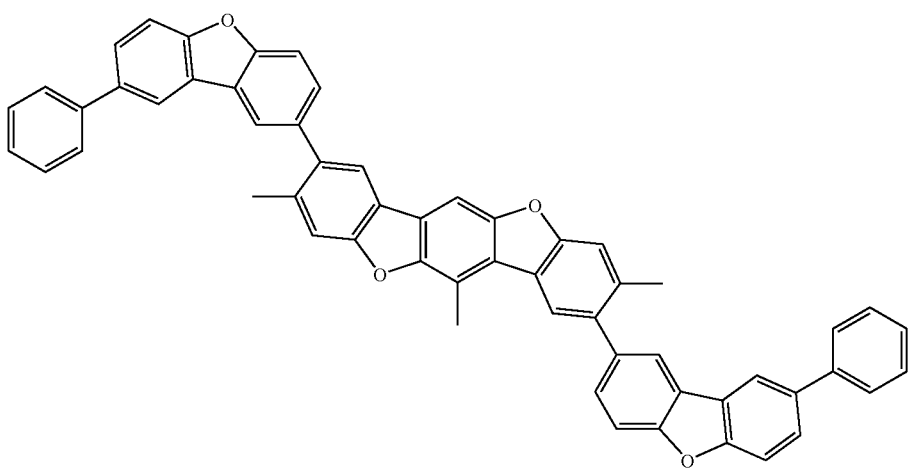

No. 41
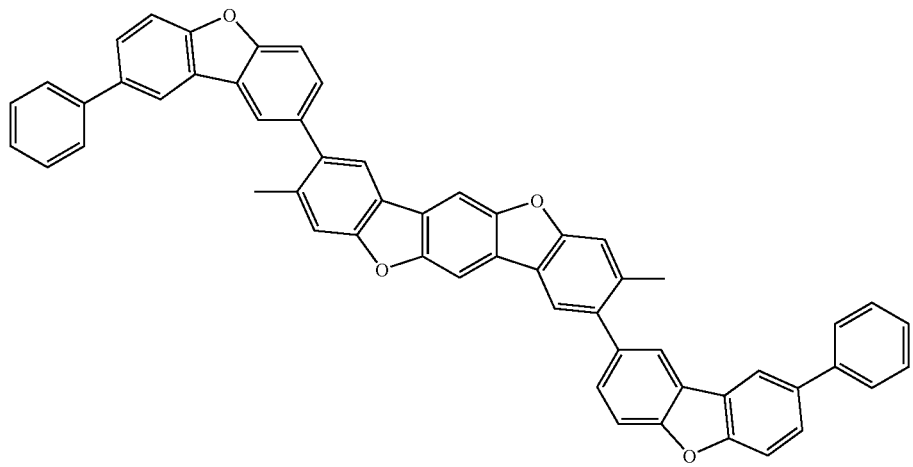
No. 42
No. 43
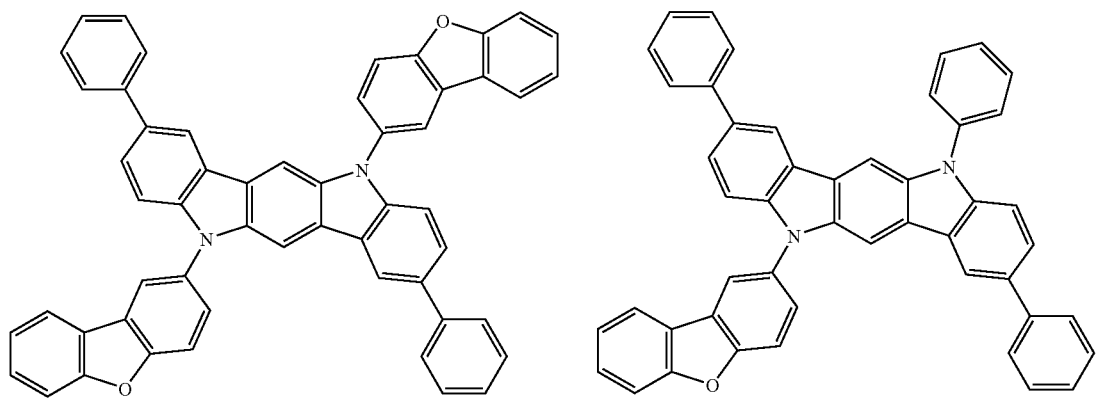
No. 44
No. 45
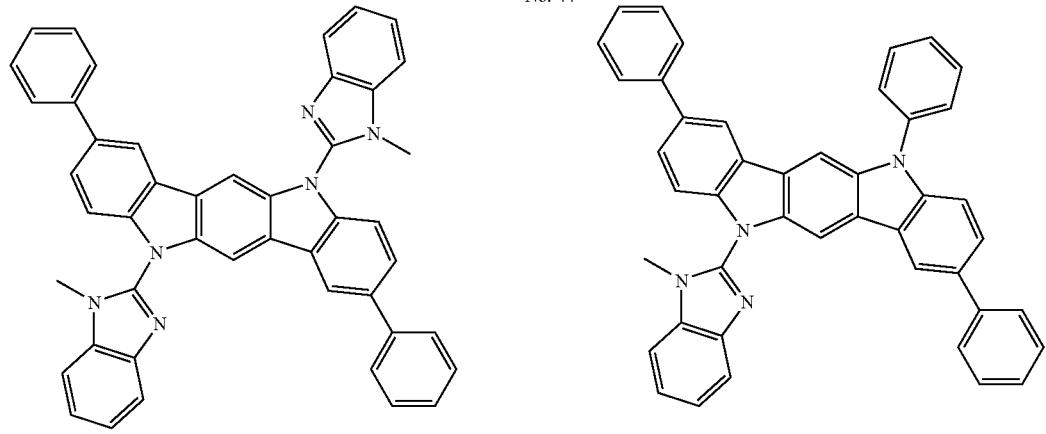

No. 46
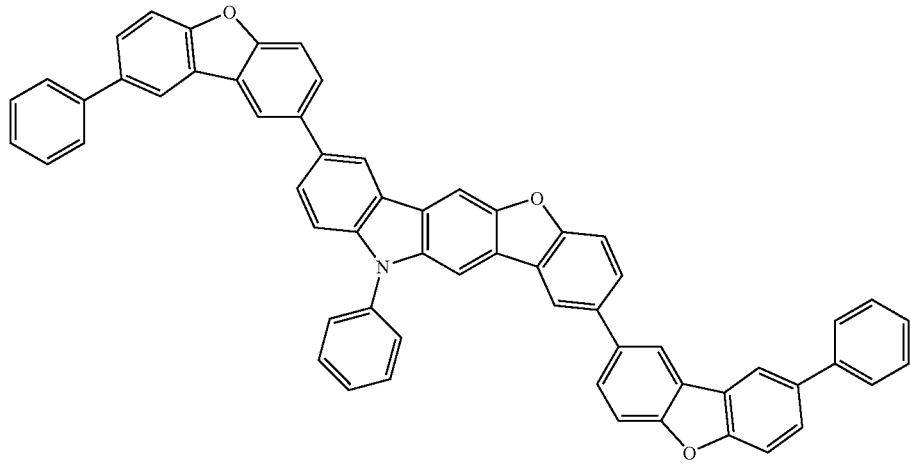
No. 47
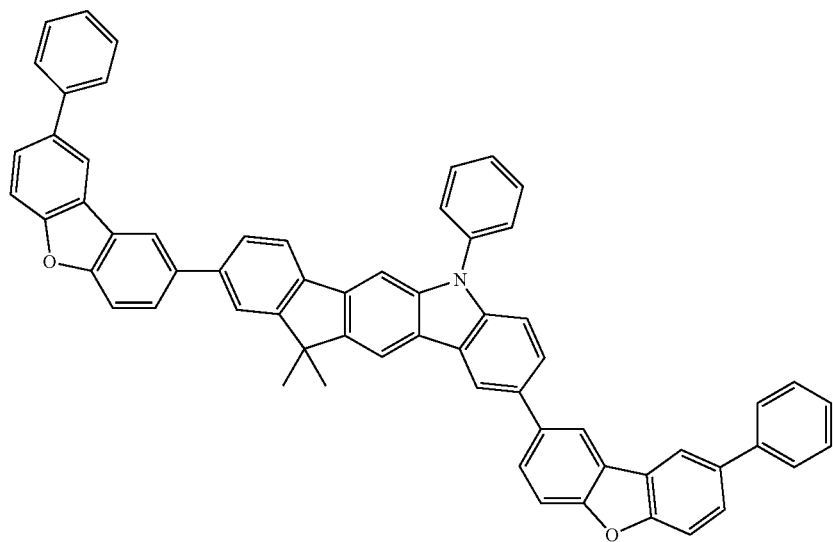
No. 48
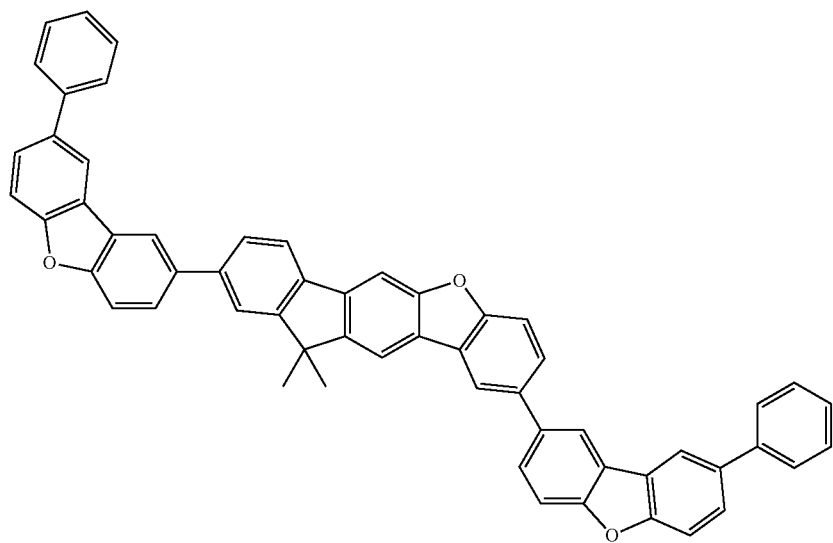

-continued
No. 49
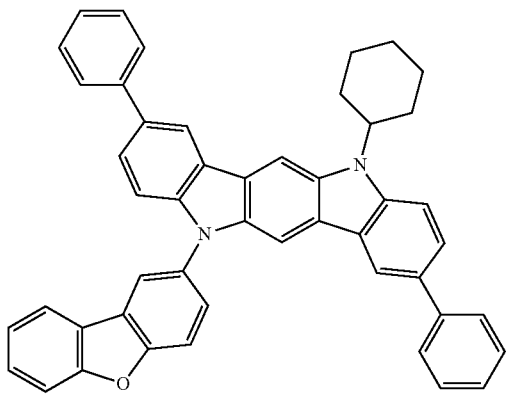
No. 50
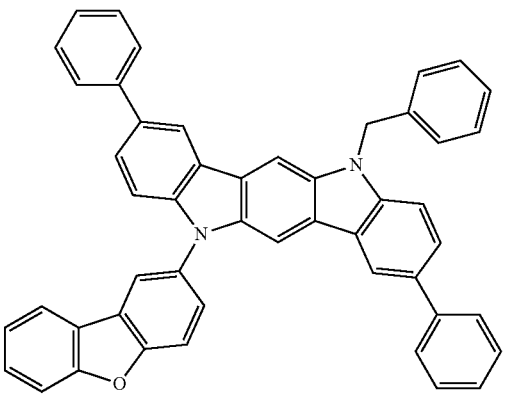
No. 51
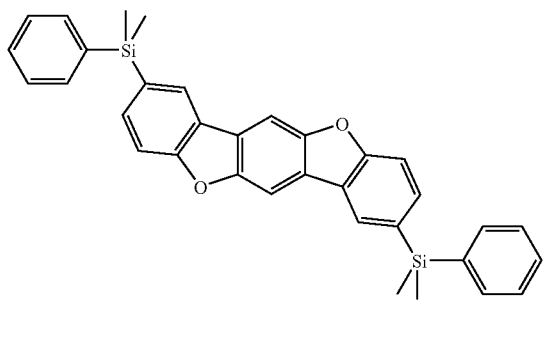
No. 52
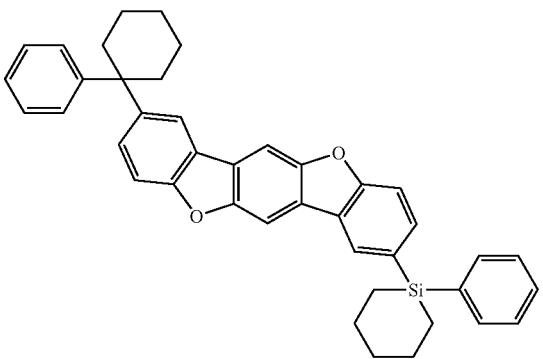
No. 53
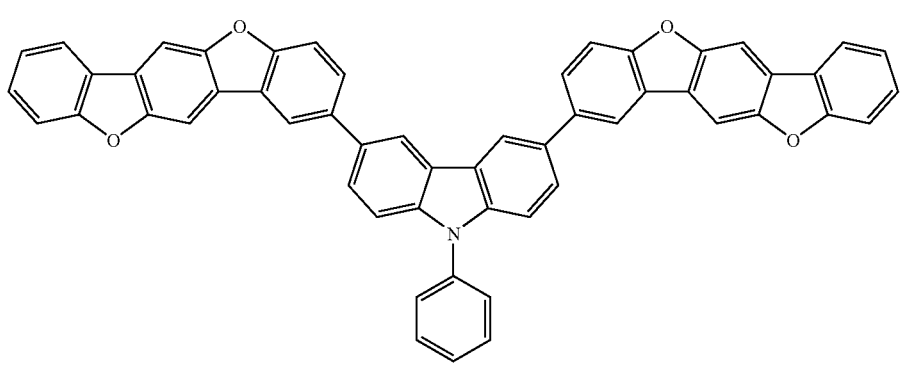
No. 54
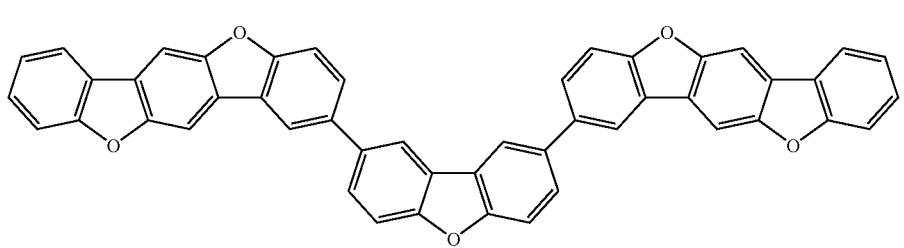

-continued
No. 55
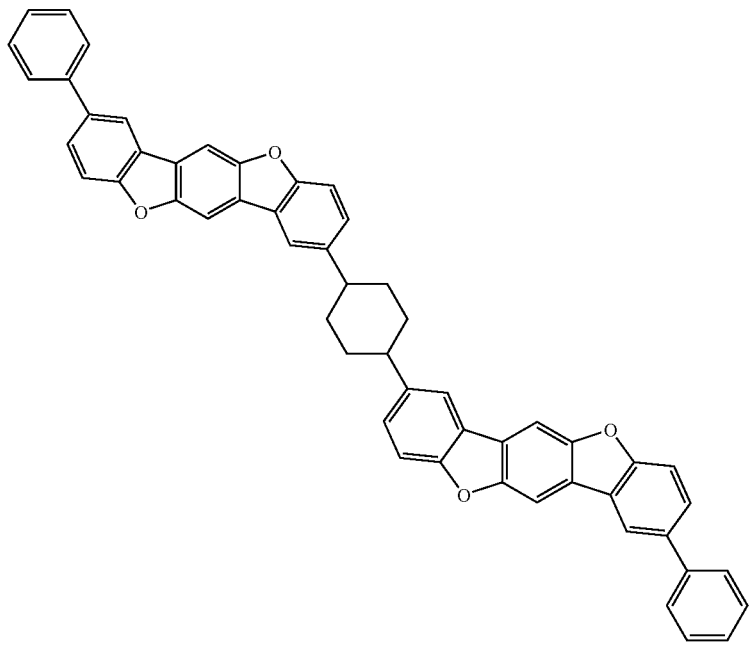
No. 56
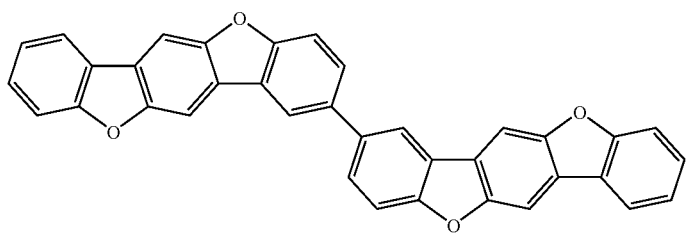
No. 57
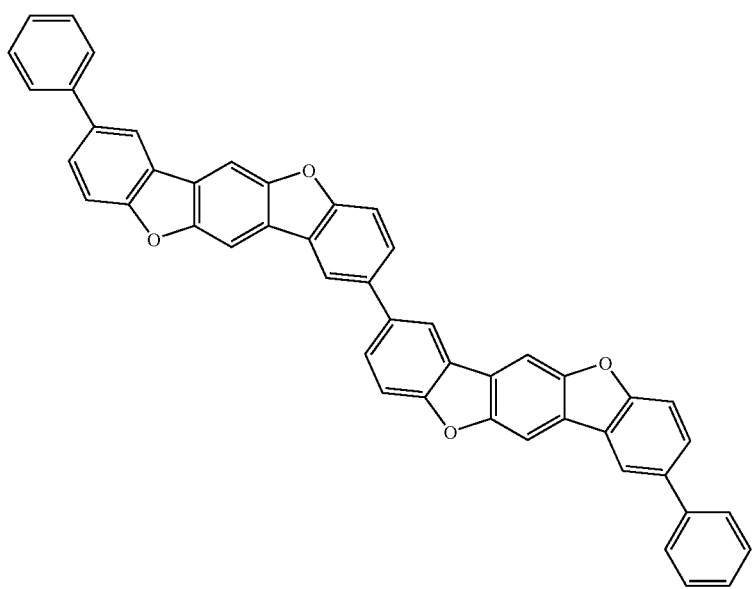

-continued
No. 58
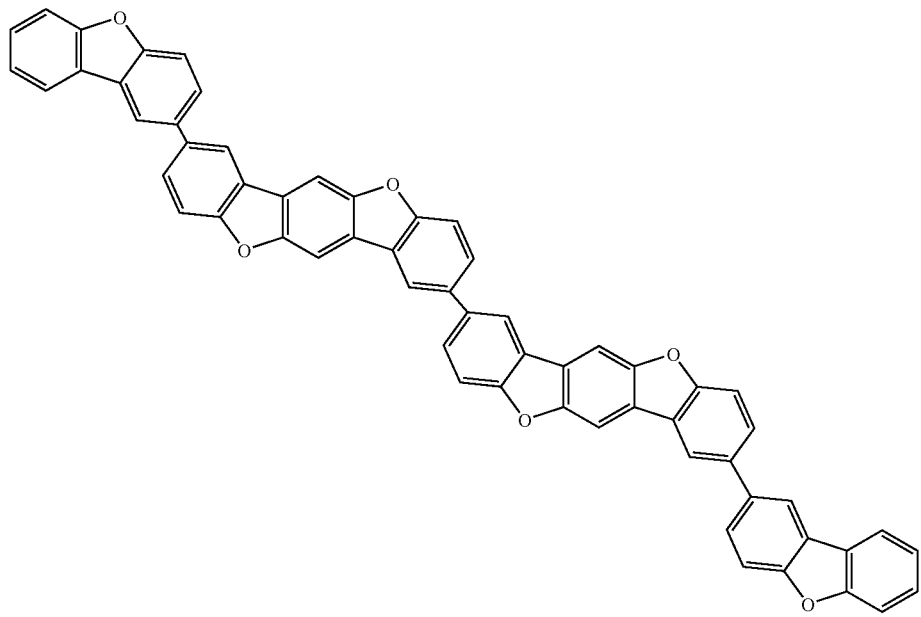
No. 59
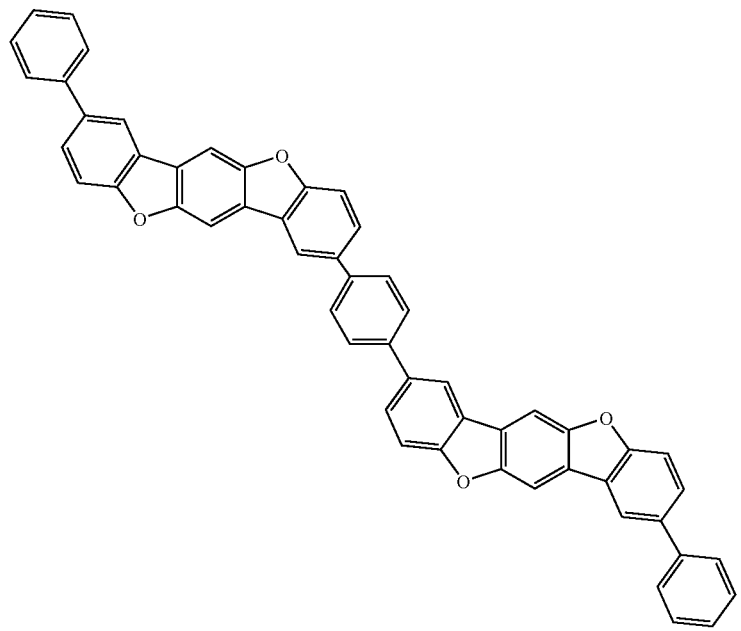
No. 60
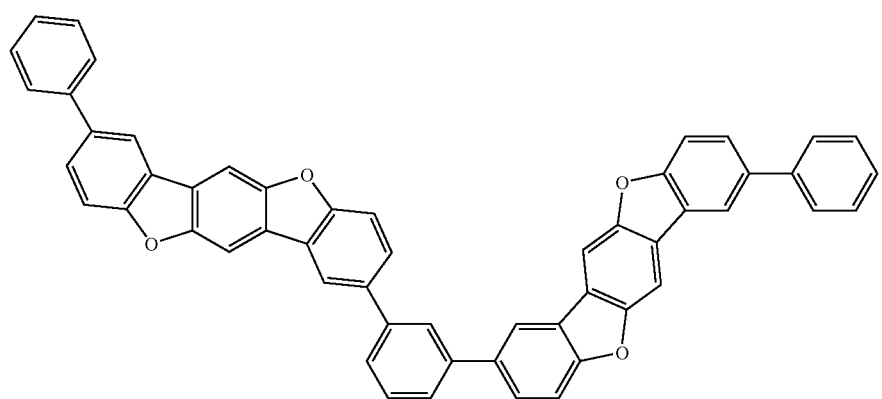

-continued
No. 61
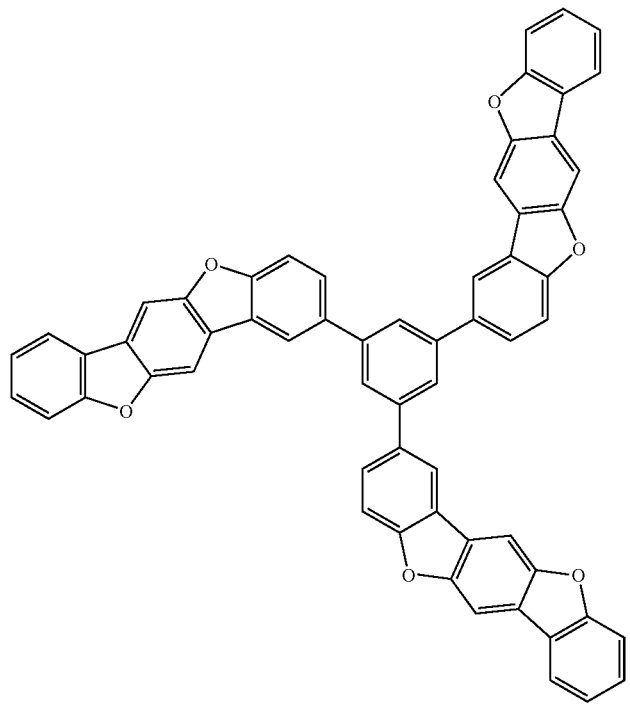
No. 62
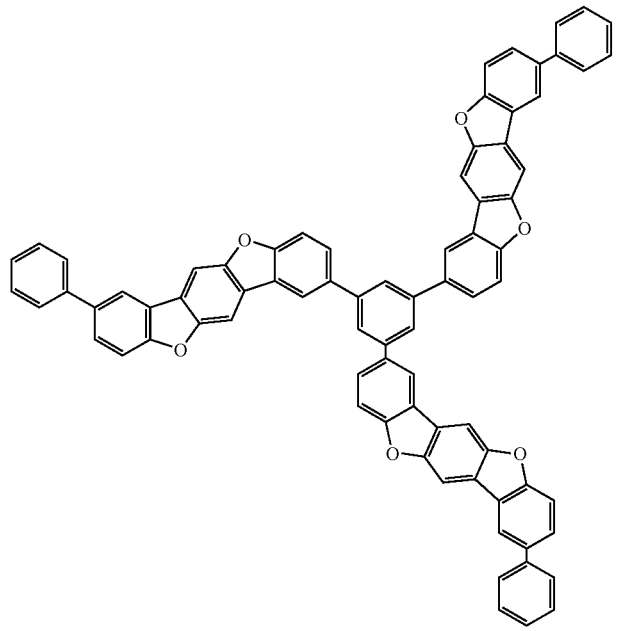

-continued
No. 63
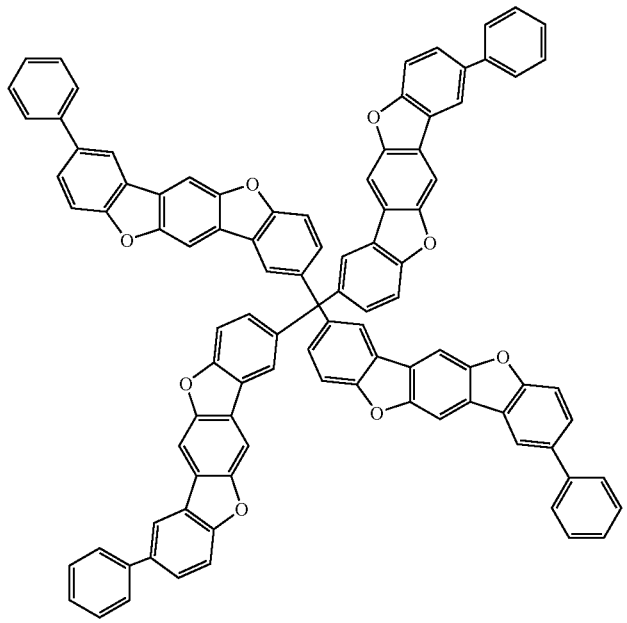
No. 64
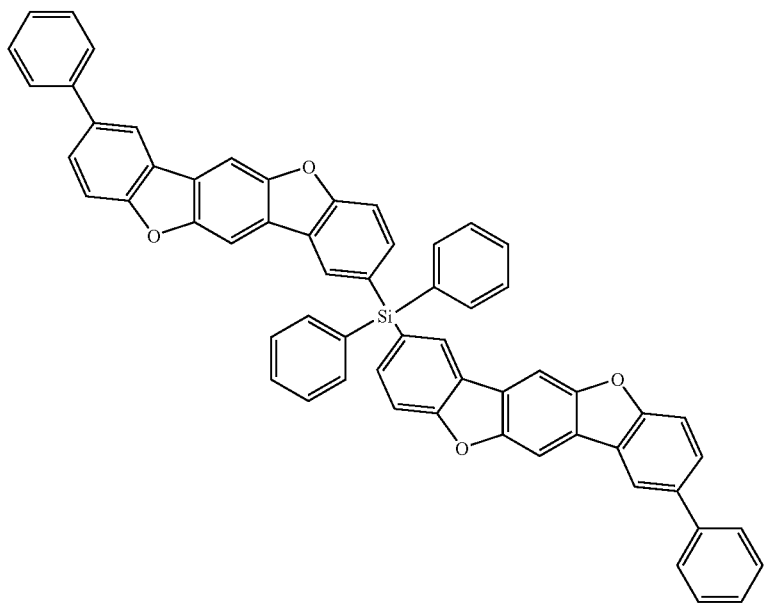

-continued
No. 65
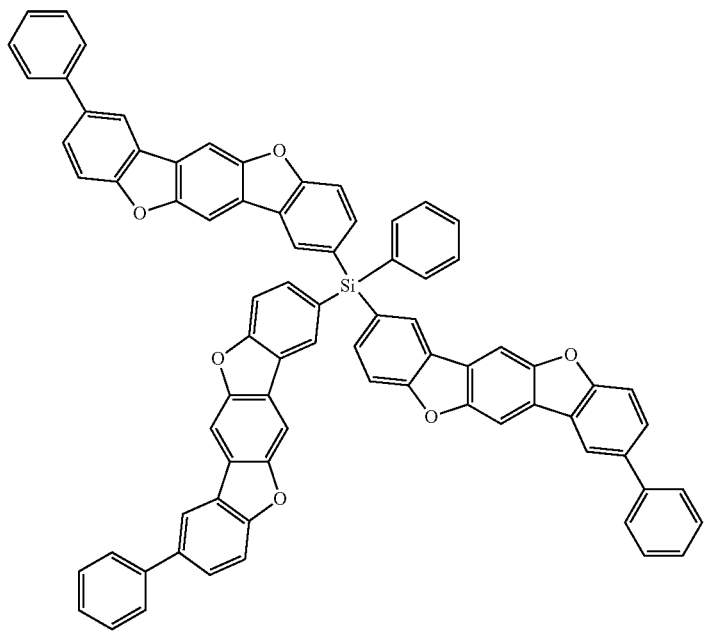
No. 66
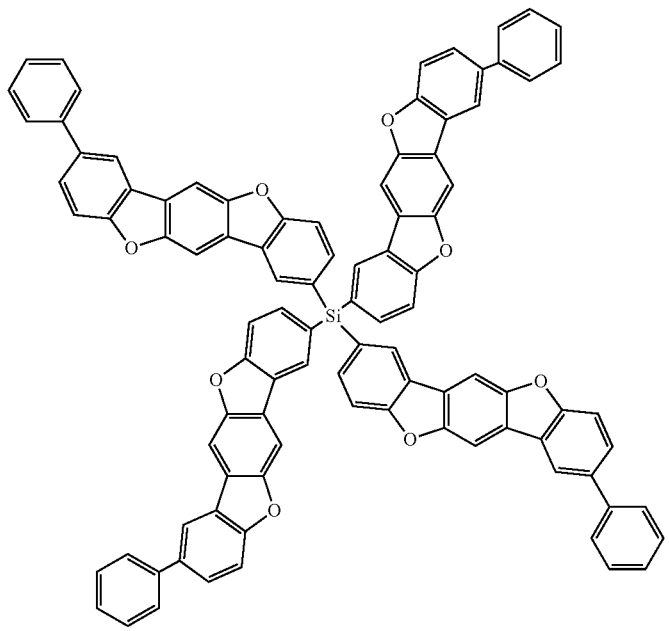
No. 67
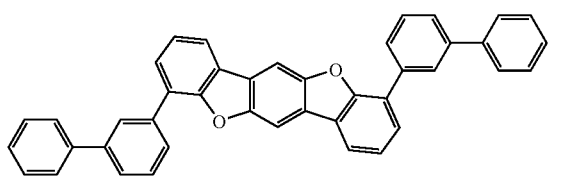
No. 68
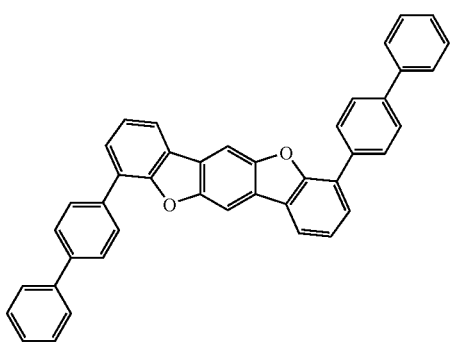

-continued
No. 69
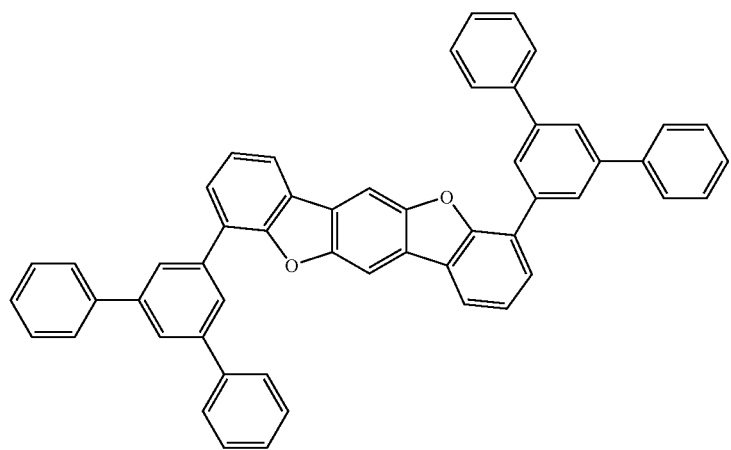
No. 70
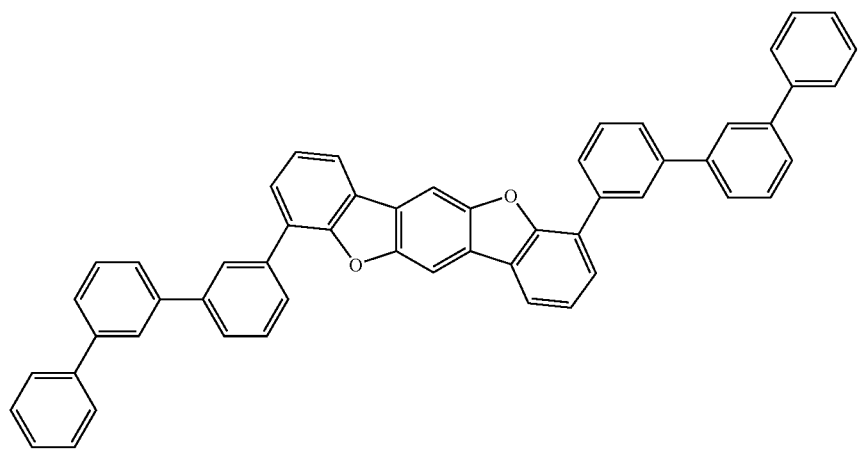
No. 71
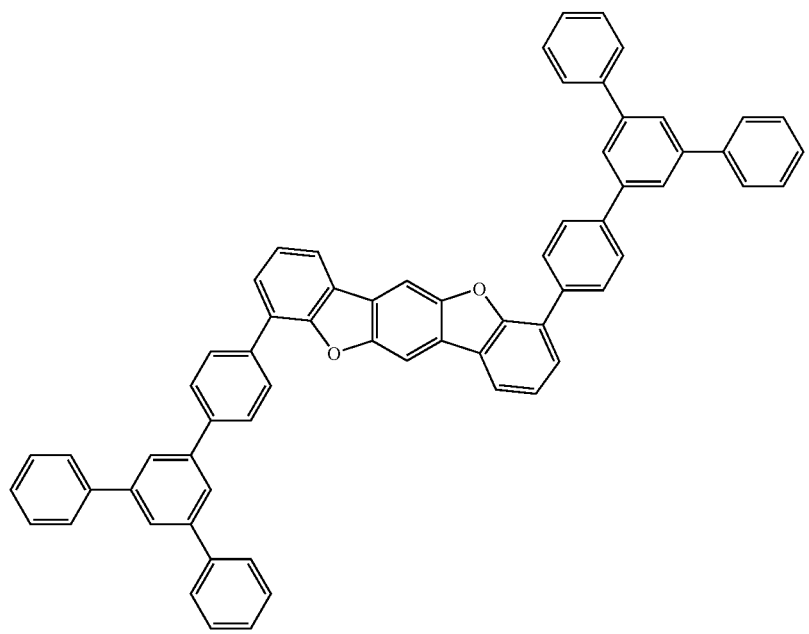

-continued
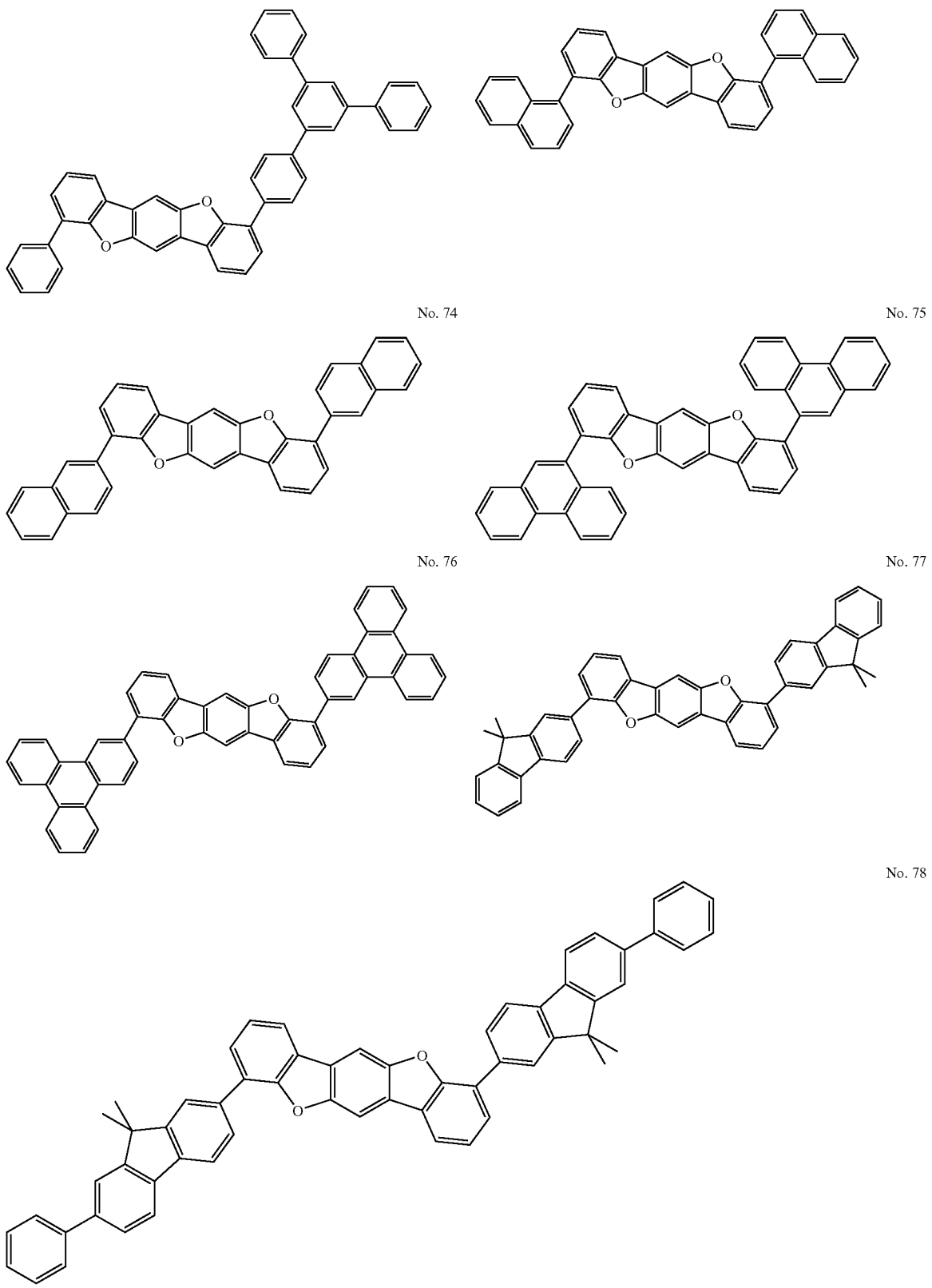

No. 79
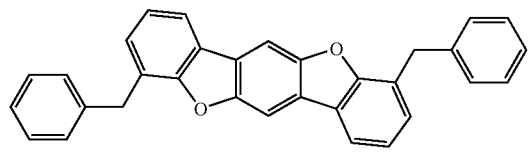
No. 80
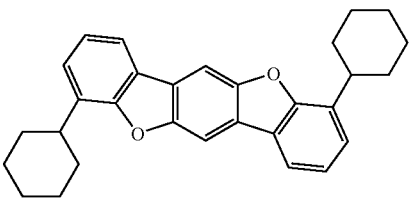
No. 81
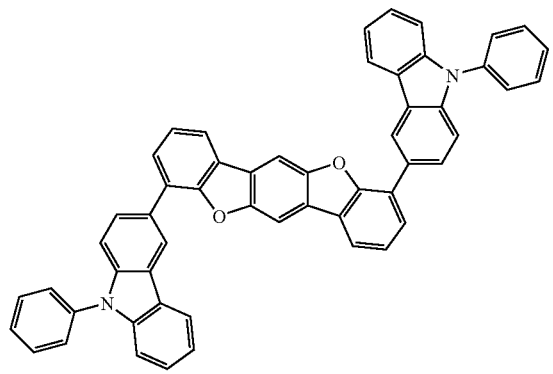
No. 82
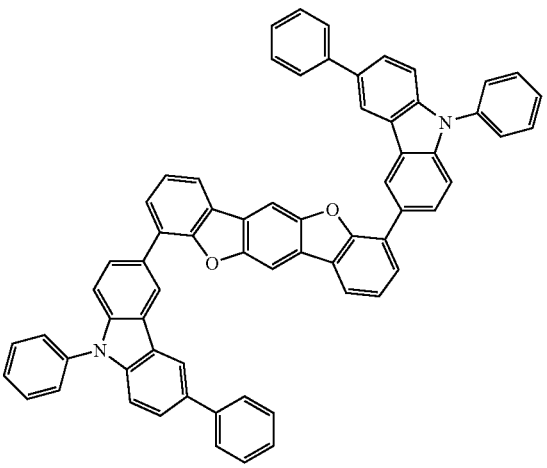
No. 83
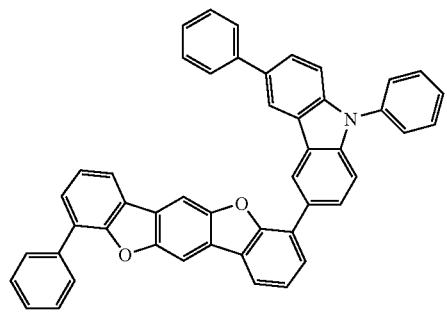
No. 84
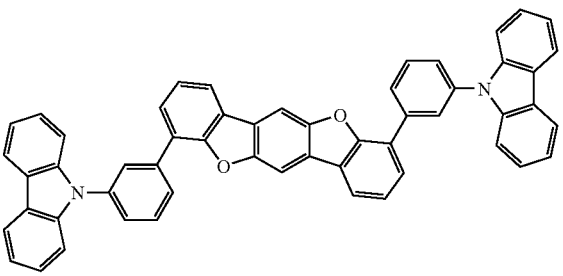
No. 85
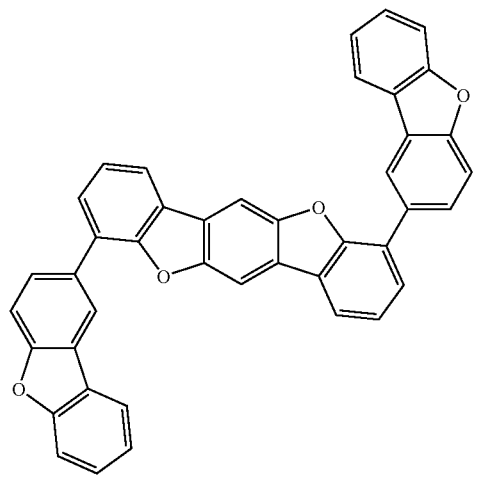
No. 86
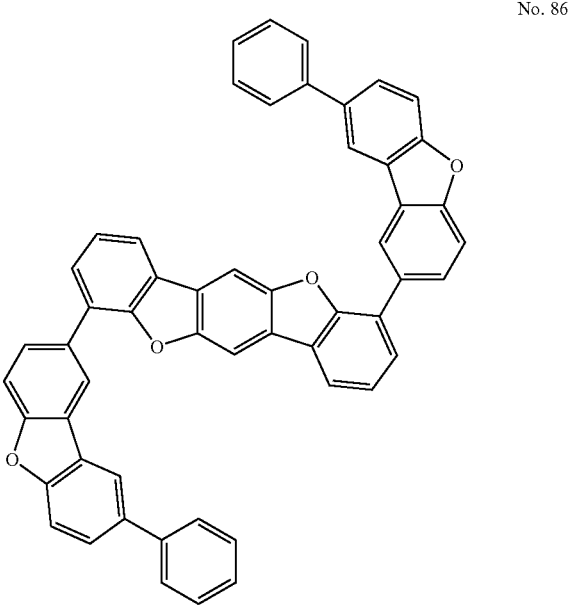

No. 87
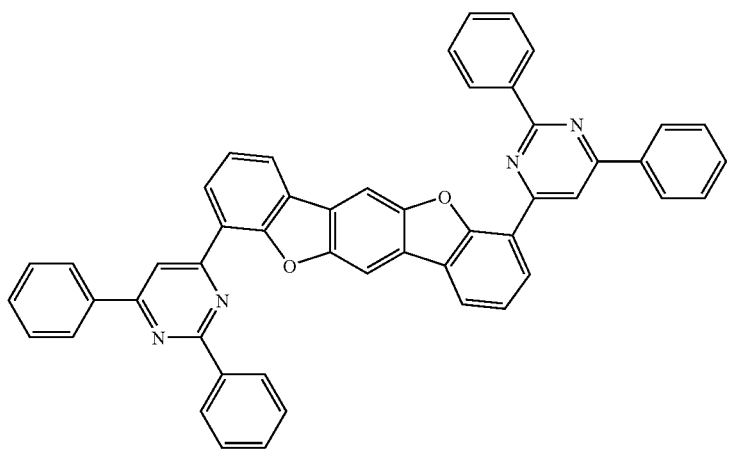
No. 88
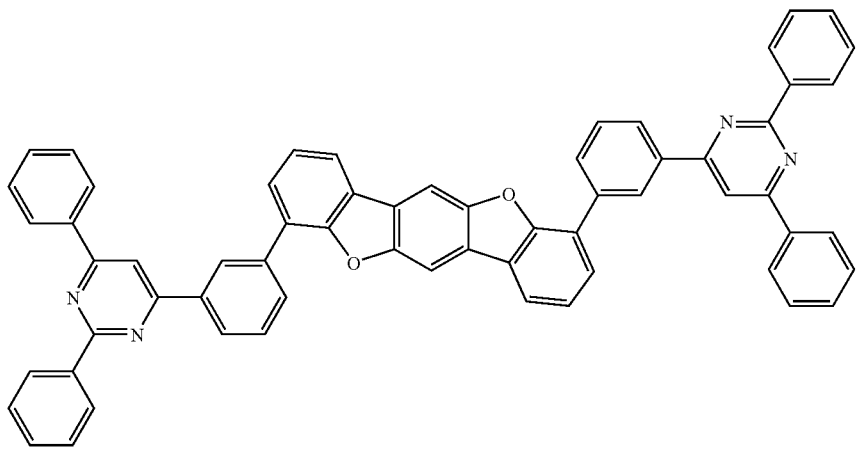
No. 89
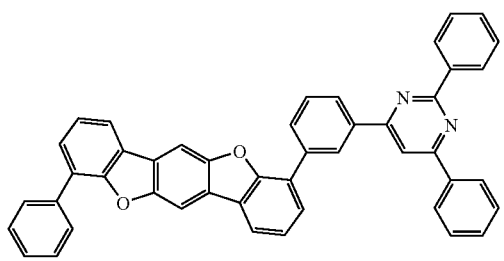
No. 90
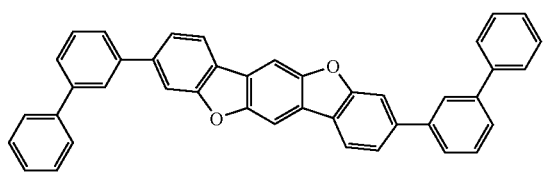
No. 91
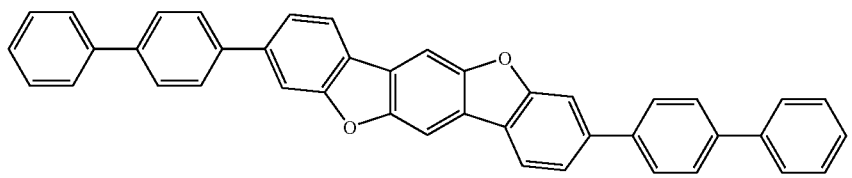

-continued
No. 92
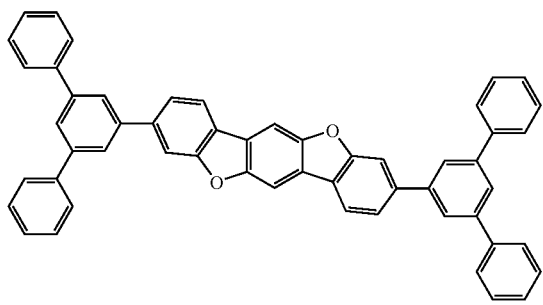
No. 93
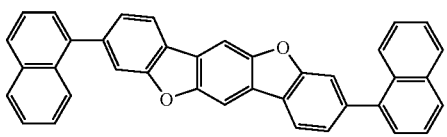
No. 94
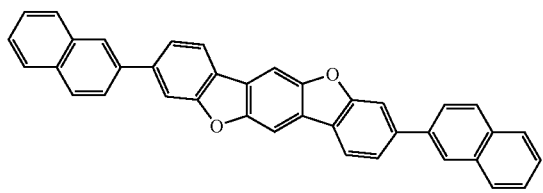
No. 95
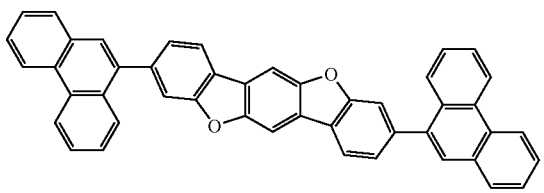
No. 96
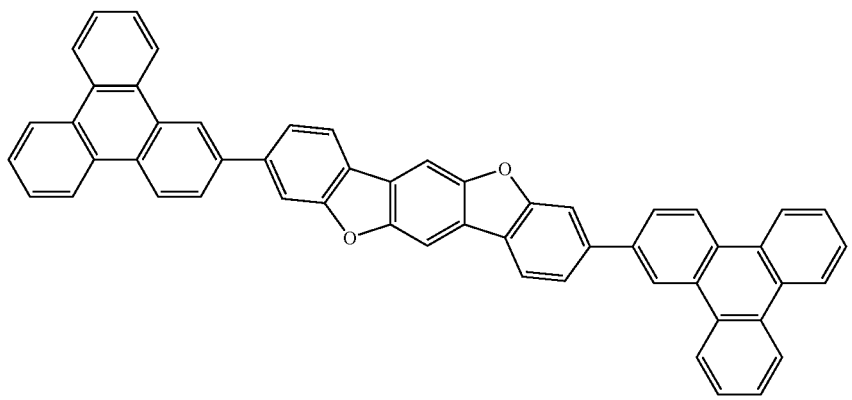
No. 97
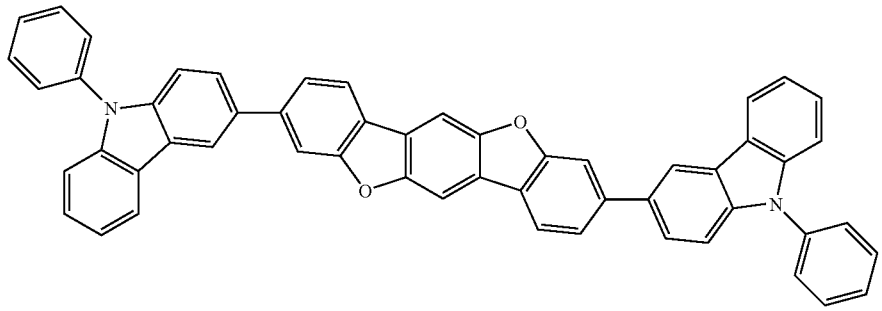

No. 98
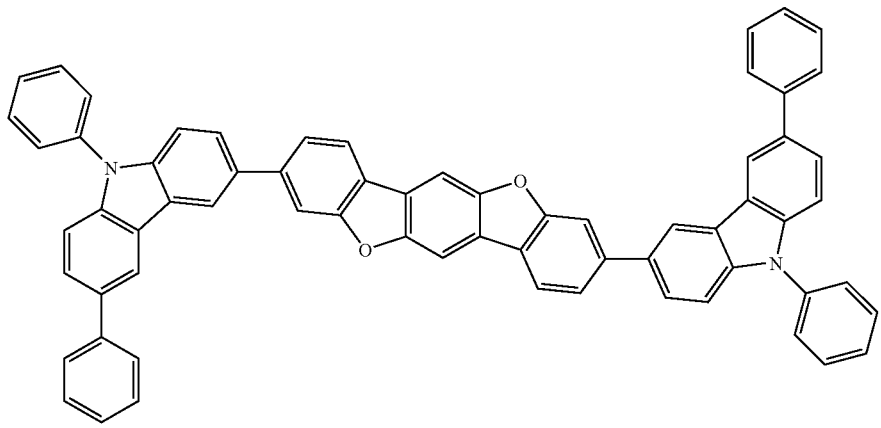
No. 99
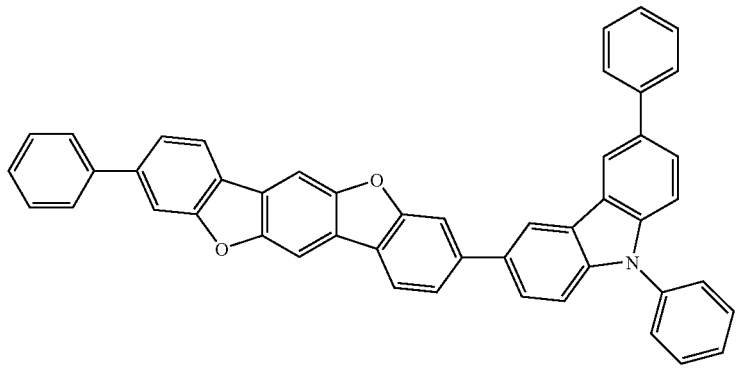
No. 100
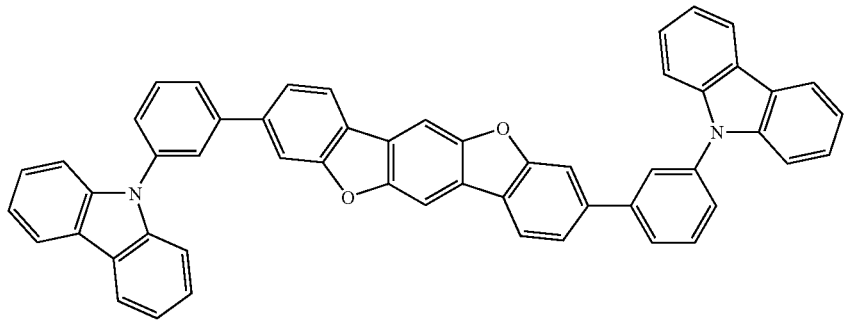
No. 101 No. 102
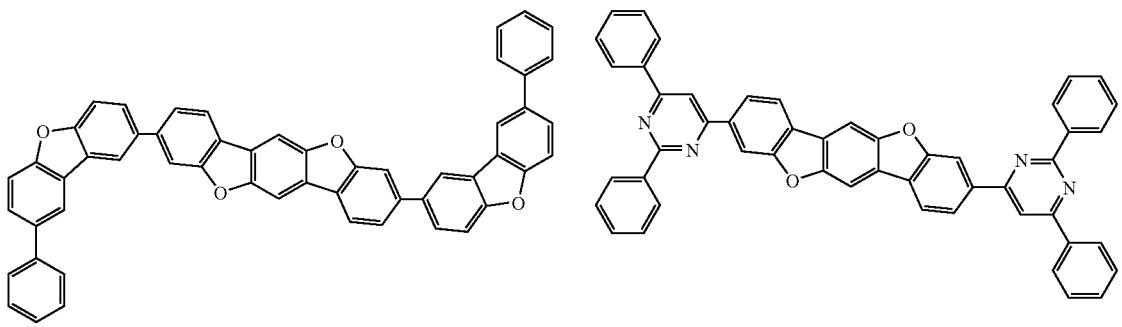

No. 103
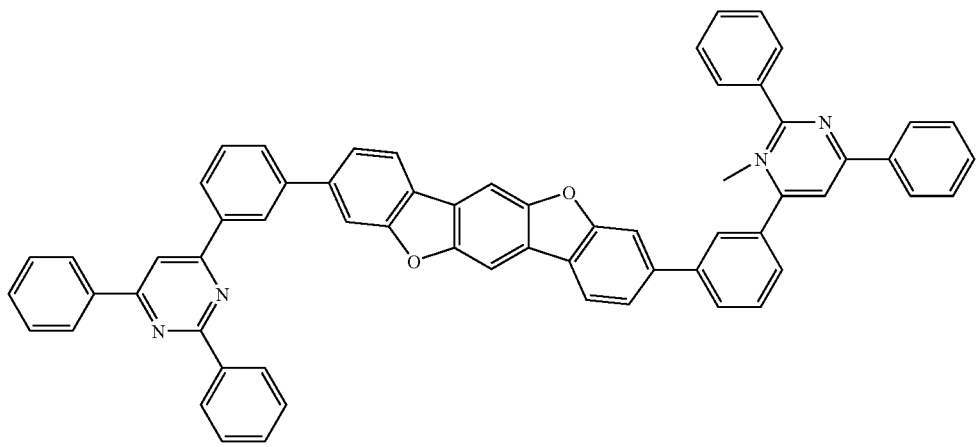
No. 104
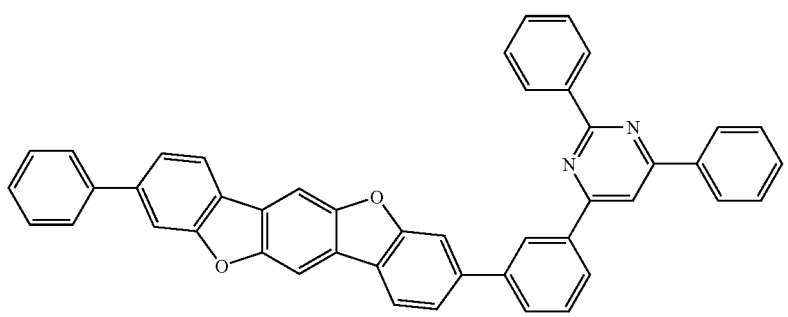
lp;1p
No. 105
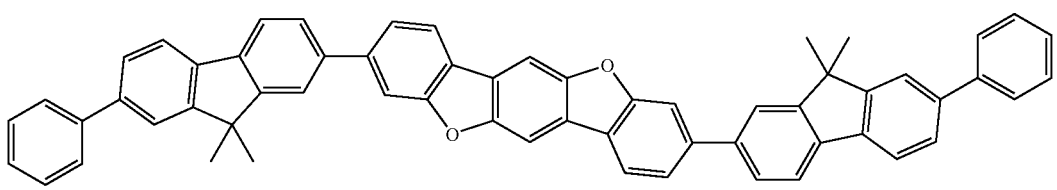
No. 106
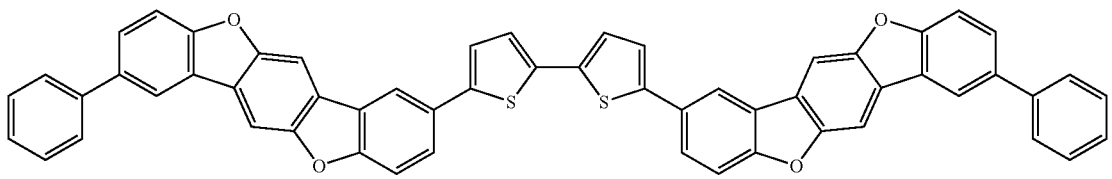
No. 107
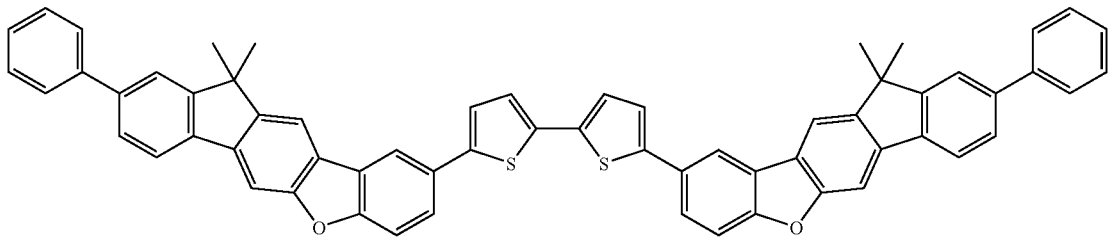

-continued
No. 108
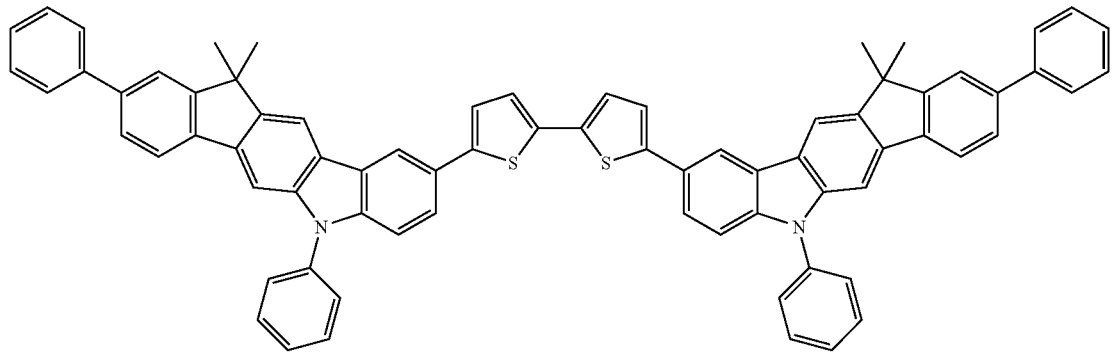
No. 109
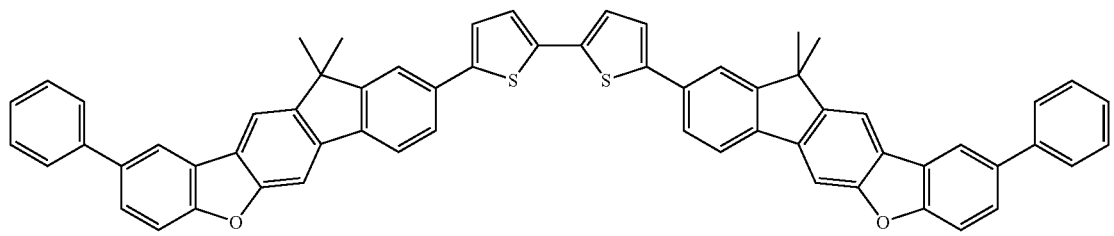
No. 110
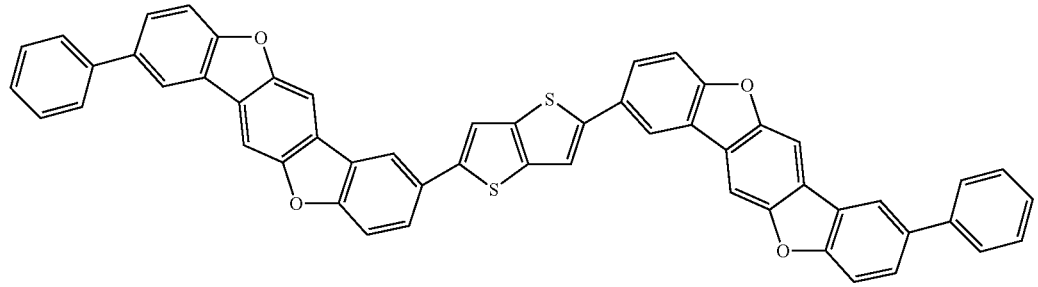
No. 111
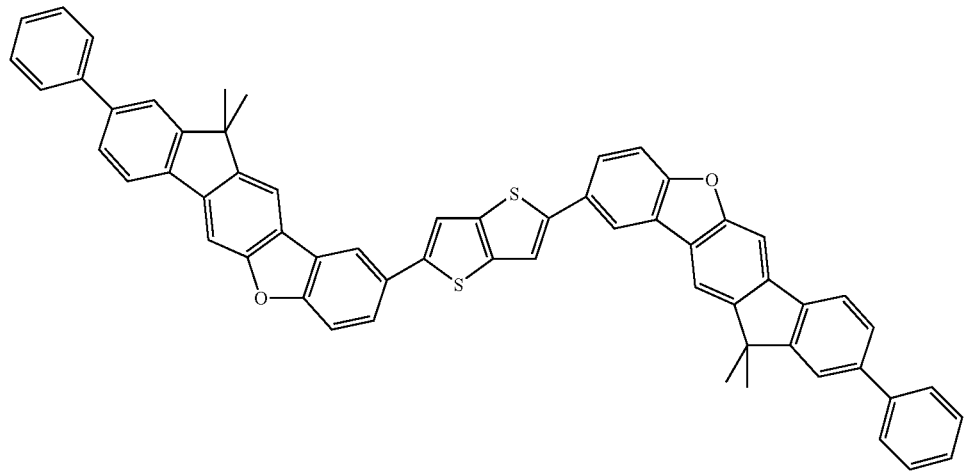
No. 112
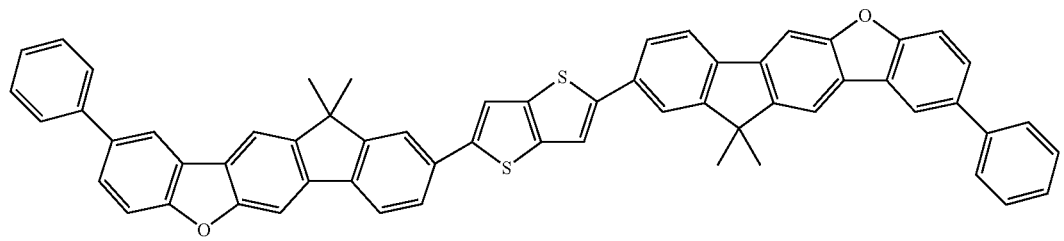

No. 113
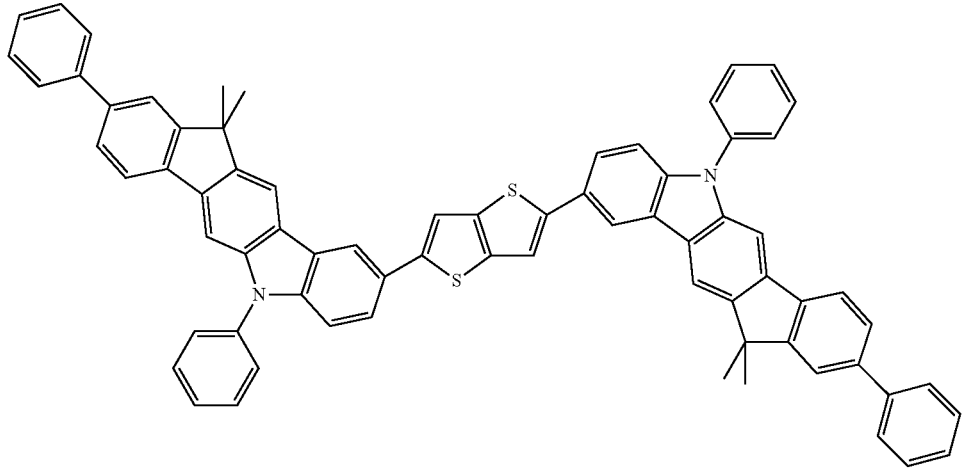
No. 114
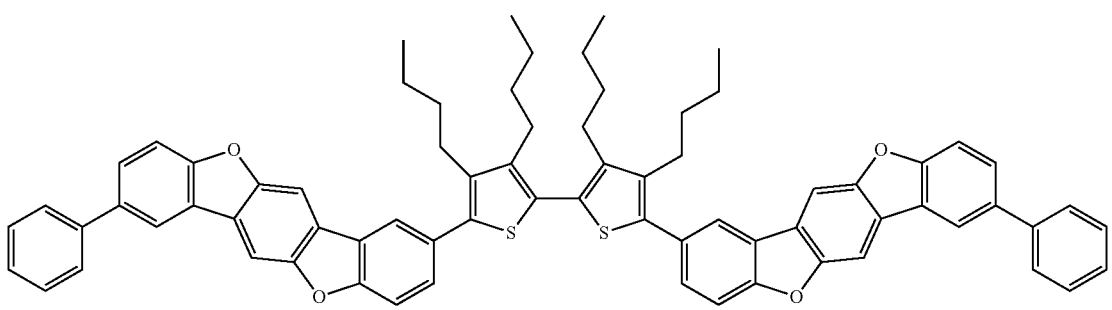
No. 115
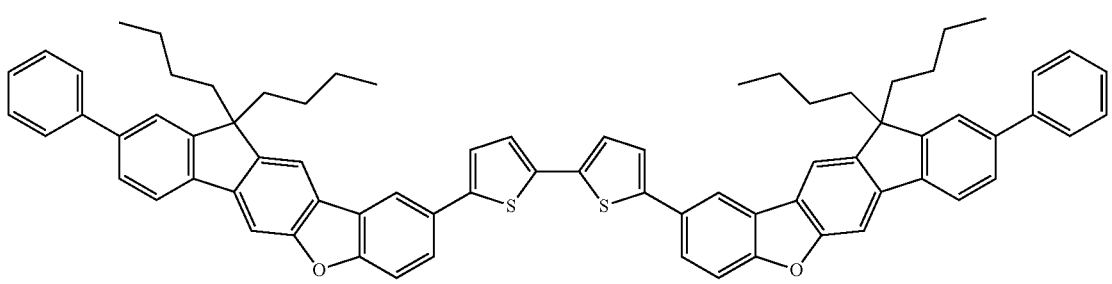
No. 116
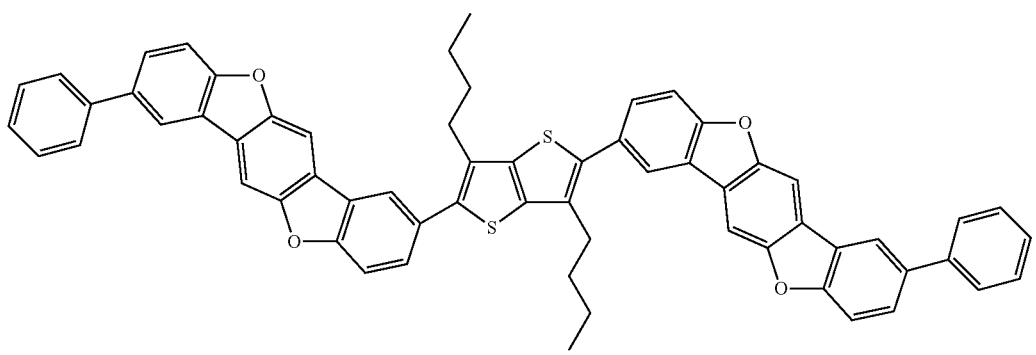

No. 117
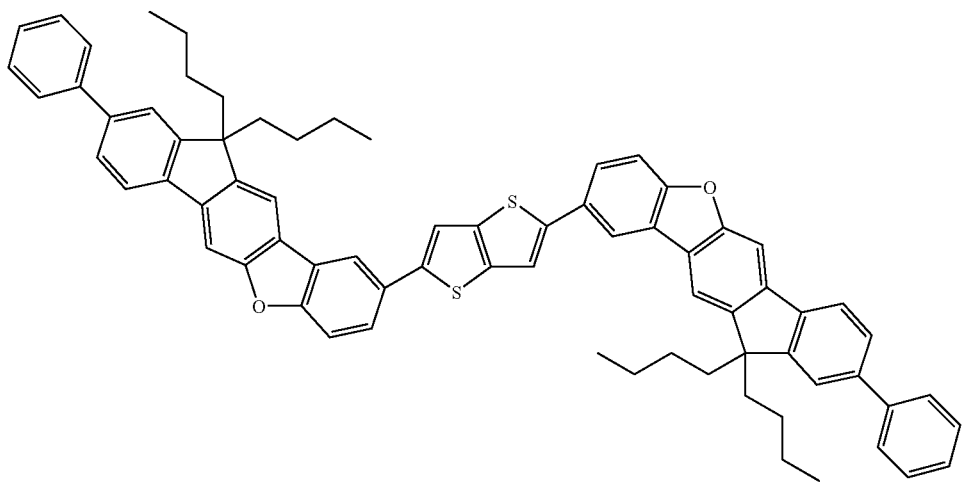
No. 118
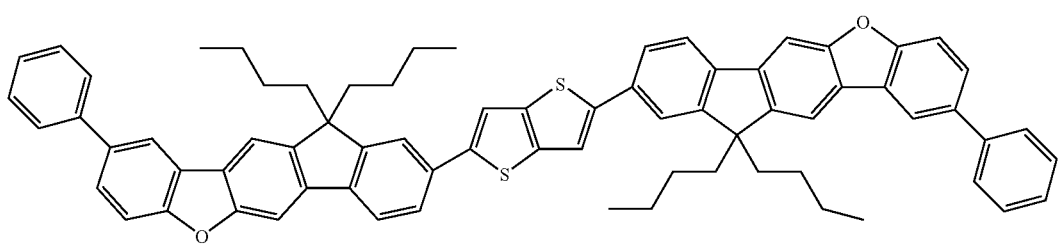
No. 119
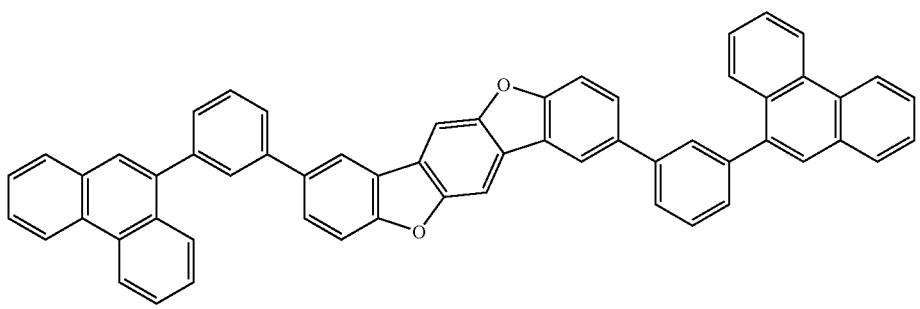
No. 120
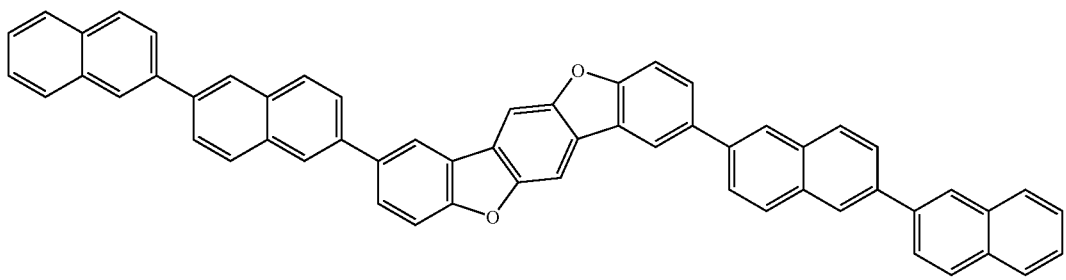
No. 121
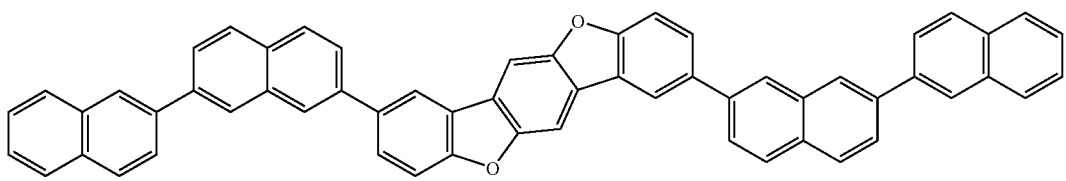

-continued
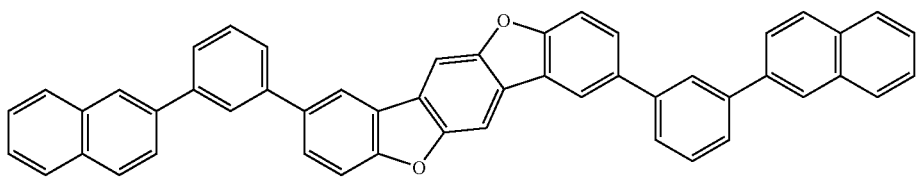
No. 122
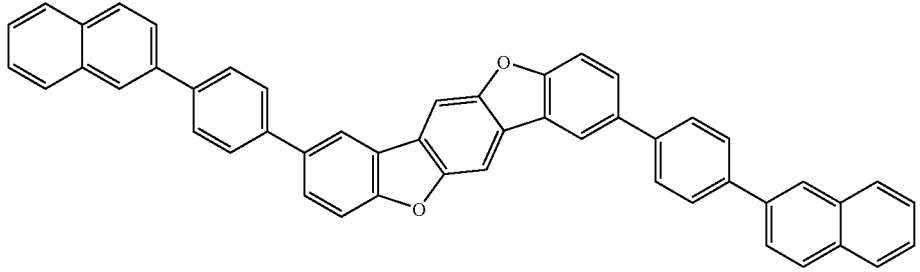
No. 123
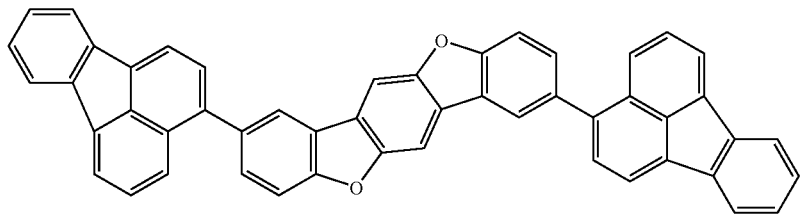
No. 124
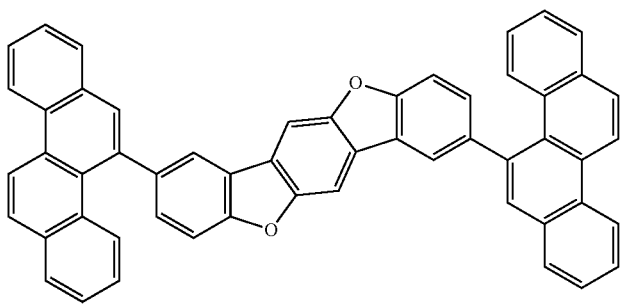
No. 125
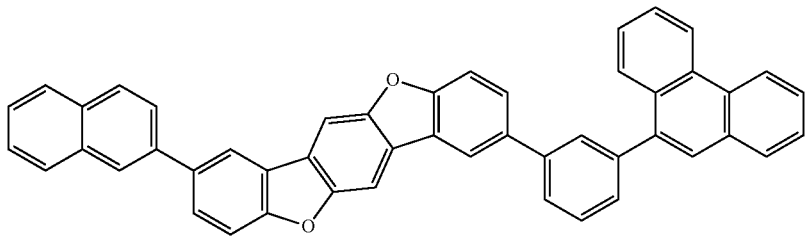
No. 126
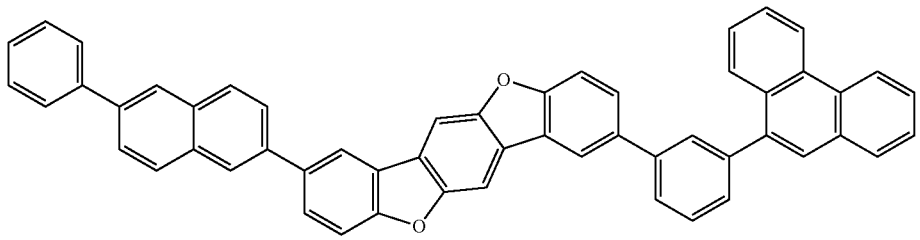
No. 127

-continued
No. 128
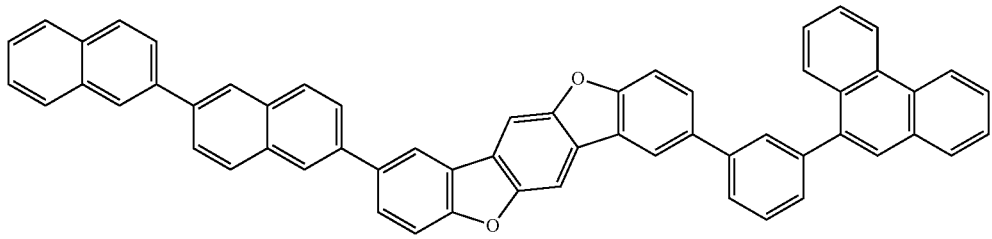
No. 129
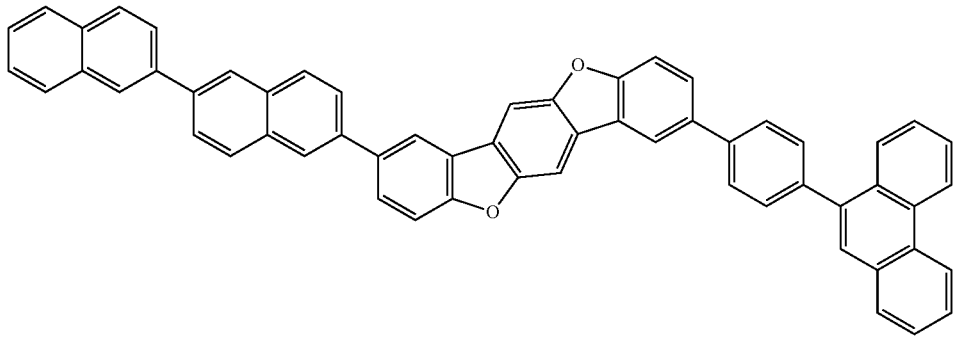
No. 130
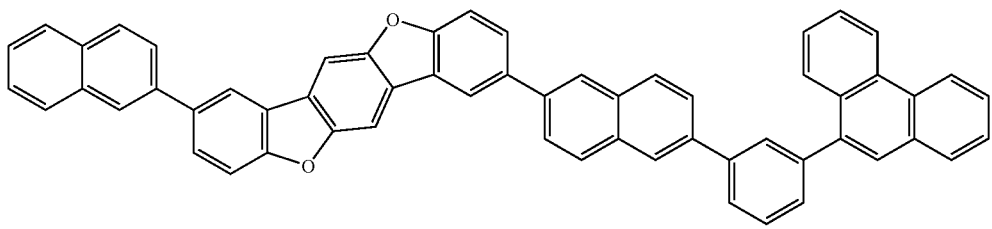
No. 131
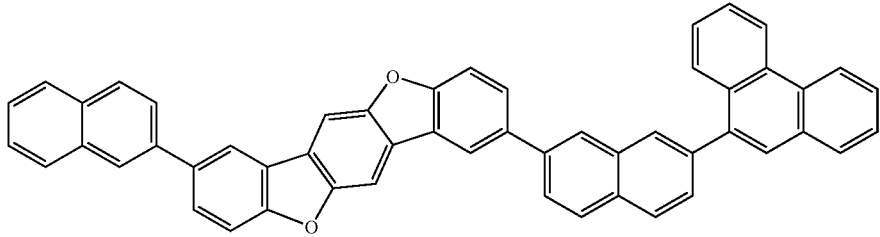
No. 132
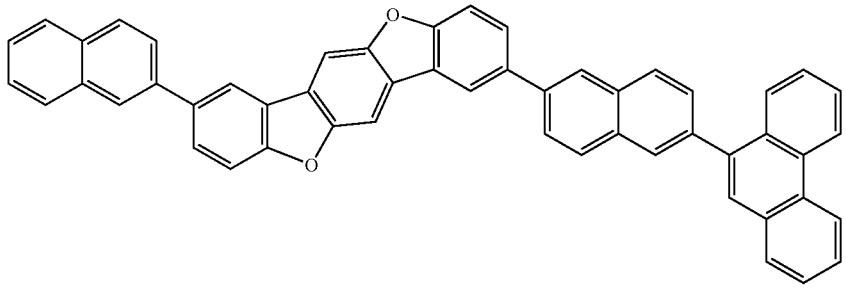
No. 133
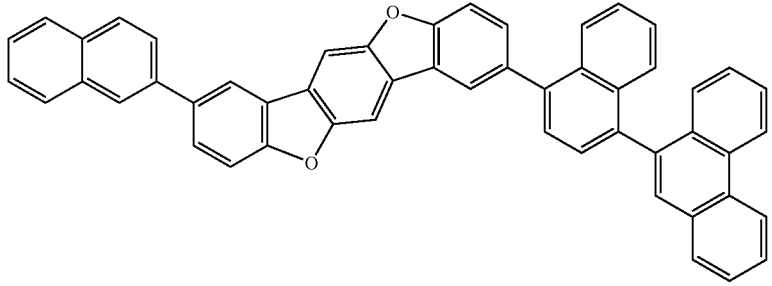

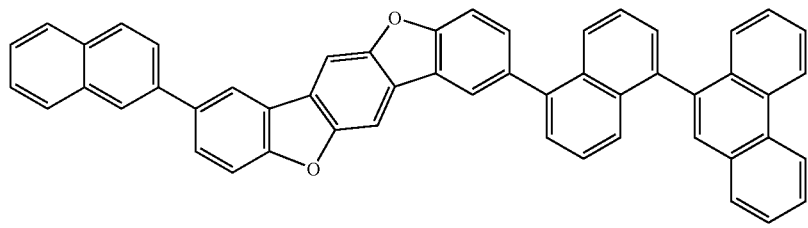

No. 134

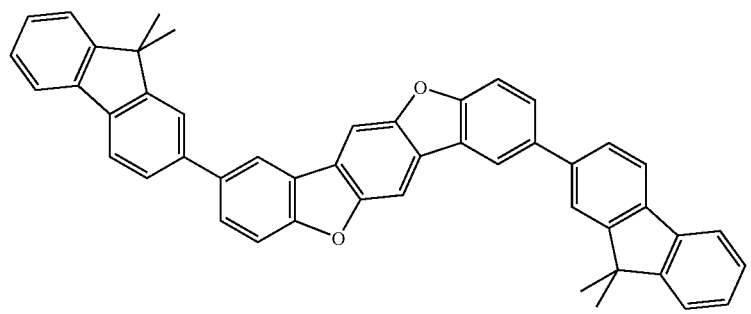

No. 135

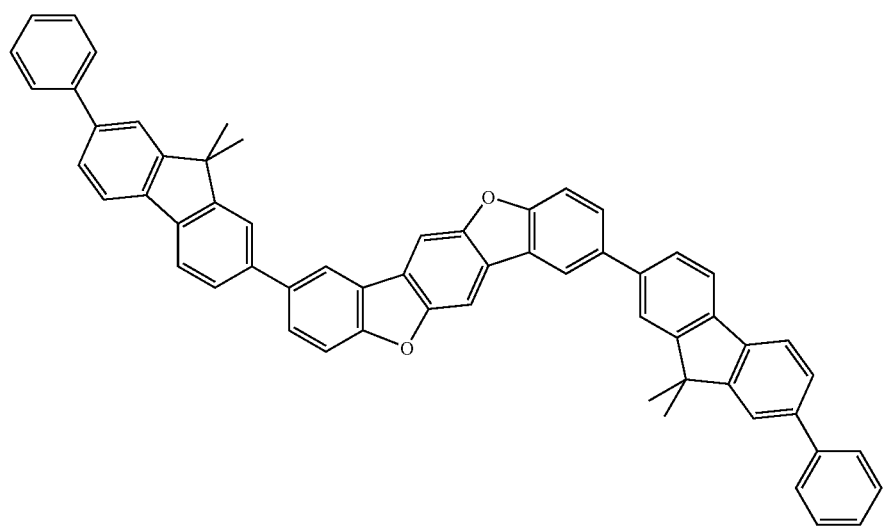

No. 136

Next, an organic EL device of the present invention will be described.

The organic EL device of the present invention has one or more organic thin film layers including a light emitting layer between a cathode and an anode, and at least one layer of the organic thin film layers contains a material for an organic EL device serving as a compound having a n-conjugated heteroacene skeleton crosslinked with a carbon atom, nitrogen atom, oxygen atom, or sulfur atom. Specific examples of the n-conjugated heteroacene skeleton are shown below.

Indenofluorene (crosslinked with a carbon atom)

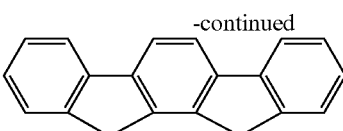

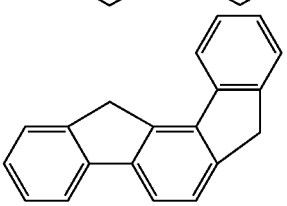

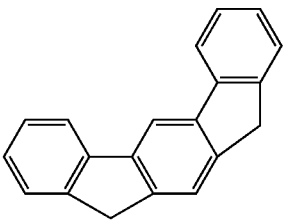

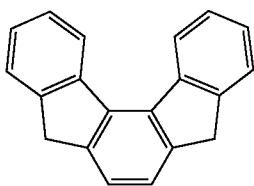
Indolocarbazole (crosslinked with a nitrogen atom)
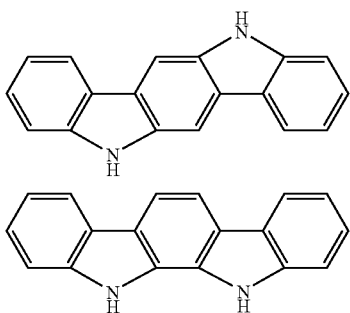
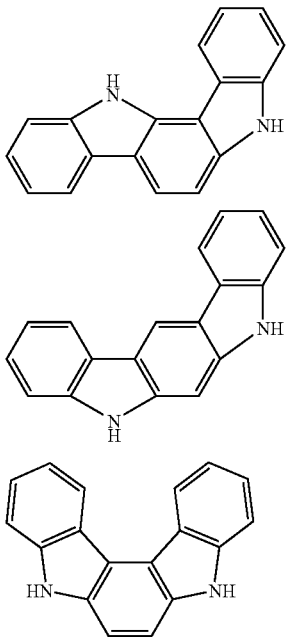
Benzofuranodibenzofuran (crosslinked with an oxygen atom)
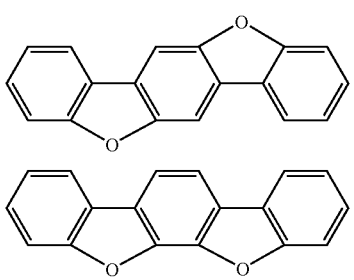
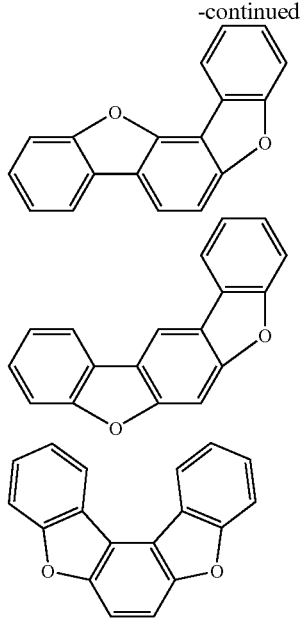
Benzothiophenodibenzothiophene (crosslinked with a sulfur atom)
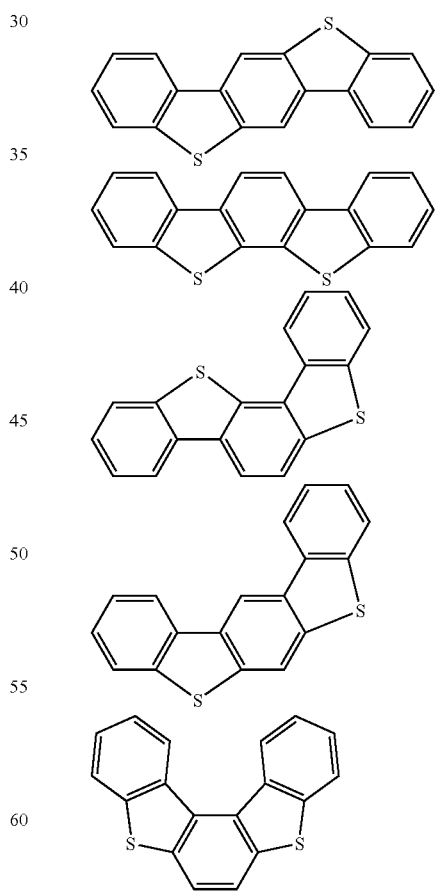
In addition to the foregoing, a π-conjugated heteroacene skeleton crosslinked with a combination of two or more of a carbon atom, a nitrogen atom, an oxygen atom, and a sulfur atom is also permitted. Specific examples of the 1-conjugated heteroacene skeleton are shown below.

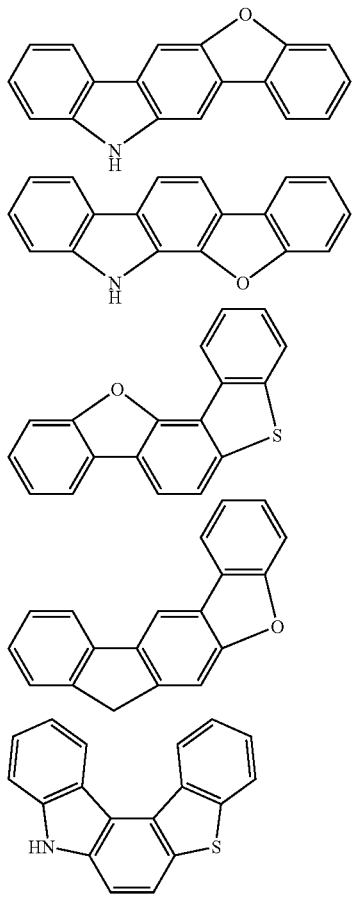

In addition, the above-mentioned material for an organic EL device of the present invention is preferably used as the material for an organic EL device.

The organic EL device may have an electron transporting layer between the light emitting layer and the cathode, and the electron transporting layer may contain the material for an organic EL device. Further, both the light emitting layer and the electron transporting layer each preferably contain the material for an organic EL device.

Alternatively, the organic EL device may have a hole transporting layer between the light emitting layer and the anode, and the hole transporting layer may contain the material for an organic EL device.

Further, the material for an organic EL device of the present invention is preferably incorporated into at least the light emitting layer. When the material is used in the light emitting layer, the lifetime of the organic EL device can be lengthened. When the material is used in the electron transporting layer or the electron injecting layer, the voltage at which the device is driven can be reduced. The material is preferably incorporated into each of two or more layers including the light emitting layer and the electron transporting layer or the electron injecting layer at the same time because both the reduced voltage and the lengthened lifetime can be achieved.

In particular, the light emitting layer as well as the electron transporting layer or electron injecting layer preferably contains, as a host material, the material for an organic EL device serving as a compound having a π-conjugated heteroacene skeleton crosslinked with a carbon atom, nitrogen atom, oxygen atom, or sulfur atom, or more preferably contains, as a host material, a material for an organic EL device represented by any one of the following general formulae (15) to (22).

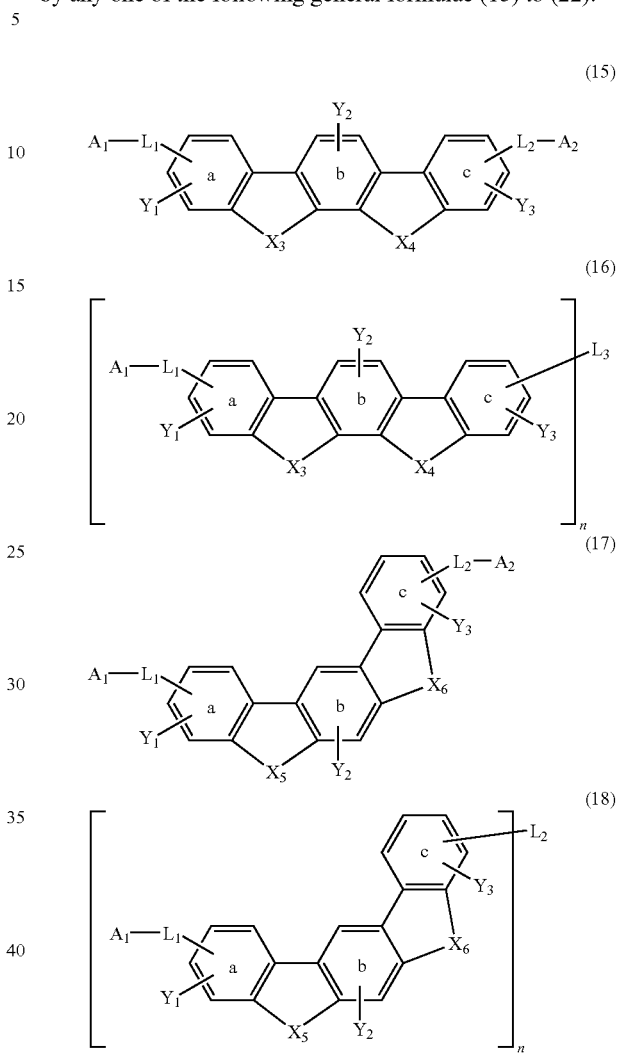

[In the formulae (15) to (18), $X_3$, $X_4$, $X_5$, and $X_6$ each independently represent O, S, N—$R_1$, or $CR_2R_3$.

In the formulae (15) to (18), $R_1$, $R_2$, and $R_3$ each independently represent an alkyl group having 1 to 20 carbon atoms, a substituted or unsubstituted cycloalkyl group having a ring formed of 3 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group having a ring formed of 3 to 24 atoms, provided that, when both $X_3$ and $X_4$, or both $X_5$ and $X_6$, represent N—$R_1$, at least one $R_1$ represents a substituted or unsubstituted, monovalent fused aromatic heterocyclic group having a ring formed of 8 to 24 atoms.

In the formulae (16) and (18), n represents 2, 3, or 4, and the material represented by one of the formulae (16) and (18) includes a dimer using $L_3$ as a linking group for n=2, a trimer using $L_3$ as a linking group for n=3, or a tetramer using $L_3$ as a linking group for n=4.

In the formulae (15) to (18), $L_1$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring a through a carbon-carbon bond.

In the formulae (15) and (17), L2 represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring c through a carbon-carbon bond, provided that, when both $X_3$ and $X_4$, or both $X_5$ and $X_6$, represent $CR_2R_3$ and both $L_1$ and $L_2$ represent a substituted or unsubstituted, monovalent or divalent aromatic hydrocarbon group having a ring formed of 6 to 24 carbon atoms, a case where $L_1$ and $L_2$ are simultaneously linked at pare positions with respect to a benzene ring b is excluded.

In the formulae (16) and (18), when n represents 2, L3 represents a single bond, an alkylene group having 1 to 20 carbon atoms, a substituted or unsubstituted cycloalkylene group having a ring formed of 3 to 20 carbon atoms, a divalent silyl group having 2 to 20 carbon atoms, a substituted or unsubstituted, divalent aromatic hydrocarbon group having a ring formed of 6 to 24 carbon atoms, or a substituted or unsubstituted, divalent aromatic heterocyclic group which has a ring formed of 3 to 24 atoms and which is linked with the benzene ring c through a carbon-carbon bond, when n represents 3, $L_3$ represents a trivalent alkane having 1 to 20 carbon atoms, a substituted or unsubstituted, trivalent cycloalkane having a ring formed of 3 to 20 carbon atoms, a trivalent silyl group having 1 to 20 carbon atoms, a substituted or unsubstituted, trivalent aromatic hydrocarbon group having a ring formed of 6 to 24 carbon atoms, or a substituted or unsubstituted, trivalent aromatic heterocyclic group which has 3 to 24 atoms and which is linked with the benzene ring c through a carbon-carbon bond, or when n represents 4, $L_3$ represents a tetravalent alkane having 1 to 20 carbon atoms, a substituted or unsubstituted, tetravalent cycloalkane having a ring formed of 3 to 20 carbon atoms, a silicon atom, a substituted or unsubstituted, tetravalent aromatic hydrocarbon group having a ring formed of 6 to 24 carbon atoms, or a substituted or unsubstituted, tetravalent aromatic heterocyclic group which has a ring formed of 3 to 24 atoms and which is linked with the benzene ring c through a carbon-carbon bond, provided that, when both $X_3$ and $X_4$ or both $X_5$ and $X_6$ represent $CR_2R_3$ and both $L_1$ and $L_3$ represent a substituted or unsubstituted, monovalent, divalent, trivalent, or tetravalent aromatic hydrocarbon group having a ring formed of 6 to 24 carbon atoms, a case where $L_1$ and $L_3$ are simultaneously linked at para positions with respect to the benzene ring b is excluded.

In the formulae (15) to (18), $A_1$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_1$ through a carbon-carbon bond, provided that, when $L_1$ represents an alkyl or alkylene group having 1 to 20 carbon atoms, a case where $A_1$ represents a hydrogen atom is excluded.

In the formulae (15) and (17), $A_2$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_2$ through a carbon-carbon bond, provided that, when $L_2$ represents an alkyl or alkylene group having 1 to 20 carbon atoms, a case where $A_2$ represents a hydrogen atom is excluded, and, when $X_3$ and $X_4$, or $X_5$ and $X_6$, each represent O, S, or $CR_2R_3$ and both $L_1$ and $L_2$ represent single bonds, a case where $A_1$ and $A_2$ simultaneously represent hydrogen atoms is excluded.

In the formulae (15) to (18), $Y_1$, $Y_2$, and $Y_3$ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with the benzene ring a, b, or c through a carbon-carbon bond, the number of each of $Y_1$ and $Y_3$ is 0, 1, 2, or 3, and the number of $Y_2$ is 0, 1, or 2.

In the formulae (15) to (18), $A_1$, $A_2$, $L_1$, $L_2$, and $L_3$ are each free of any carbonyl group.]

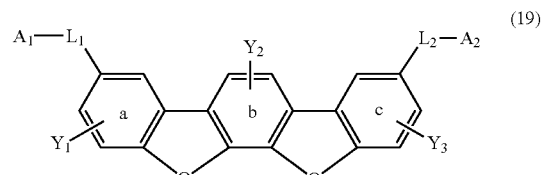

(19)

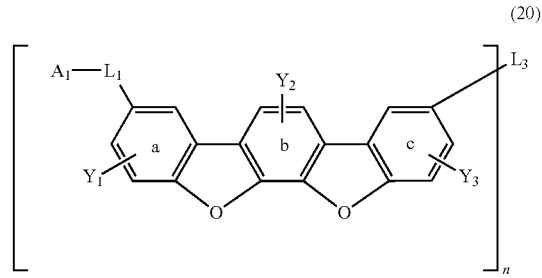

(20)

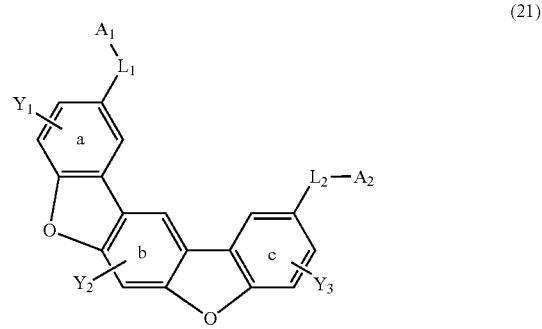

(21)

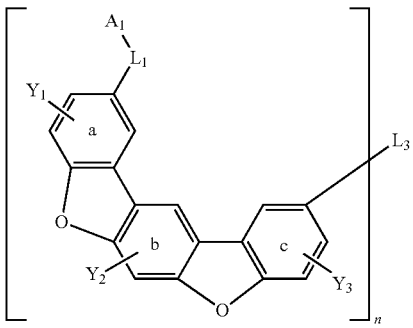

(22)

[In the formulae (20) and (22), n represents 2, 3, or 4, and the material represented by one of the formulae (20) and (22) includes a dimer using $L_3$ as a linking group for n=2, a trimer using $L_3$ as a linking group for n=3, or a tetramer using $L_3$ as a linking group for n=4.

In the formulae (19) to (22), $L_1$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring a through a carbon-carbon bond.

In the formulae (19) and (21), $L_2$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring c through a carbon-carbon bond.

In the formulae (20) and (22), when n represents 2, $L_3$ represents a single bond, an alkylene group having 1 to 20 carbon atoms, a substituted or unsubstituted cycloalkylene group having a ring formed of 3 to 20 carbon atoms, a divalent silyl group having 2 to 20 carbon atoms, a substituted or unsubstituted, divalent aromatic hydrocarbon group having a ring formed of 6 to 24 carbon atoms, or a substituted or unsubstituted, divalent aromatic heterocyclic group which has a ring formed of 3 to 24 atoms and which is linked with the benzene ring c through a carbon-carbon bond, when n represents 3, $L_3$ represents a trivalent alkane having 1 to 20 carbon atoms, a substituted or unsubstituted, trivalent cycloalkane having a ring formed of 3 to 20 carbon atoms, a trivalent silyl group having 1 to 20 carbon atoms, a substituted or unsubstituted, trivalent aromatic hydrocarbon group having a ring formed of 6 to 24 carbon atoms, or a substituted or unsubstituted, trivalent aromatic heterocyclic group which has 3 to 24 atoms and which is linked with the benzene ring c through a carbon-carbon bond, or when n represents 4, $L_3$ represents a tetravalent alkane having 1 to 20 carbon atoms, a substituted or unsubstituted, tetravalent cycloalkane having a ring formed of 3 to 20 carbon atoms, a silicon atom, a substituted or unsubstituted, tetravalent aromatic hydrocarbon group having a ring formed of 6 to 24 carbon atoms, or a substituted or unsubstituted, tetravalent aromatic heterocyclic group which has a ring formed of 3 to 24 atoms and which is linked with the benzene ring c through a carbon-carbon bond.

In the formulae (19) to (22), $A_1$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_1$ through a carbon-carbon bond, provided that, when $L_1$ represents an alkyl or alkylene group having 1 to 20 carbon atoms, a case where $A_1$ represents a hydrogen atom is excluded.

In the formulae (19) and (21), $A_2$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_2$ through a carbon-carbon bond, provided that, when $L_2$ represents an alkyl or alkylene group having 1 to 20 carbon atoms, a case where $A_2$ represents a hydrogen atom is excluded, and, when both $L_1$ and $L_2$ represent single bonds, a case where $A_1$ and $A_2$ simultaneously represent hydrogen atoms is excluded.

In the formulae (19) to (22), $Y_1$, $Y_2$, and $Y_3$ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with the benzene ring a, b, or c through a carbon-carbon bond, the number of each of $Y_1$ and $Y_3$ is 0, 1, 2, or 3, and the number of $Y_2$ is 0, 1, or 2.

In the formulae (19) to (22), $A_1$, $A_2$, $L_1$, $L_2$, and $L_3$ are each free of any carbonyl group.]

Examples of the respective groups represented by $Y_1$ to $Y_3$, $R_1$ to $R_3$, $L_1$ to $L_3$, and $A_1$ and $A_2$ in the general formulae (15) to (22), and examples of the substituents for the groups include examples similar to those listed for the general formulae (1) to (14).

Specific examples of the material for an organic EL device represented by any one of the general formulae (15) to (22) of the present invention are shown below. However, the present invention is not limited to these exemplified compounds.

No. 137
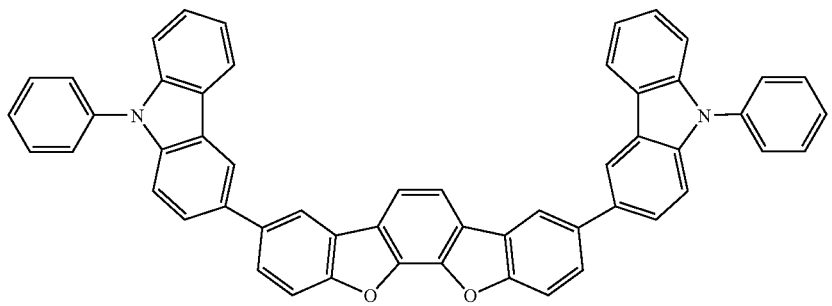
No. 138
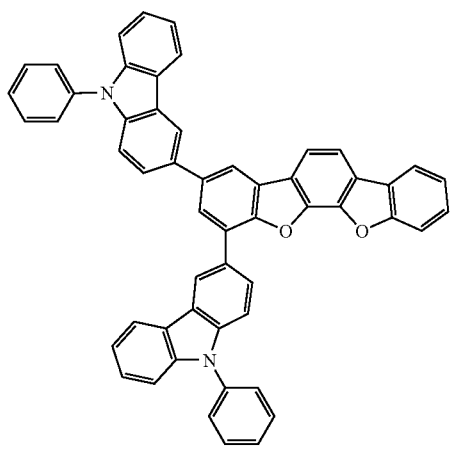
No. 139
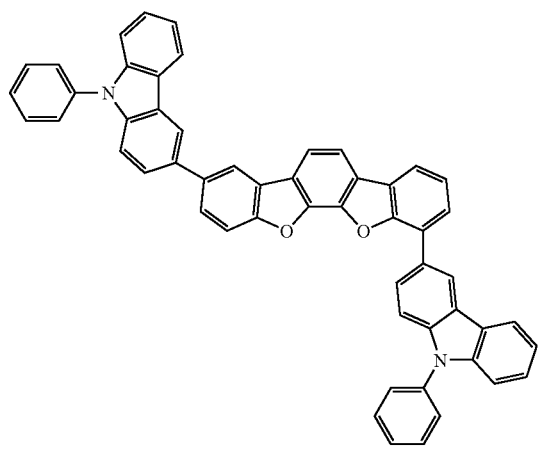
No. 140
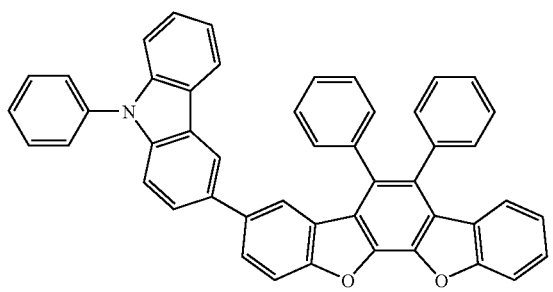
No. 141
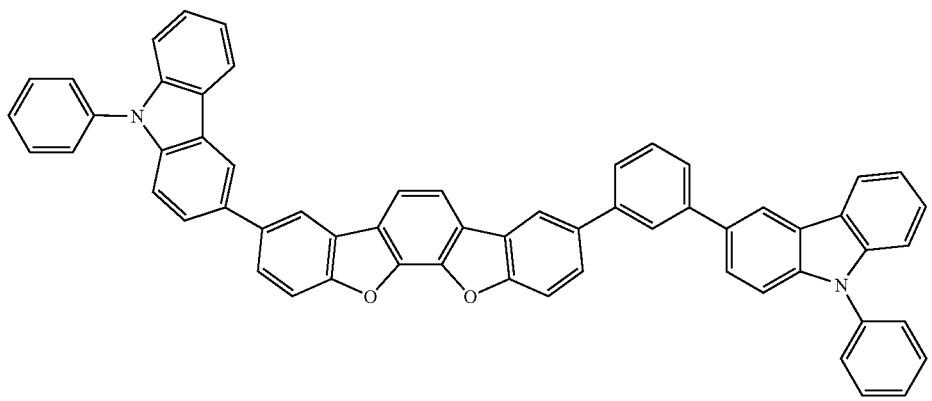

-continued
No. 142
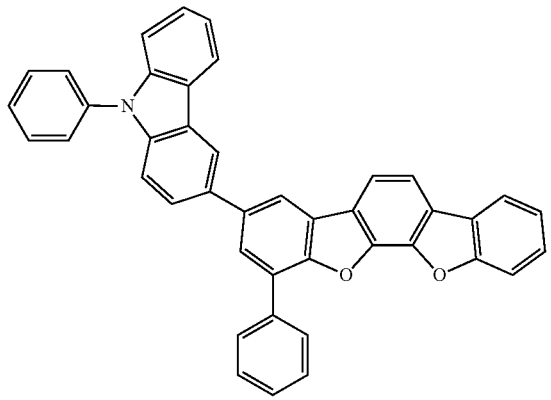
No. 143
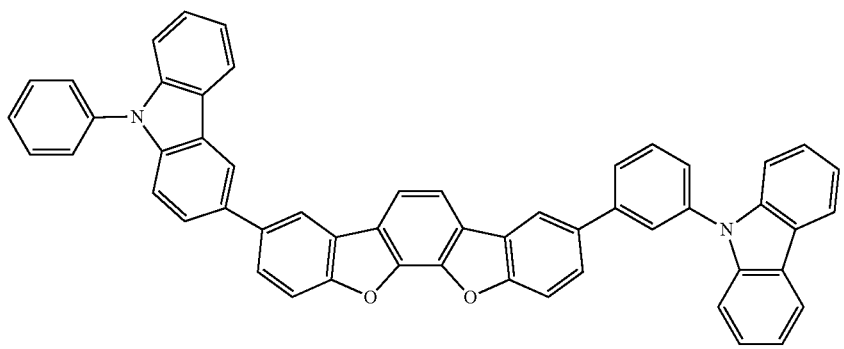
No. 144
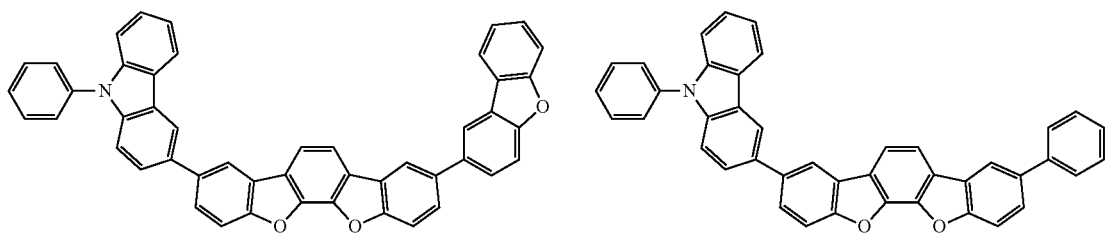
No. 145
No. 146
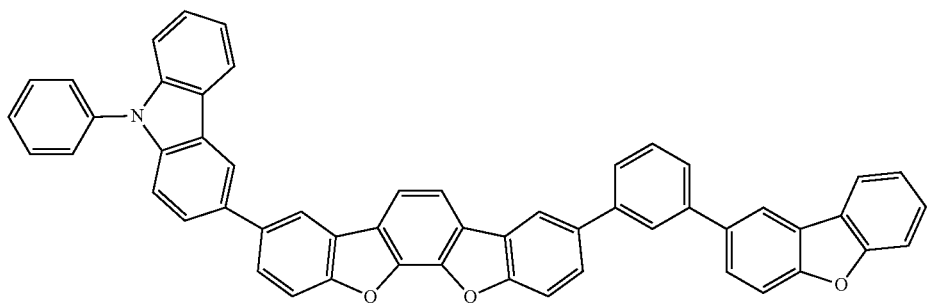
No. 147
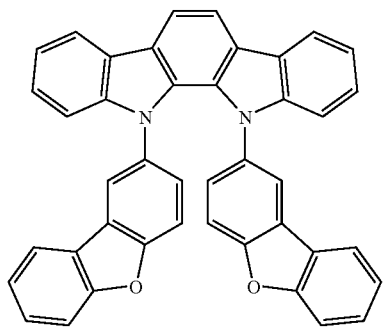
No. 148
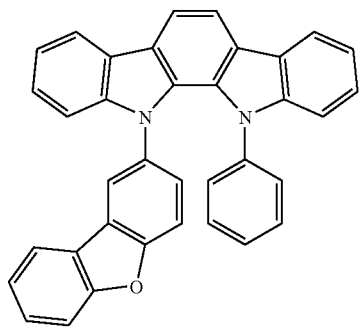

-continued
No. 149
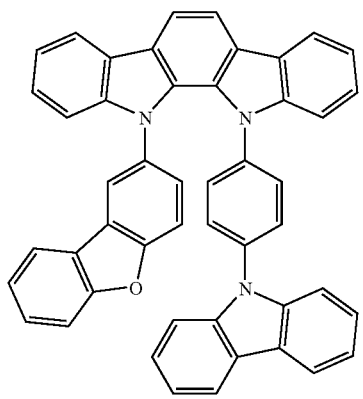
No. 150
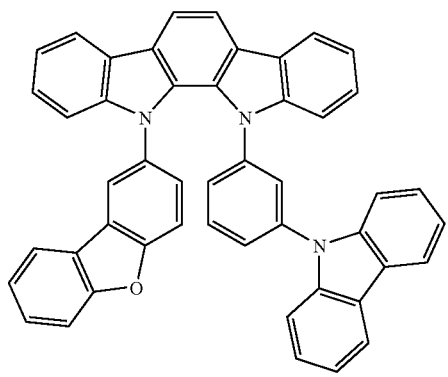
No. 151
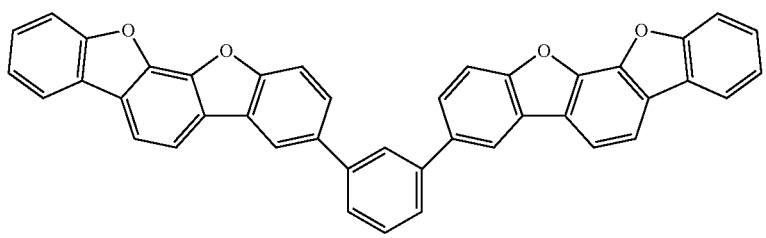
No. 152
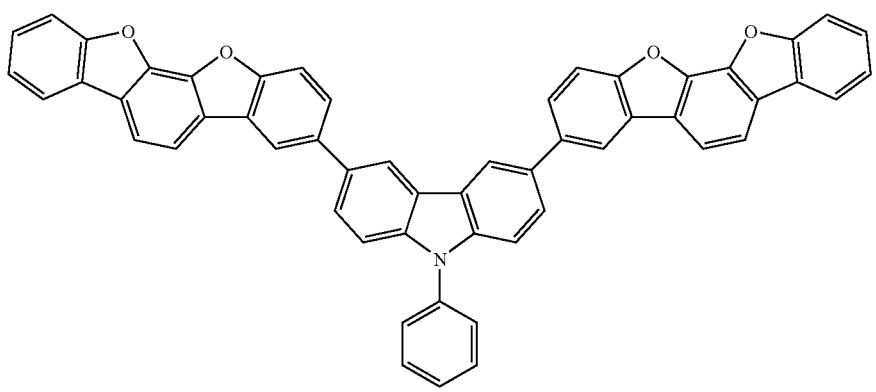
No. 153
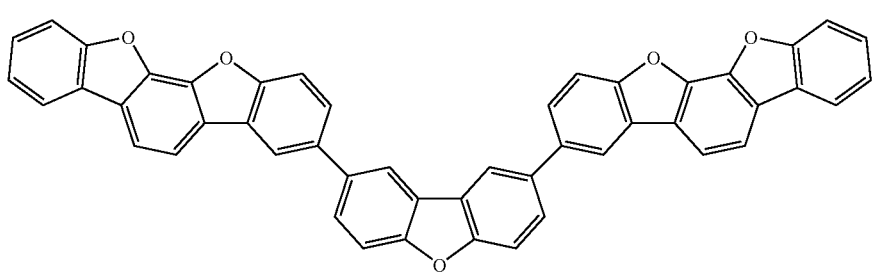
No. 154
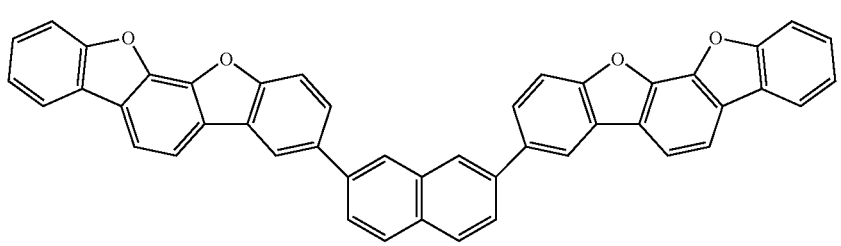

-continued
No. 155
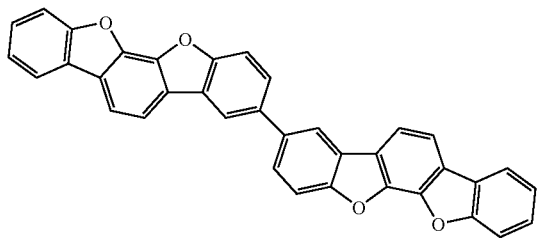
No. 156
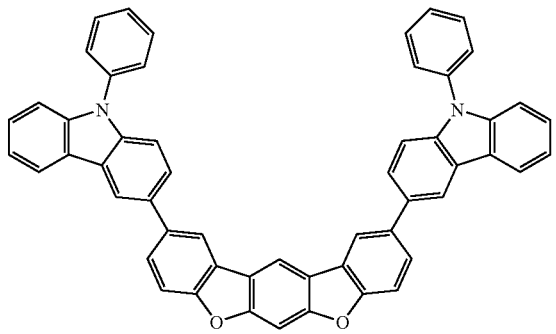
No. 157
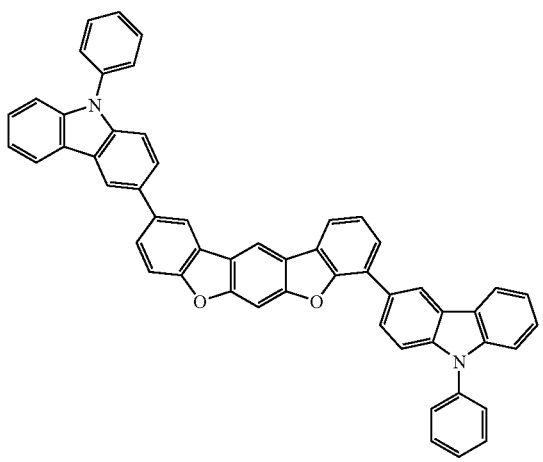
No. 158
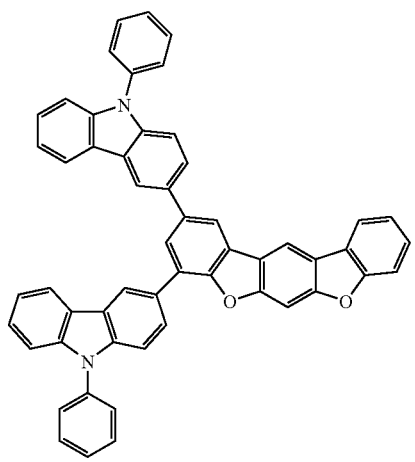
No. 159
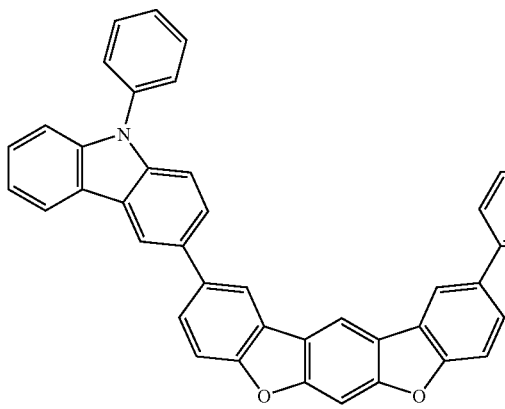
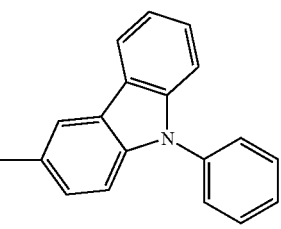
No. 160
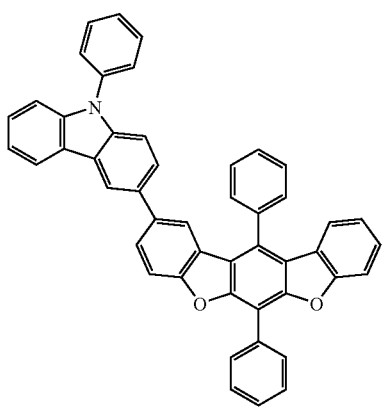
No. 161
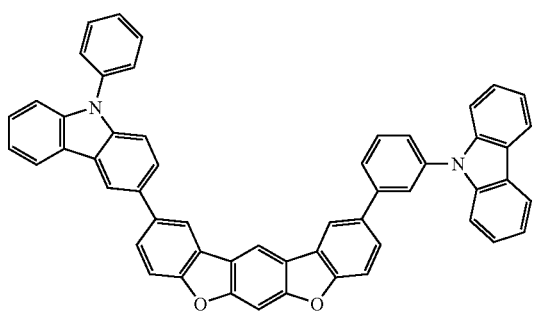

-continued
No. 162
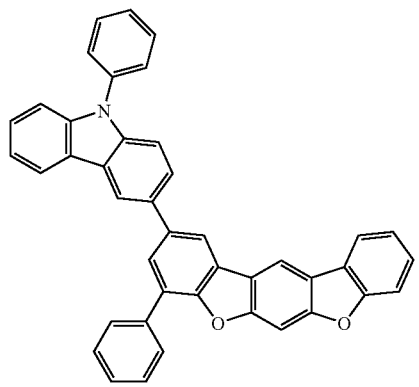
No. 163
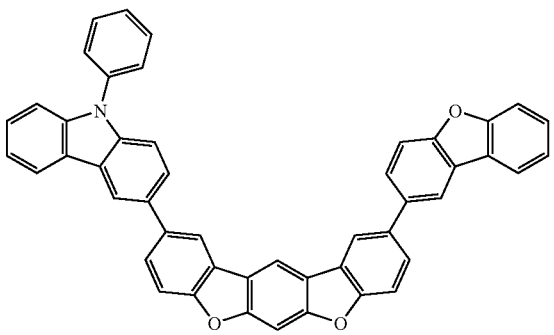
No. 164
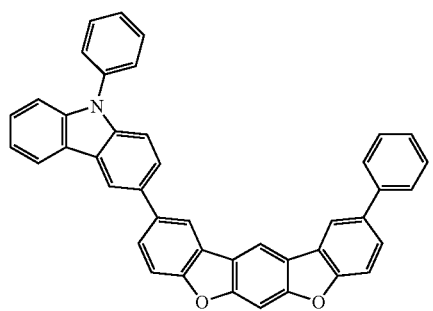
No. 165
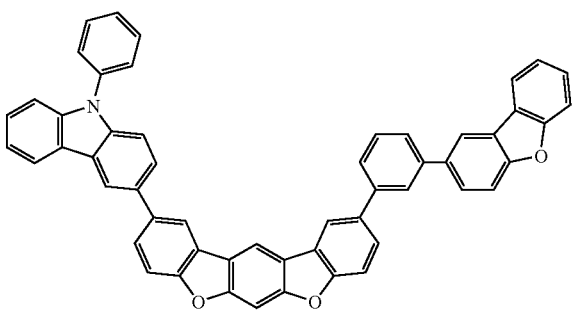
No. 166
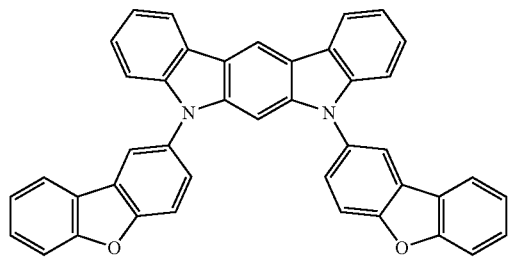
No. 167
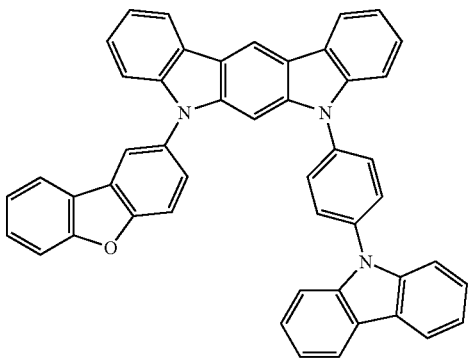
No. 168
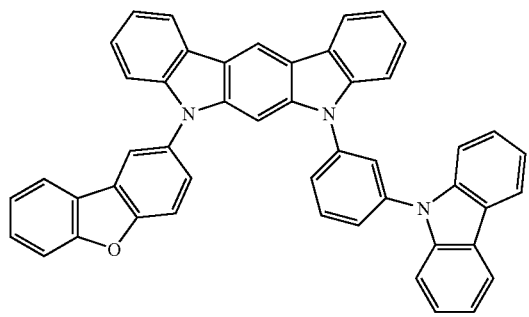
No. 169
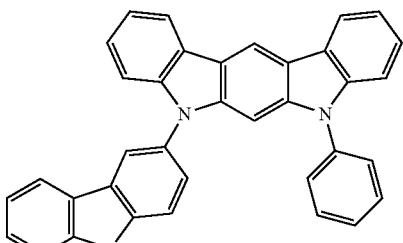

-continued
No. 170
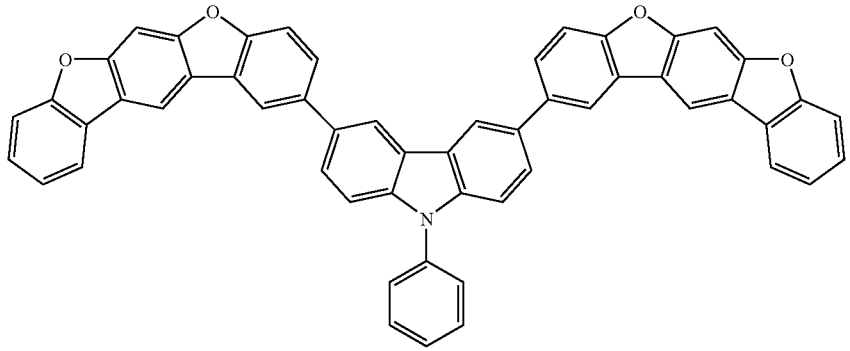
No. 171
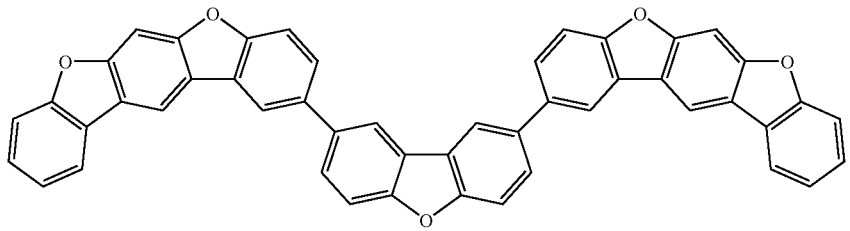
No. 172
No. 173
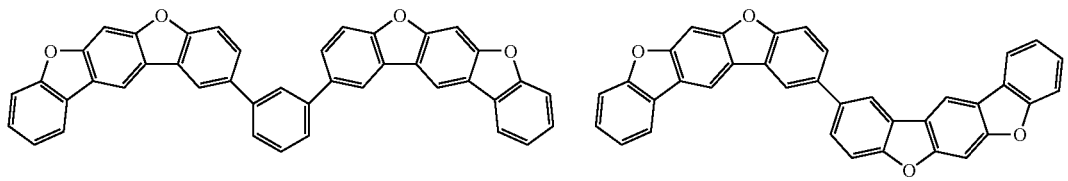
No. 174
No. 175
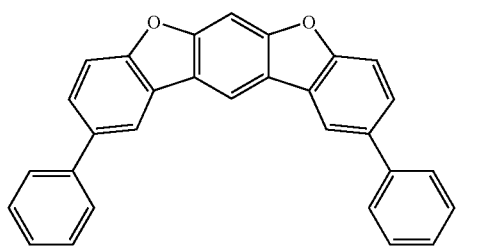
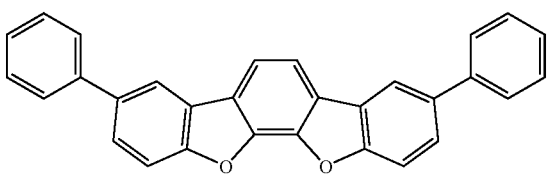
No. 176
No. 177
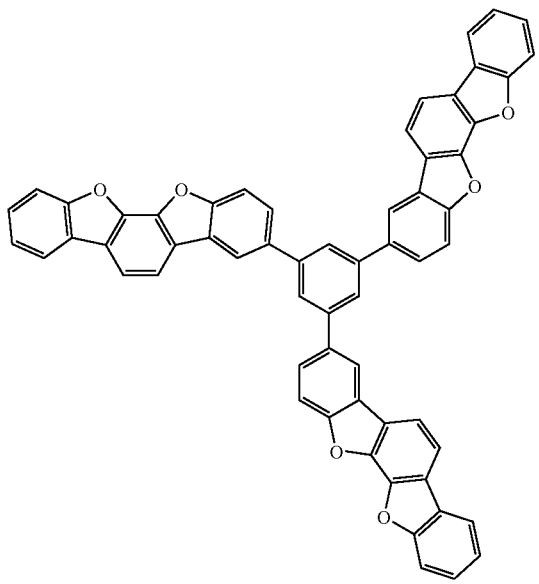
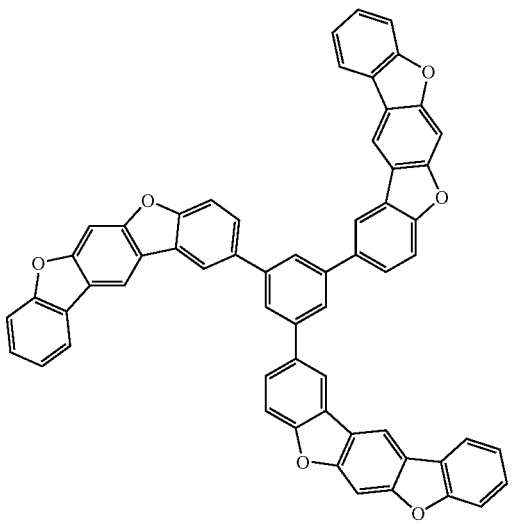

-continued
No. 178
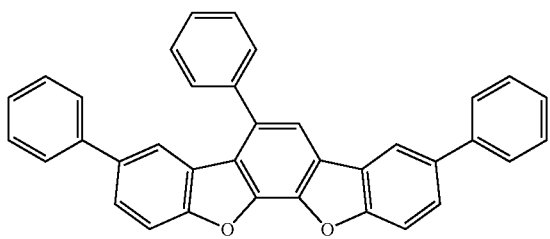
No. 179
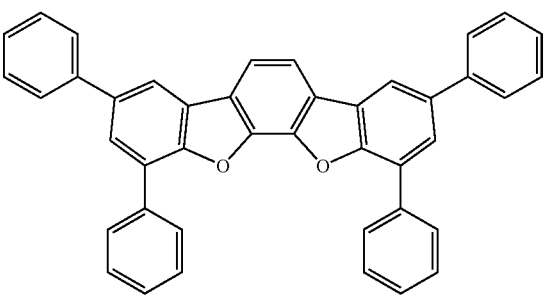
No. 180
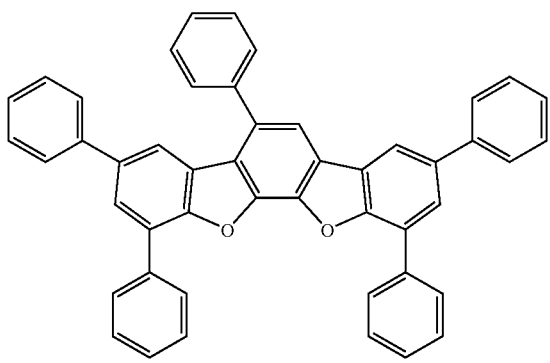
No. 181
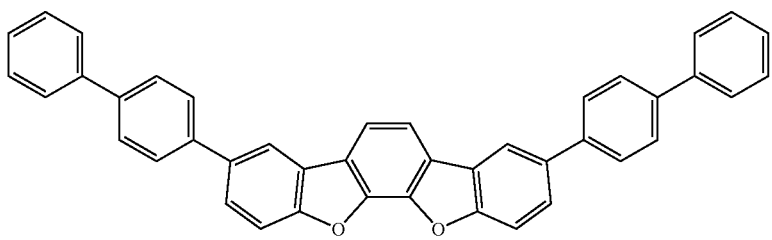
No. 182
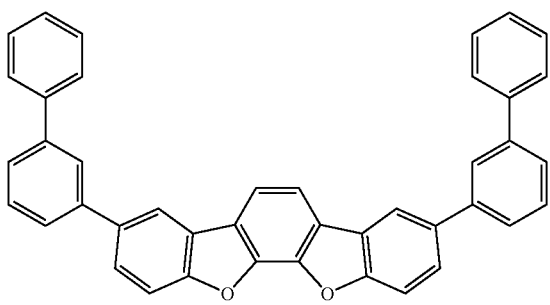
No. 183
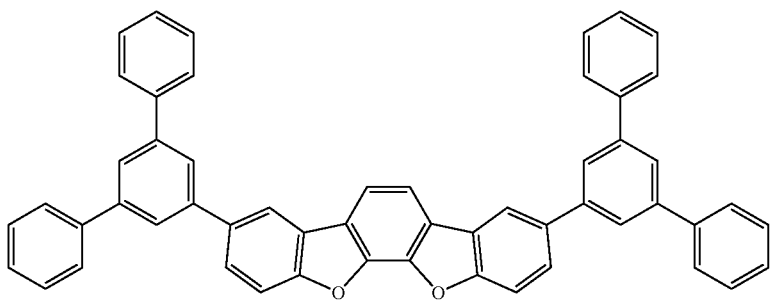

-continued
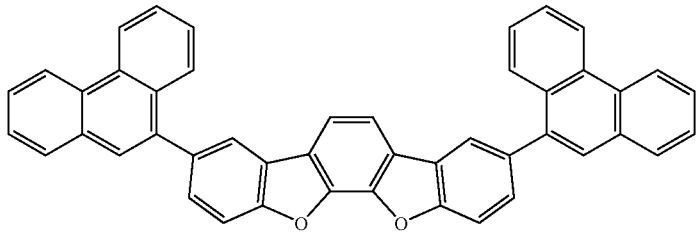
No. 184
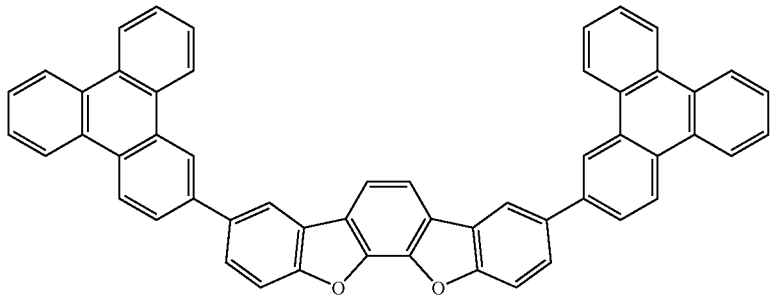
No. 185
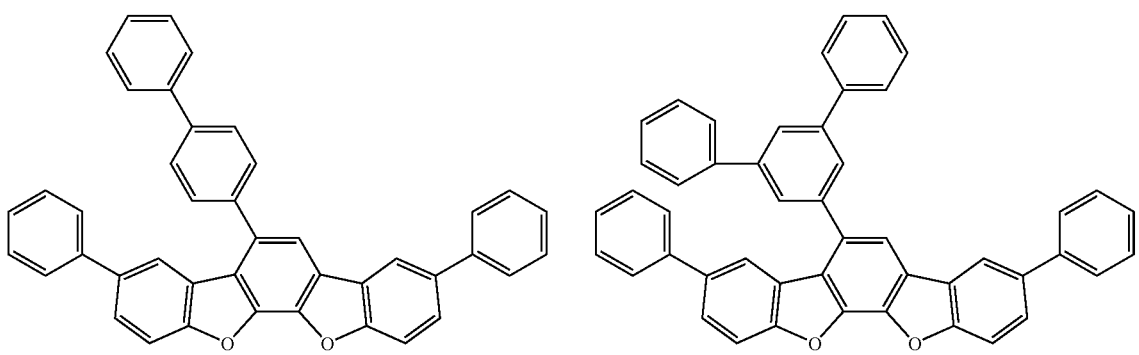
No. 186                                      No. 187
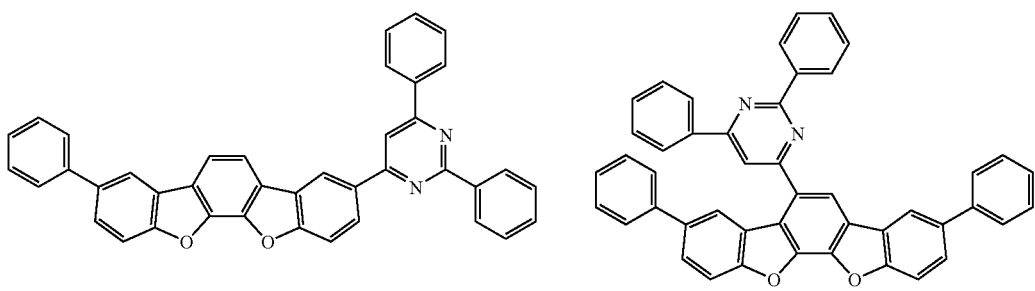
No. 188                                      No. 189
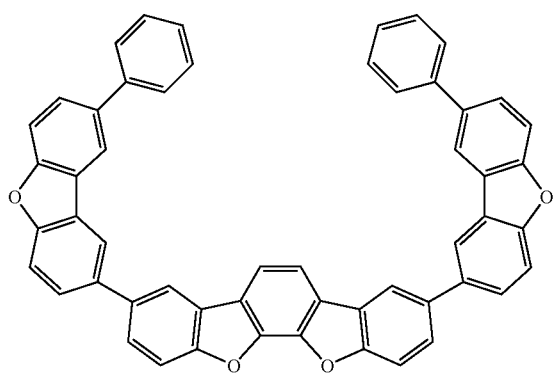
No. 190

-continued
No. 191
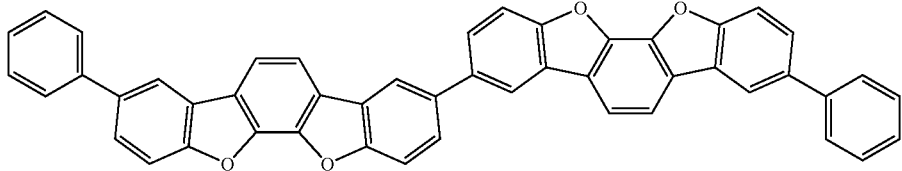
No. 192
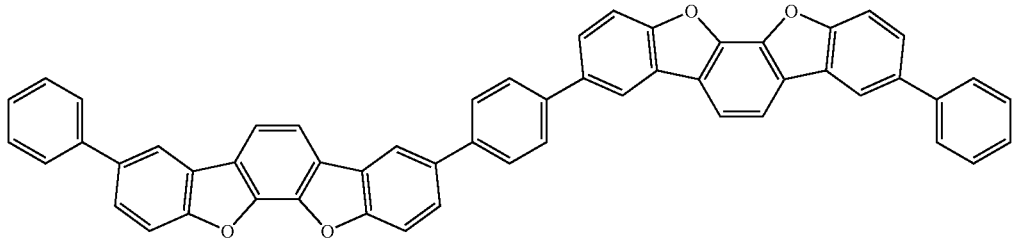
No. 193
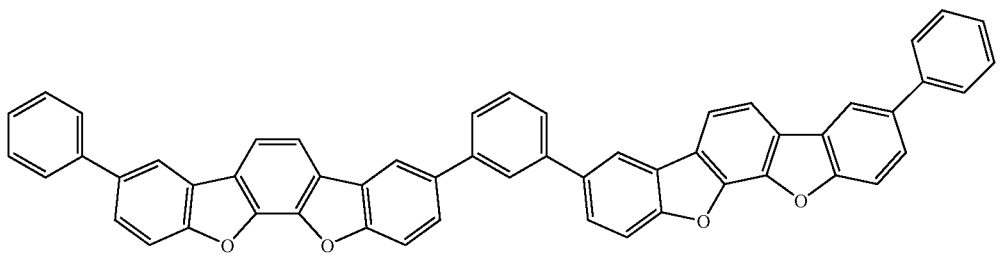
No. 194 No. 195
No. 196 No. 197
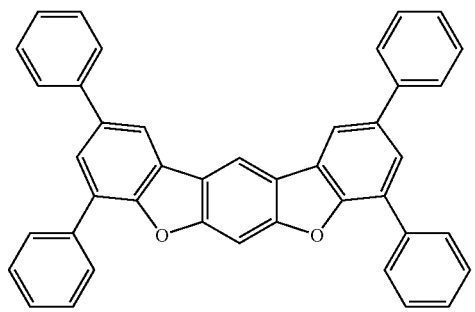
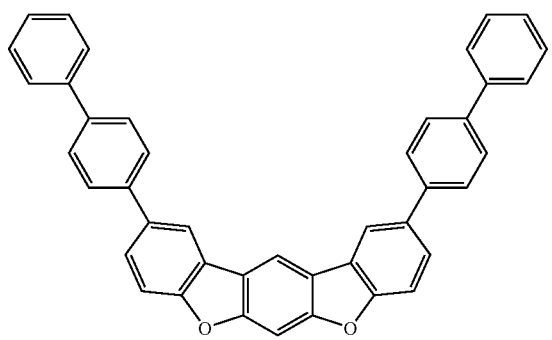

-continued
No. 198
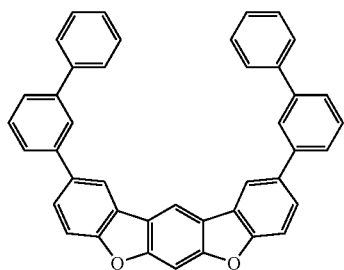
No. 199
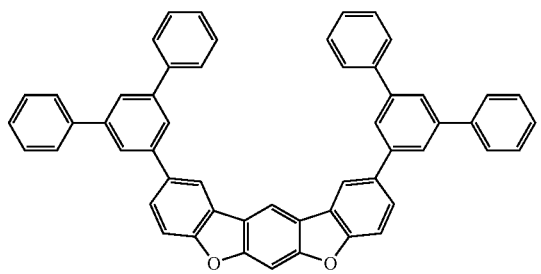
No. 200
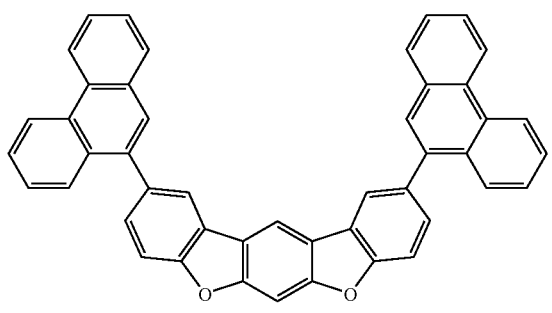
No. 201
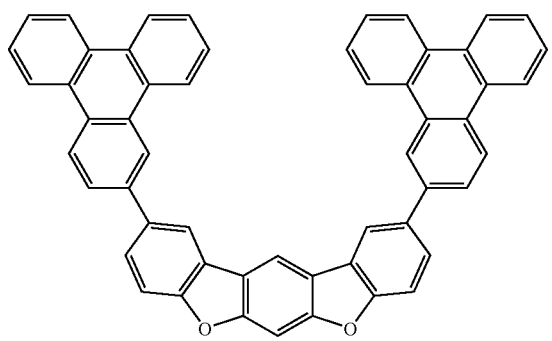
No. 202
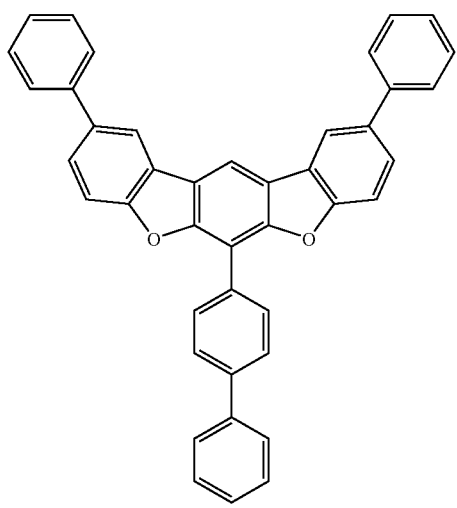
No. 203
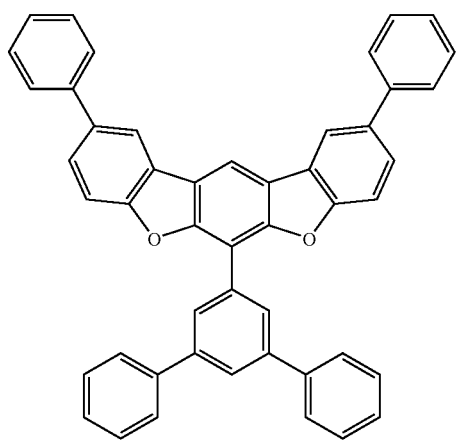
No. 204
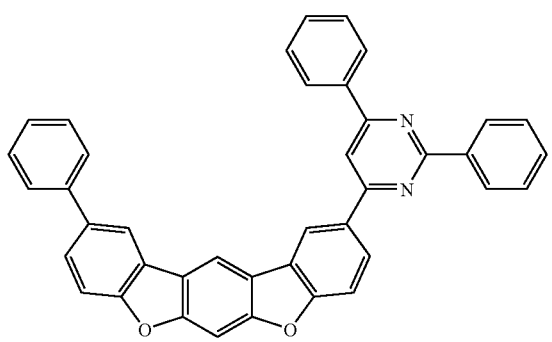
No. 205
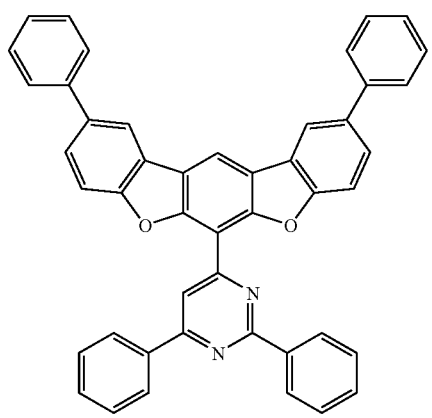

-continued
No. 206
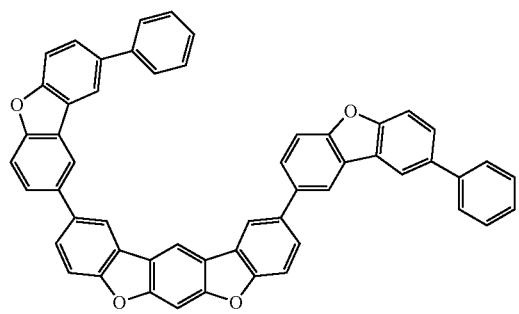
No. 207
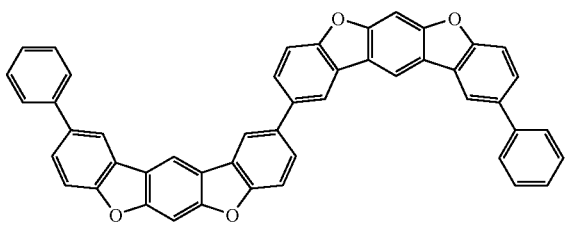
No. 208
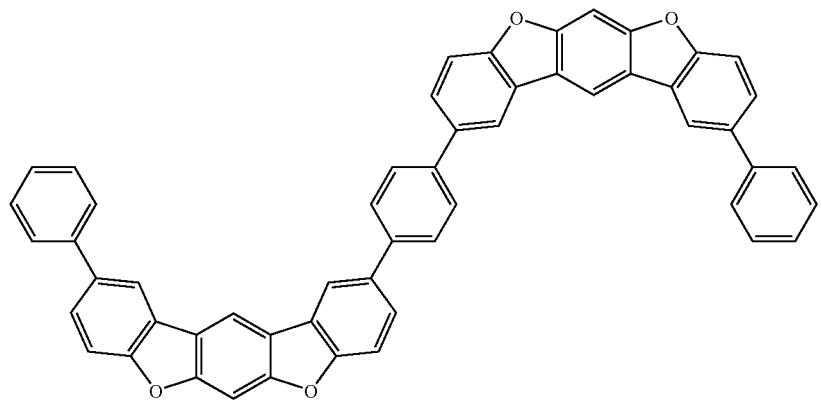
No. 209
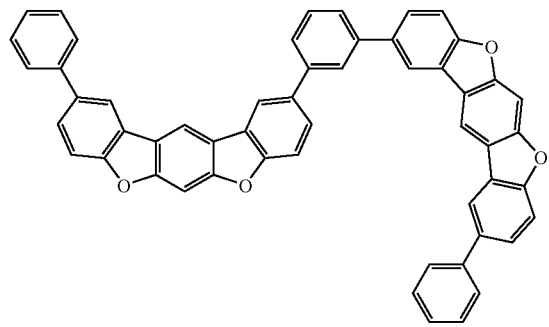
No. 210
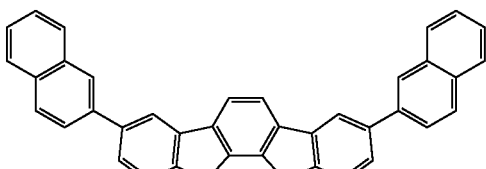
No. 211
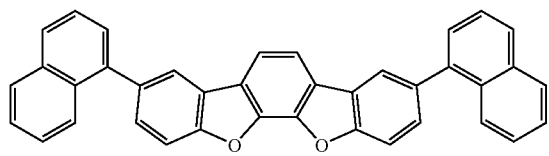
No. 212
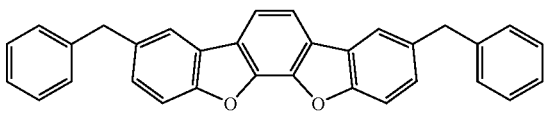
No. 213
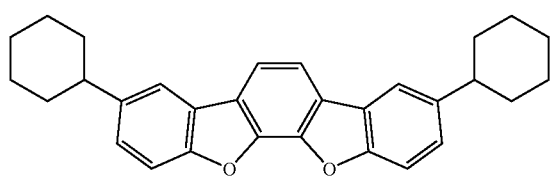

-continued
No. 214
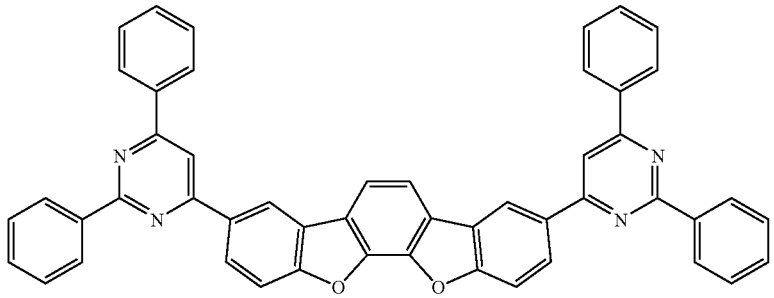
No. 215
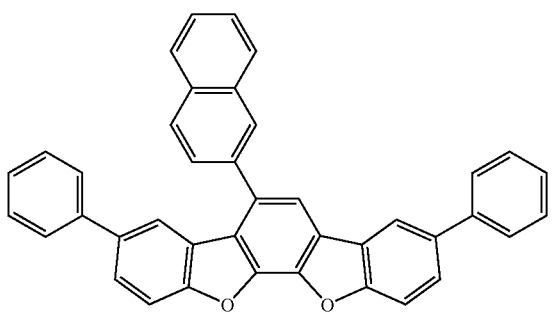
No. 216
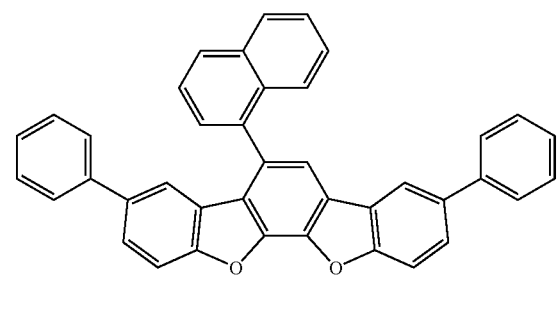
No. 217
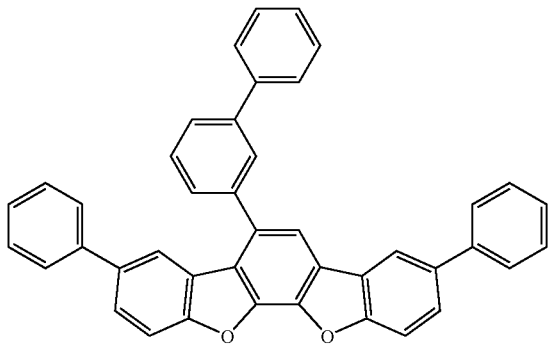
No. 218
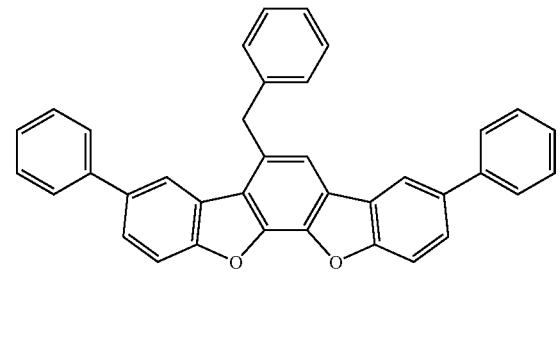
No. 219
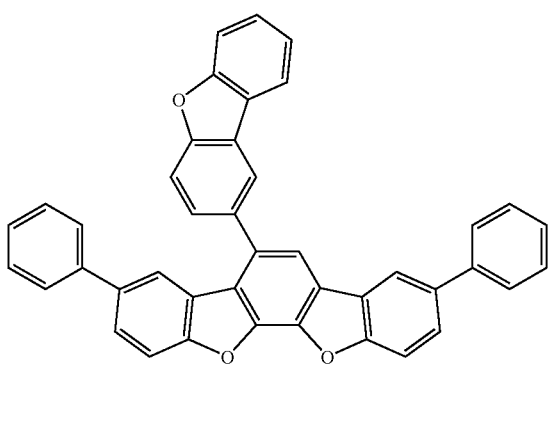
No. 220
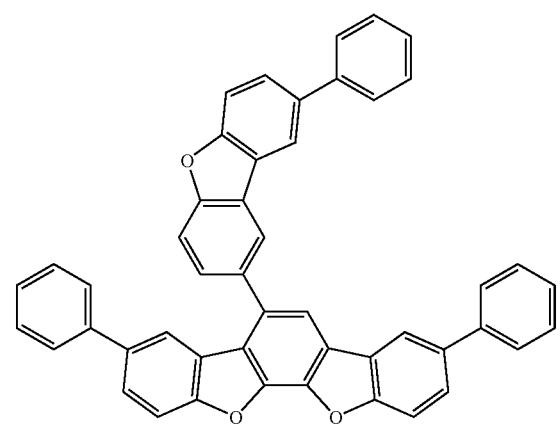

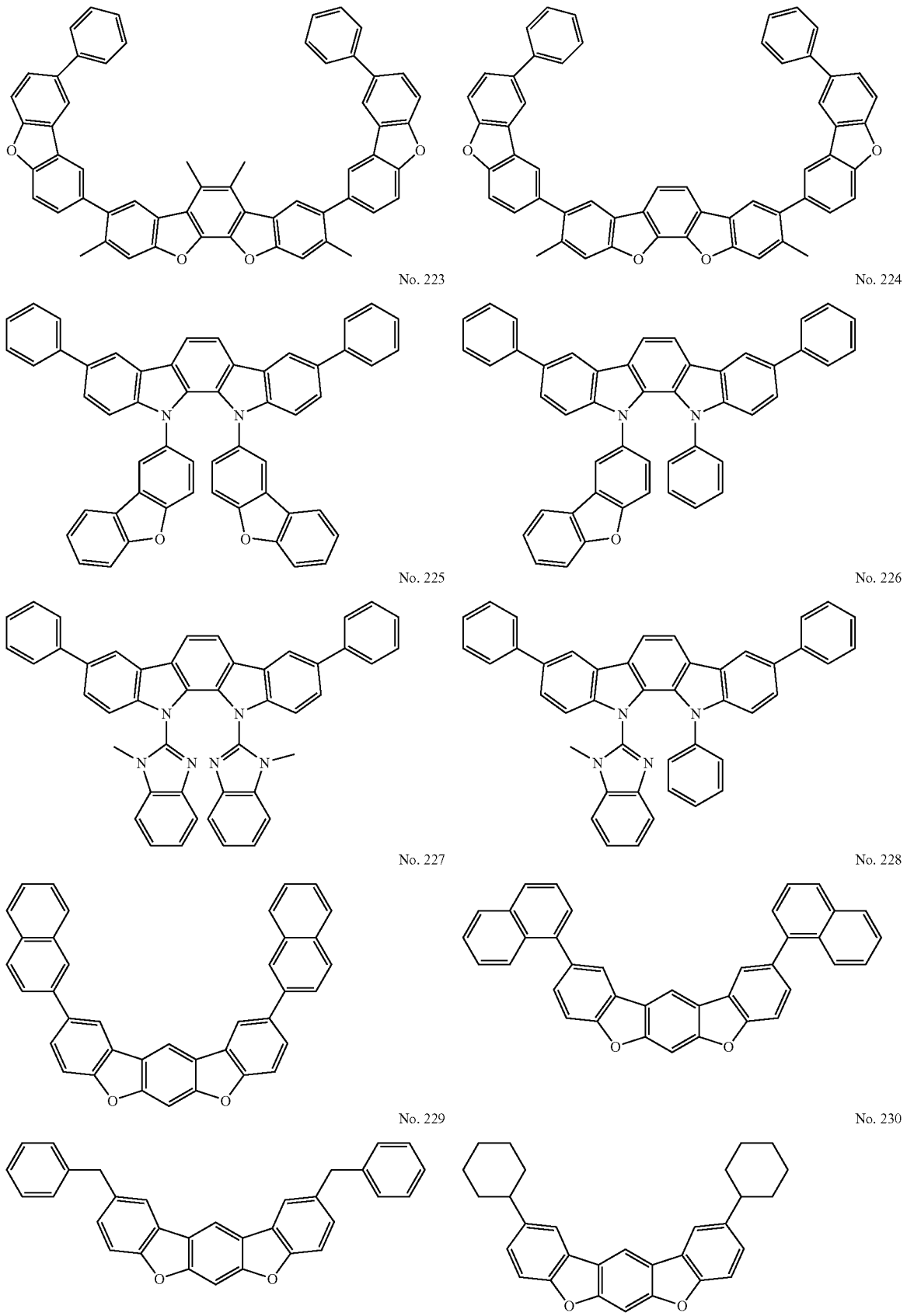

-continued
No. 231
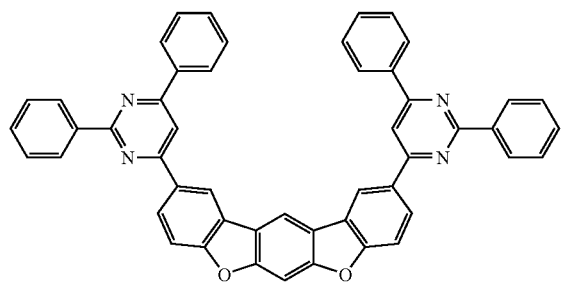
No. 232
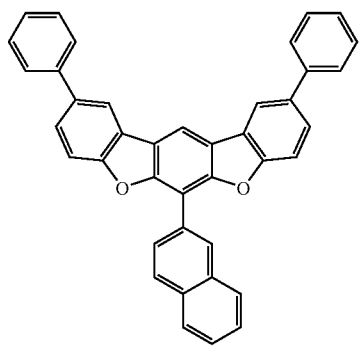
No. 233
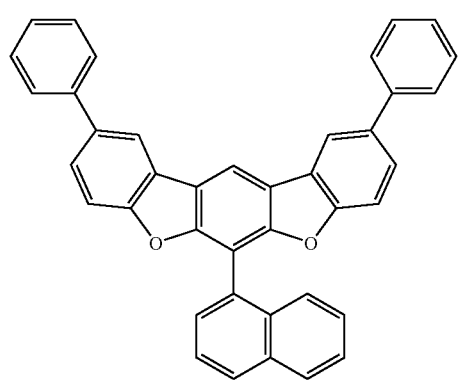
No. 234
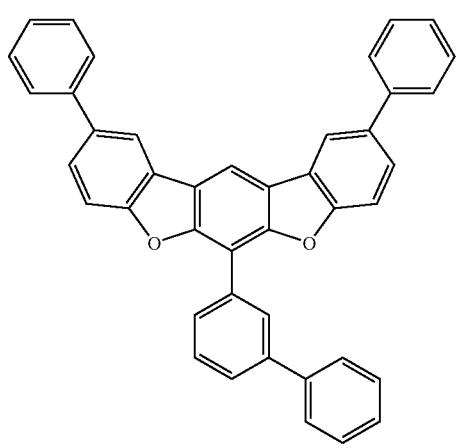
No. 235
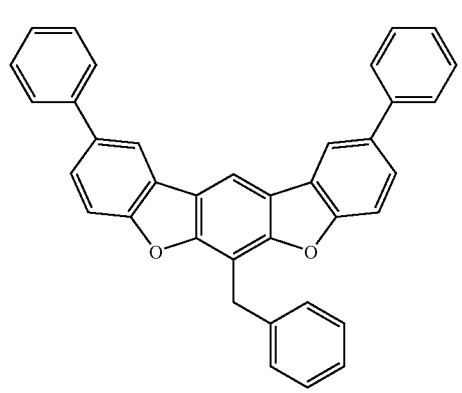
No. 236
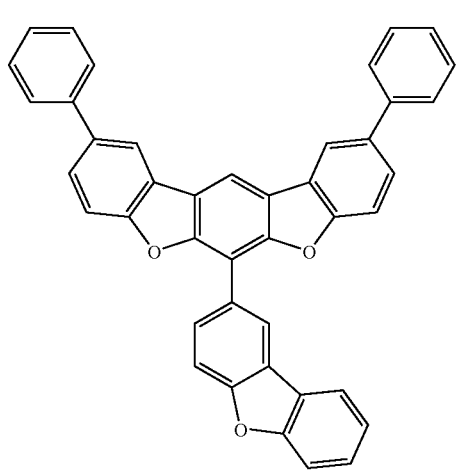
No. 237
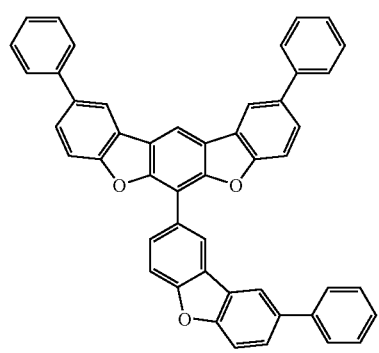
No. 238
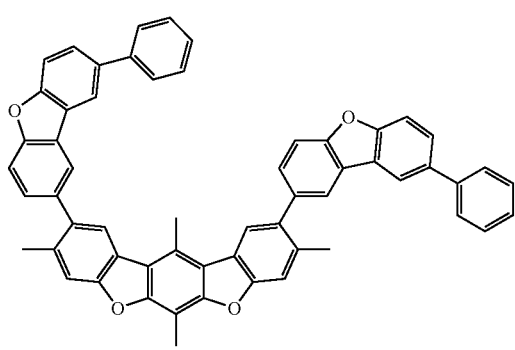

-continued
No. 239
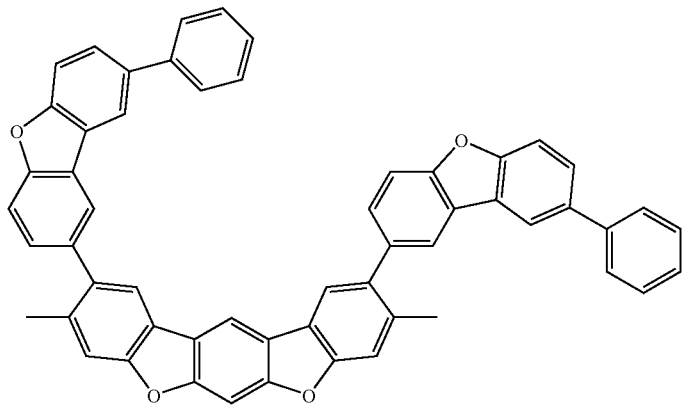
No. 240
No. 241
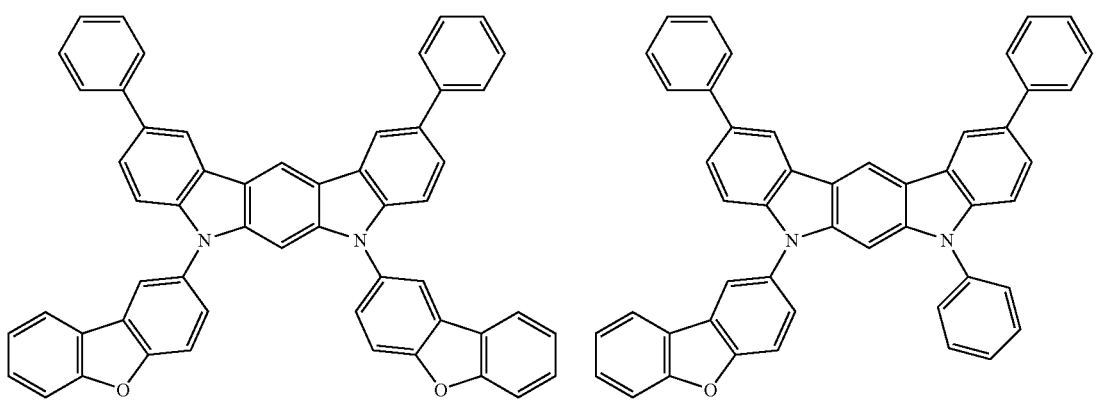
No. 242
No. 243
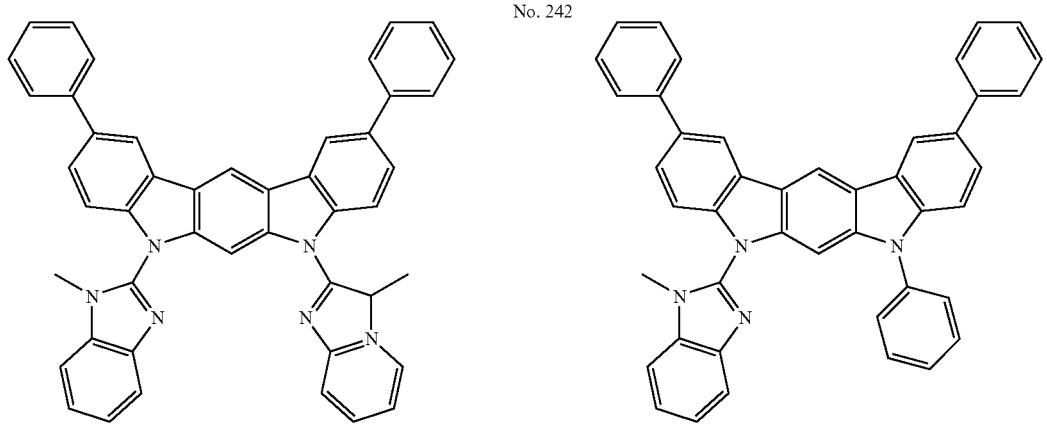

-continued
No. 244
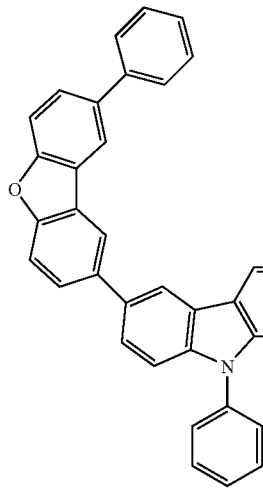
No. 245
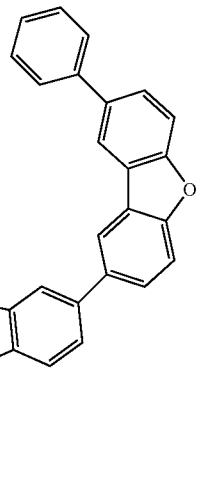
No. 246
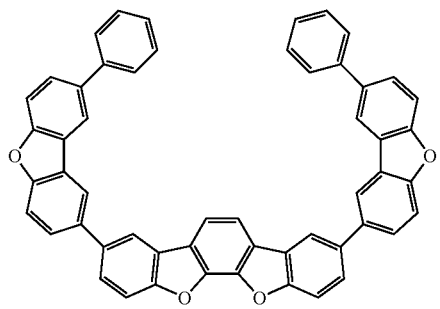
No. 247
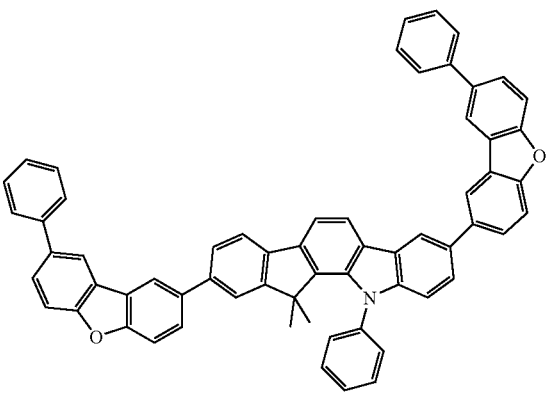
No. 248
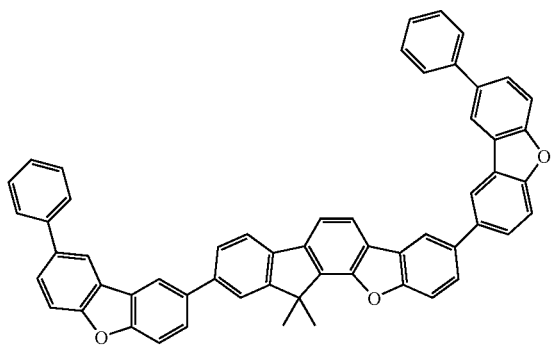
No. 249
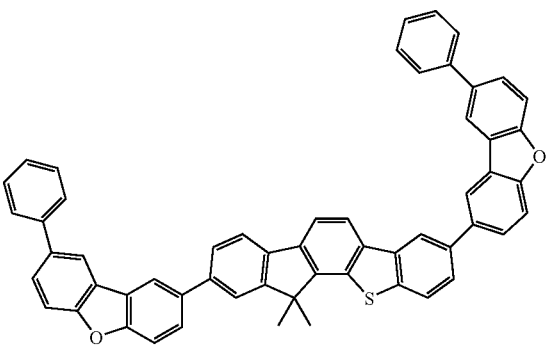

-continued
No. 250
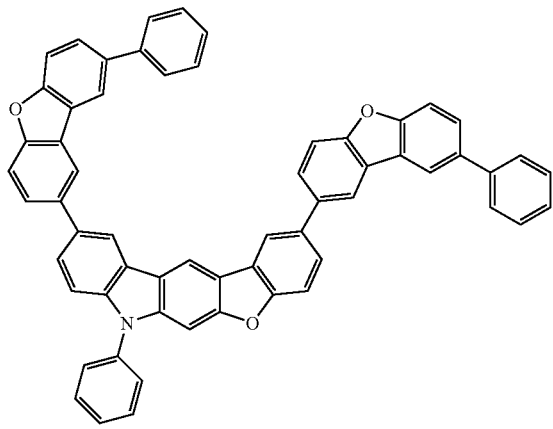
No. 251
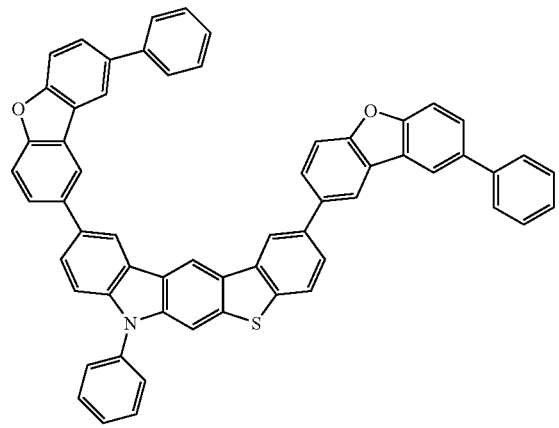
No. 252
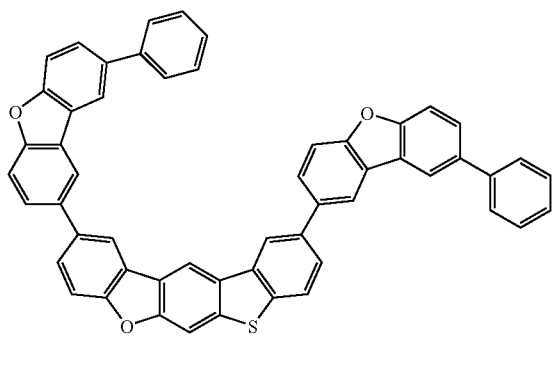
No. 253
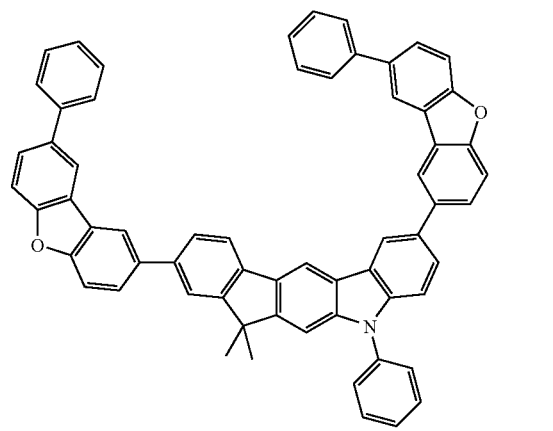
No. 254
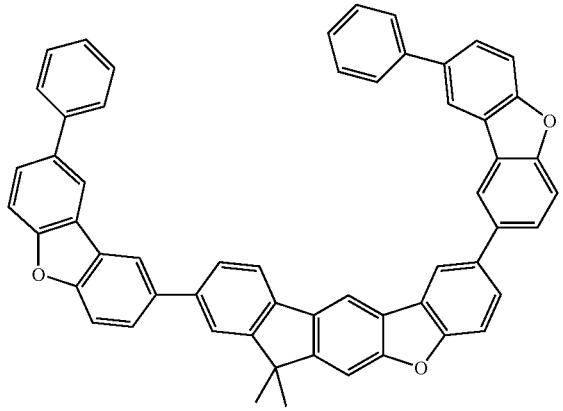
No. 255
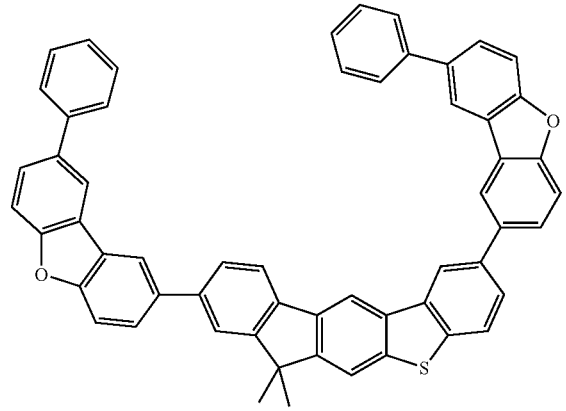
No. 256
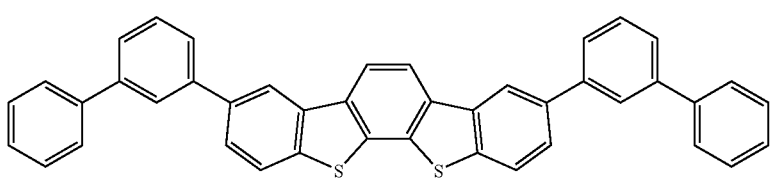

-continued
No. 257
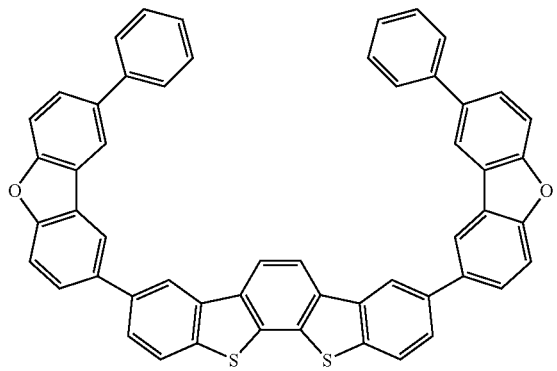
No. 258
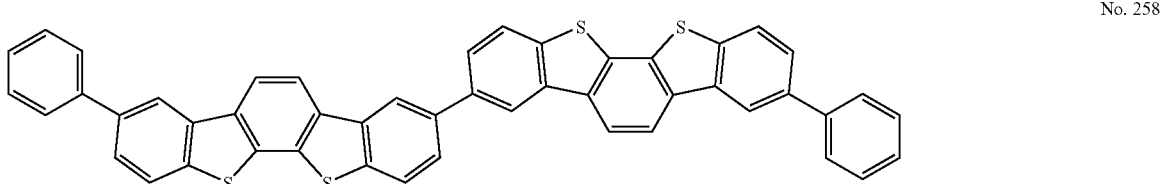
No. 259
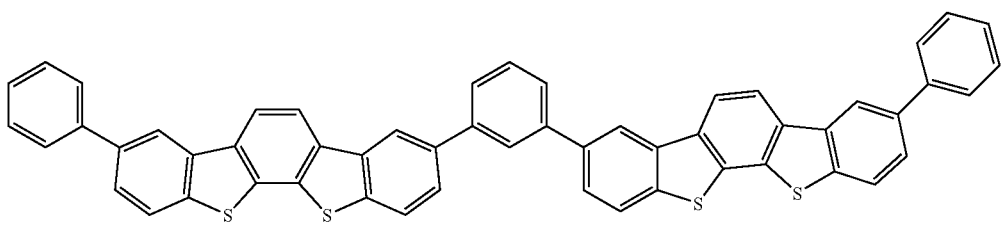
No. 260
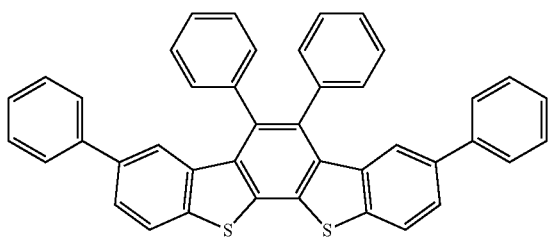
No. 261
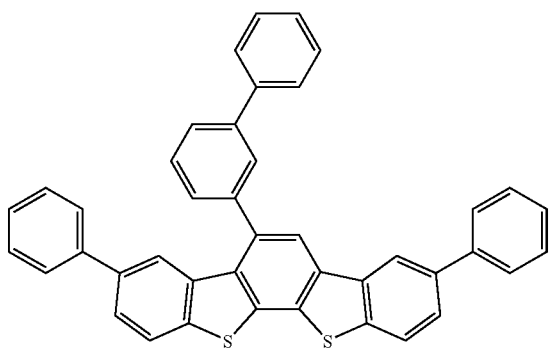
No. 262
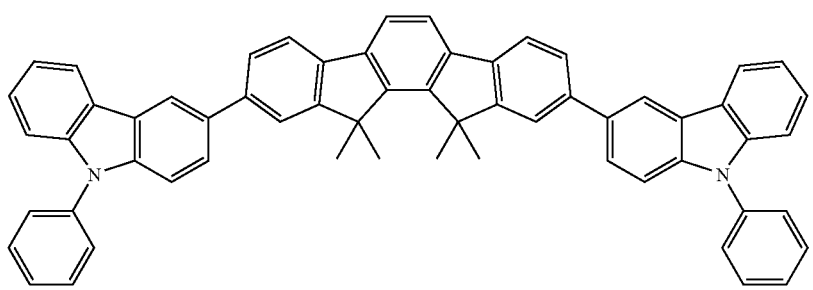

-continued
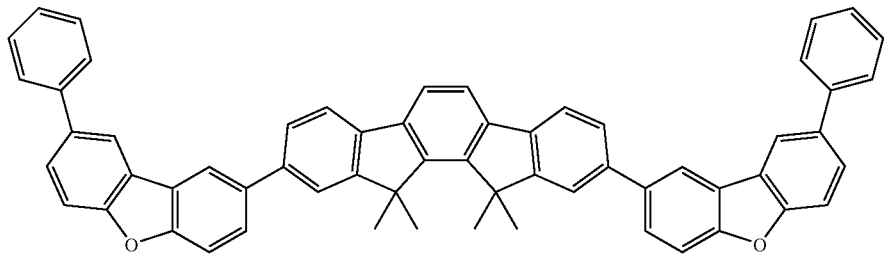
No. 263
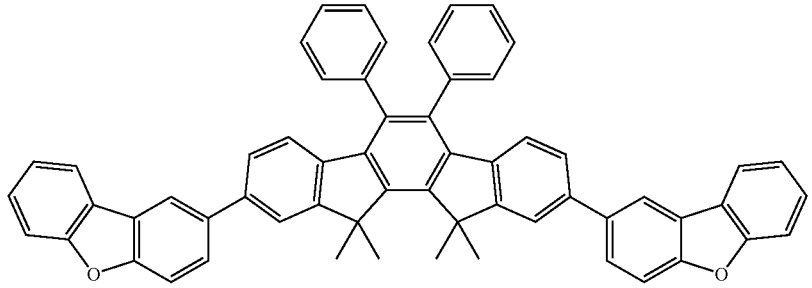
No. 264
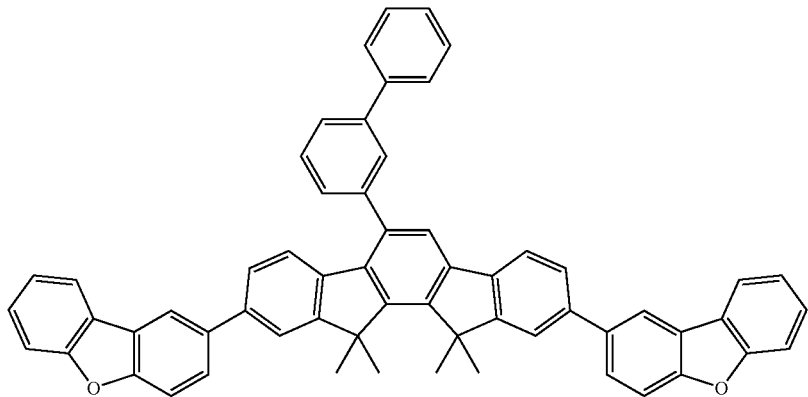
No. 265
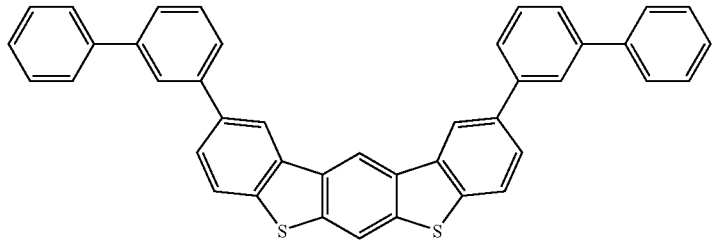
No. 266
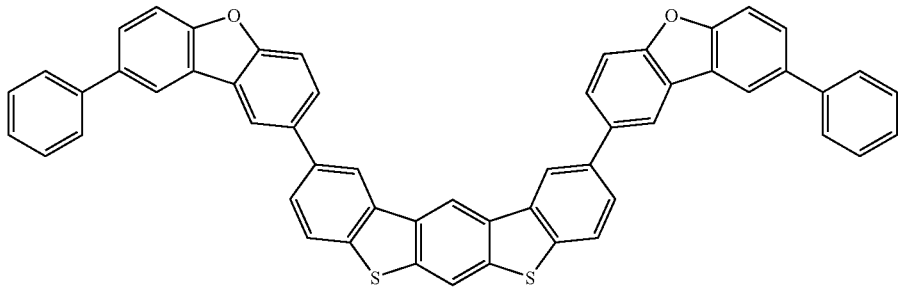
No. 267

-continued
No. 268
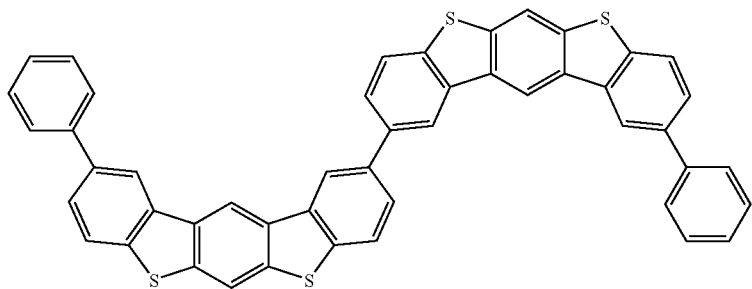
No. 269
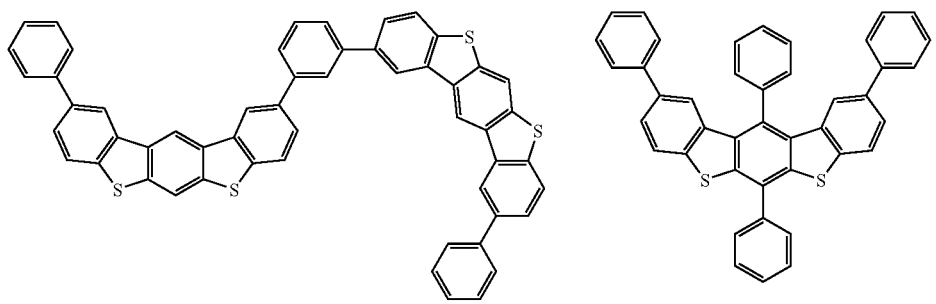
No. 270
No. 271
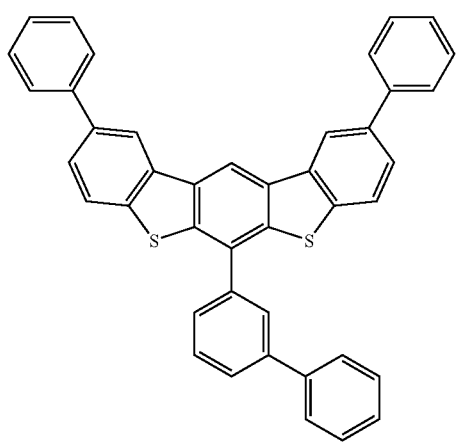
No. 272
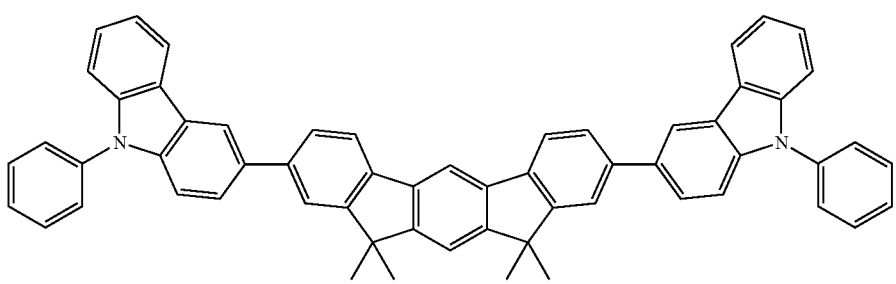
No. 273
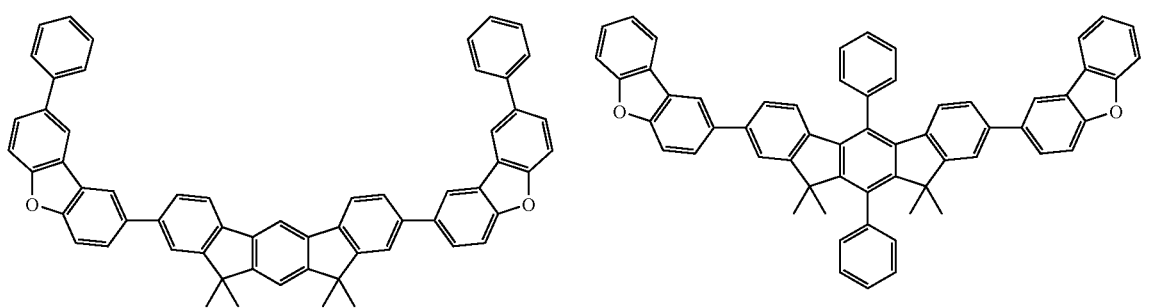
No. 274

-continued
No. 275
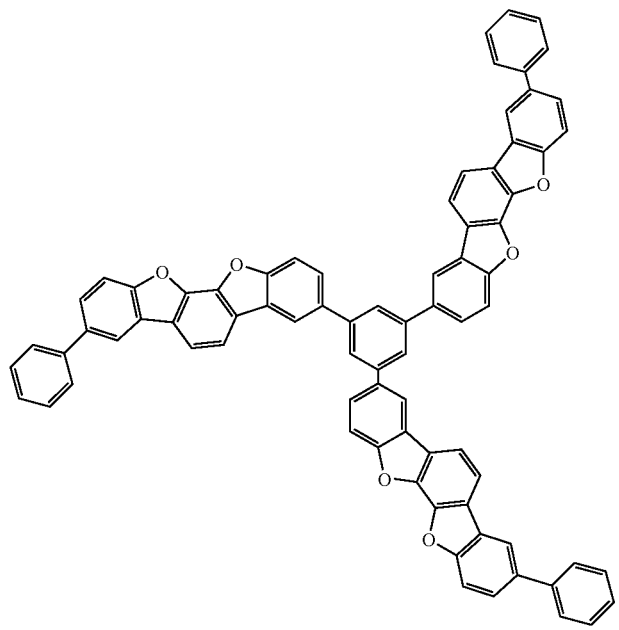
No. 276
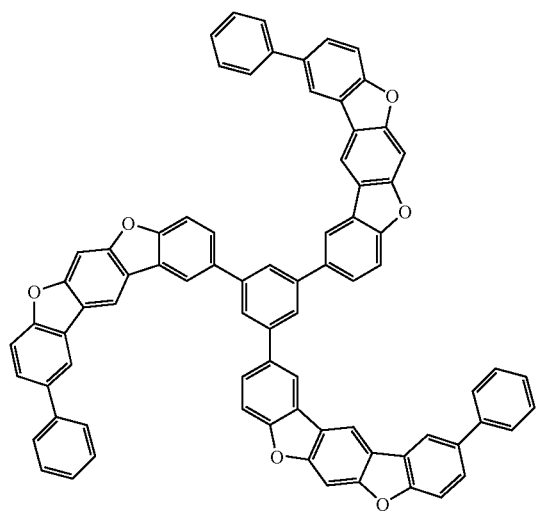
No. 277
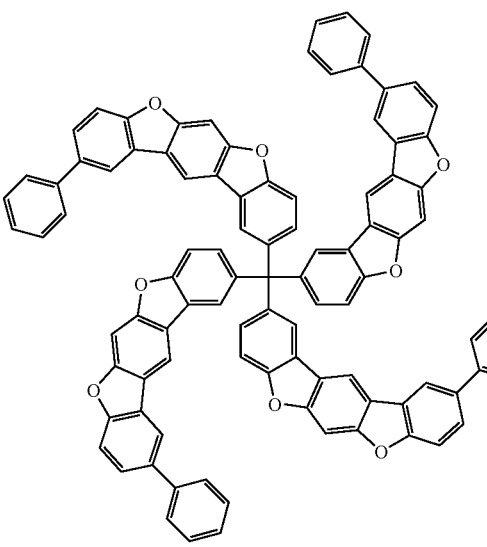
No. 278
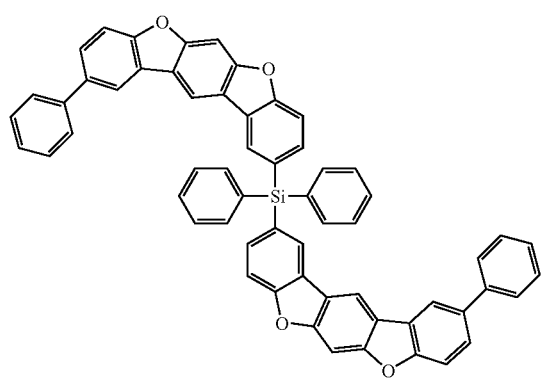
No. 279
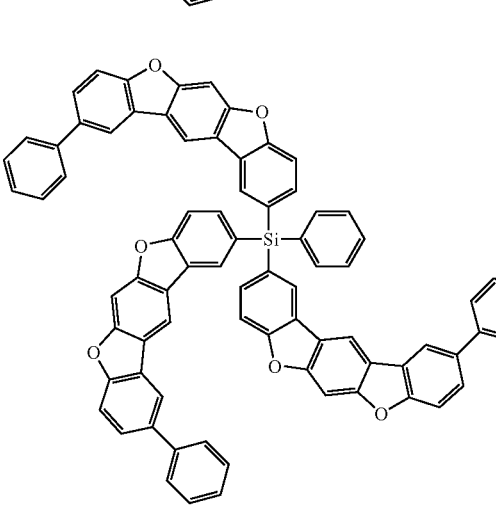

-continued
No. 280
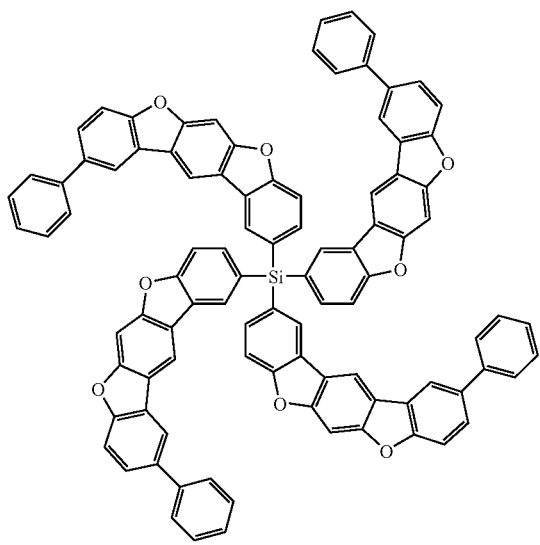
No. 281
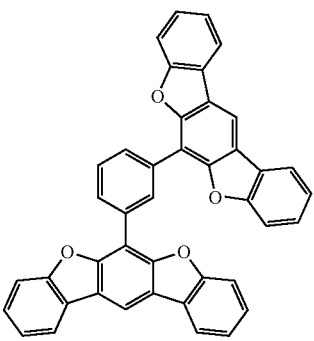
No. 282
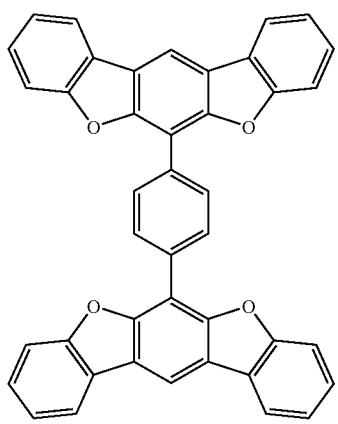
No. 283
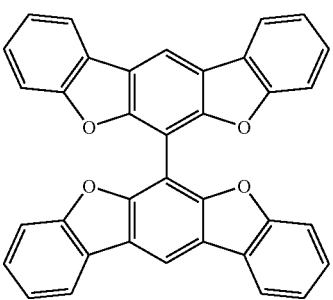
No. 284
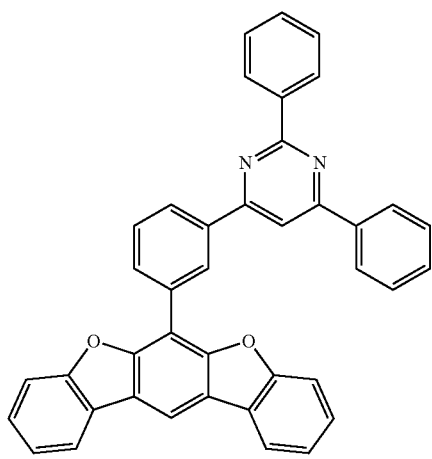
No. 285
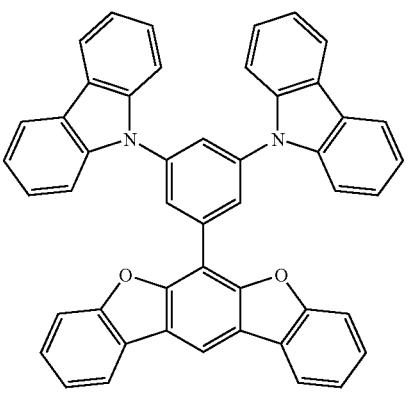
No. 286
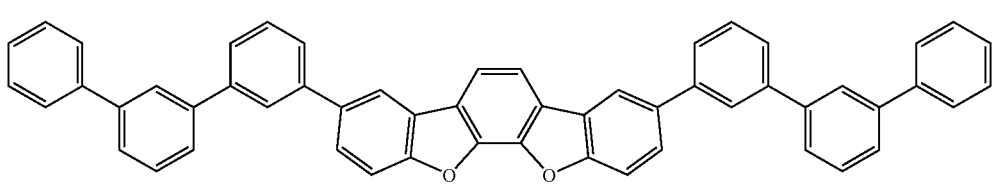

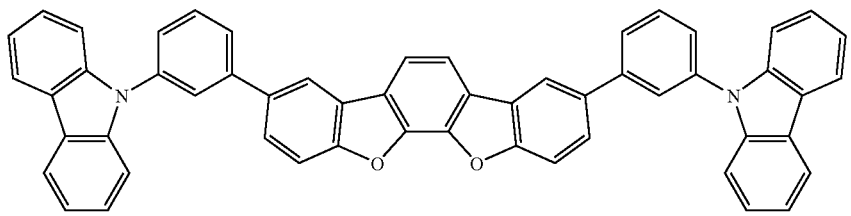
No. 287
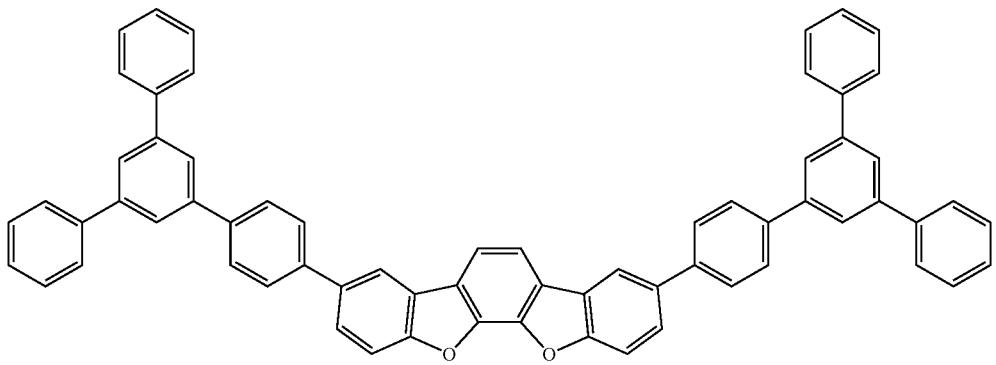
No. 288
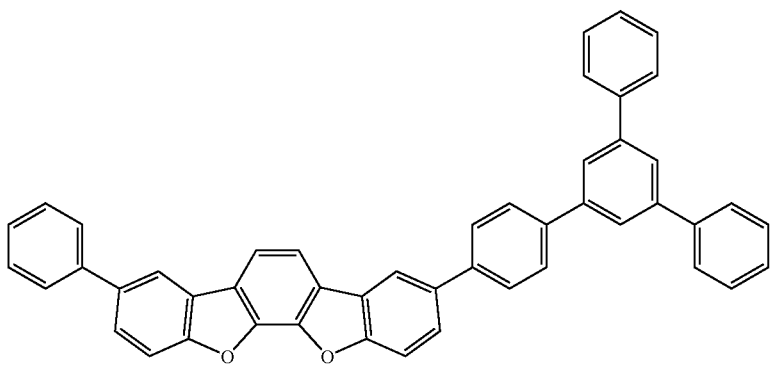
No. 289
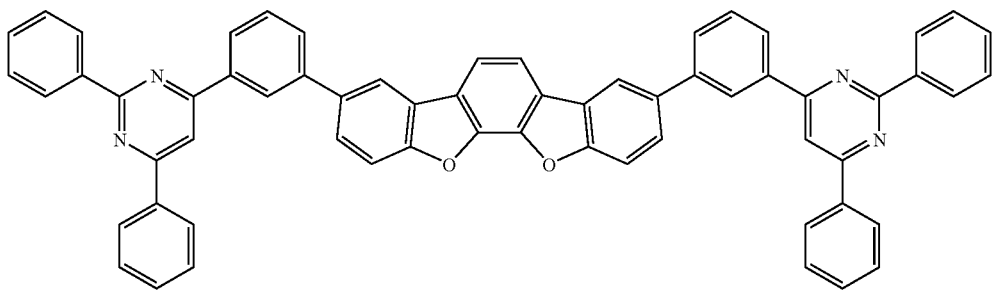
No. 290
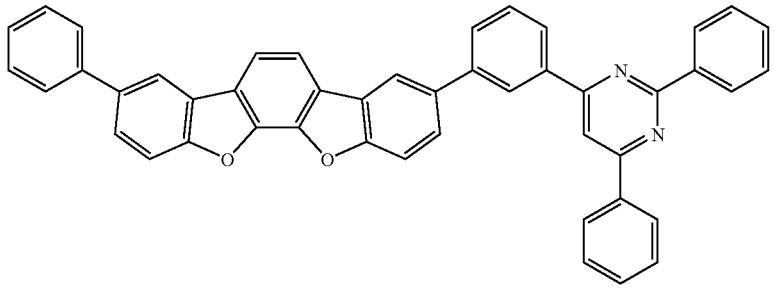
No. 291

-continued
No. 292
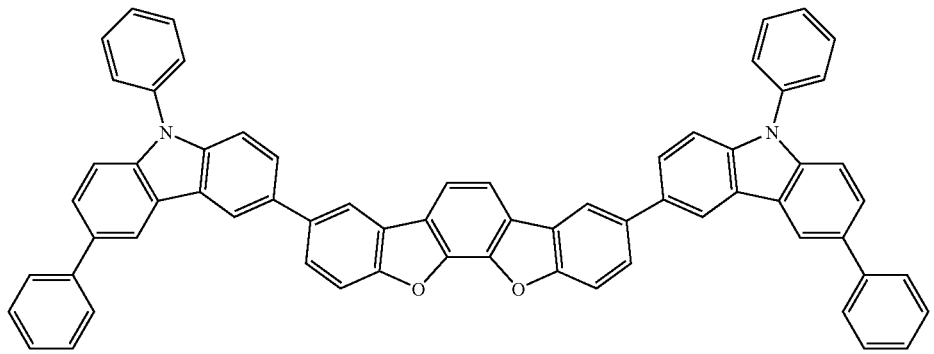
No. 293
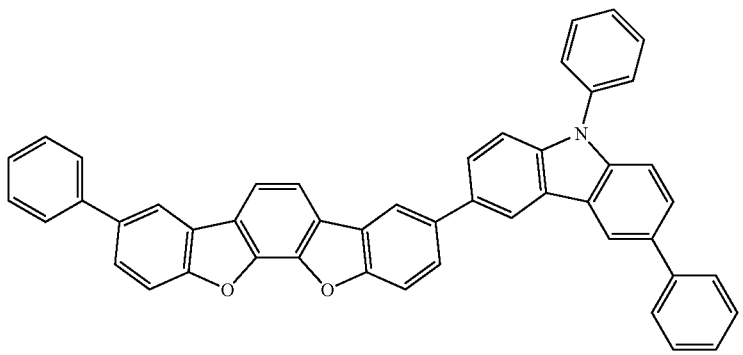
No. 294
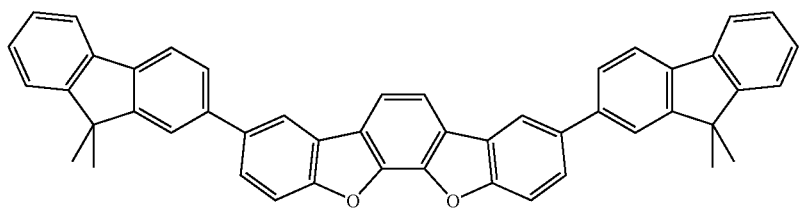
No. 295
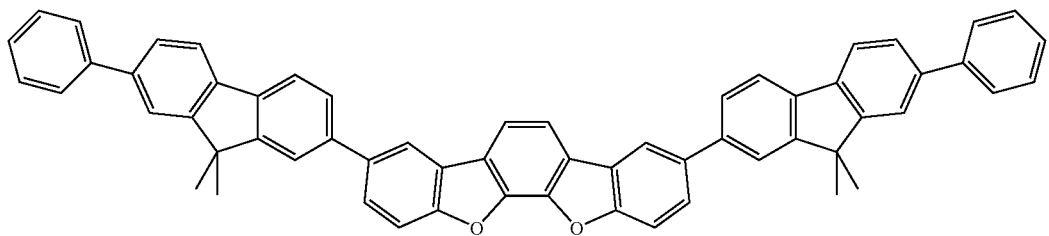
No. 296
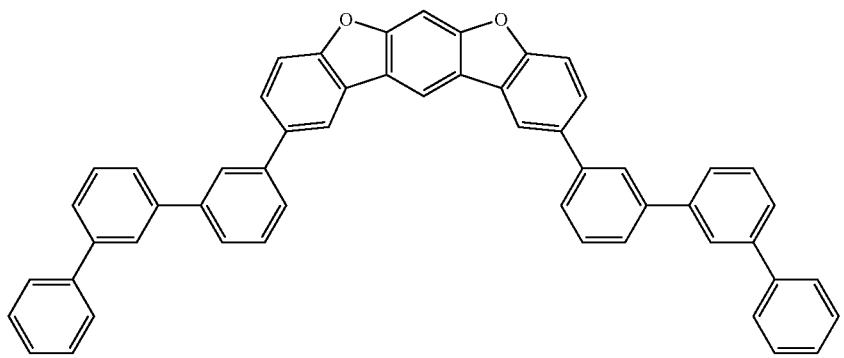

-continued
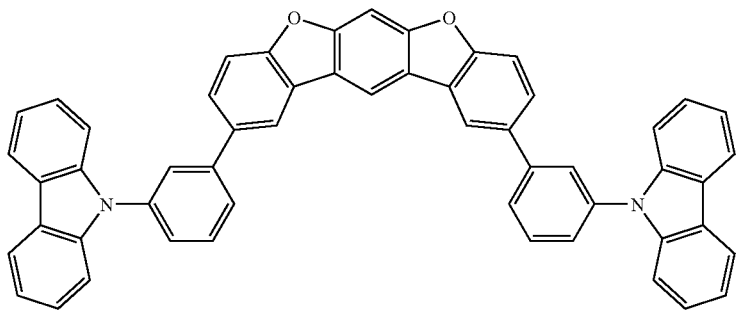
No. 297
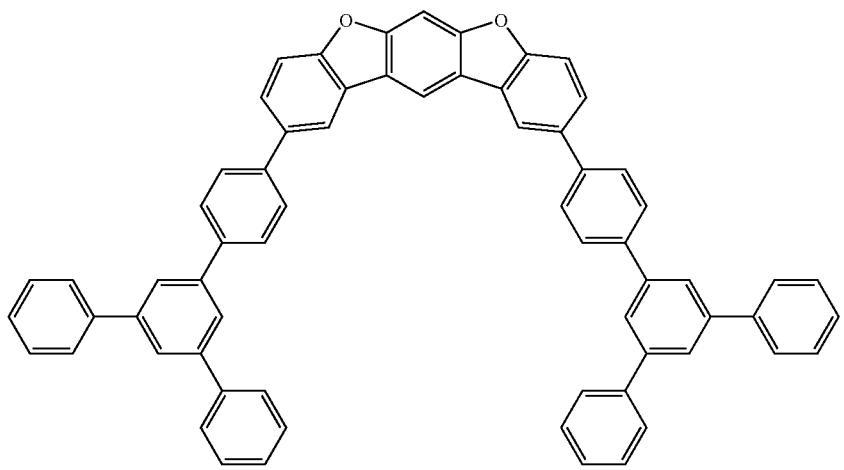
No. 298
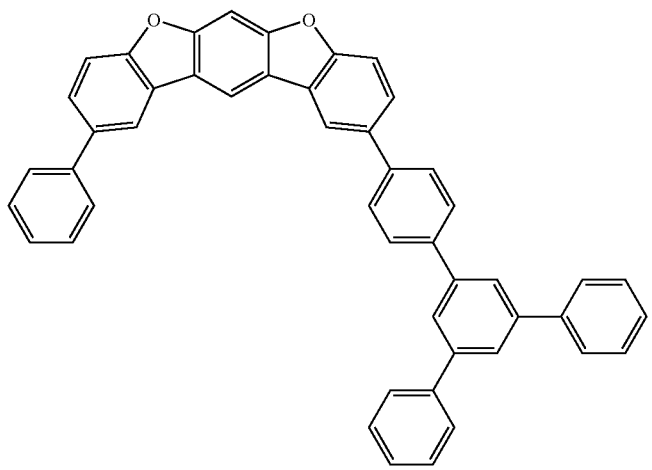
No. 299
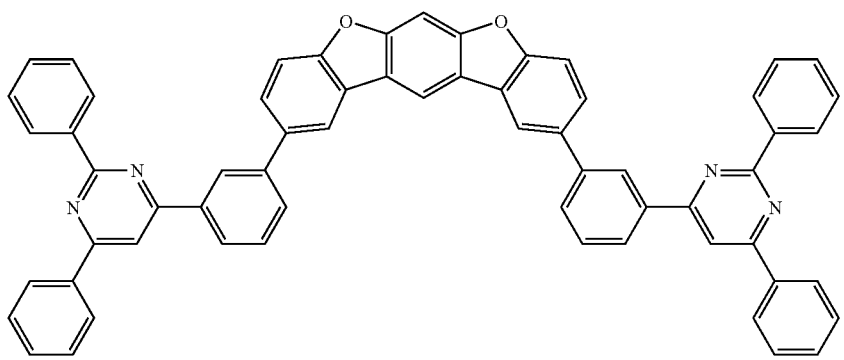
No. 300

No. 301
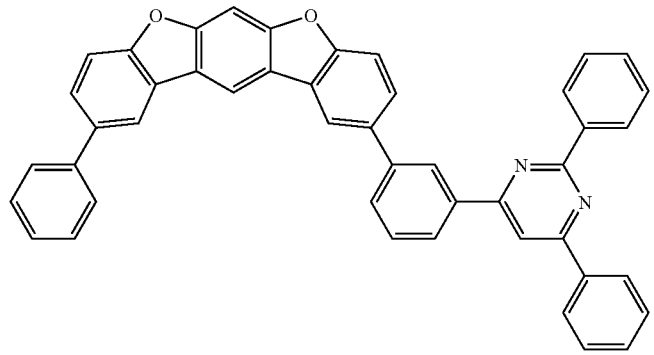
No. 302
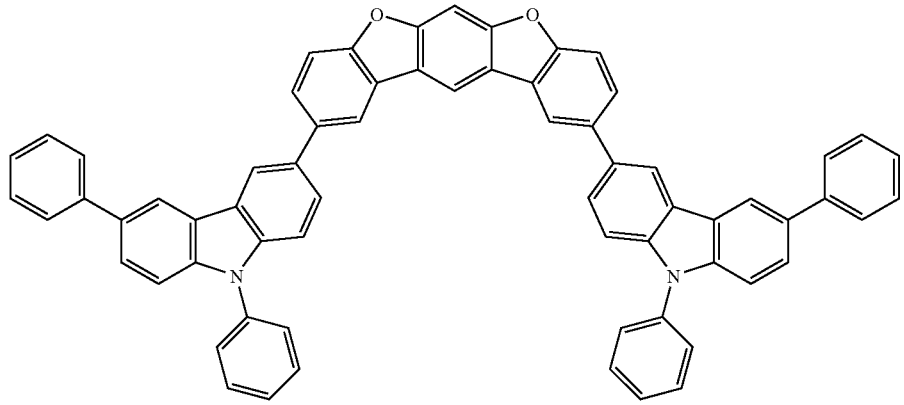
No. 303
No. 304
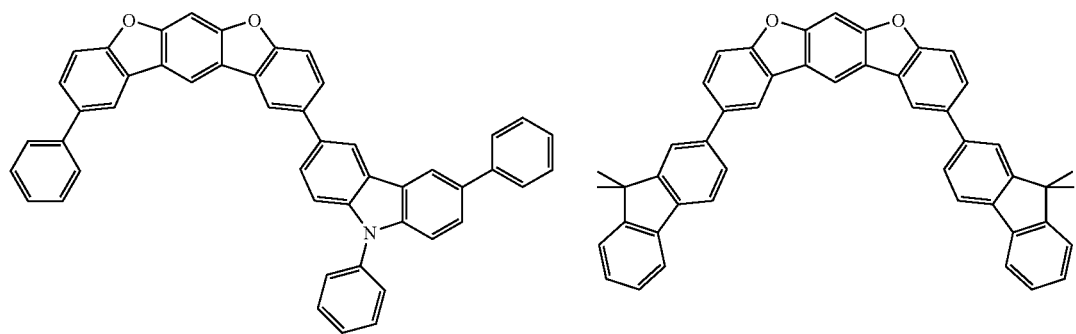
No. 305
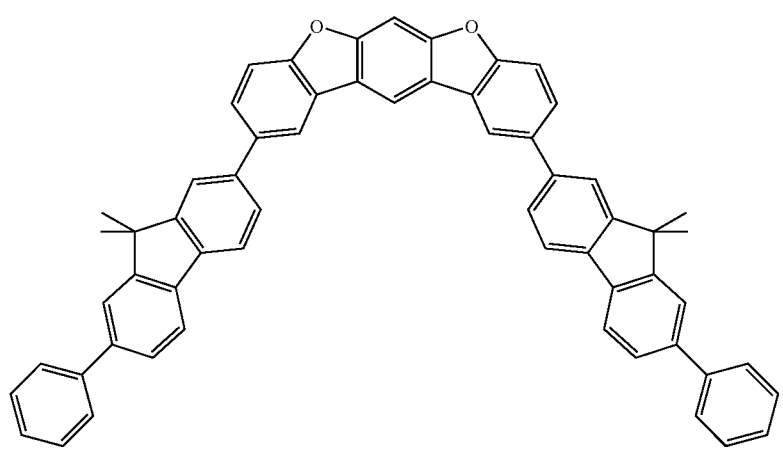

-continued
No. 306
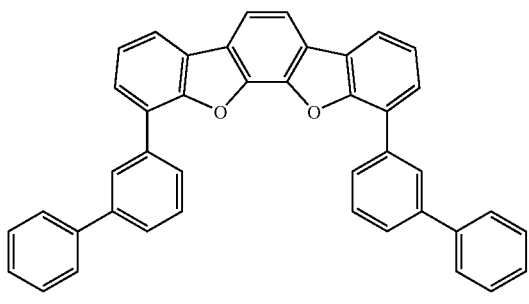
No. 307
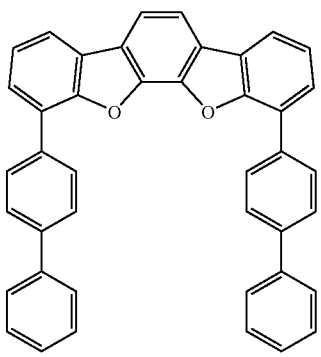
No. 308
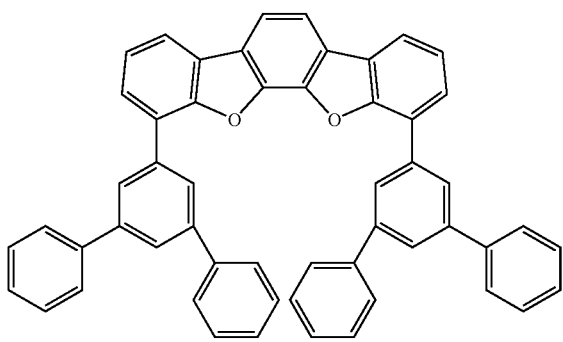
No. 309
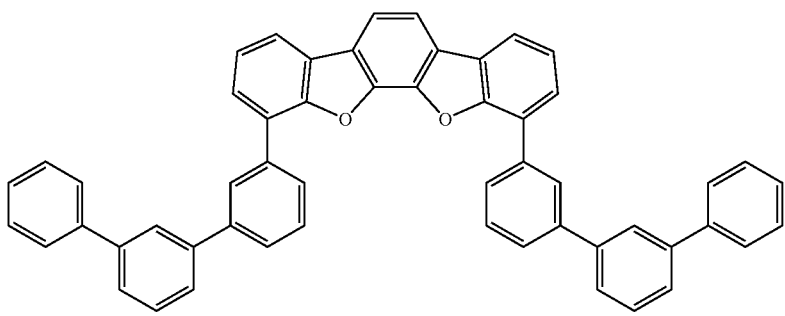
No. 310
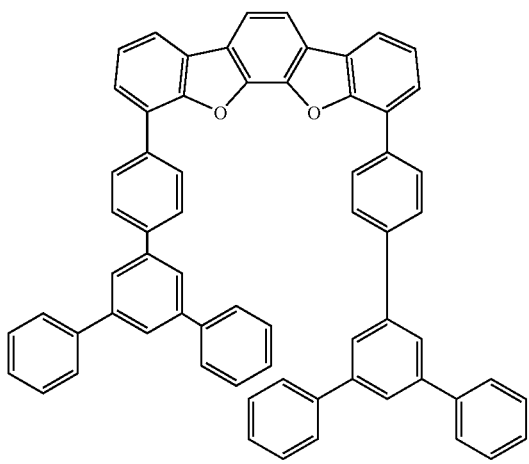
No. 311
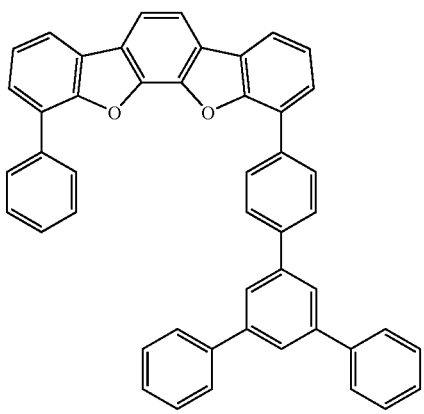

-continued
No. 312
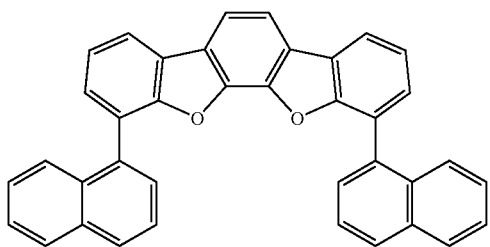
No. 313
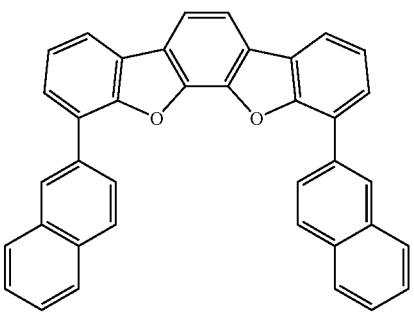
No. 314
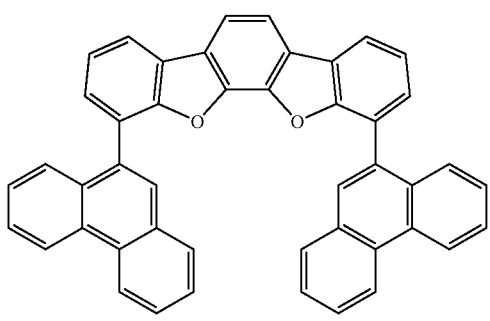
No. 315
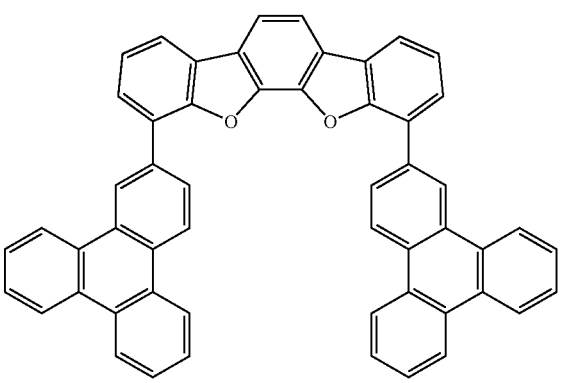
No. 316
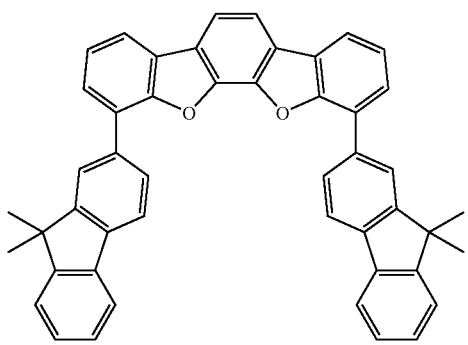
No. 317
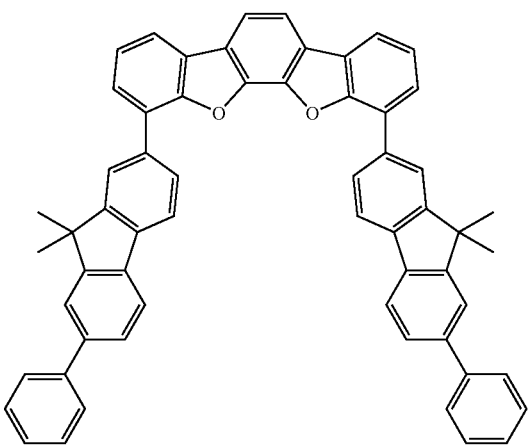
No. 318
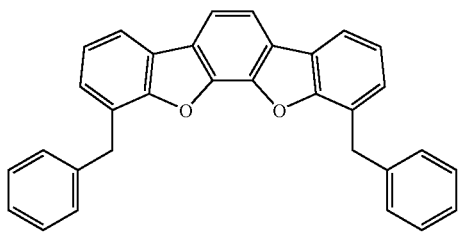
No. 319
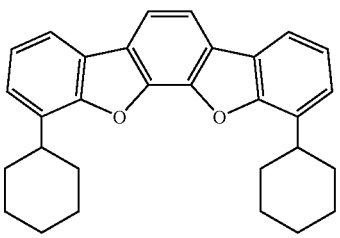

-continued
No. 320
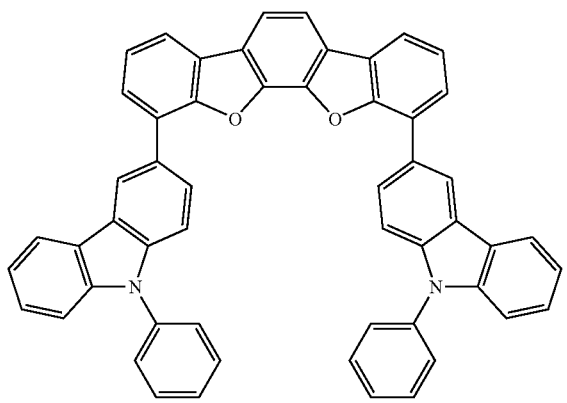
No. 321
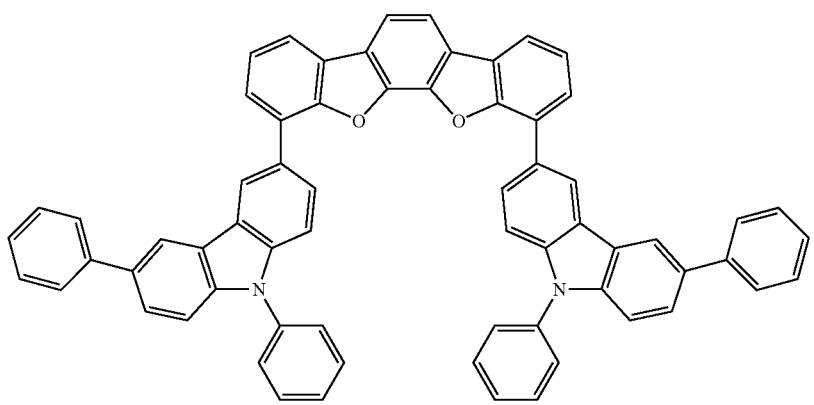
No. 322
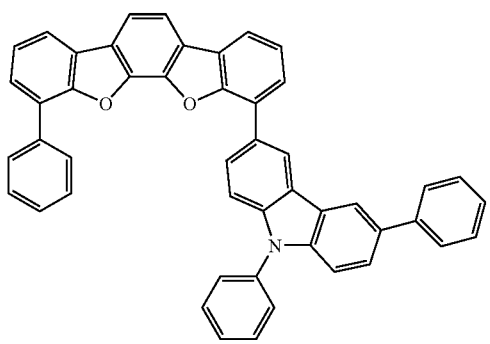
No. 323
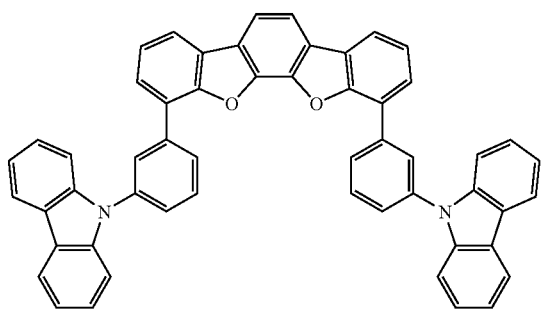
No. 324
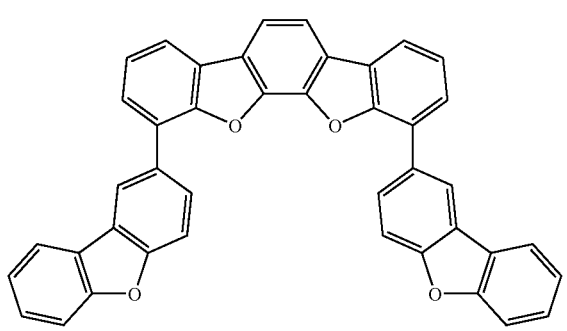

-continued
No. 325
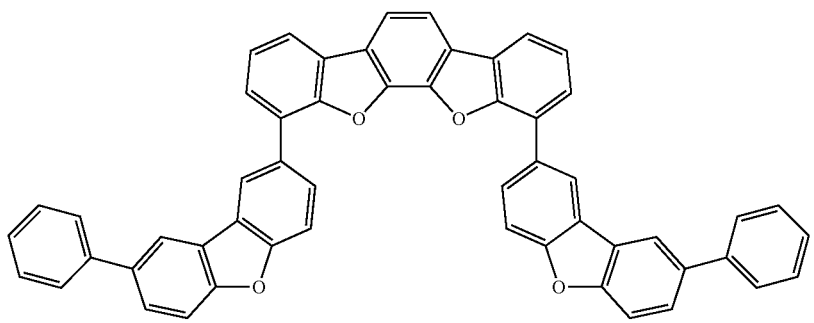
No. 326
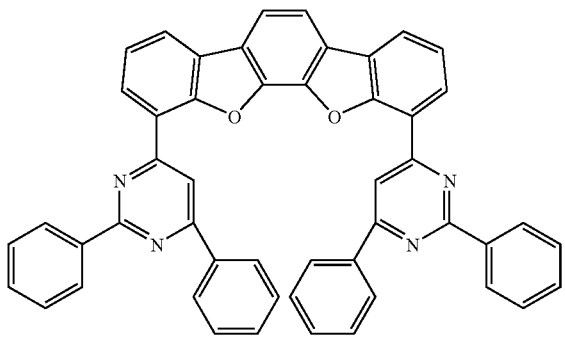
No. 327
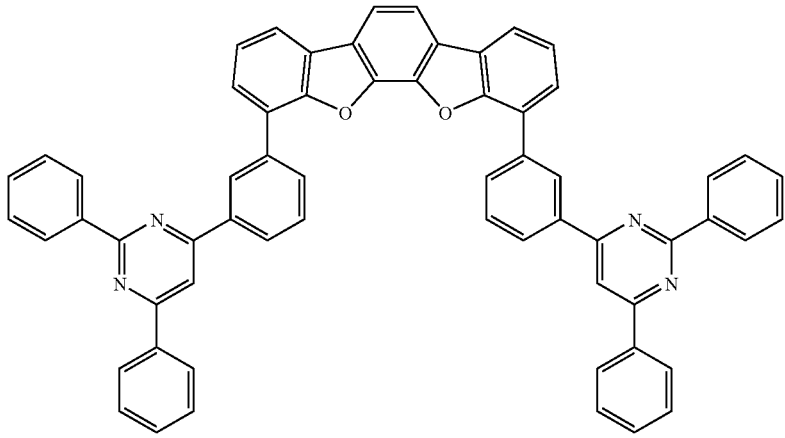
No. 328
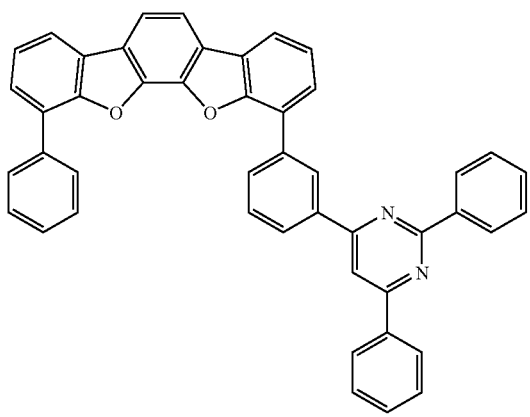
No. 329
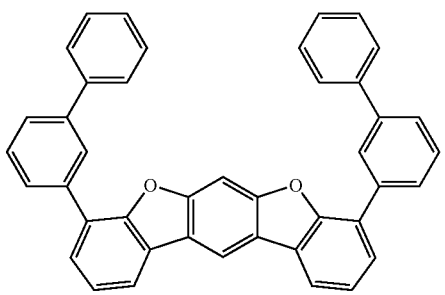

-continued
No. 330
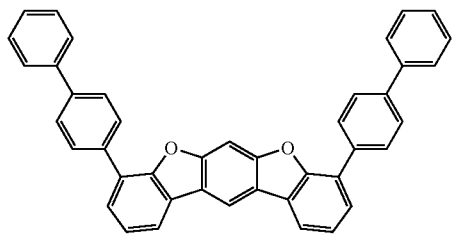
No. 331
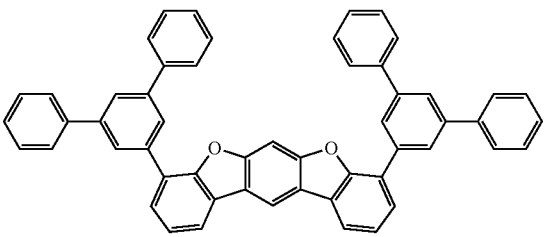
No. 332
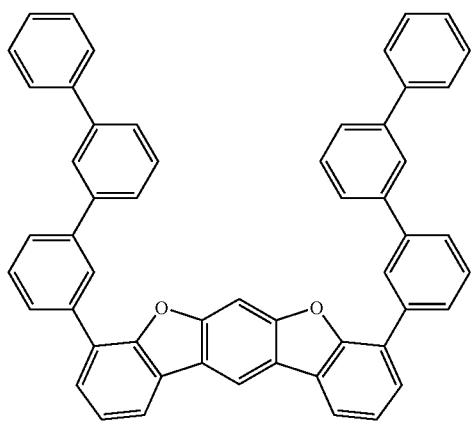
No. 333
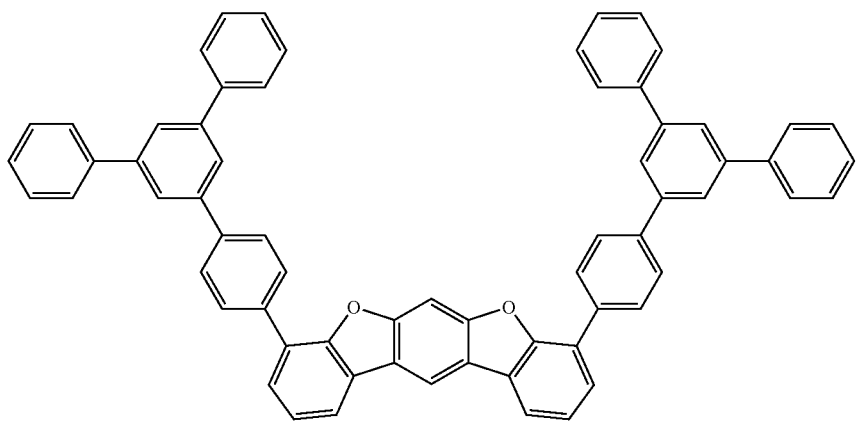
No. 334
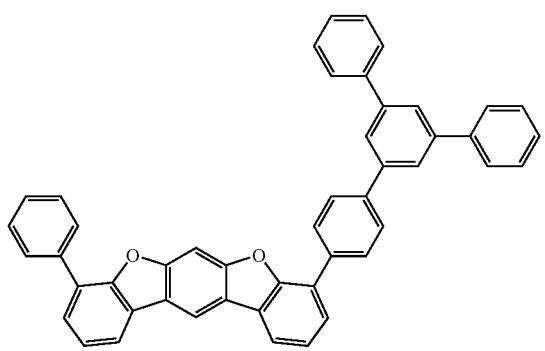
No. 335
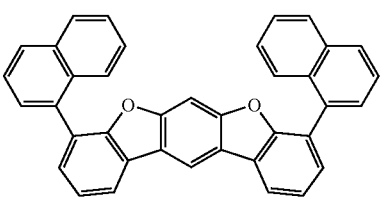

-continued
No. 336
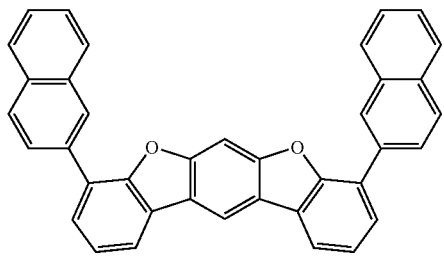
No. 337
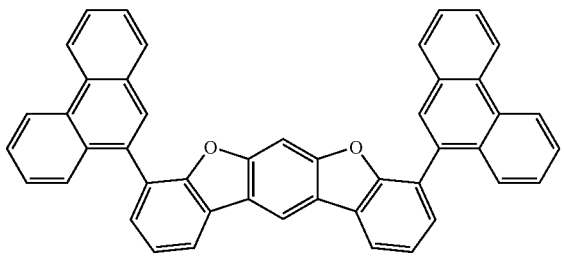
No. 338
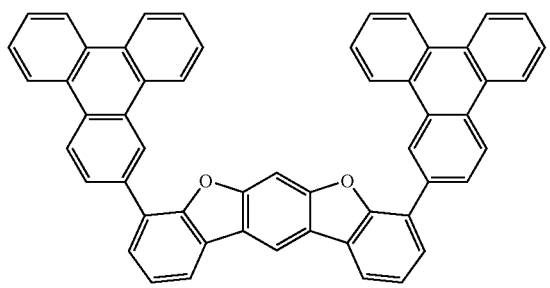
No. 339
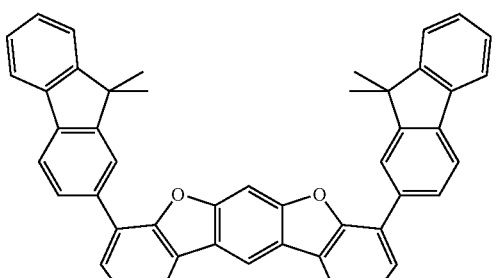
No. 340
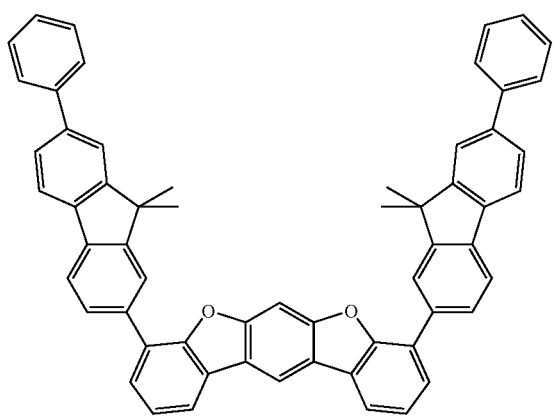
No. 341
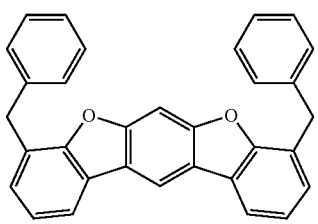
No. 342
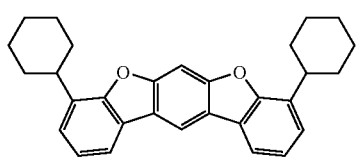
No. 343
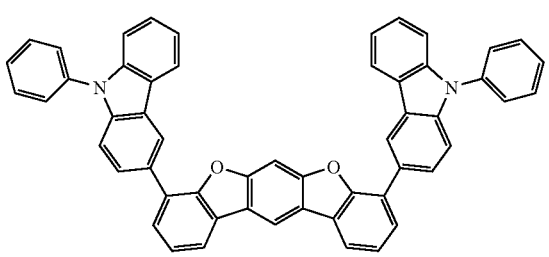
No. 344
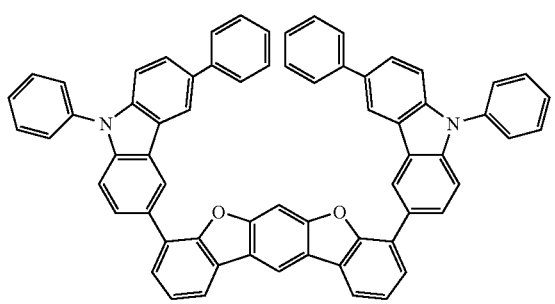
No. 345
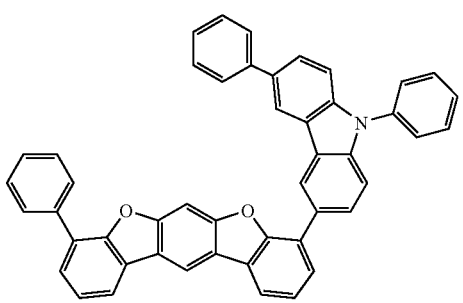

-continued
No. 346
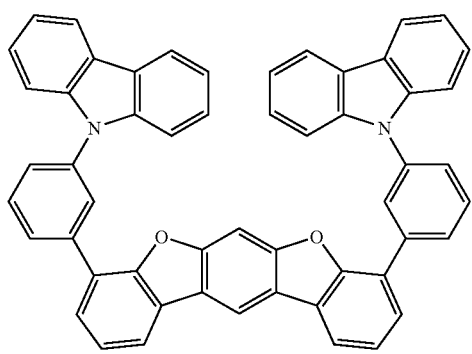
No. 347
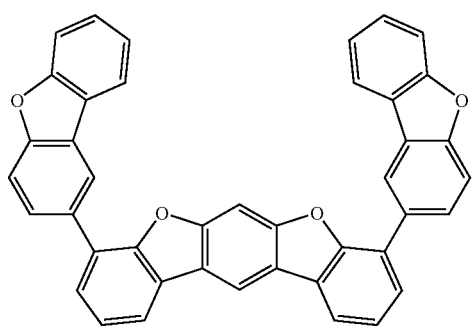
No. 348
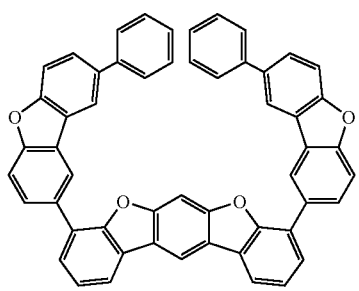
No. 349
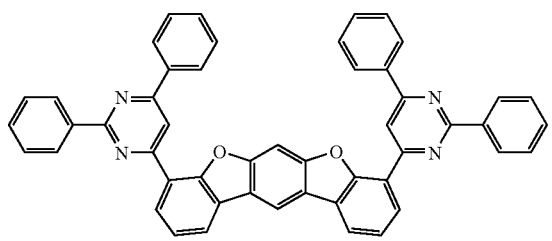
No. 350
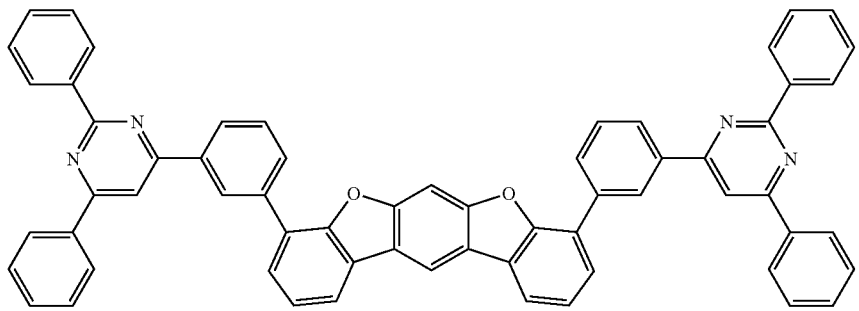
No. 351
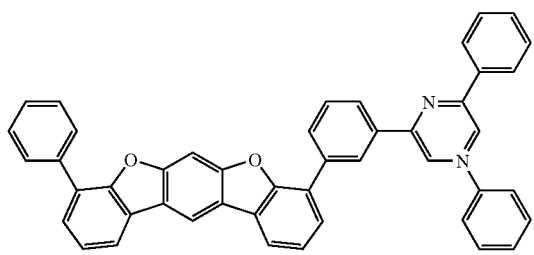
No. 352
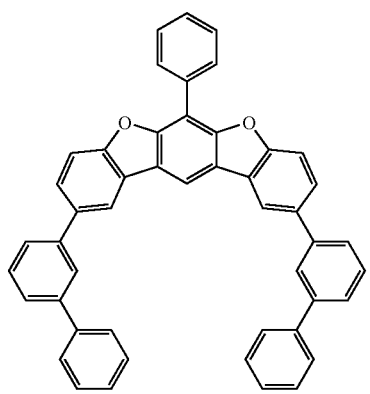

-continued
No. 353
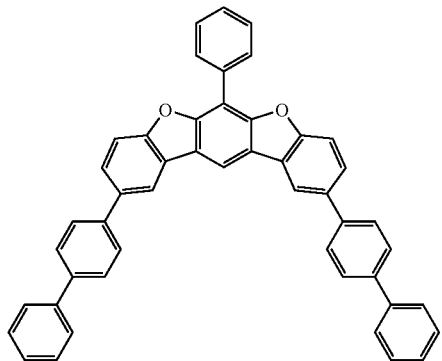
No. 354
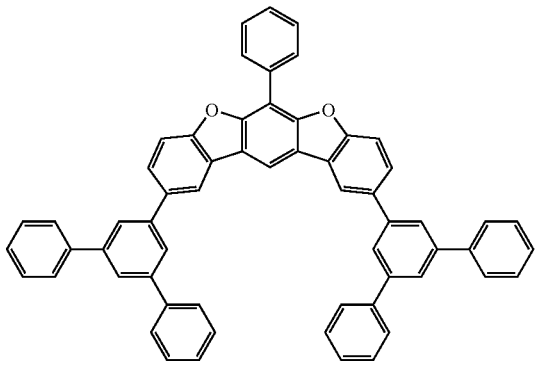
No. 355
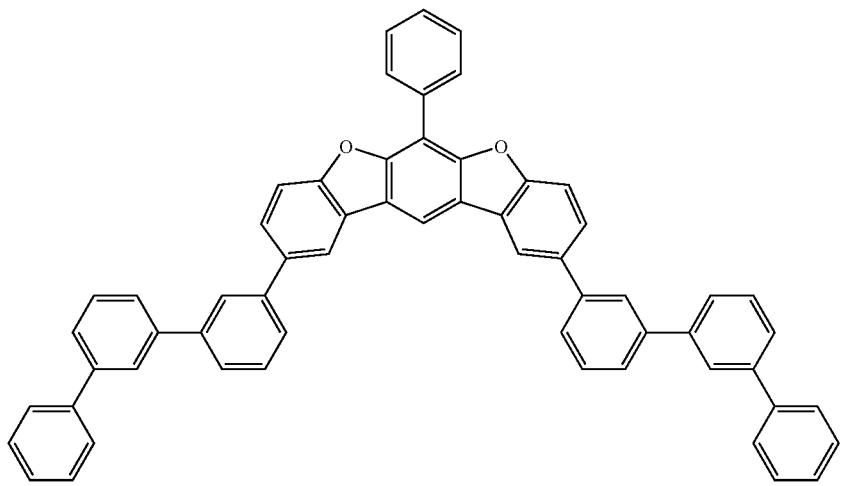
No. 356
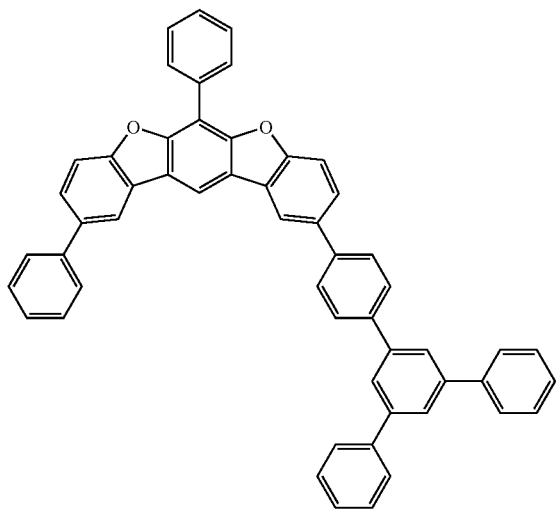
No. 357
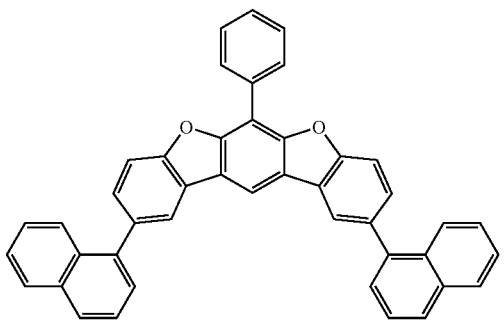

-continued
No. 358
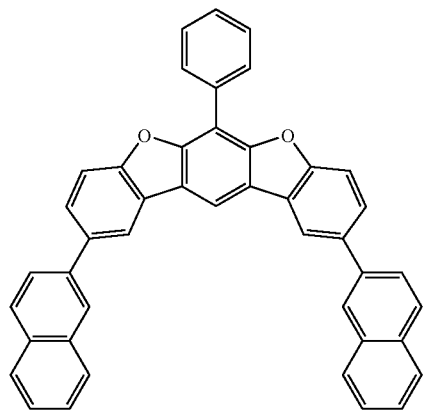
No. 359
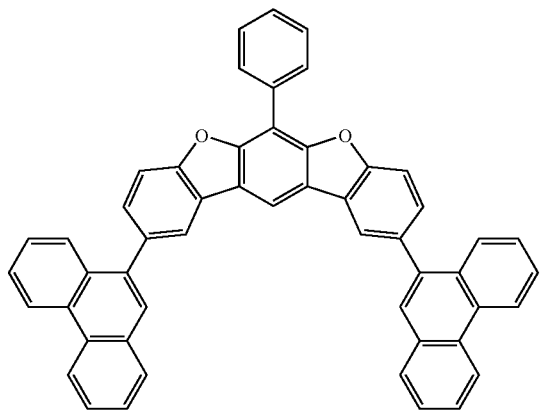
No. 360
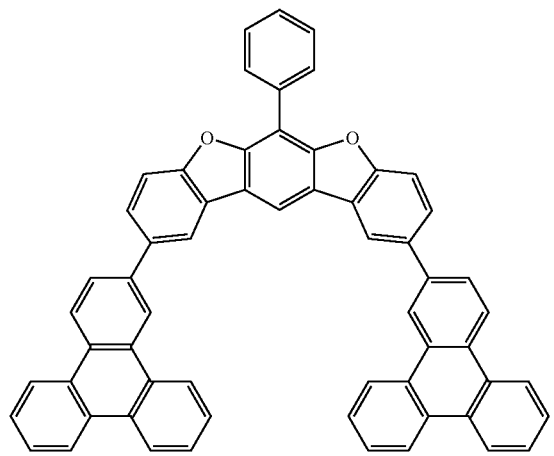
No. 361
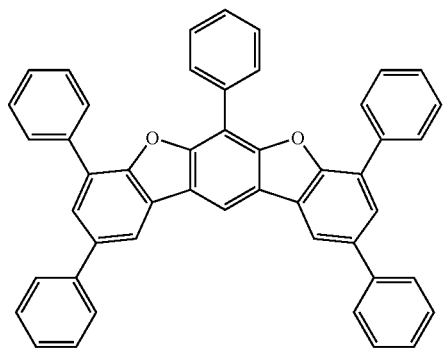
No. 362
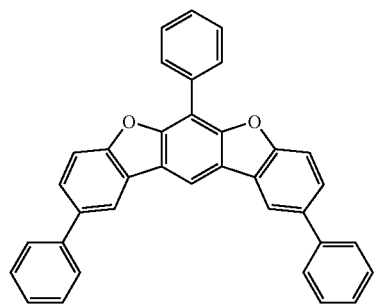
No. 363
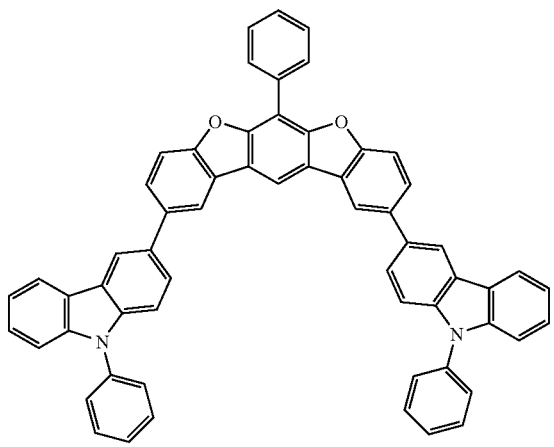

-continued
No. 364
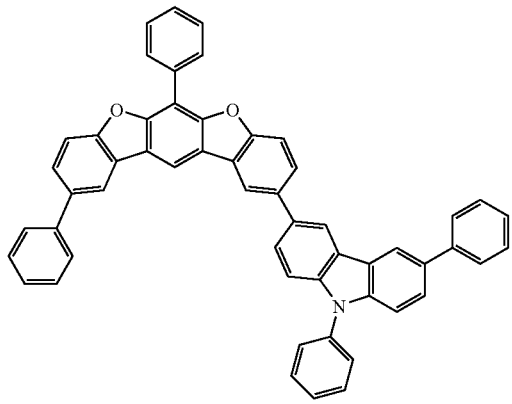
No. 365
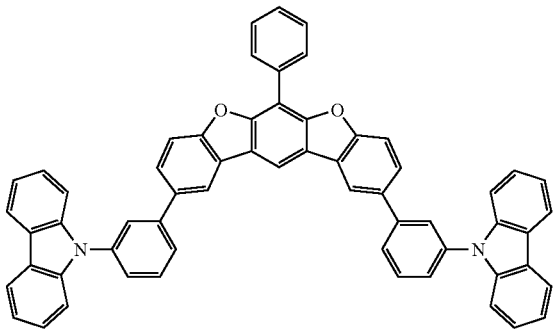
No. 366
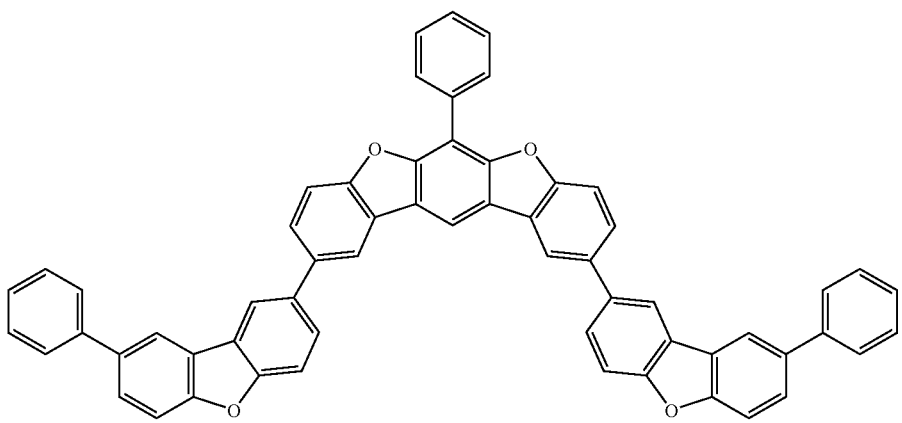
No. 367
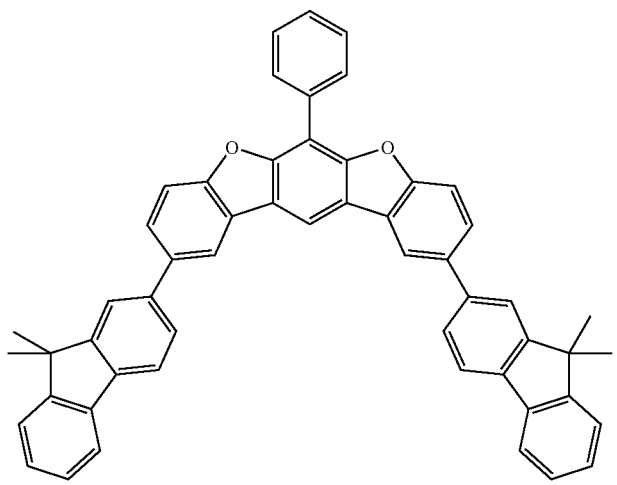

No. 368
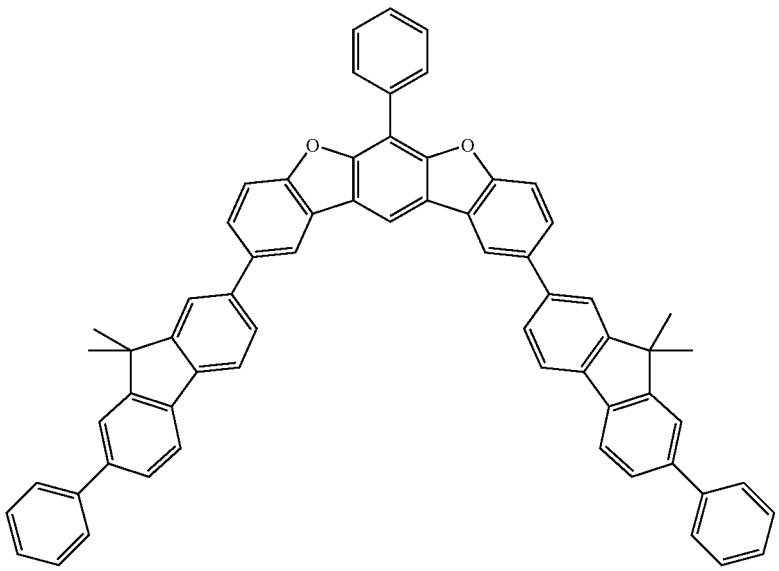
No. 369
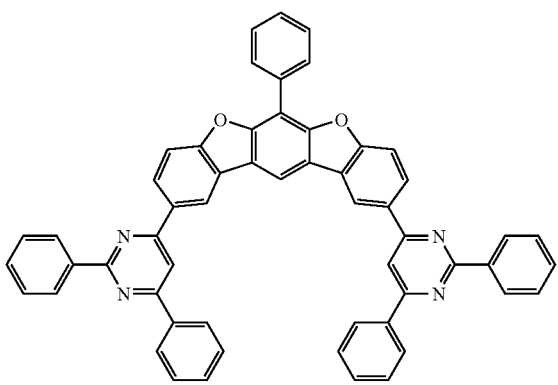
No. 370
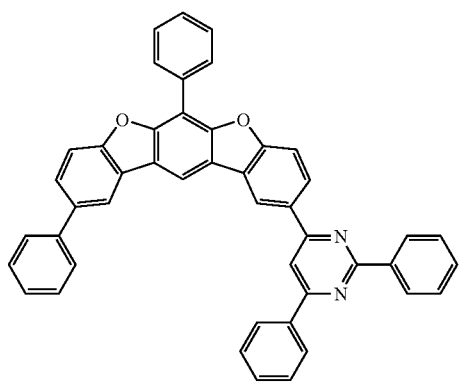
No. 371
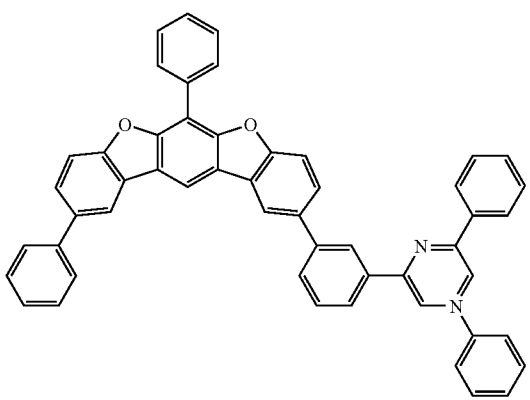
No. 372
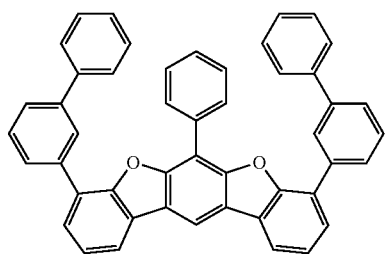
No. 373
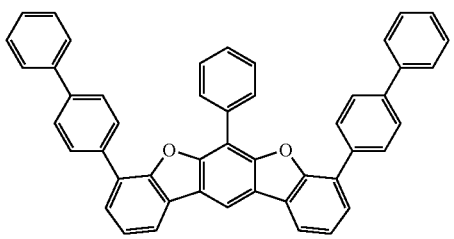
No. 374
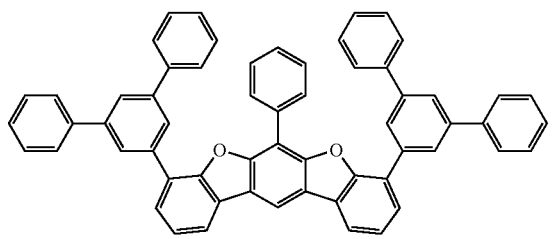

-continued
No. 375
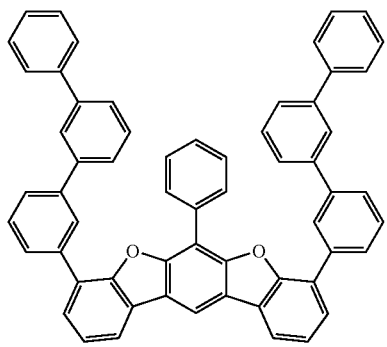
No. 376
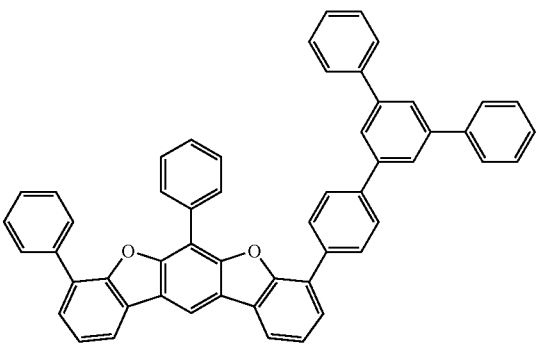
No. 377
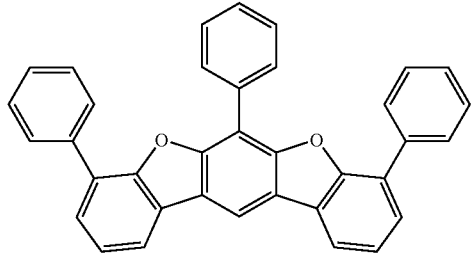
No. 378
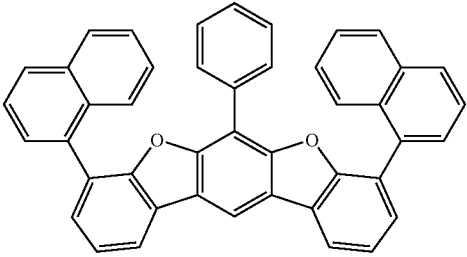
No. 379
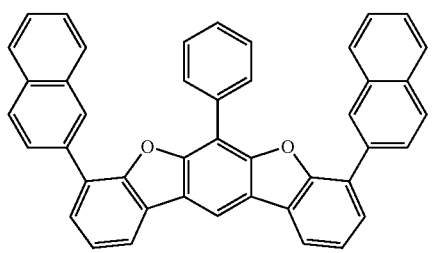
No. 380
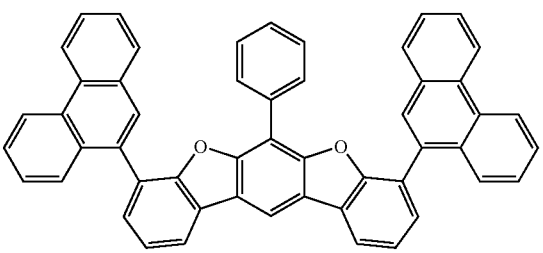
No. 381
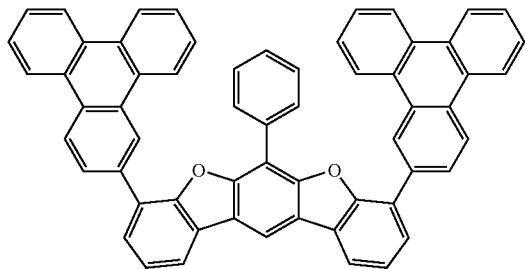
No. 382
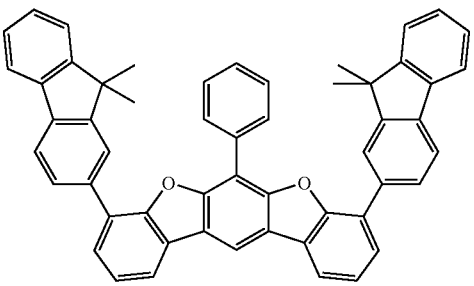
No. 383
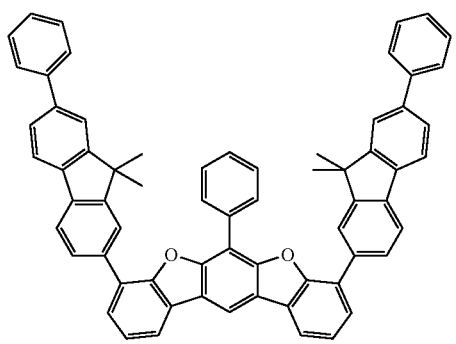
No. 384
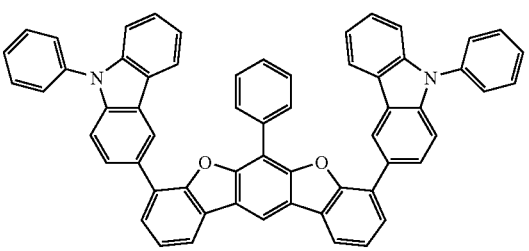

-continued
No. 385
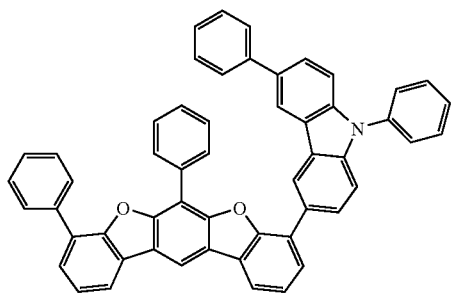
No. 386
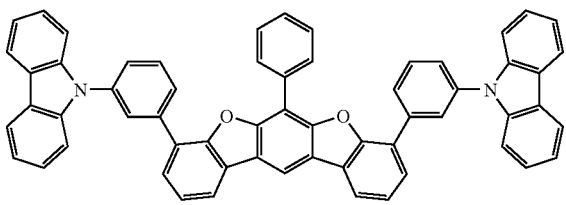
No. 387
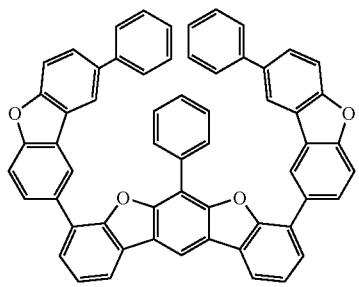
No. 388
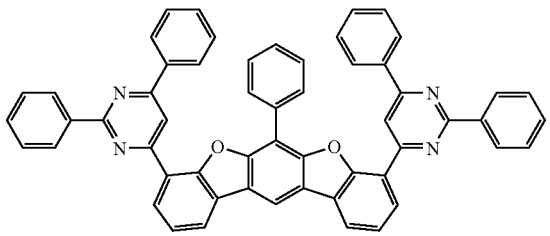
No. 389
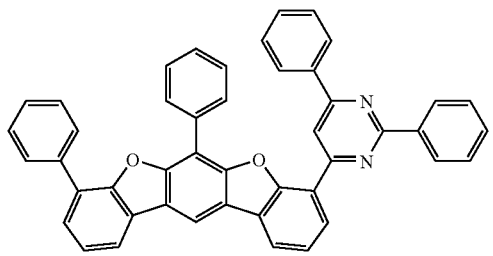
No. 390
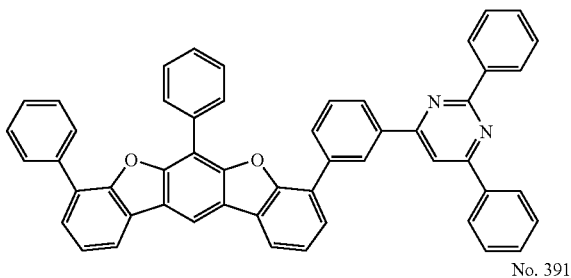
No. 391
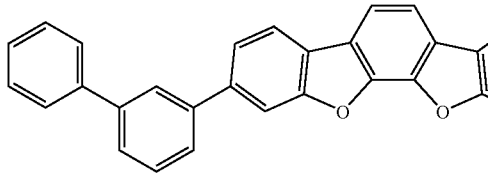
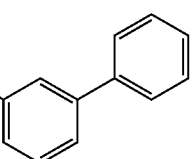
No. 392
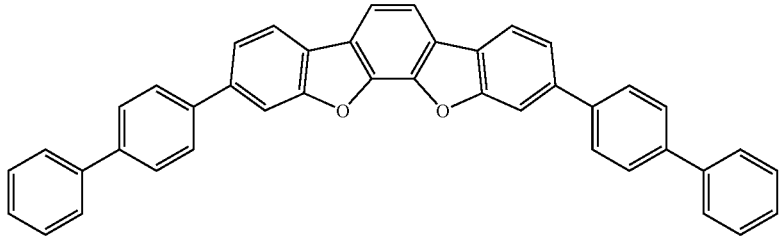
No. 393
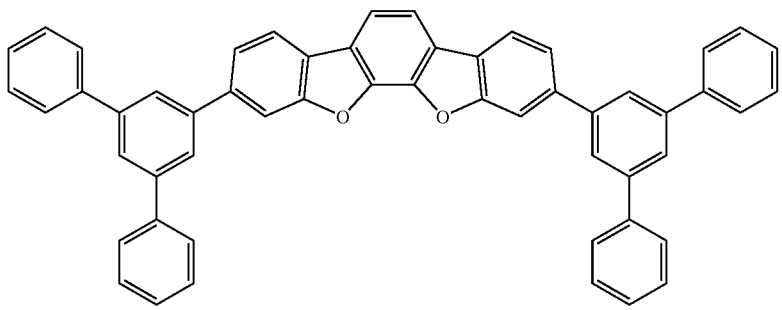

-continued
No. 394
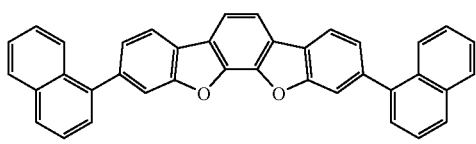
No. 395
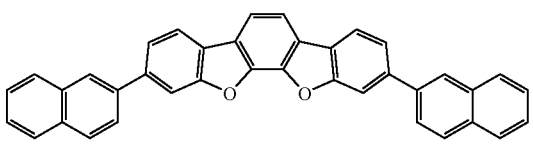
No. 396
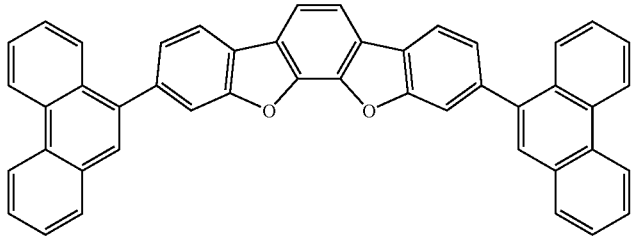
No. 397
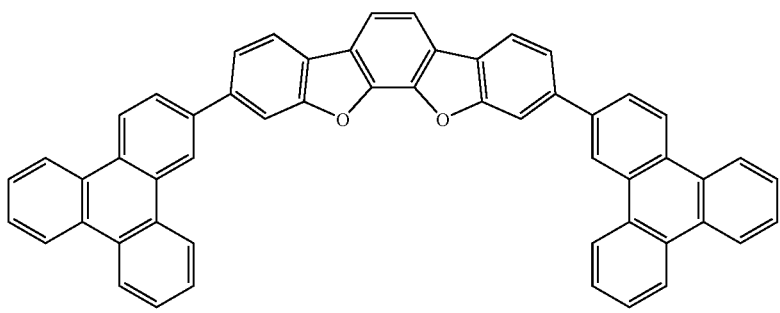
No. 398
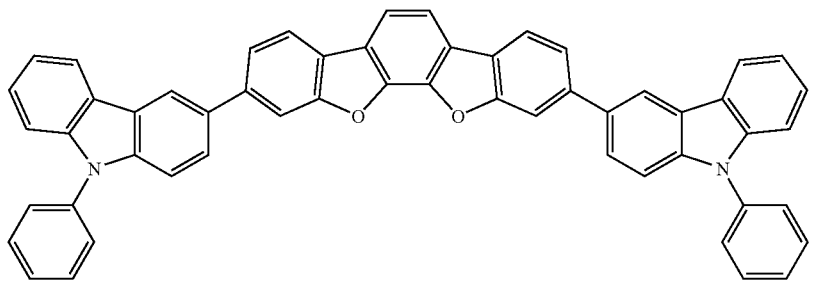
No. 399
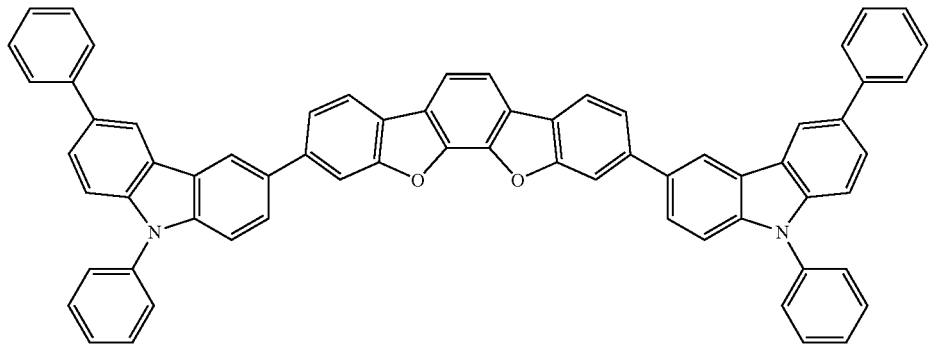

-continued
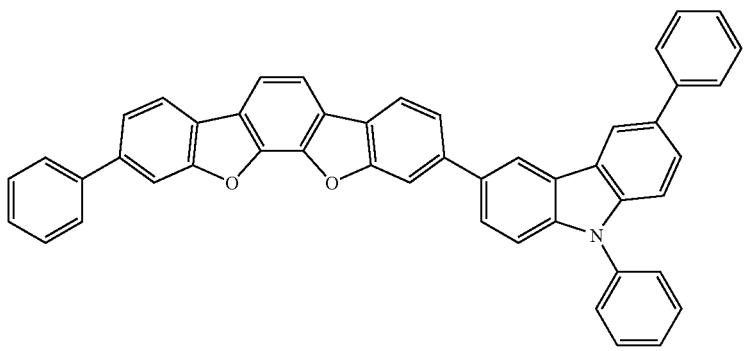
No. 400
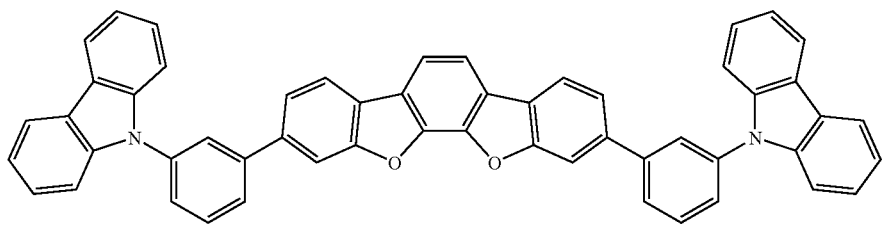
No. 401
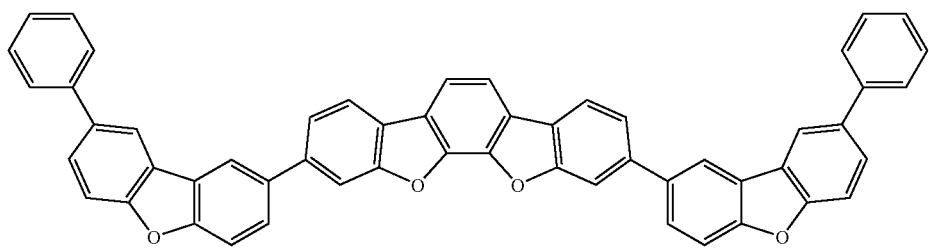
No. 402
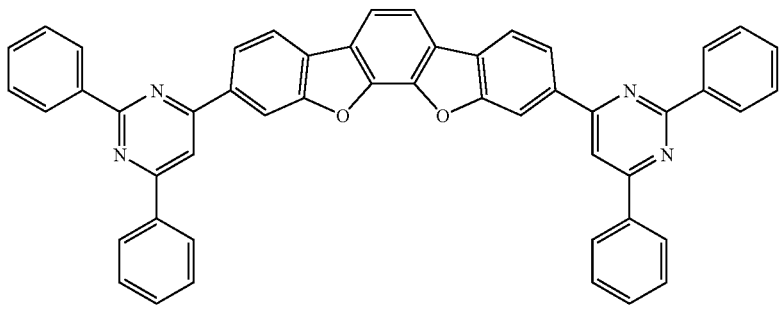
No. 403
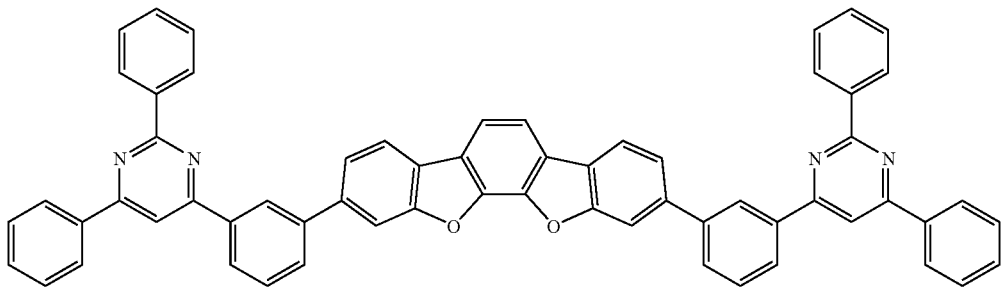
No. 404

-continued
No. 405
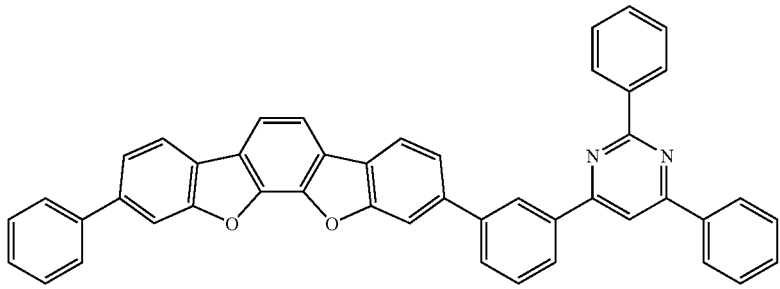
No. 406
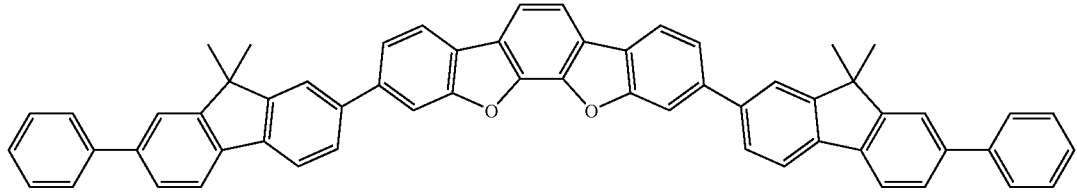
No. 407
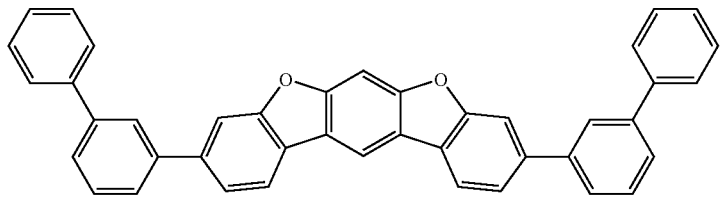
No. 408
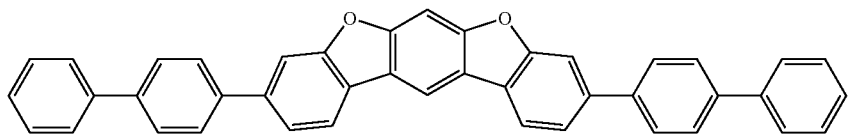
No. 409　　　　　　No. 410
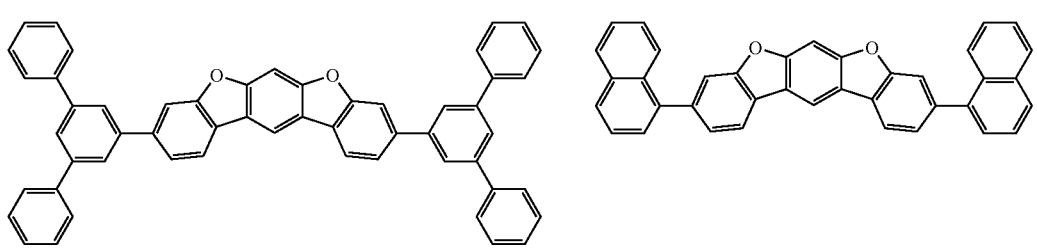
No. 411　　　　　　No. 412
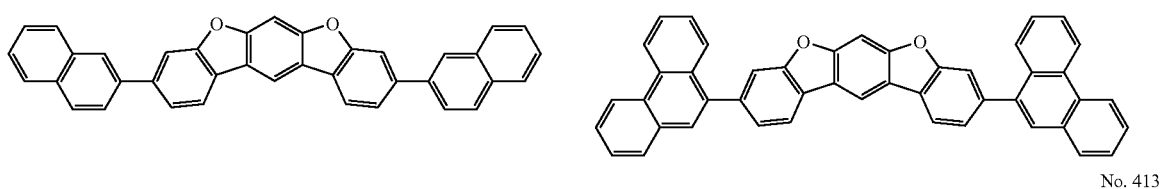
No. 413
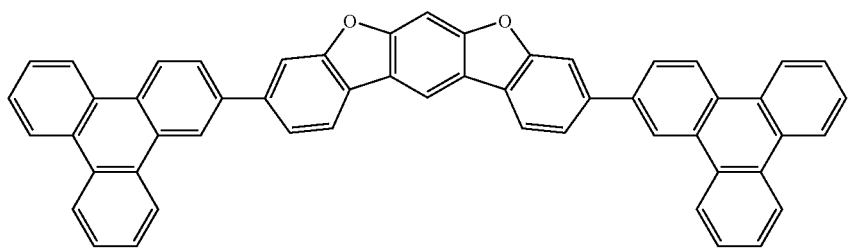

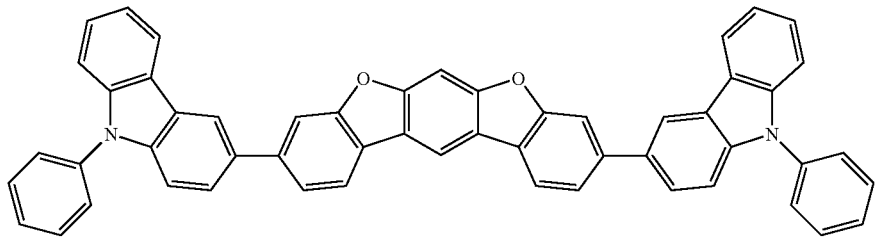
No. 414
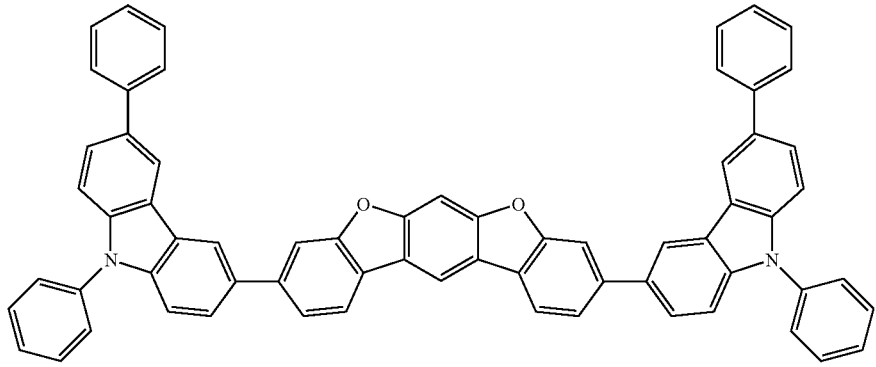
No. 415
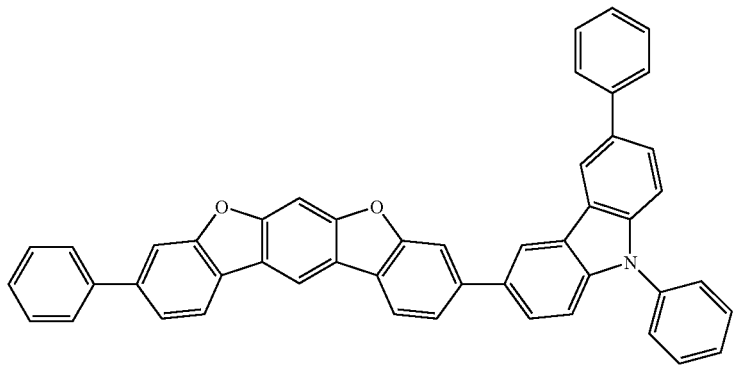
No. 416
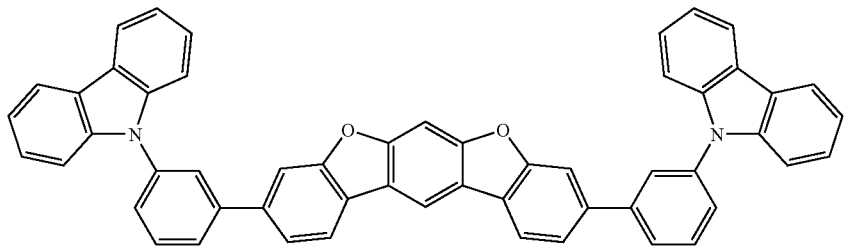
No. 417
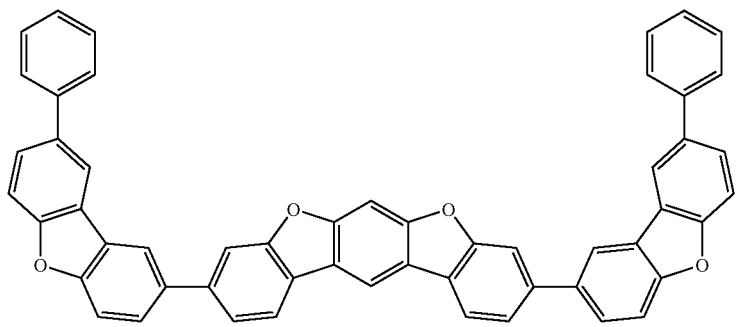
No. 418

No. 419
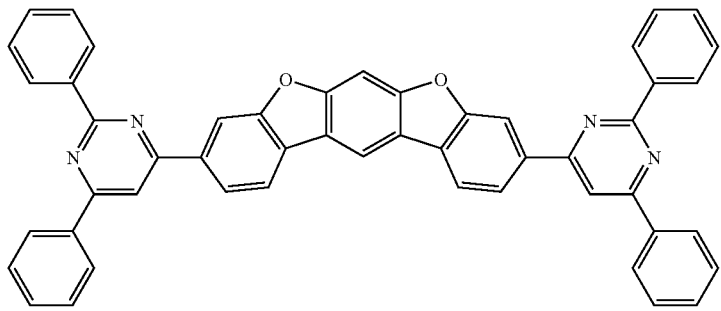
No. 420
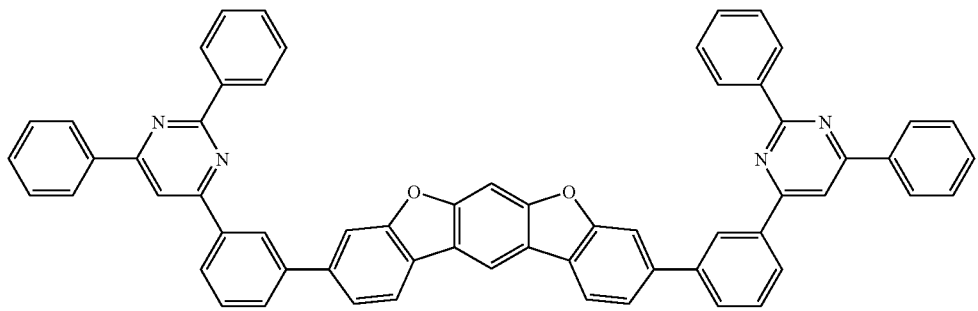
No. 421
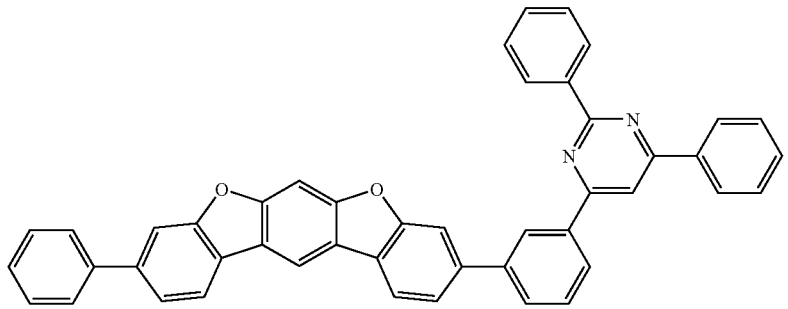
No. 422
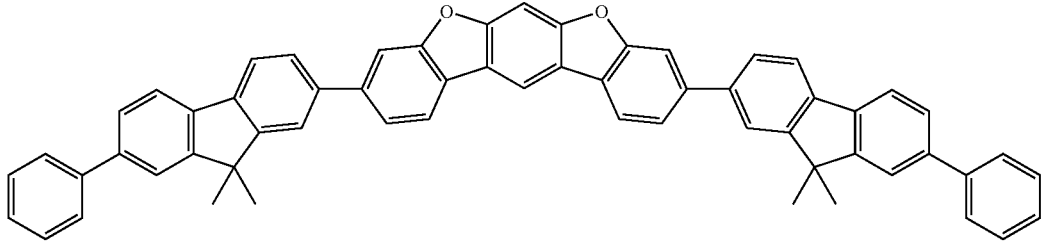
No. 423
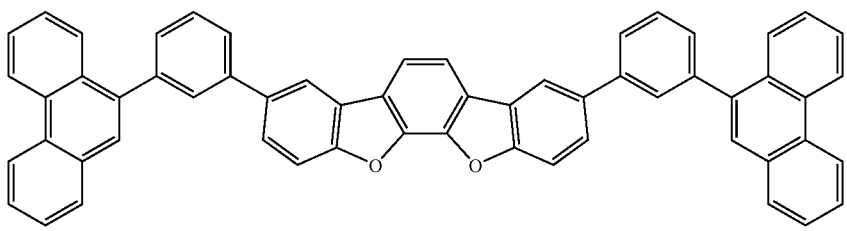
No. 424
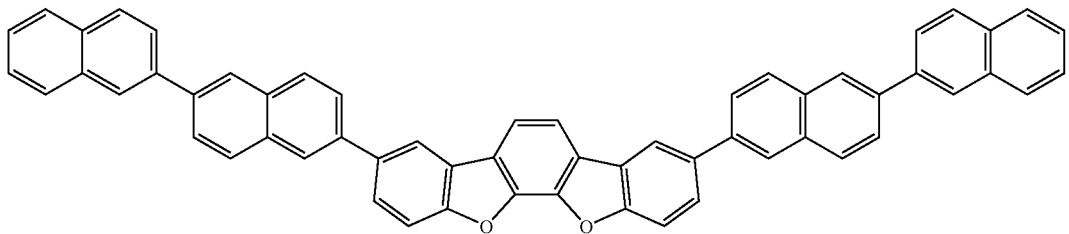

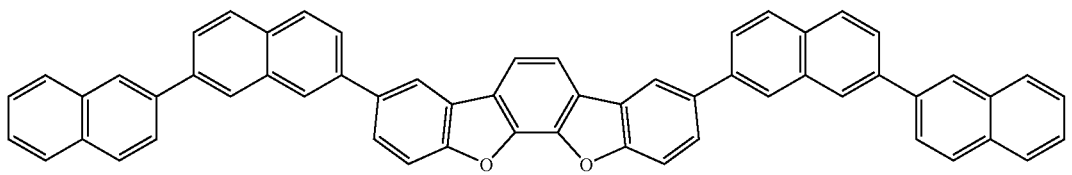
No. 425
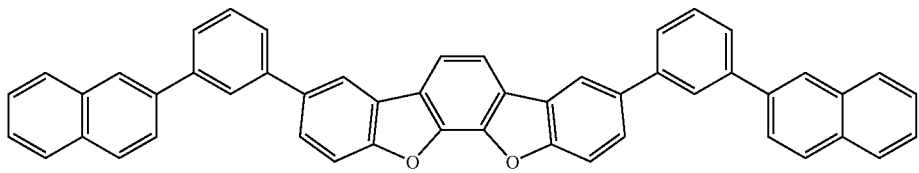
No. 426
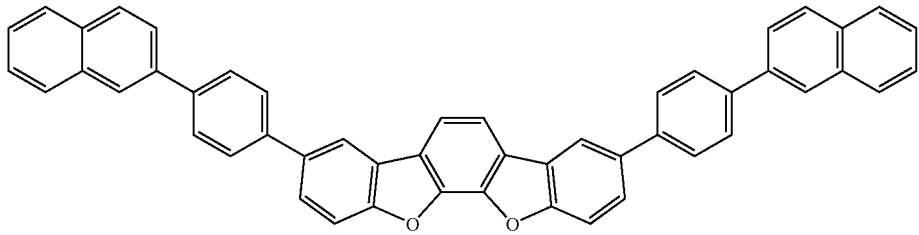
No. 427
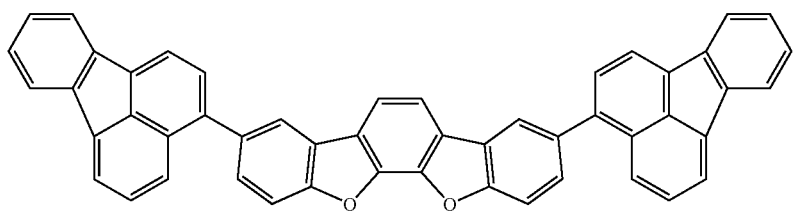
No. 428
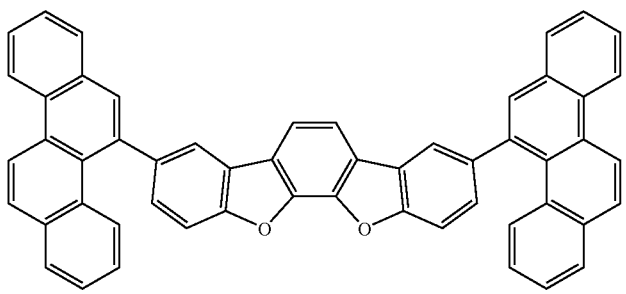
No. 429
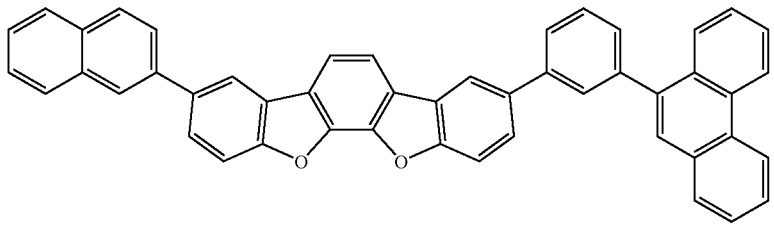
No. 430
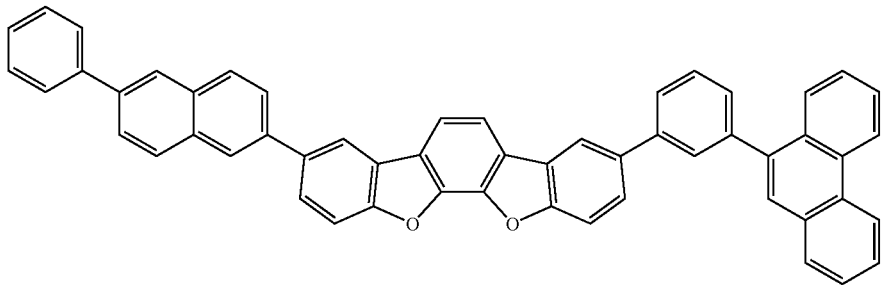
No. 431

-continued
No. 432
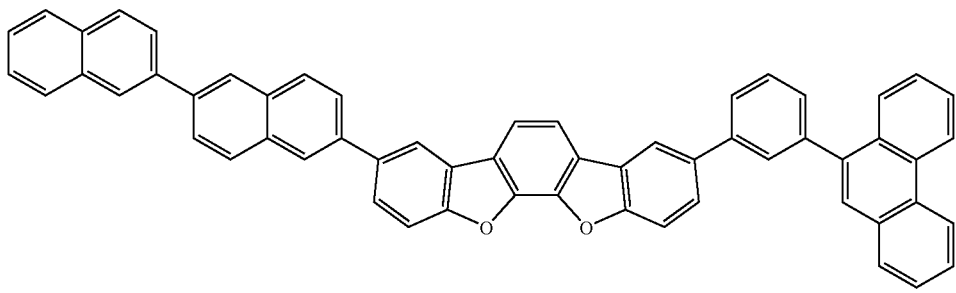
No. 433
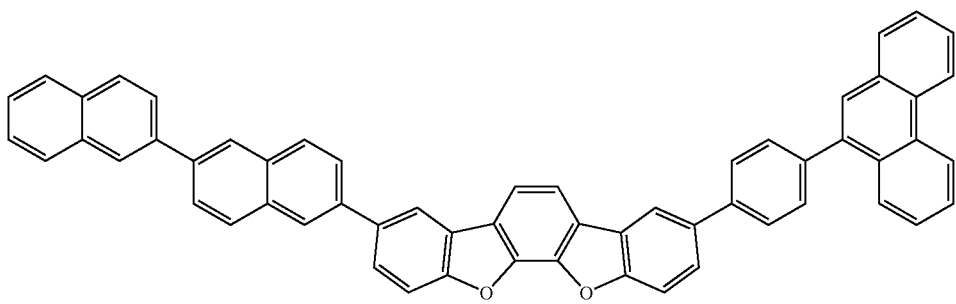
No. 434
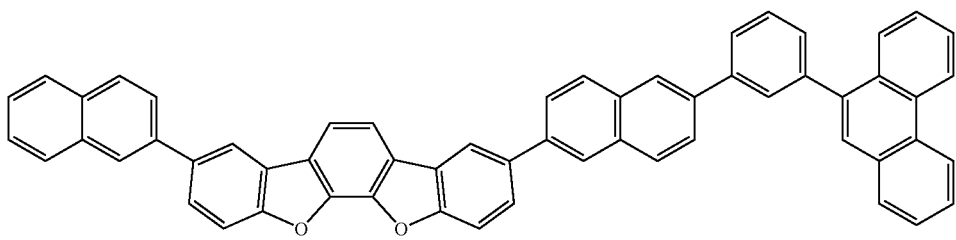
No. 435
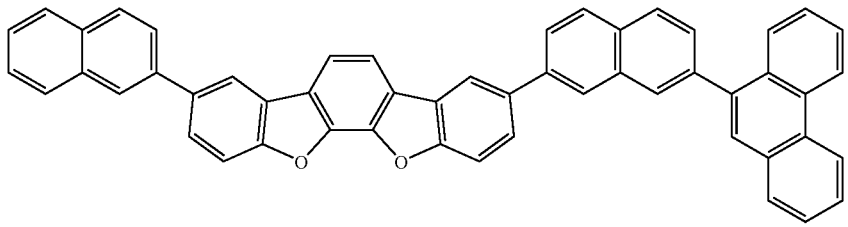
No. 436
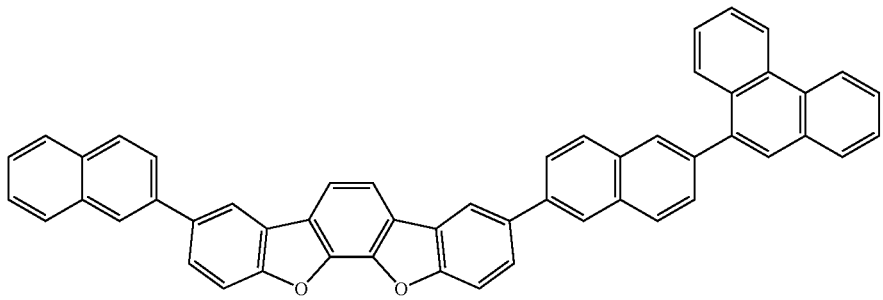

-continued
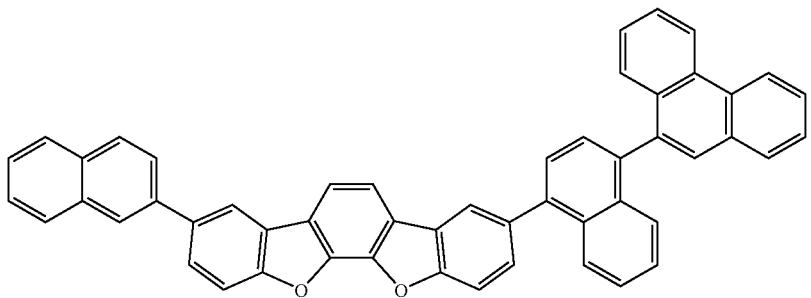
No. 437
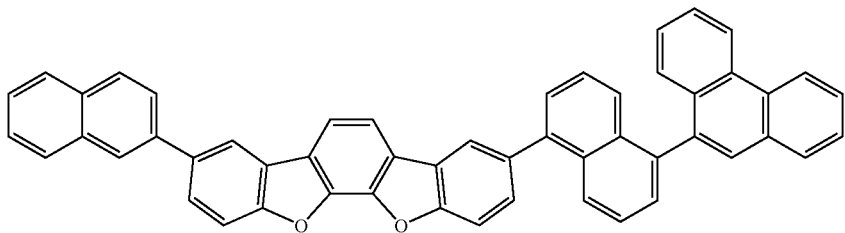
No. 438
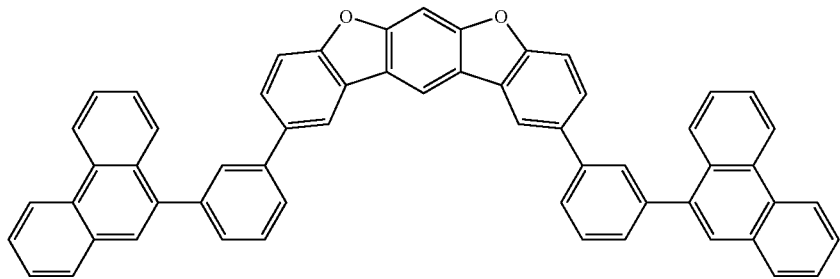
No. 439
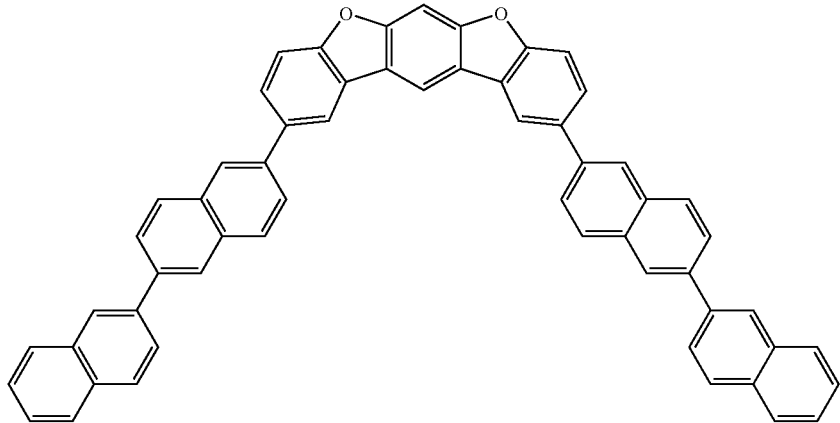
No. 440
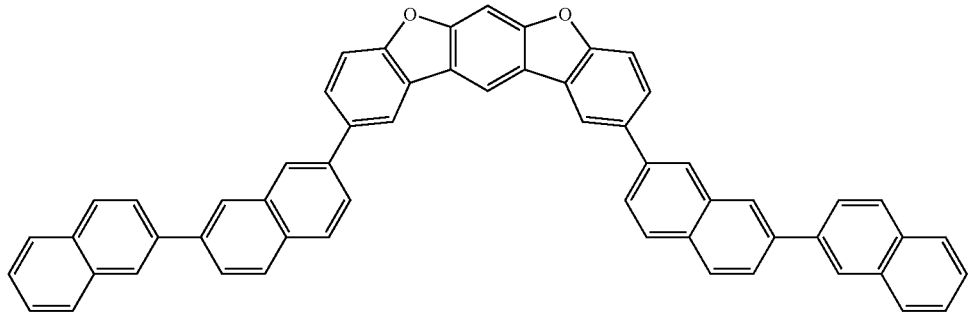
No. 441

-continued
No. 442
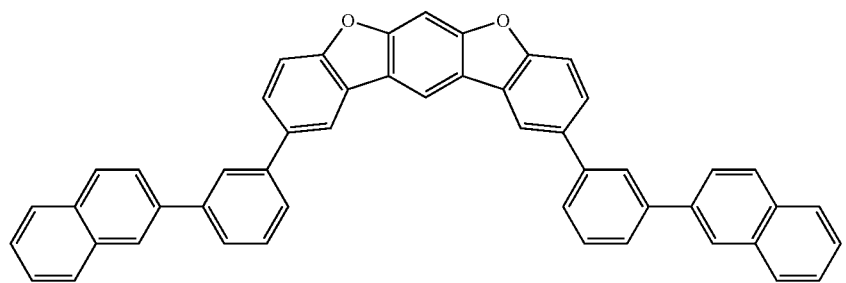
No. 443
No. 444
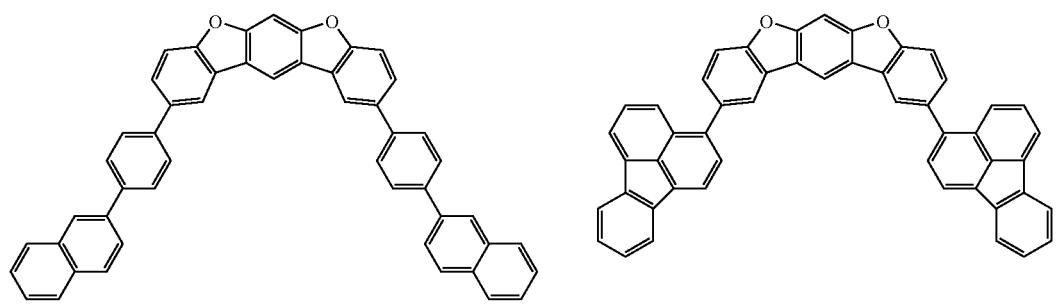
No. 445
No. 446
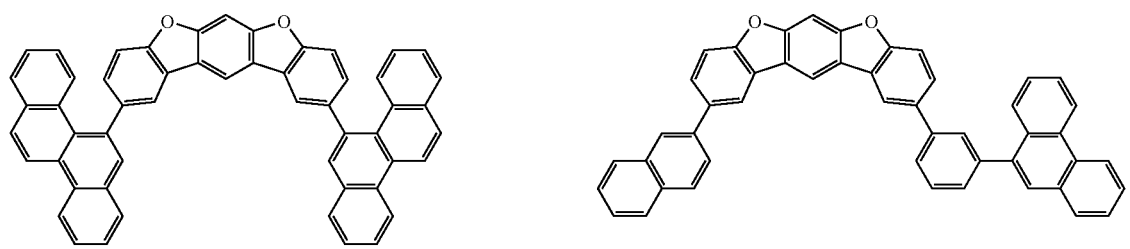
No. 447
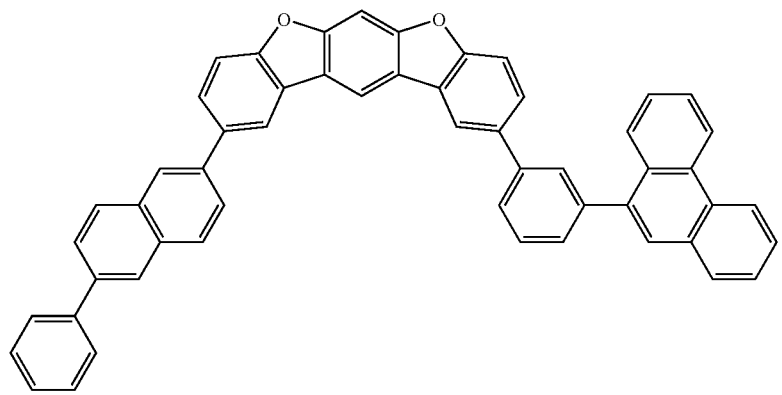

-continued
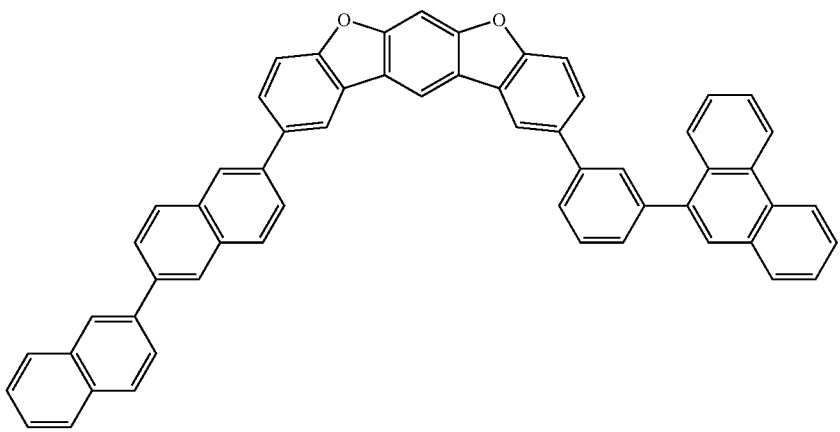
No. 448
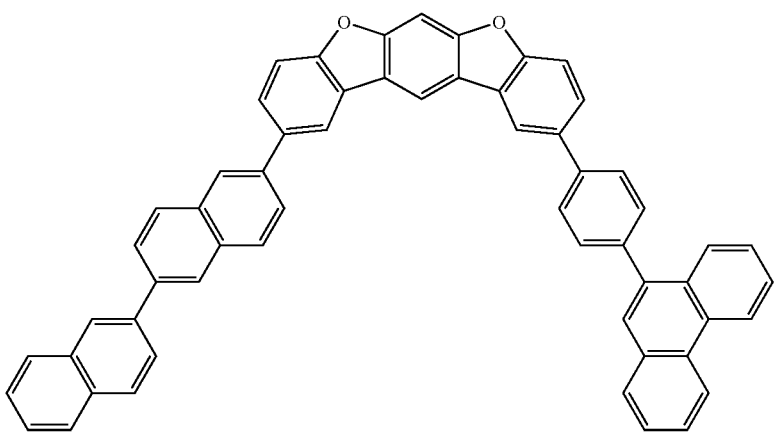
No. 449
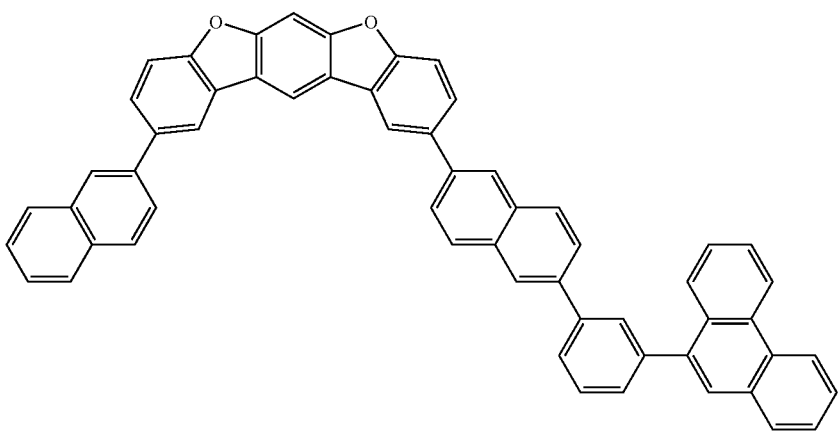
No. 450
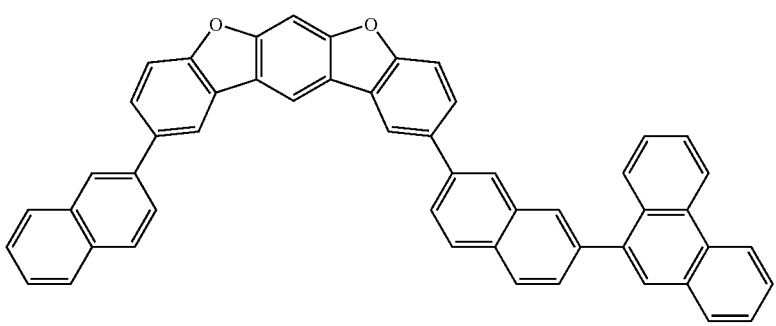
No. 451

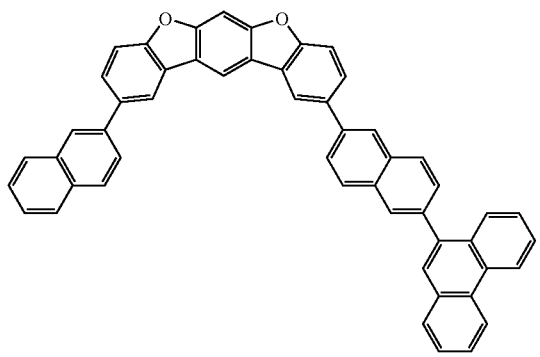

No. 452

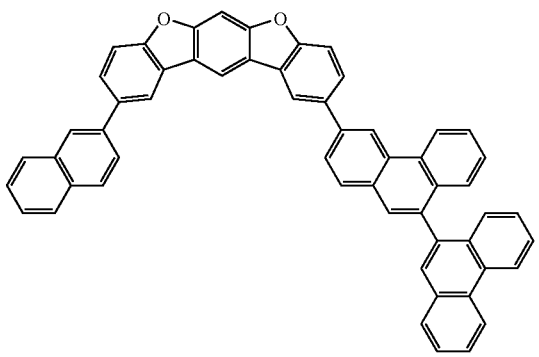

No. 453

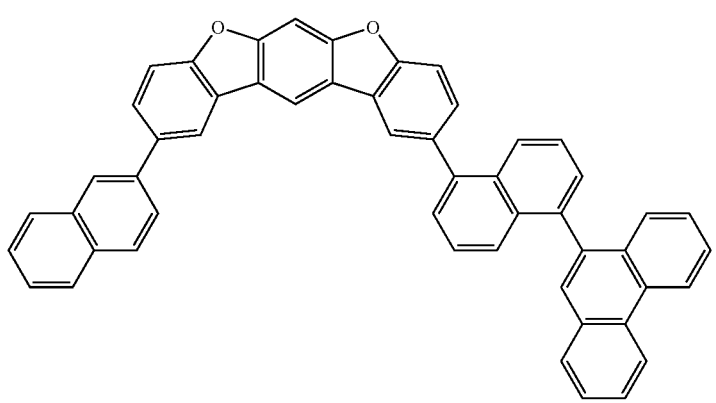

No. 454

A multi-layer type organic EL device is obtained by laminating multiple layers; for example, the device is formed of an anode, a hole transporting layer (a hole injecting layer), a light emitting layer, and a cathode, of an anode, a light emitting layer, an electron transporting layer (an electron injecting layer), and a cathode, of an anode, a hole transporting layer (a hole injecting layer), a light emitting layer, an electron transporting layer (an electron injecting layer), and a cathode, or of an anode, a hole transporting layer (a hole injecting layer), a light emitting layer, a hole barrier layer, an electron transporting layer (an electron injecting layer), and a cathode.

In the organic EL device of the present invention, the light emitting layer preferably contains the material for an organic EL device as a host material. In addition, it is preferred that the light emitting layer be composed of a host material and a phosphorescent material, and the host material be the material for an organic EL device.

In addition, the material for an organic EL device may be a host material to be used together with a phosphorescent material, or may be an electron transporting material to be used together with a phosphorescent material. The material has a triplet energy gap of preferably 2.2 to 3.2 eV, or more preferably 2.5 to 3.2 eV.

The phosphorescent material is preferably a compound containing iridium (Ir), osmium (Os), ruthenium (Ru), or platinum (Pt) because the compound has a high phosphorescent quantum yield, and can additionally improve the external quantum efficiency of the light emitting device. The material is more preferably a metal complex such as an iridium complex, an osmium complex, a ruthenium complex, or a platinum complex. Of those, the iridium complex and the platinum complex are still more preferable, and an orthometalated iridium complex is most preferable. Specific examples of the metal complex such as an iridium complex, an osmium complex, a ruthenium complex, or a platinum complex are shown below.

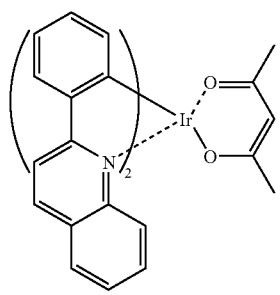

PQIr

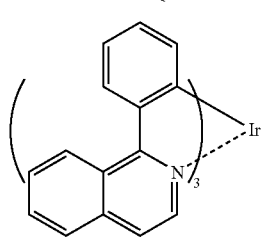

181
-continued
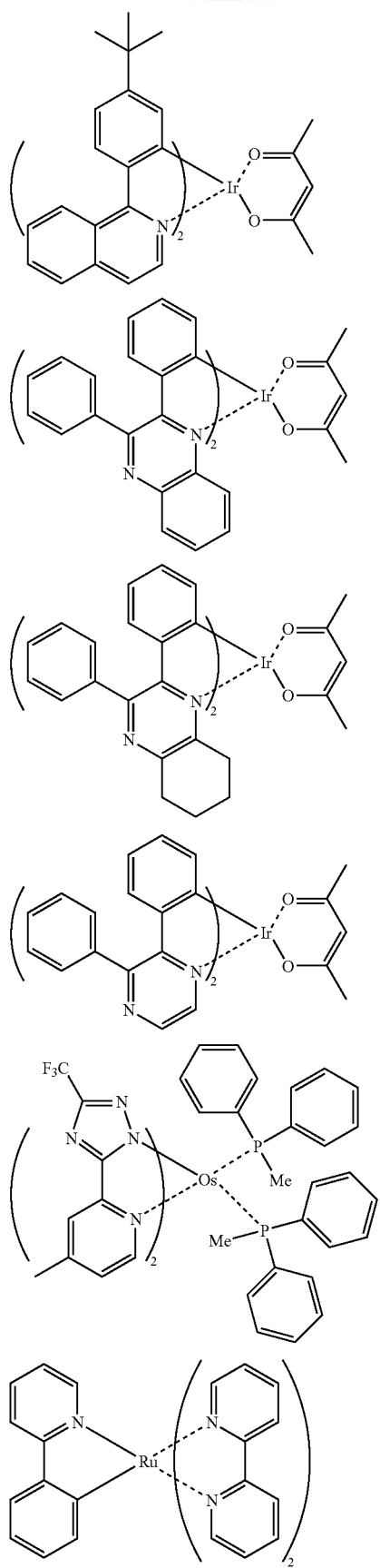
182
-continued
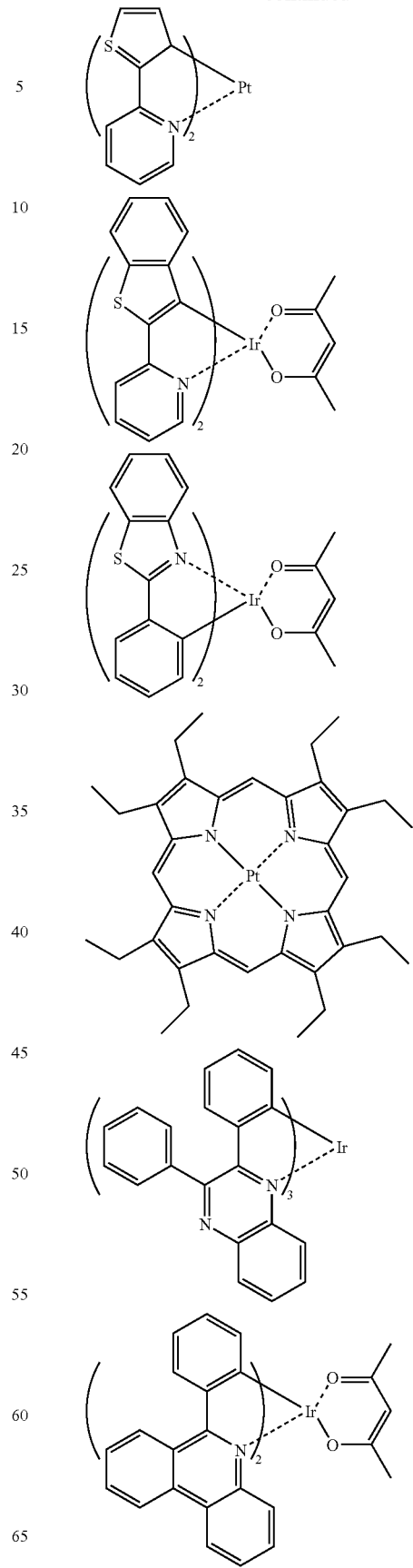

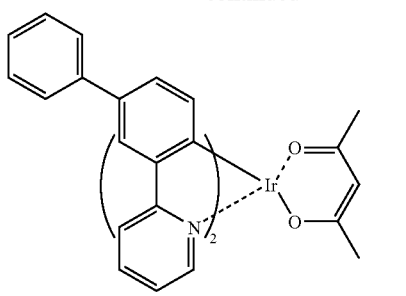
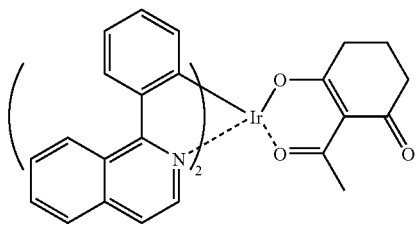
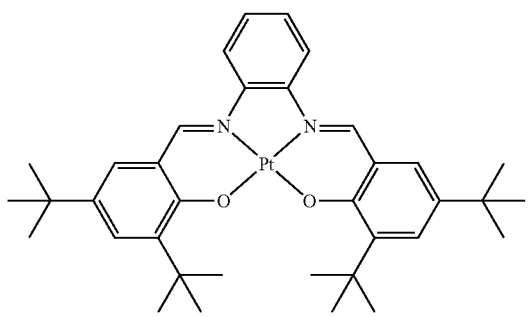
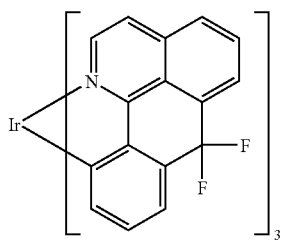
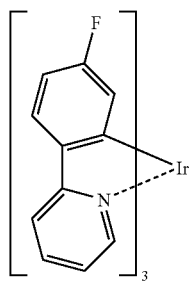
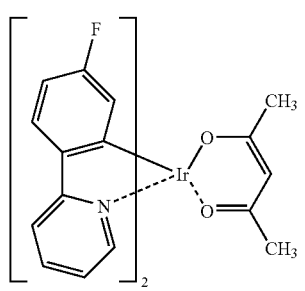
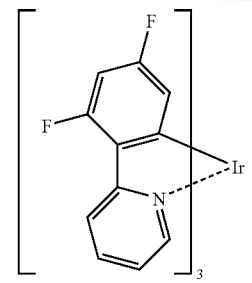
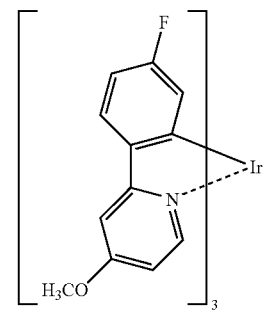
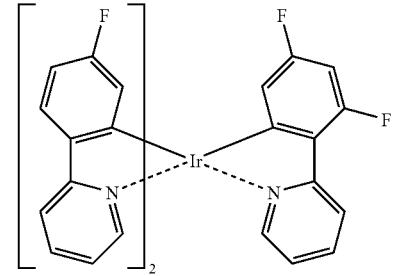
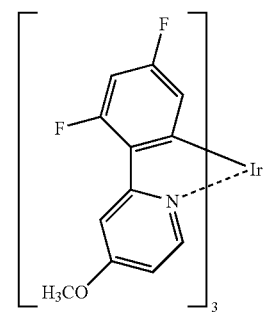
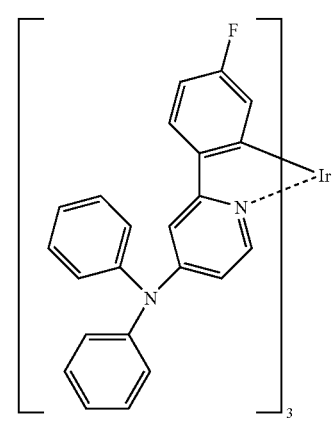

-continued
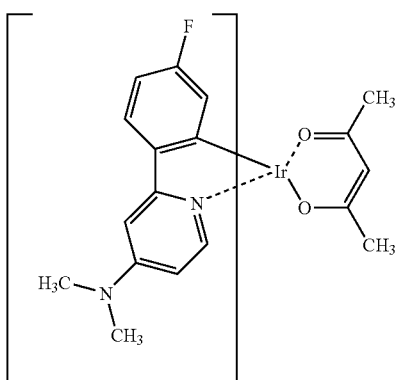
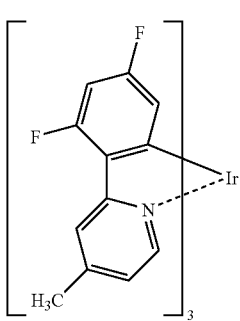
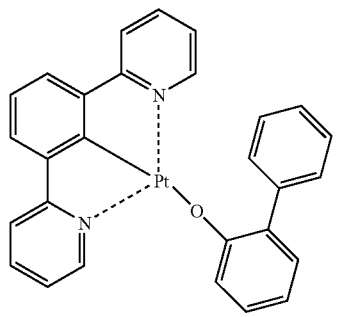
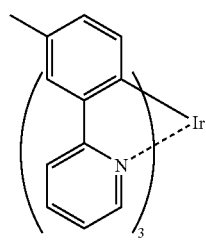
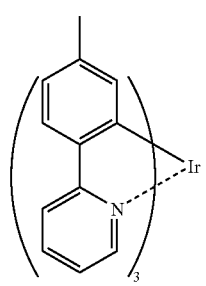
-continued
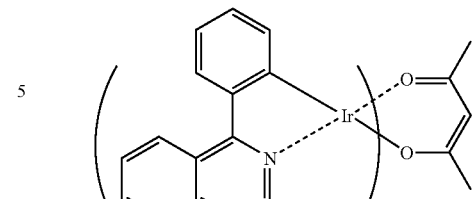
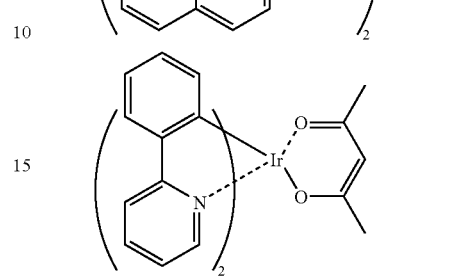
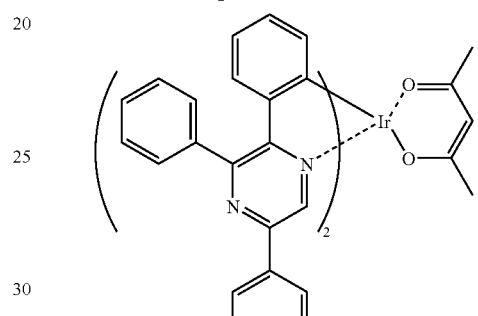
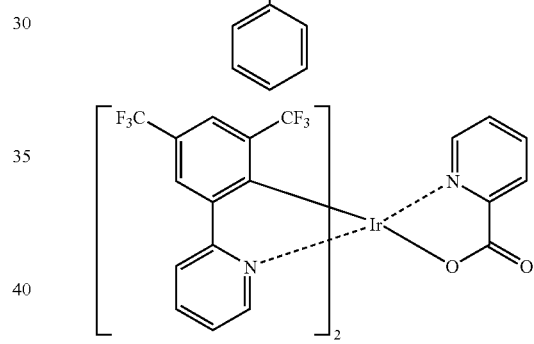
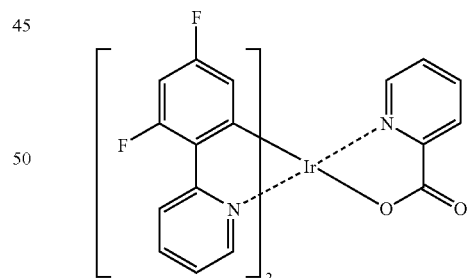
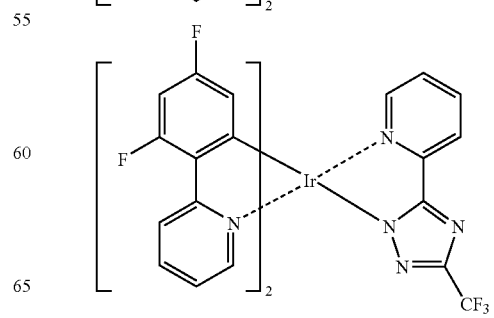

187
-continued
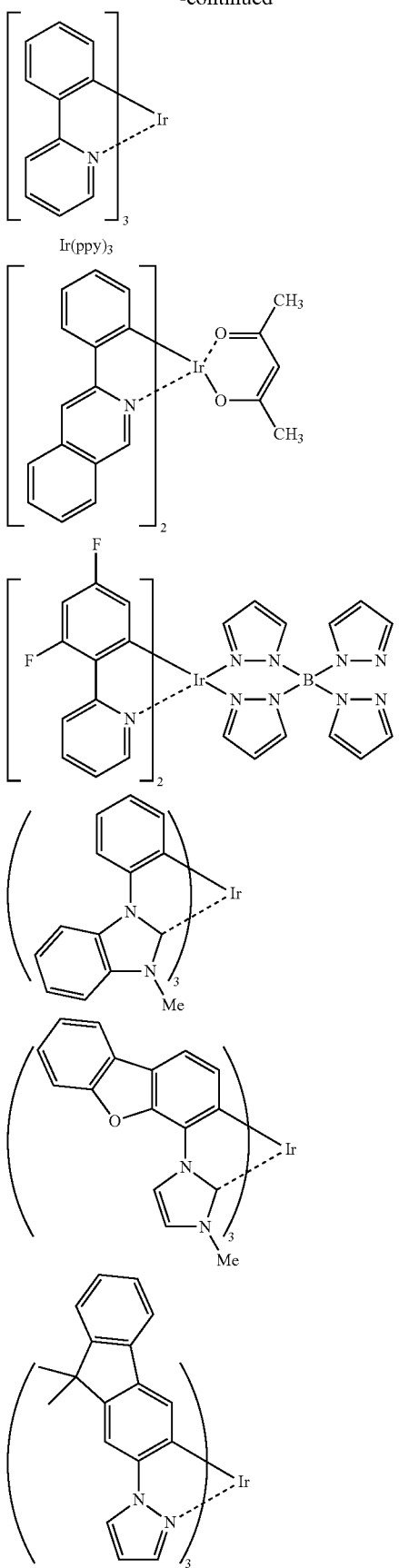
Ir(ppy)₃
188
-continued
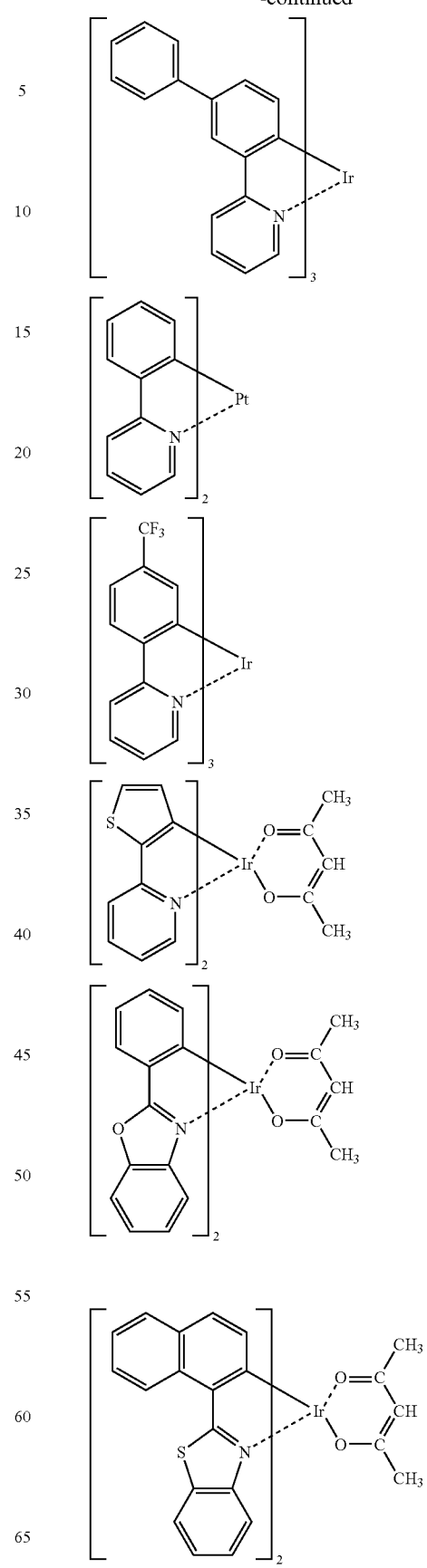

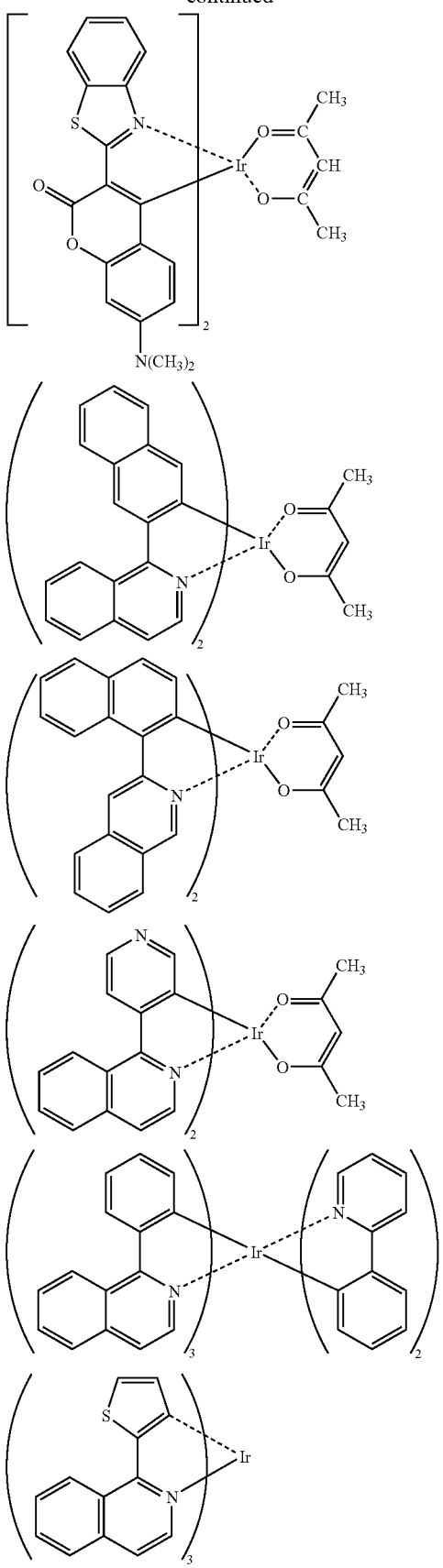

In addition, the organic EL device of the present invention is preferably such that the light emitting layer contains a host material and a phosphorescent material, and contains a metal complex having a local maximum luminous wavelength of 500 nm or less. Further, the material of the present invention can be used together with a fluorescent dopant. The material can be used together with a blue, green, or red fluorescent dopant. In particular, the material can be more preferably used together with the blue or green fluorescent dopant. Further, the material can be preferably used also as an electron transporting material for a fluorescent organic EL device.

The organic EL device of the present invention preferably has a reductive dopant in an interfacial region between the cathode and an organic thin layer (for example, an electron injecting layer or a light emitting layer). Examples of the reductive dopant include at least one kind selected from an alkali metal, an alkali metal complex, an alkali metal compound, an alkaline earth metal, an alkaline earth metal complex, an alkaline earth metal compound, a rare earth metal, a rare earth metal complex, and a rare earth metal compound.

Preferred examples of the alkali metal include an alkali metal having a work function of 2.9 eV or less, such as Na having a work function of 2.36 eV, K having a work function of 2.28 eV, Rb having a work function of 2.16 eV, and Cs having a work function of 1.95 eV. Of those, K, Rb, and Cs are more preferable, Rb or Cs is still more preferable, and Cs is most preferable.

Preferred examples of the alkali earth metal include an alkali earth metal having a work function of 2.9 eV or less, such as Ca having a work function of 2.9 eV, Sr having a work function of 2.0 to 2.5 eV, and Ba having a work function of 2.52 eV.

Preferred examples of the rare earth metal include a rare earth metal having a work function of 2.9 eV or less, such as Sc, Y, Ce, Tb, and Yb.

Of those metals, a preferable metal has a particularly high reductive ability, so improvement of light emission intensity and long life of organic EL device can be attained by adding a relatively small amount of the metal to an electron injecting region.

Examples of the alkali metal compound include an alkali oxide such as $Li_2O$, $Cs_2O$, or $K_2O$, and an alkali halide such as LiF, NaF, CsF, or KF. Of those, LiF, $Li_2O$, or NaF is preferable.

Examples of the alkali earth metal compound include BaO, SrO, CaO, and mixtures thereof such as $Ba_mSr_{1-m}O$ (0<m<1) and $Ba_mCa_{1-m}O$ (0<m<1) Of those, BaO, SrO, and CaO are preferable.

Examples of the rare earth metal compound include $YbF_3$, $ScF_3$, $ScO_3$, $Y_2O_3$, $Ce_2O_3$, $GdF_3$, and $TbF_3$. Of those, $YbF_3$, $ScF_3$, and $TbF_3$ are preferable.

The alkali metal complex, alkali earth metal complex, and rare metal complex are not particularly limited as long as they each include as a metal ion at least one of alkali metal ions, alkali earth metal ions, and rare earth metal ions. Meanwhile, preferable examples of a ligand include, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzoimidazole, hydroxybenzotriazole, hydroxyfluborane, bipyridyl, phenanthroline, phthalocyanine, porphyrin, cyclopentadiene, β-diketones, azomethines, and derivatives thereof.

For the addition form of the reductive dopant, it is preferable that the reductive dopant be formed in a shape of a layer or an island in the interfacial region. A preferable example of the forming method includes a method in which an organic substance which is a light emitting material or an electron injecting material for forming the interfacial region is deposited at the same time as the reductive dopant is deposited by a resistant heating deposition method, thereby dispersing the reductive dopant in the organic substance. The disperse concentration by molar ratio of the organic compound to the reductive dopant is 100:1 to 1:100, and is preferably 5:1 to 1:5.

In a case where the reductive dopant is formed into the shape of a layer, the light emitting material or electron injecting material which serves as an organic layer in the interface is formed into the shape of a layer. After that, the reductive dopant is solely deposited by the resistant heating deposition method to form a layer preferably having a thickness of 0.1 to 15 nm.

In a case where the reductive dopant is formed into the shape of an island, the light emitting material or electron injecting material which serves as an organic layer in the interface is formed into the shape of an island. After that, the reductive dopant is solely deposited by the resistant heating deposition method to form an island preferably having a thickness of 0.05 to 1 nm.

When the organic EL device of the present invention has an electron injecting layer between the light emitting layer and the cathode, an electron transporting material to be used in the electron injecting layer is preferably an aromatic heterocyclic compound containing one or more heteroatoms in any one of its molecules, or particularly preferably a nitrogen-containing ring derivative.

The nitrogen-containing ring derivative is preferably, for example, a nitrogen-containing ring metal chelate complex represented by the following general formula (A).

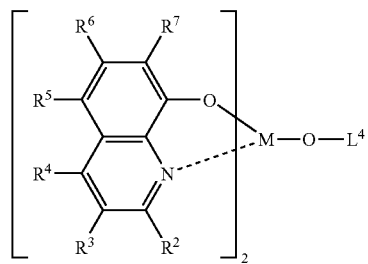

(A)

$R^2$ to $R^7$ each independently represent a hydrogen atom, a halogen atom, an amino group, a hydrocarbon group each having 1 to 40 carbon atoms, an alkoxy group, an aryloxy group, an alkoxycarbonyl group, or a heterocyclic group, each of which may be substituted.

Examples of the halogen atom represented by $R^2$ to $R^7$ include a fluorine atom, a chlorine atom, a bromine atom, and an iodine atom.

Examples of the amino group that may be substituted and represented by $R^2$ to $R^7$ include an alkylamino group, an arylamino group, and an aralkylamino group. Examples of the alkyl group in the alkylamino group include alkyl groups each having 1 to 40 carbon atoms such as a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an neopentyl group, a 1-methylpentyl group, a 2-methylpentyl group, a 1-pentylhexyl group, a 1-butylpentyl group, a 1-heptyloctyl group, a 3-methylpentyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, a iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, 1,3-dicyanoisopropyl group, a 2,3-dicyano-t-butyl group, a 1,2,3-tricyanopropyl group, a nitromethyl group, a 1-nitroethyl group, a 2-nitroethyl group, a 1,2-dinitroethyl group, a 2,3-dinitro-t-butyl group, and a 1,2,3-trinitropropyl group. Preferred are alkyl groups each having 1 to 20 carbon atoms and more preferred are alkyl groups each having 1 to 10 carbon atoms.

Examples of the aryl group in the arylamino group include aryl groups each having a ring formed of 6 to 40 carbon atoms such as a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, a an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, and a 4"-t-butyl-p-terphenyl-4-yl group. Preferred are aryl groups each having a ring formed of 6 to 20 carbon atoms and more preferred are aryl groups each having a ring formed of 6 to 10 carbon atoms.

Examples of the aralkyl group in the aralkylamino group include aralkyl groups each having 7 to 40 carbon atoms such as a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, 2-(1-pyrrolyl)ethyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenylisopropyl group, and a 1-chloro-2-phenylisopropyl group. Preferred are aralkyl groups each having 7 to 20 carbon atoms and more preferred are aralkyl groups each having 7 to 10 carbon atoms.

Examples of the hydrocarbon groups each having 1 to 40 carbon atoms represented by $R^2$ to $R^7$ include substituted or unsubstituted alkyl groups, alkenyl groups, cycloalkyl groups, aryl groups, and aralkyl groups.

As the alkyl groups, the same examples of the alkyl groups in the above-mentioned alkylamino group are given, and alkyl groups each having 1 to 20 carbon atoms are preferred and alkyl groups each having 1 to 10 carbon atoms are more preferred.

Examples of the alkenyl group include alkenyl groups each having 2 to 40 carbon atoms such as a vinyl group, an allyl group, a 1-butenyl group, a 2-butenyl group, a 3-butenyl group, a 1,3-butanedienyl group, a 1-methylvinyl group, a styryl group, a 2,2-diphenylvinyl group, a 1,2-diphenylvinyl group, a 1-methylaryl group, a 1,1-dimethylaryl group, a 2-methylallyl group, a 1-phenylallyl group, a 2-phenylallyl group, a 3-phenylallyl group, a 3,3-diphenylallyl group, a 1,2-dimethylallyl group, a 1-phenyl-1-butenyl group, and a 3-phenyl-1-butenyl group. Preferred are alkenyl groups each having 2 to 20 carbon atoms and more preferred are alkenyl groups each having 2 to 10 carbon atoms.

Examples of the cycloalkyl groups include cycloalkyl groups each having a ring formed of 3 to 40 carbon atoms such as a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group. Preferred are cycloalkyl groups each having a ring formed of 3 to 10 carbon atoms are preferred.

As the aryl groups, the same examples of the aryl groups in the above-mentioned arylamino groups are given. Preferred are aryl groups each having a ring formed of 6 to 20 carbon atoms and more preferred are aryl groups each having a ring formed of 6 to 10 carbon atoms.

As the aralkyl groups, the same examples of the aralkyl groups in the above-mentioned aralkylamino groups are given. Preferred are aralkyl groups each having 7 to 20 carbon atoms and more preferred are aralkyl groups each having 7 to 10 carbon atoms.

As the alkoxy group that represented by $R^2$ to $R^7$ and may be substituted, the same examples of the alkyl groups in the above-mentioned alkylamino groups are given as alkyl group moieties. Preferred are alkoxy groups each having 1 to 20 carbon atoms and more preferred alkoxy groups having 1 to 10 carbon atoms.

As the aryloxy group that represented by $R^2$ to $R^7$ and may be substituted, aryl oxy groups each having the same aryl group in the above-mentioned alkylamino group as an aryl group moiety are given. Preferred are aryl groups each having a ring formed of 6 to 20 carbon atoms and more preferred are aryl groups each having a ring formed of 6 to 10 carbon atoms.

As the alkoxycarbonyl group that represented by $R^2$ to $R^7$ and may be substituted, alkoxycarbonyl groups each having the same alkyl group in the above-mentioned alkylamino group as the alkyl group moiety are given. Preferred are alkoxycarbonyl groups each having 2 to 20 carbon atoms and more preferred are alkoxycarbonyl groups each having 2 to 10 carbon atoms.

The heterocyclic group that represented by $R^2$ to $R^7$ and may be substituted is a monocycle or a fused ring. The heterocyclic group preferably has a ring formed of 1 to 20 carbon atoms, more preferably has a ring formed of 1 to 12 carbon atoms, and still more preferably has a ring formed of 2 to 10 carbon atoms. The heterocyclic group is an aromatic heterocyclic group having at least one hetero atom selected form a nitrogen atom, an oxygen atom, a sulfur atom, and selenium atom. Examples of the heterocyclic group include groups derived from pyrrolidine, piperidine, piperazine, morpholine, thiophene, selenophene, furan, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phanazine, tetrazole, benzoimidazole, benzoxazole, benzothiazole, benzotriazole, tetrazaindene, carbazole, and azepine. Preferred are groups derived from furan, thiophene, pyridine, pyrazine, pyrimidine, pyridazine, triazine, quinoline, phthalazine, naphthyridine, quinoxaline, and quinazoline, more preferred are groups derived from furan, thiophene, pyridine, and quinoline, and still more preferred is a quinolinyl group.

M represents aluminum (Al), gallium (Ga), or indium (In). Indium is preferred.

$L^4$ in the formula (A) is a group represented by the following formula (A') or (A").

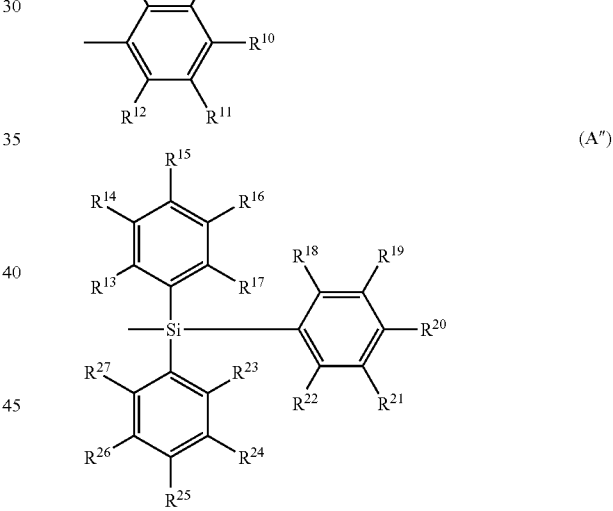

(In the formula, $R^8$ to $R^{12}$ each independently represent a hydrogen atom, or a substituted or unsubstituted hydrocarbon atoms having 1 to 40 carbon atoms, and adjacent groups may form a cyclic structure. In addition, $R^{13}$ to $R^{27}$ each independently represent a hydrogen atom, or a substituted or unsubstituted hydrocarbon group having 1 to 40 carbon atoms, and adjacent groups may form a cyclic structure.

As the hydrocarbon group having 1 to 40 carbon atoms represented by $R^8$ to $R^{12}$ in the formula (A') and $R^{13}$ to $R^{27}$ in the formula (A"), the same specific examples of $R^2$ to $R^7$ are given.

In addition, examples of the divalent group in $R^8$ to $R^{12}$ and $R^{13}$ to $R^{27}$ in the case where adjacent groups form a cyclic structure include a tetra methylene group, a penta methylene group, a hexa methylene group, a diphenylmethane-2,2'-diyl group, a diphenyethane-3,3'-diyl group, and diphenylpropane-4,4'-diyl group.

Specific examples of the nitrogen-containing ring metal chelate complex represented by the formula (A) are shown below. However, the present invention is not limited to these exemplified compounds.
(A-1)
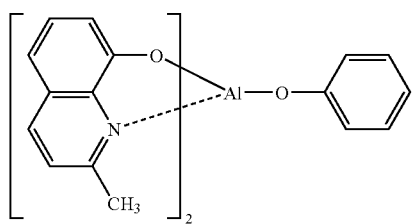
(A-2)
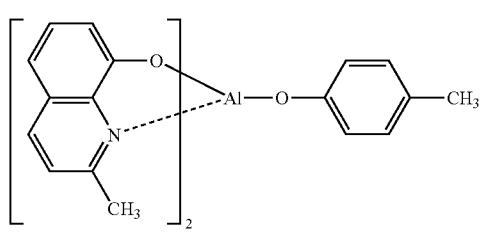
(A-3)
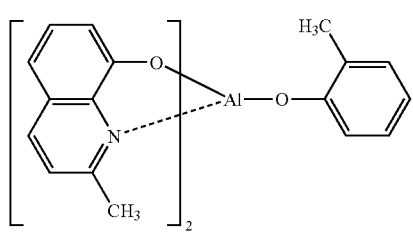
(A-4)
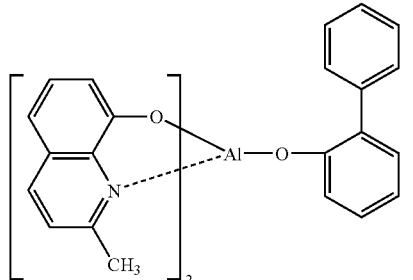
(A-5)
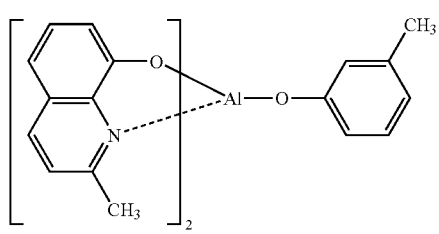
(A-6)
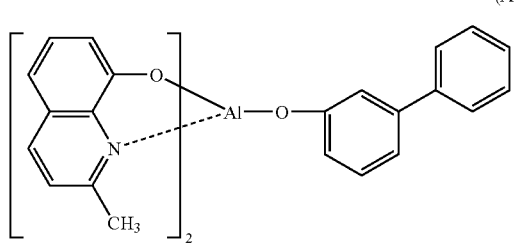
(A-7)
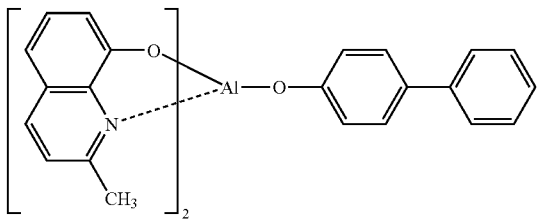
(A-8)
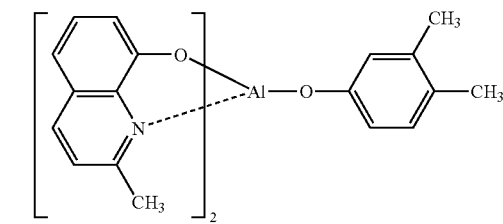
(A-9)
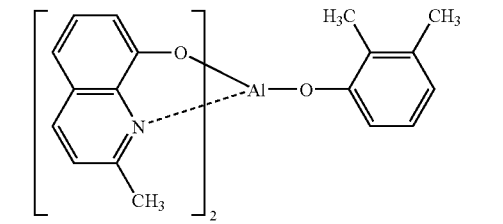
(A-10)
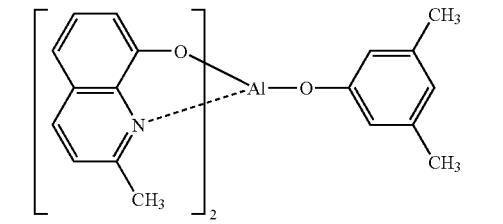
(A-11)
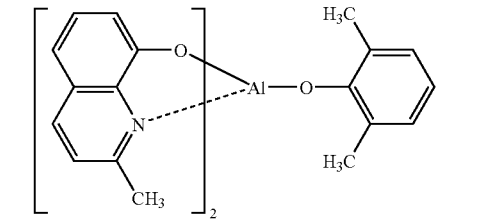
(A-12)
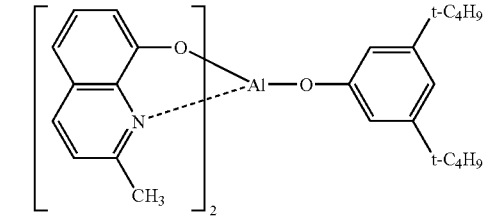
(A-13)

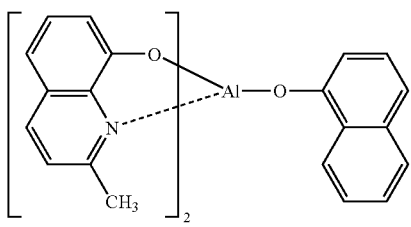
(A-14)
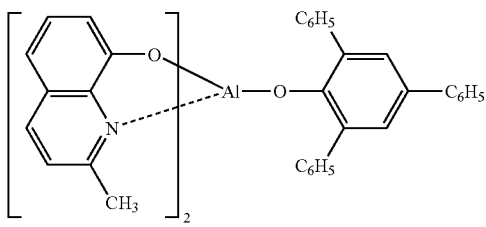
(A-15)
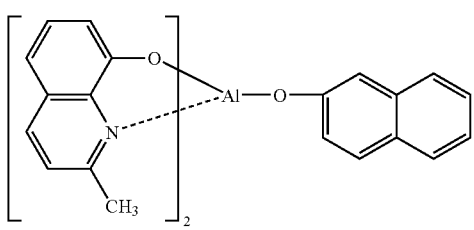
(A-16)
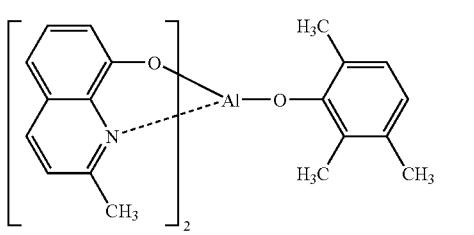
(A-17)
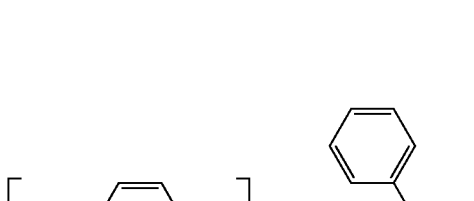
(A-18)
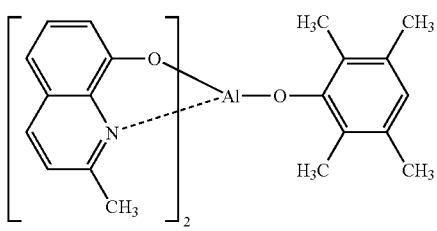
(A-19)
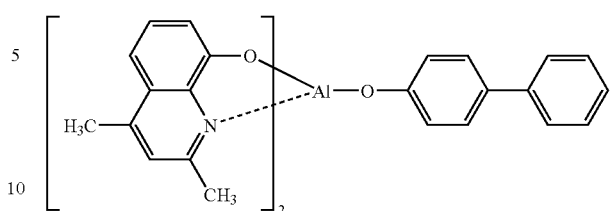
(A-20)
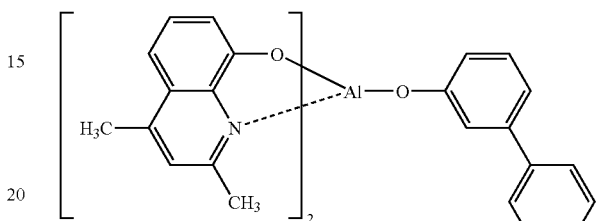
(A-21)
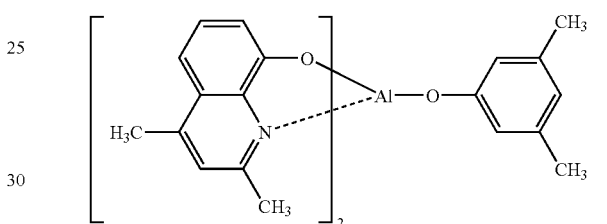
(A-22)
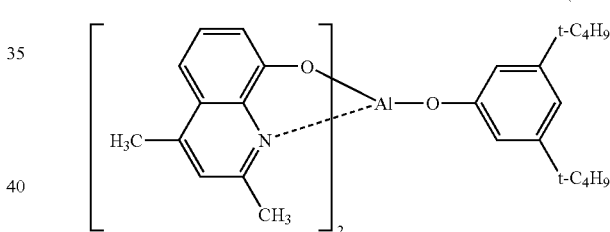
(A-23)
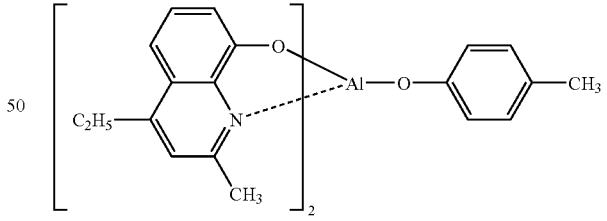
(A-24)
(A-25)

(A-26) 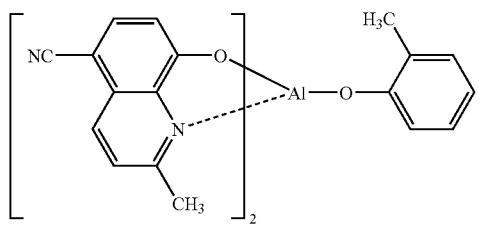

(A-31) 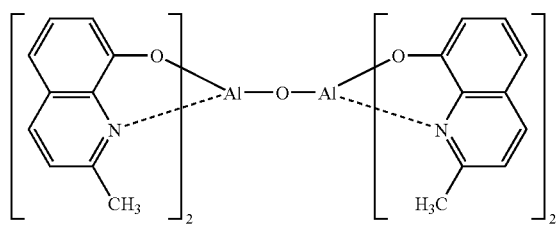

(A-27) 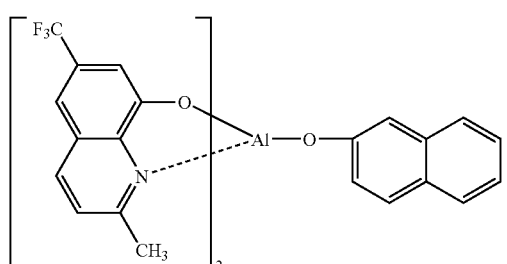

(A-32) 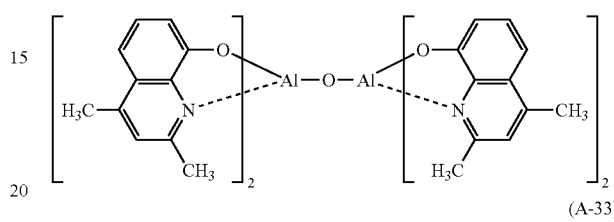

(A-33) 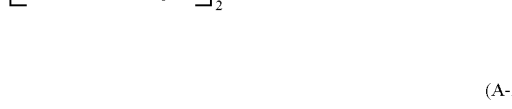

(A-28) 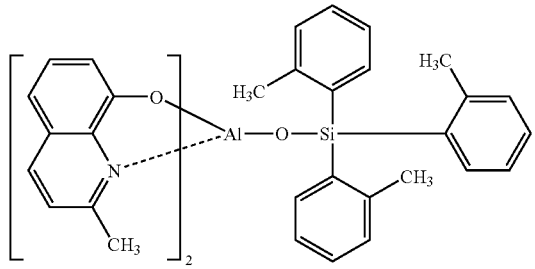

(A-34) 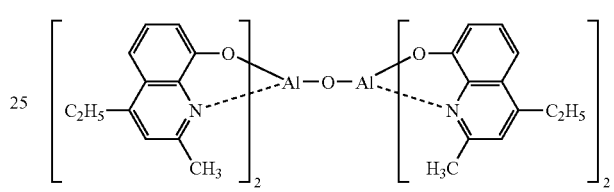

(A-35) 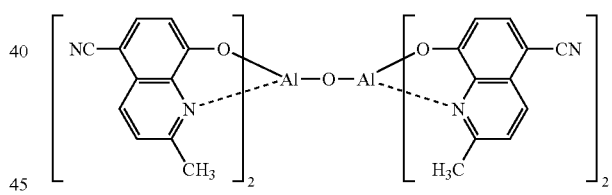

(A-29) 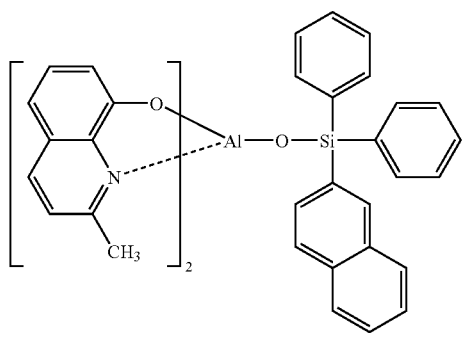

(A-36) 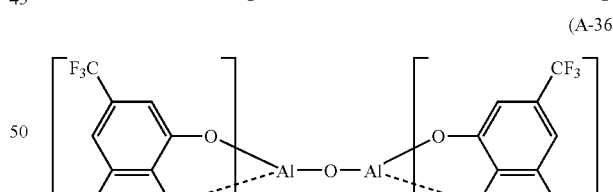

(A-30) 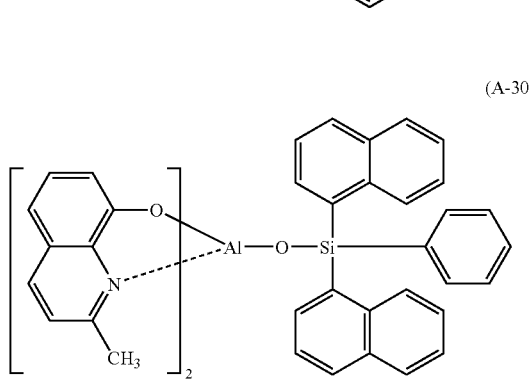

A nitrogen-containing heterocyclic derivative is a nitrogen-containing heterocyclic derivative composed of an organic compound having any one of the following general formulae, and a nitrogen-containing compound which is not a metal complex is also an example of the derivative. Examples of the derivative include a five- or six-membered ring containing a skeleton represented by the following formula (a) and a derivative of a structure represented by the following formula (b).

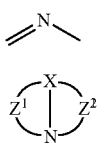

(a)

(b)

(In the formula (b), X represents a carbon atom or a nitrogen atom, and $Z^1$ and $Z^2$ each independently represent an atomic group capable of forming a nitrogen-containing heterocycle.)

(c)

An organic compound having a nitrogen-containing aromatic polycycle composed of a five- or six-membered ring is preferable. In the case of such nitrogen-containing aromatic polycycle having multiple nitrogen atoms, a nitrogen-containing aromatic polycyclic aromatic organic compound having a skeleton obtained by combining the above formulae (a) and (b) or the above formulae (a) and (c) is more preferable.

The nitrogen-containing group of the nitrogen-containing organic compound is selected from, for example, nitrogen-containing heterocyclic groups represented by the following general formulae.

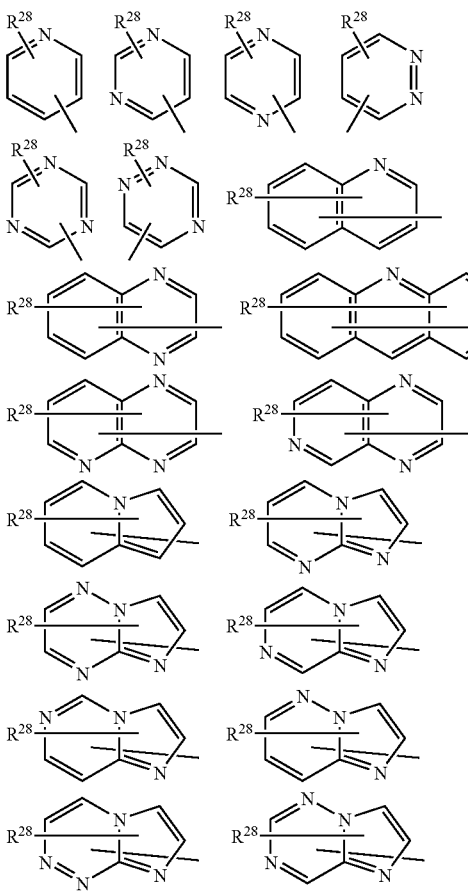

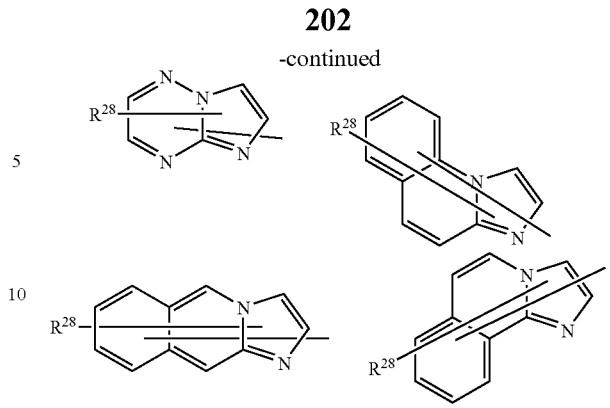

In each of the formulae, $R^{28}$ represents an aryl group having 6 to 40 carbon atoms, a heteroaryl group having 3 to 40 carbon atoms, an alkyl group having 1 to 20 carbon atoms, or an alkoxy group having 1 to 20 carbon atoms, n represents an integer of 0 to 5, and, when n represents an integer of 2 or more, when $R^{28}$ is multiple, multiple $R^{28}$s may be identical to or different from each other.

Further, a preferable specific compound is, for example, a nitrogen-containing heterocyclic derivative represented by the following formula.

$$HAr^a\text{-}L^6\text{-}Ar^b\text{---}Ar^c$$

(In the formula, $HAr^a$ represents a nitrogen-containing heterocycle which has 3 to 40 carbon atoms and which may have a substituent, $L^6$ represents a single bond, an arylene group which has 6 to 40 carbon atoms and which may have a substituent, or a heteroarylene group which has 3 to 40 carbon atoms and which may have a substituent, $Ar^b$ represents a divalent aromatic hydrocarbon group which has 6 to 40 carbon atoms and which may have a substituent, and $Ar^c$ represents an aryl group which has 6 to 40 carbon atoms and which may have a substituent, or a heteroaryl group which has 3 to 40 carbon atoms and which may have a substituent.)

$HAr^a$ is selected from, for example, the following group.

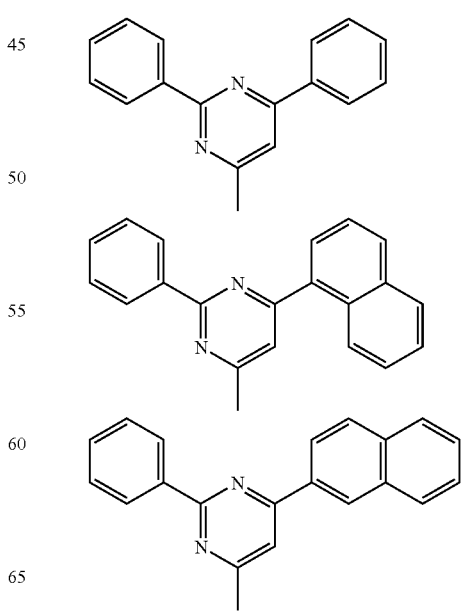

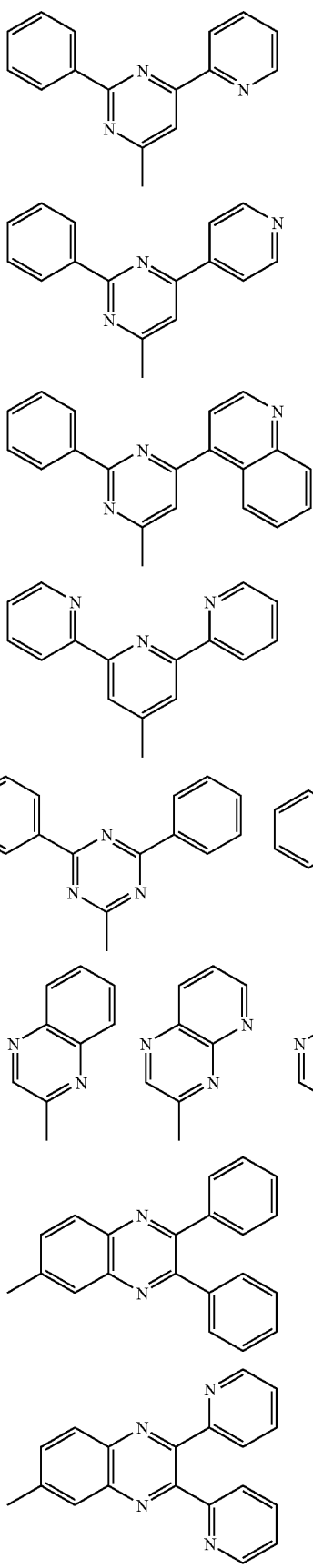
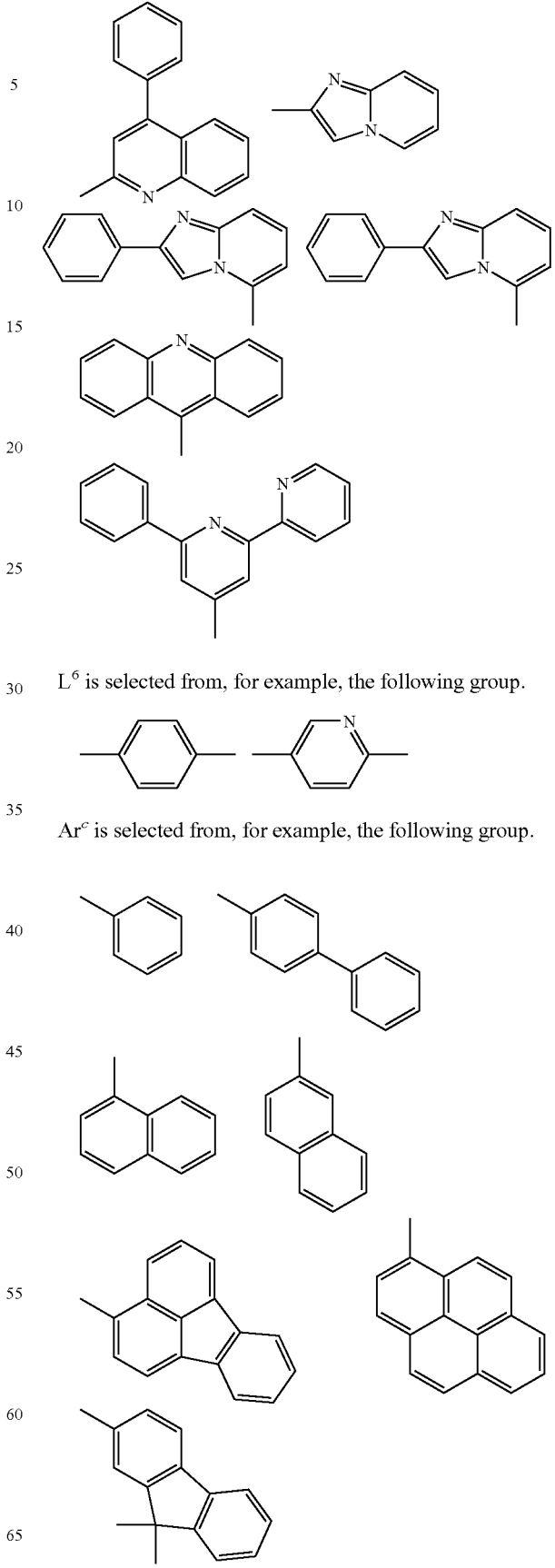
$L^6$ is selected from, for example, the following group.
$Ar^c$ is selected from, for example, the following group.

$Ar^b$ is selected from, for example, the following arylanthranil group.

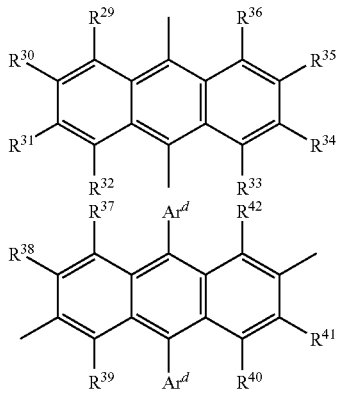

(In the formulae, $R^{29}$ to $R^{42}$ each independently represent a hydrogen atom, a halogen atom, an alkyl group having 1 to 20 carbon atoms, an alkoxy group having 1 to 20 carbon atoms, an aryloxy group having 6 to 40 carbon atoms, an aryl group which has 6 to 40 carbon atoms and which may have a substituent, or a heteroaryl group having 3 to 40 carbon atoms, and $Ar^d$ represents an aryl group which has 6 to 40 carbon atoms and which may have a substituent, or a heteroaryl group having 3 to 40 carbon atoms.)

In addition, a nitrogen-containing heterocyclic derivative in which $R^{29}$ to $R^{36}$ in $Ar^b$ represented by the above formula each represent a hydrogen atom is preferable.

In addition to the foregoing, the following compound (see JP 09-3448 A) is also suitably used.

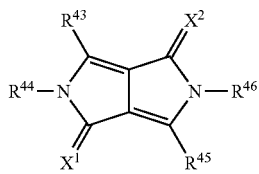

(In the formula, $R^{43}$ to $R^{46}$ each independently represent a hydrogen atom, a substituted or unsubstituted aliphatic group, a substituted or unsubstituted alicyclic group, a substituted or unsubstituted carbocyclic aromatic ring group, or a substituted or unsubstituted heterocyclic group, and $X^1$ and $X^2$ each independently represent an oxygen atom, a sulfur atom, or a dicyanomethylene group.)

In addition to the foregoing, the following compound (see JP 2000-173774 A) is also suitably used.

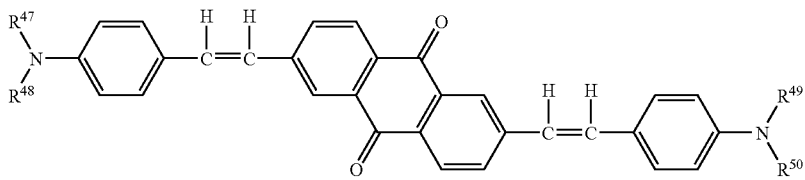

In the formula, $R^{47}$, $R^{48}$, $R^{49}$, and $R^{50}$ represent groups identical to or different from one another, and each represent an aryl group represented by the following formula.

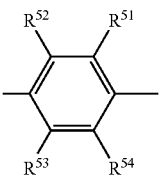

(In the formula, $R^{51}$, $R^{52}$, $R^{53}$, $R^{54}$, and $R^{55}$ represent groups identical to or different from one another, and each may represent a hydrogen atom, or at least one of them may represent a saturated or unsaturated alkoxyl, alkyl, amino, or alkylamino group.

Further, a polymer compound containing the nitrogen-containing heterocyclic group or nitrogen-containing heterocyclic derivative is also permitted.

In addition, the electron transporting layer preferably contains at least one of the nitrogen-containing heterocyclic derivatives represented by the following general formulae (201) to (203).

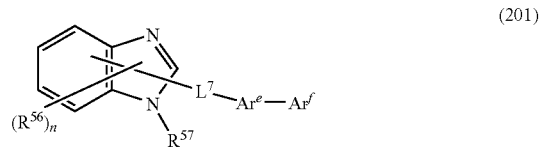
(201)

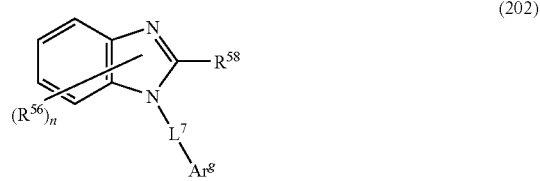
(202)

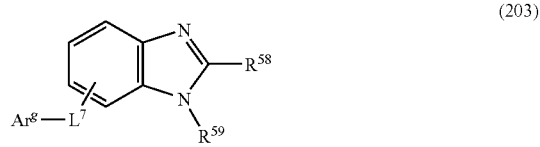
(203)

In the formulae (201) to (203), $R^{56}$ represents a hydrogen atom, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent, n represents an integer of 0 to 4, $R^{57}$ represents an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group having 1 to 20 carbon atoms, $R^{58}$ and $R^{59}$ each independently represent a hydrogen atom, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent, $L^7$ represents a single bond, an arylene group which has 6 to 60 carbon atoms and which may have a substituent, a pyridinylene group which may have a substituent, a quinolinylene group which may have a substituent, or a fluorenylene group which may have a substituent, $Ar^e$ represents an arylene group which has 6 to 60 carbon atoms and which may have a substituent, a pyridinylene group which may have a substituent, or a quinolinylene group which may have a substituent, and $Ar^f$ represents a hydrogen atom, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent.

In the formulae, $Ar^g$ represents an aryl group which has 6 to 60 carbon atoms and which may have a substituent, a pyridyl group which may have a substituent, a quinolyl group which may have a substituent, an alkyl group which has 1 to 20 carbon atoms and which may have a substituent, an alkoxy group which has 1 to 20 carbon atoms and which may have a substituent, or a group represented by —$Ar^e$—$Ar^f$ ($Ar^e$ and $Ar^f$ each have the same meaning as that described above).

It should be noted that, in the formulae (201) to (203), $R^{56}$ represents a hydrogen atom, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent.

The aryl group which has 6 to 60 carbon atoms is preferably an aryl group having 6 to 40 carbon atoms, or more preferably an aryl group having 6 to 20 carbon atoms, and specific examples of such groups include a phenyl group, a naphthyl group, an anthryl group, a phenanthryl group, a naphthacenyl group, a chrysenyl group, a pyrenyl group, a biphenyl group, a terphenyl group, a tolyl group, a t-butylphenyl group, a (2-phenylpropyl)phenyl group, a fluoranthenyl group, a fluorenyl group, a monovalent group composed of spirobifluorene, a perfluorophenyl group, a perfluoronaphthyl group, a perfluoroanthryl group, a perfluorobiphenyl group, a monovalent group composed of 9-phenylanthracene, a monovalent group composed of 9-(1'-naphthyl)anthracene, a monovalent group composed of 9-(2'-naphthyl)anthracene, a monovalent group composed of 6-phenylchrysene, and a monovalent group composed of 9-[4-(diphenylamino)phenyl]anthracene; a phenyl group, a naphthyl group, a biphenyl group, a terphenyl group, a 9-(10-phenyl)anthryl group, a 9-[10-(1'-naphthyl)]anthryl group, a 9-[10-(2'-naphthyl)]anthryl group, or the like is preferable.

The alkyl group which has 1 to 20 carbon atoms is preferably an alkyl group having 1 to 6 carbon atoms, and specific examples of such group include a methyl group, an ethyl group, a propyl group, a butyl group, a pentyl group, a hexyl group, and a haloalkyl group such as a trifluoromethyl group. An alkyl group having 3 or more carbon atoms may be linear, cyclic, or branched.

The alkoxy group which has 1 to 20 carbon atoms is preferably an alkoxy group having 1 to 6 carbon atoms, and specific examples of such group include a methoxy group, an ethoxy group, a propoxy group, a butoxy group, a pentyloxy group, and a hexyloxy group. An alkoxy group having 3 or more carbon atoms may be linear, cyclic, or branched.

Examples of the substituent of each group represented by $R^{56}$ include a halogen atom, an alkyl group which has 1 to 20 carbon atoms and which may have a substituent, an alkoxy group which has 1 to 20 carbon atoms and which may have a substituent, an aryloxy group which has 6 to 40 carbon atoms and which may have a substituent, an aryl group which has 6 to 40 carbon atoms and which may have a substituent, or a heteroaryl group which has 3 to 40 carbon atoms and which may have a substituent.

Examples of the halogen atom include fluorine, chlorine, bromine, and iodine.

Examples of the alkyl group which has 1 to 20 carbon atoms, the alkoxy group which has 1 to 20 carbon atoms, and the aryl group which has 6 to 40 carbon atoms include the same examples as those described above.

Examples of the aryloxy group which has 6 to 40 carbon atoms include a phenoxy group and a biphenyloxy group.

Examples of the heteroaryl group which has 3 to 40 carbon atoms include a pyrrolyl group, a furyl group, a thienyl group, a silolyl group, a pyridyl group, a quinolyl group, an isoquinolyl group, a benzofuryl group, an imidazolyl group, a pyrimidyl group, a carbazolyl group, a selenophenyl group, an oxadiazolyl group, and a triazolyl group.

n represents an integer of 0 to 4, or preferably 0 to 2.

In the formula (201), $R^{57}$ represents an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group having 1 to 20 carbon atoms.

Specific examples of the respective groups, and preferable carbon numbers and preferable substituents of those groups are the same as those described for $R^{56}$.

In the formulae (202) and (203), $R^{58}$ and $R^{59}$ each independently represent a hydrogen atom, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent.

Specific examples of the respective groups, and preferable carbon numbers and preferable substituents of those groups are the same as those described for $R^{56}$ In the formulae (201) to (203), $L^7$ represents a single bond, an arylene group which has 6 to 60 carbon atoms and which may have a substituent, a pyridinylene group which may have a substituent, a quinolinylene group which may have a substituent, or a fluorenylene group which may have a substituent.

The arylene group which has 6 to 60 carbon atoms is preferably an arylene group having 6 to 40 carbon atoms, or more preferably an arylene group having 6 to 20 carbon atoms, and specific examples of such groups include divalent groups each formed by removing one hydrogen atom from the aryl group described for $R^{56}$. Examples of the substituent of each group represented by $L^7$ include the same examples as those described for $R^{56}$ In addition, $L^7$ preferably represents a group selected from the group consisting of the following groups.

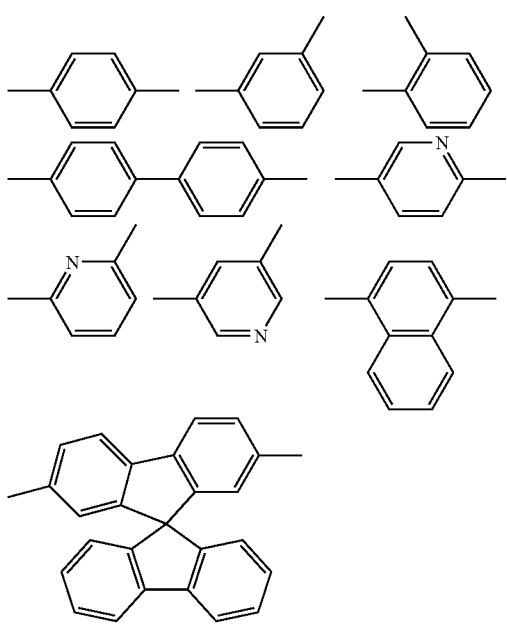

In the formula (201), $Ar^e$ represents an arylene group which has 6 to 60 carbon atoms and which may have a substituent, a pyridinylene group which may have a substituent, or a quinolinylene group which may have a substituent. Examples of the substituents of the respective groups represented by $Ar^e$ and $Ar^g$ include the same examples as those described for $R^{56}$.

In addition, $Ar^e$ preferably represents a group selected from fused ring groups represented by the following formulae (101) to (110).

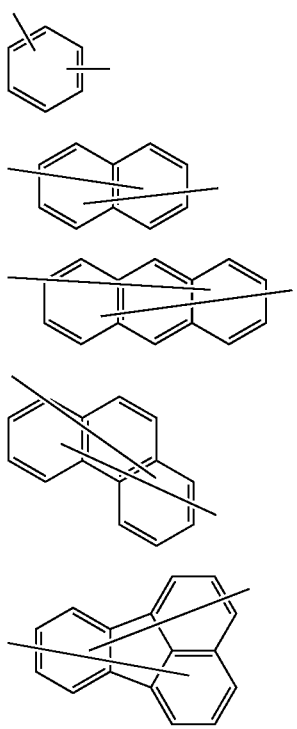

(101)
(102)
(103)
(104)
(105)
(106)
(107)
(108)
(109)

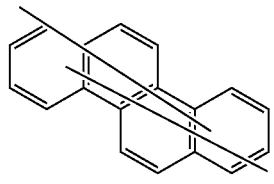

(106)

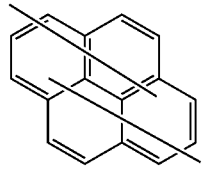

(107)

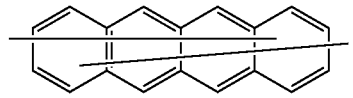

(108)

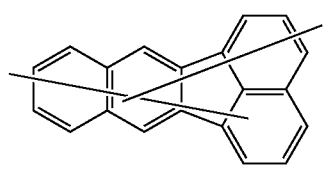

(109)

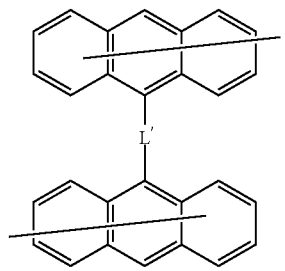

(110)

In the formulae (101) to (110), each fused ring may be bonded with a bonding group composed of a halogen atom, an alkyl group which has 1 to 20 carbon atoms and which may have a substituent, an alkoxy group which has 1 to 20 carbon atoms and which may have a substituent, an aryloxy group which has 6 to 40 carbon atoms and which may have a substituent, an aryl group which has 6 to 40 carbon atoms and which may have a substituent, or a heteroaryl group which has 3 to 40 carbon atoms and which may have a substituent, and, when multiple bonding groups of this kind are present, the bonding groups may be identical to or different from each other. Specific examples of the respective groups include the same examples as those described above.

In the formula (110), L' represents a single bond or a group selected from the group consisting of the following groups.

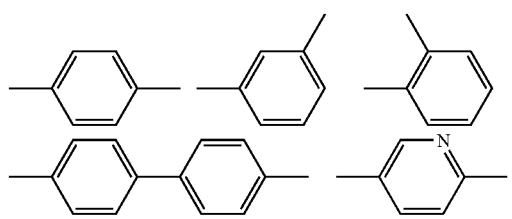

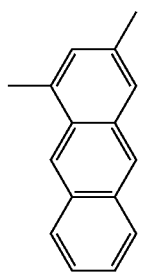
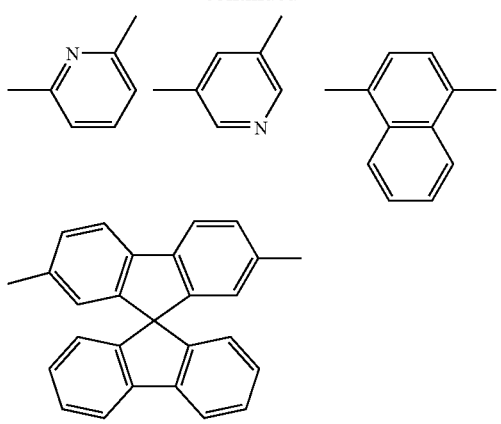
The formula (103) represented by Ar$^e$ is preferably a fused ring group represented by the following formulae (111) to (125).
(111)
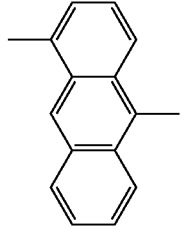
(112)
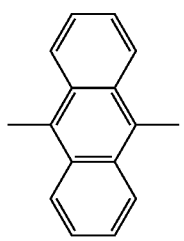
(113)
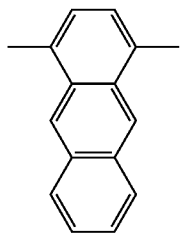
(114)
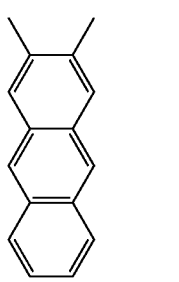
(115)
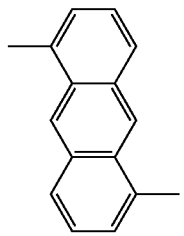
(116)
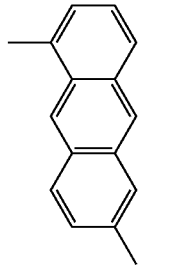
(117)
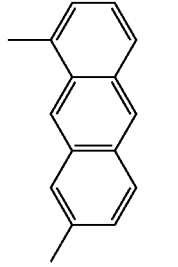
(118)
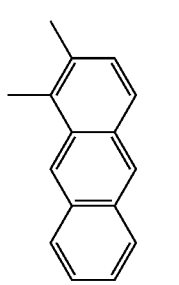
(119)
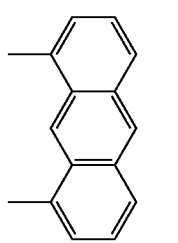
(120)

-continued (121)
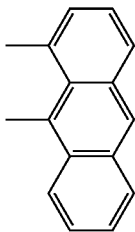

(122)
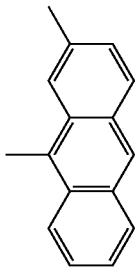

(123)
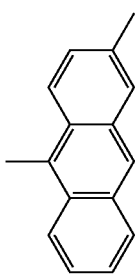

(124)
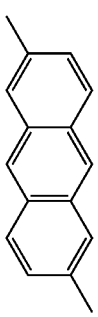

(125)
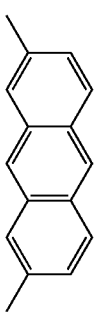

In the formulae (111) to (125), each fused ring may be bonded with a bonding group composed of a halogen atom, an alkyl group which has 1 to 20 carbon atoms and which may have a substituent, an alkoxy group which has 1 to 20 carbon atoms and which may have a substituent, an aryloxy group which has 6 to 40 carbon atoms and which may have a substituent, an aryl group which has 6 to 40 carbon atoms and which may have a substituent, or a heteroaryl group which has 3 to 40 carbon atoms and which may have a substituent, and, when multiple bonding groups of this kind are present, the bonding groups may be identical to or different from each other. Specific examples of the respective groups include the same examples as those described above.

In the formula (201), $Ar^f$ represents a hydrogen atom, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent.

Specific examples of the respective groups, and preferable carbon numbers and preferable substituents of those groups are the same as those described for $R^{56}$.

In the formulae (202) and (203), $Ar^g$ represents an aryl group which has 6 to 60 carbon atoms and which may have a substituent, a pyridyl group which may have a substituent, a quinolyl group which may have a substituent, an alkyl group which has 1 to 20 carbon atoms and which may have a substituent, an alkoxy group which has 1 to 20 carbon atoms and which may have a substituent, or a group represented by —$Ar^e$—$Ar^f$ ($Ar^e$ and $Ar^f$ each have the same meaning as that described above).

Specific examples of the respective groups, and preferable carbon numbers and preferable substituents of those groups are the same as those described for $R^{56}$.

In addition, $Ar^g$ preferably represents a group selected from fused ring groups represented by the following formulae (126) to (135).

(126)
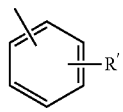

(127)
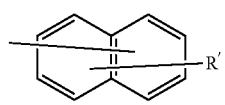

(128)
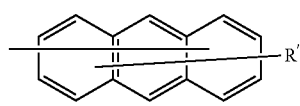

(129)
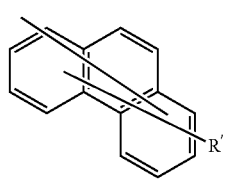

(130)
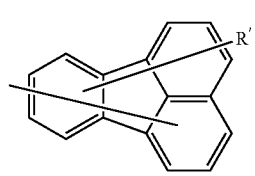

-continued

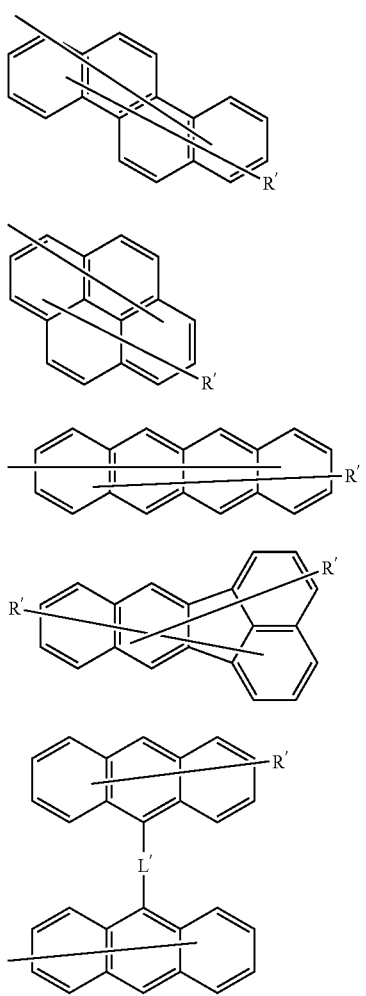

(131)

(132)

(133)

(134)

(135)

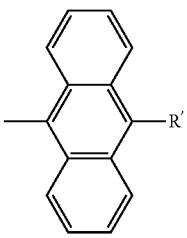

(136)

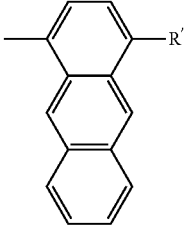

(137)

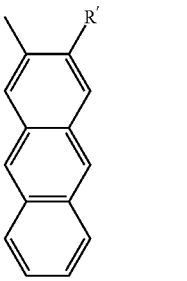

(138)

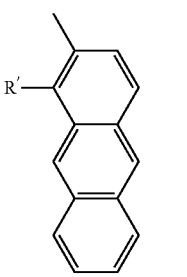

(139)

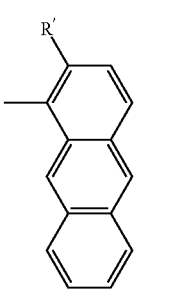

(140)

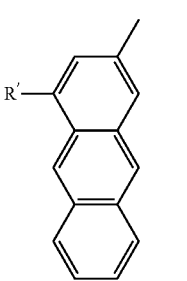

(141)

In the formulae (126) to (135), each fused ring may be bonded with a bonding group composed of a halogen atom, an alkyl group which has 1 to 20 carbon atoms and which may have a substituent, an alkoxy group which has 1 to 20 carbon atoms and which may have a substituent, an aryloxy group which has 6 to 40 carbon atoms and which may have a substituent, an aryl group which has 6 to 40 carbon atoms and which may have a substituent, or a heteroaryl group which has 3 to 40 carbon atoms and which may have a substituent, and, when multiple bonding groups of this kind are present, the bonding groups may be identical to or different from each other. Specific examples of the respective groups include the same examples as those described above.

In the formula (135), L' is the same as that described above.

In the formulae (126) to (135), R' represents a hydrogen atom, an alkyl group which has 1 to 20 carbon atoms and which may have a substituent, an aryl group which has 6 to 40 carbon atoms and which may have a substituent, or a heteroaryl group which has 3 to 40 carbon atoms and which may have a substituent. Specific examples of the respective groups include the same examples as those described above.

The general formula (128) represented by $Ar^g$ is preferably a fused ring group represented by the following formulae (136) to (158).

-continued
(142) 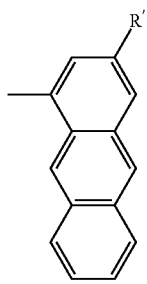
(143) 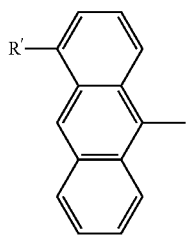
(144) 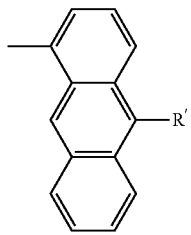
(145) 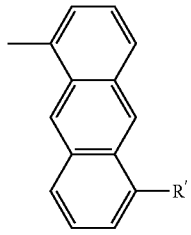
(146) 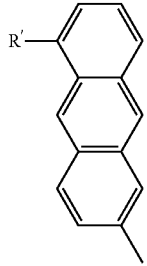
(147) 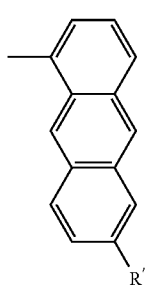
-continued
(148) 
(149) 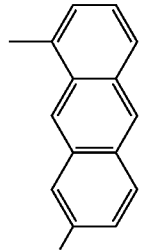
(150) 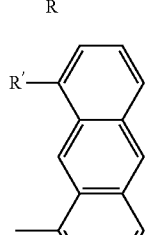
(151) 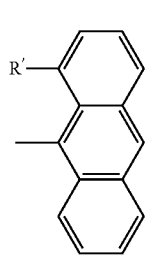
(152) 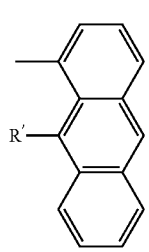
(153) 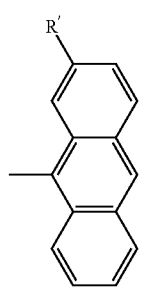

(154)

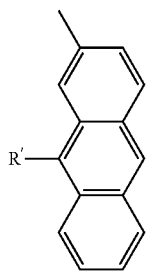

(155)

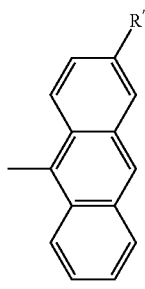

(156)

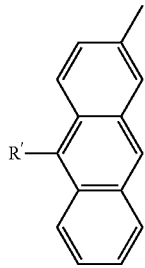

(157)

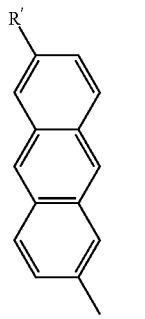

(158)

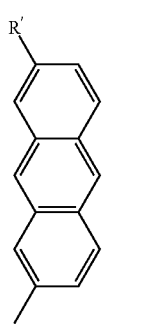

In the formulae (136) to (158), each fused ring may be bonded with a bonding group composed of a halogen atom, an alkyl group which has 1 to 20 carbon atoms and which may have a substituent, an alkoxy group which has 1 to 20 carbon atoms and which may have a substituent, an aryloxy group which has 6 to 40 carbon atoms and which may have a substituent, an aryl group which has 6 to 40 carbon atoms and which may have a substituent, or a heteroaryl group which has 3 to 40 carbon atoms and which may have a substituent, and, when multiple bonding groups of this kind are present, the bonding groups may be identical to or different from each other. Specific examples of the respective groups include the same examples as those described above. R' is the same as that described above.

In addition, it is preferred that $Ar^f$ and $Ar^g$ each independently represent a group selected from the group consisting of the following groups.

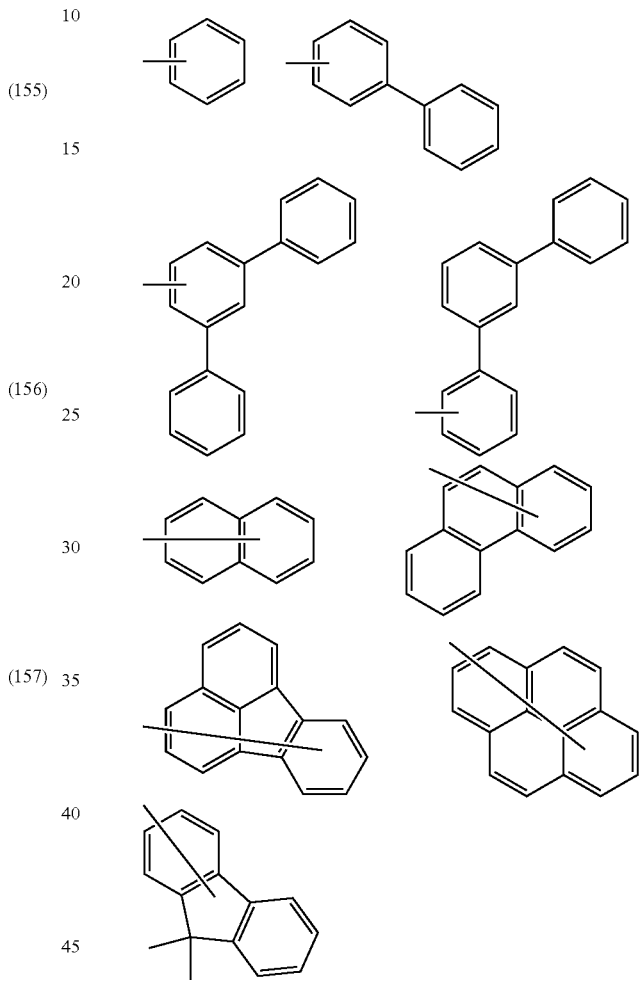

Specific examples of the nitrogen-containing heterocyclic derivatives represented by the formulae (201) to (203) of the present invention are shown below. However, the present invention is not limited to these exemplified compounds.

It should be noted that HAr in the following tables represent any one of the following parts in the formulae (201) to (203).

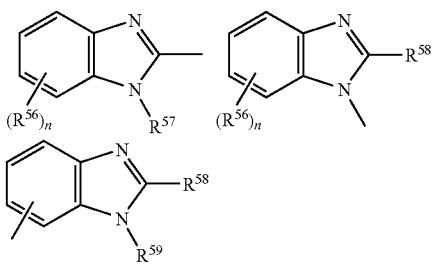

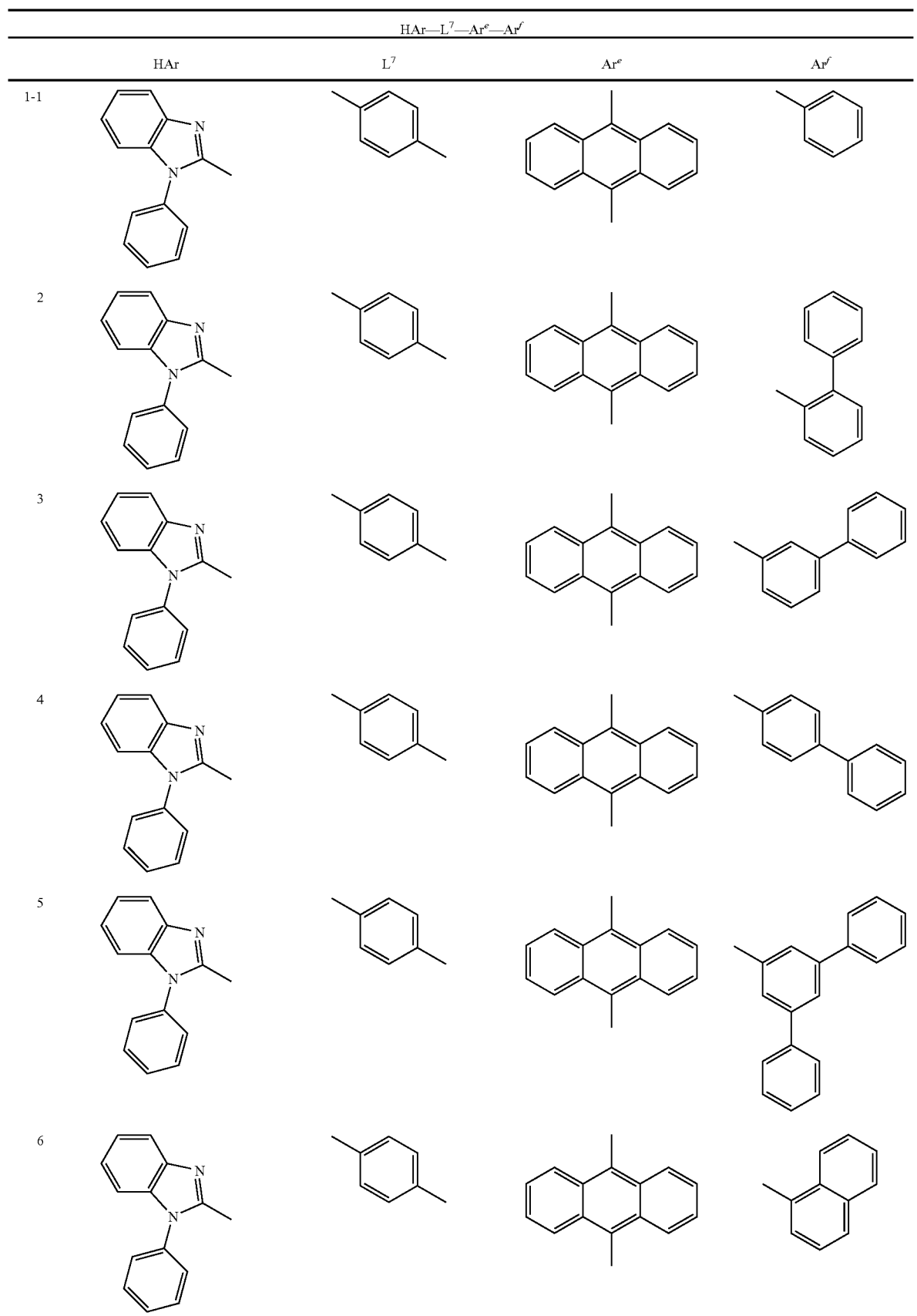

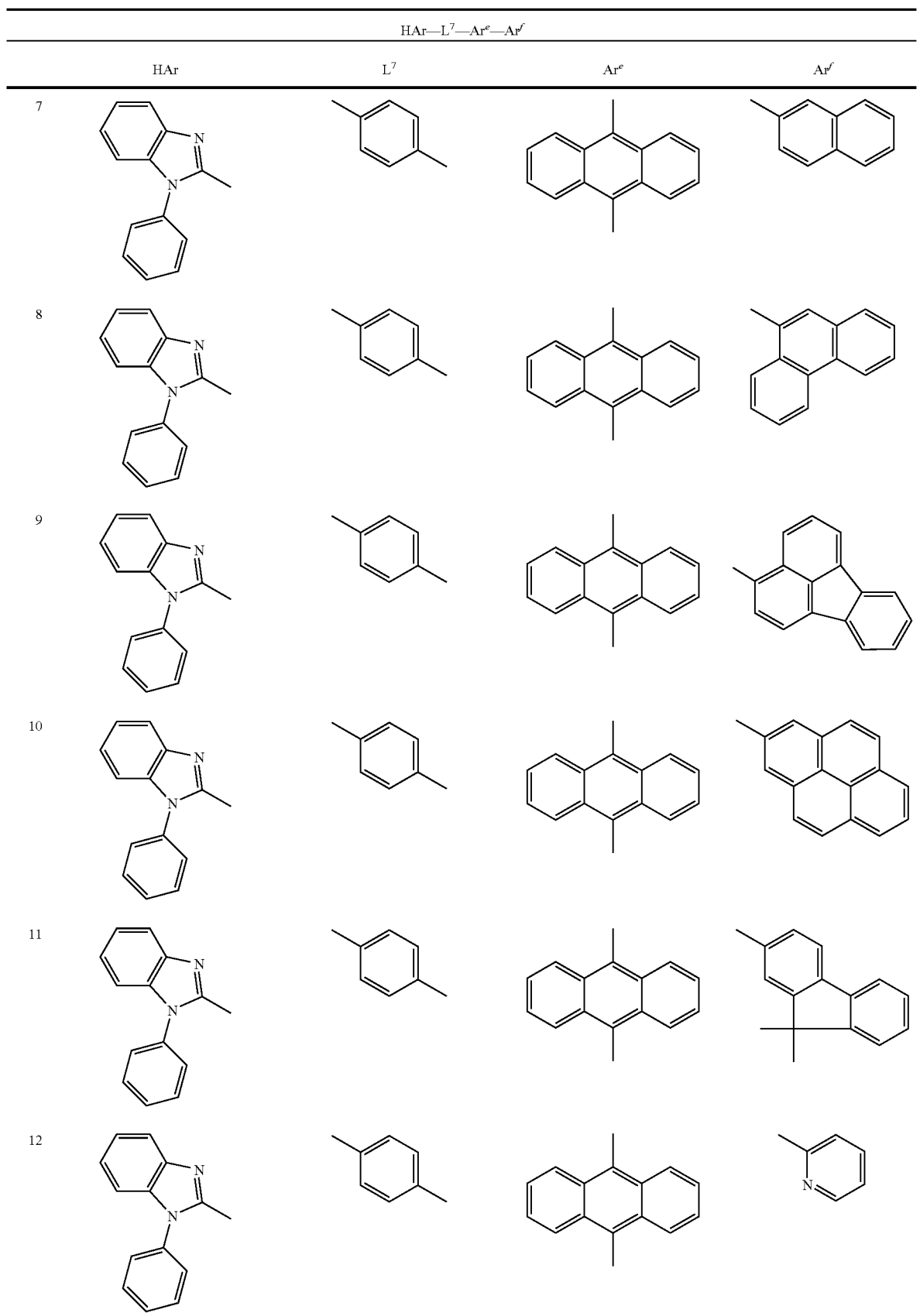

-continued
| | HAr | L⁷ | Arᵉ | Arᶠ |
|---|---|---|---|---|
| 13 | 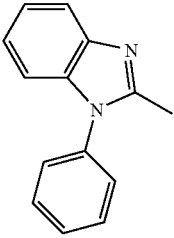 | 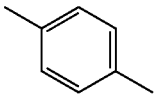 | 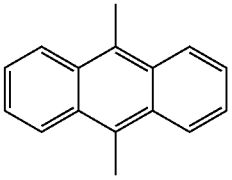 | 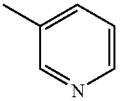 |
| 14 | 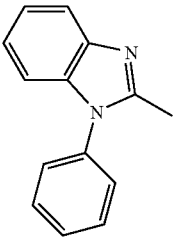 | 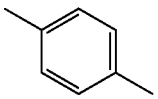 | 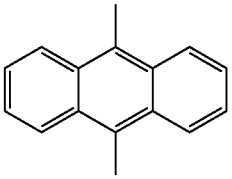 | 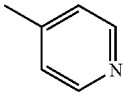 |
| 2-1 | 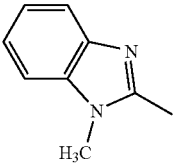 | 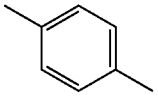 | 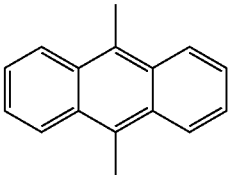 | 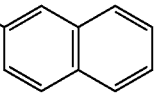 |
| 2 | 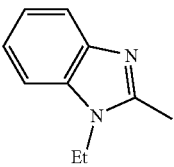 | 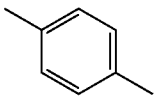 | 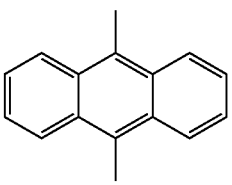 | 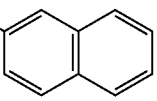 |
| 3 | 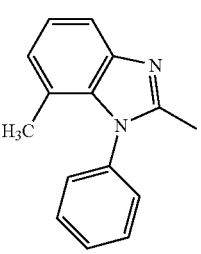 | 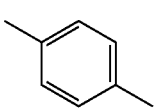 | 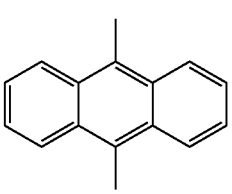 | 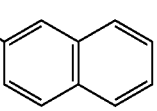 |
| 4 | 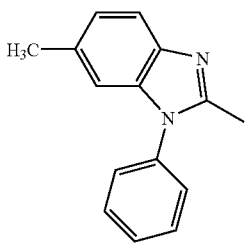 | 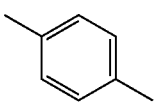 | 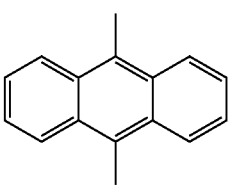 | 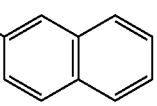 |

-continued
| | HAr | L⁷ | Arᵉ | Ar^f |
|---|---|---|---|---|
| 5 | 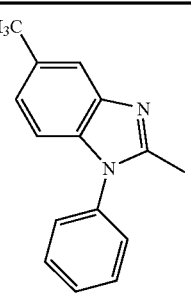 | 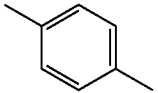 | 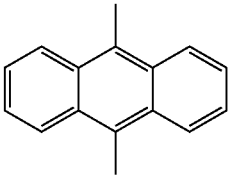 | 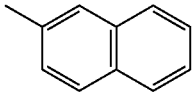 |
| 6 | 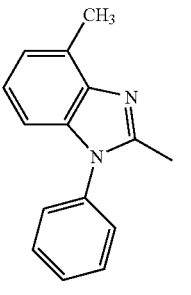 | 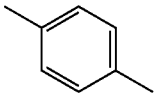 | 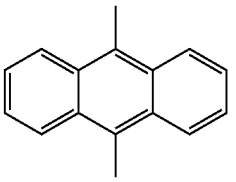 | 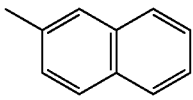 |
| 7 | 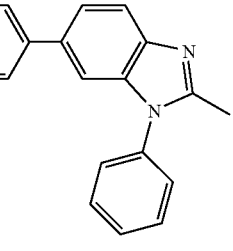 | 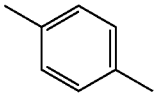 | 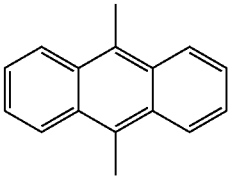 | 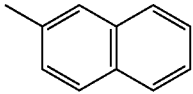 |
| 8 | 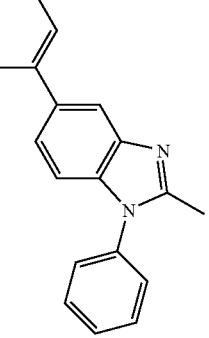 | 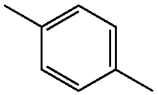 | 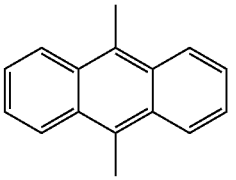 | 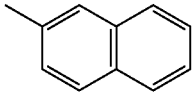 |
| 9 | 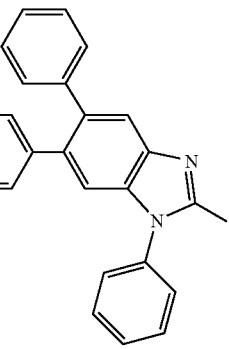 | 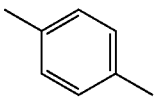 | 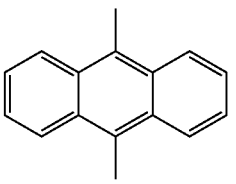 | 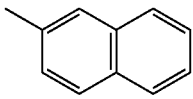 |

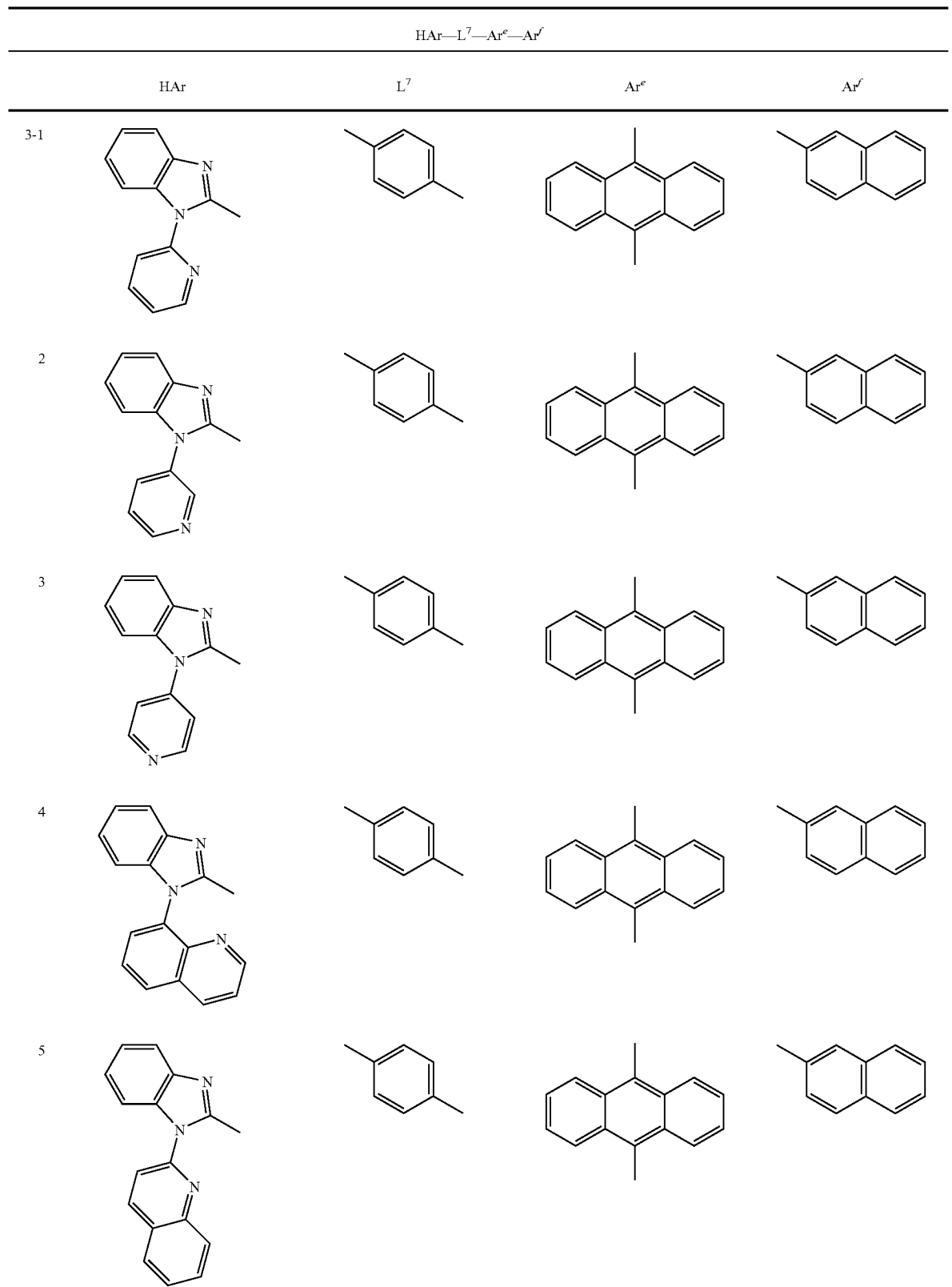

-continued
| | HAr | L[7] | Ar[e] | Ar[f] |
|---|---|---|---|---|
| 6 | 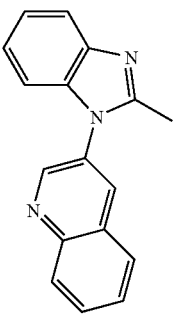 | 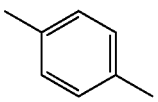 | 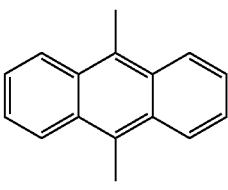 | 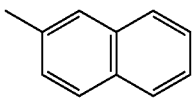 |
| 4-1 | 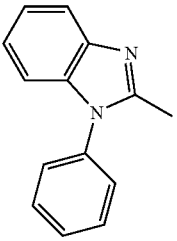 |  | 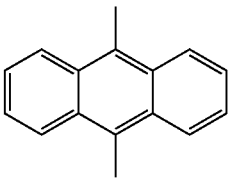 | 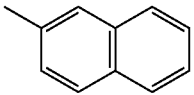 |
| 2 | 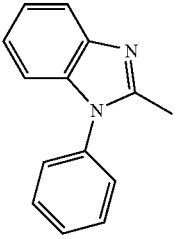 | 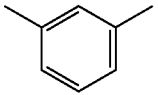 | 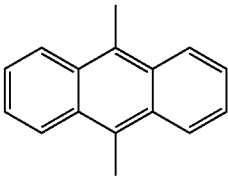 | 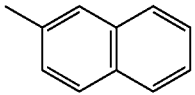 |
| 3 | 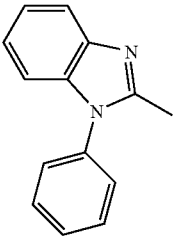 | 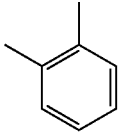 | 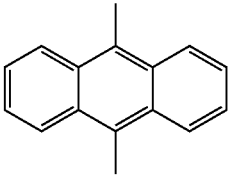 | 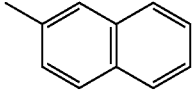 |
| 4 | 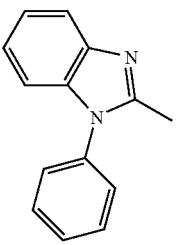 | 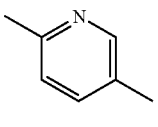 | 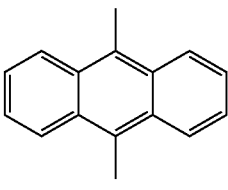 | 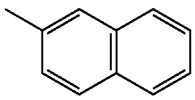 |
| 5 | 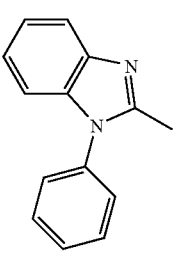 | 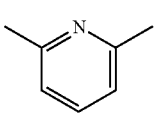 | 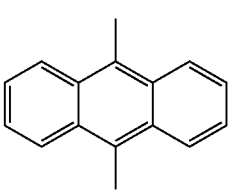 | 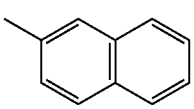 |

-continued
| | HAr | L⁷ | Arᵉ | Arᶠ |
|---|---|---|---|---|
| 6 | 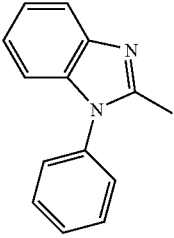 | 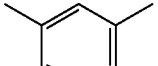 | 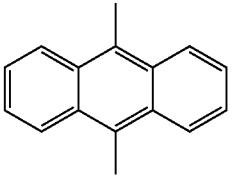 | 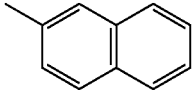 |
| 7 | 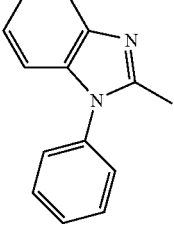 | 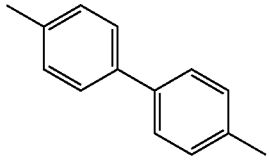 | 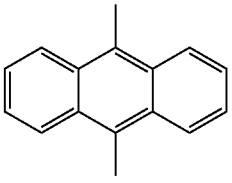 | 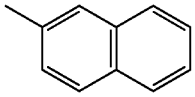 |
| 8 | 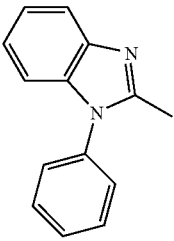 | 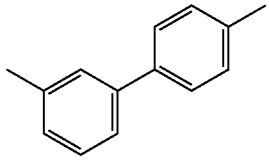 | 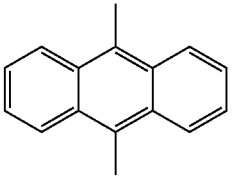 | 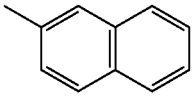 |
| 9 | 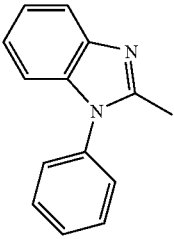 | 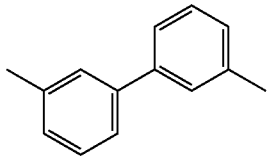 | 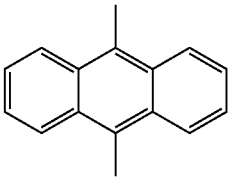 | 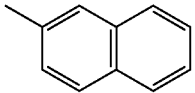 |
| 10 | 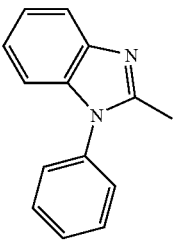 | 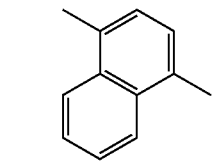 | 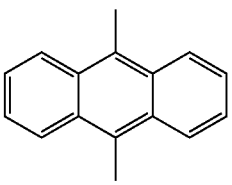 | 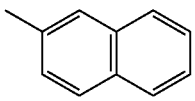 |
| 11 | 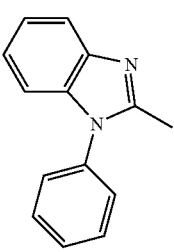 | 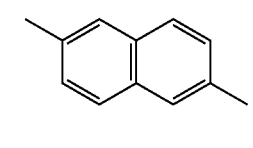 | 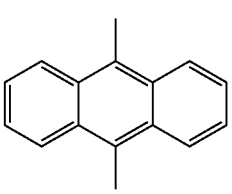 | 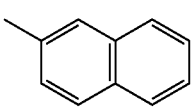 |

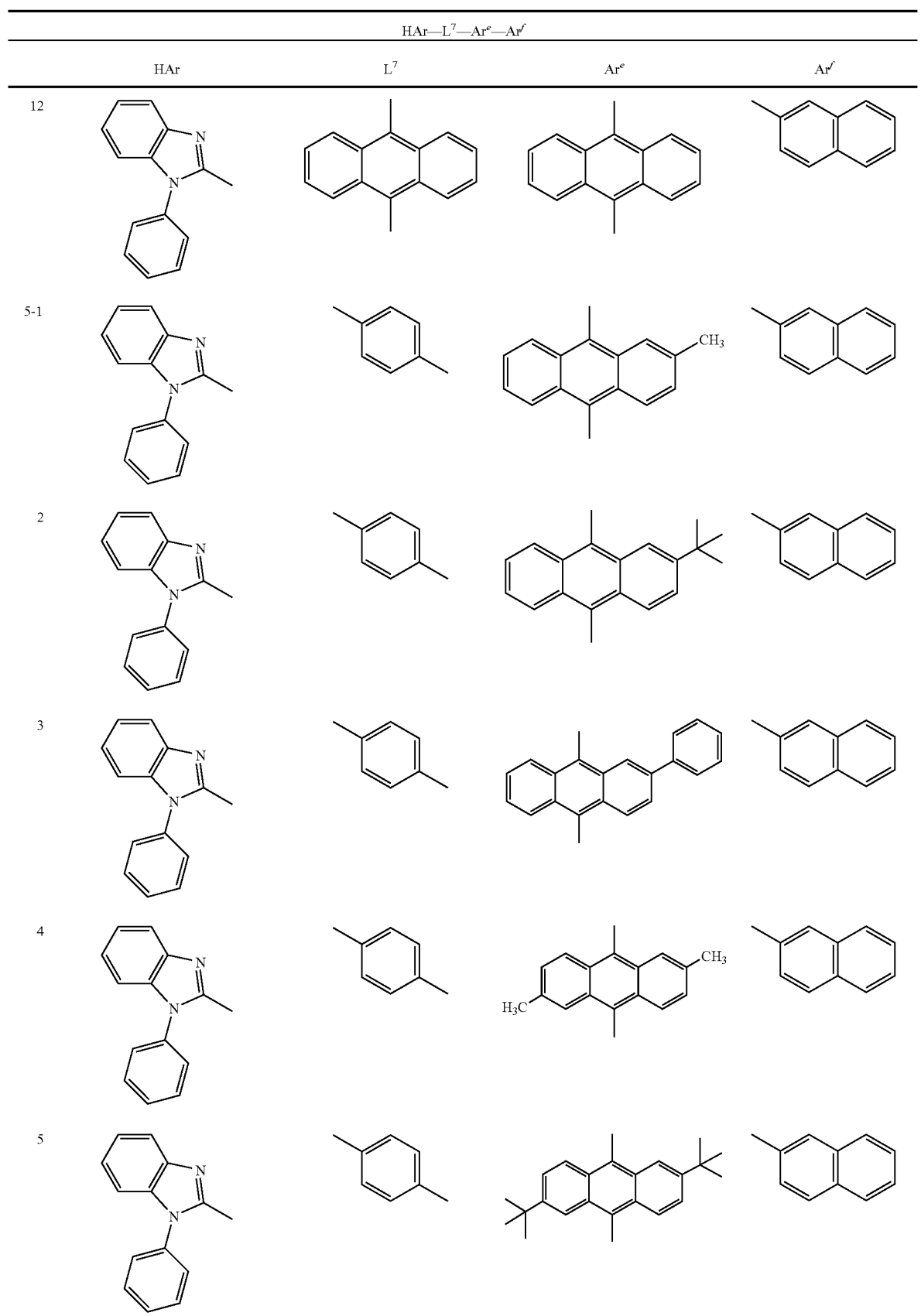

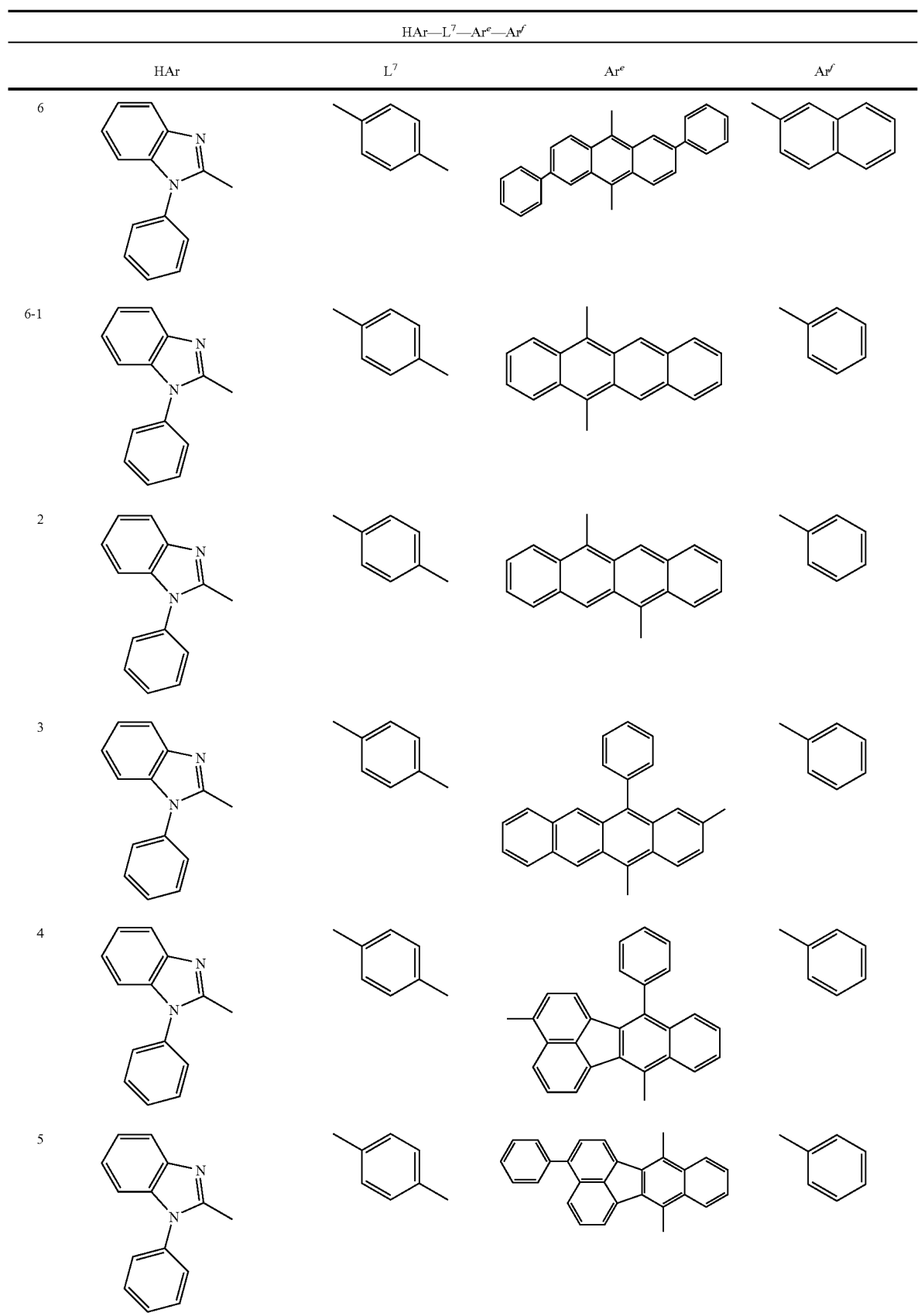

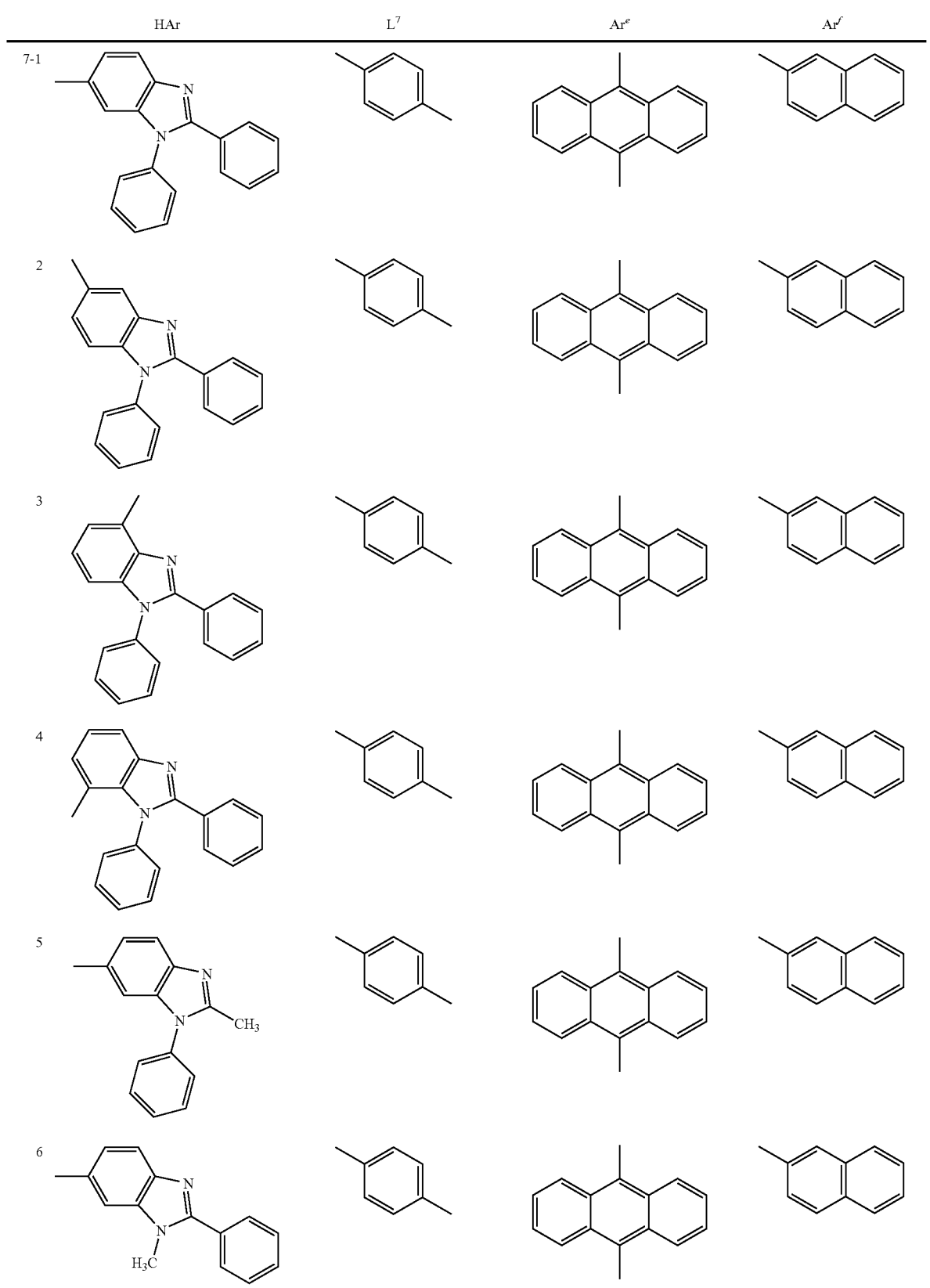

| | HAr | L⁷ | Arᵉ | Arᶠ |
|---|---|---|---|---|
| 7 | | | | |
| 8 | | | | |
| 9 | | | | |
| 10 | | | | |
| 8-1 | | | | |
| 2 | | | | |

-continued
| | HAr | L⁷ | Arᵉ | Arᶠ |
|---|---|---|---|---|
| 3 | 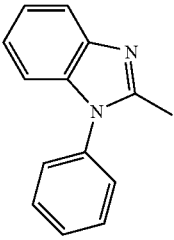 | 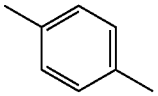 | 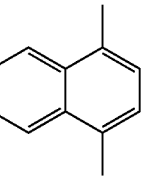 | 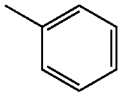 |
| 4 | 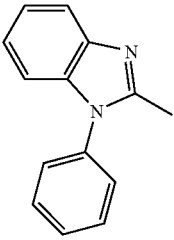 | 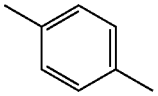 | 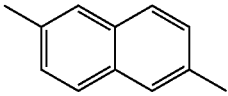 | 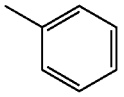 |
| 5 | 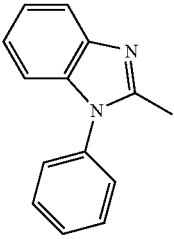 | 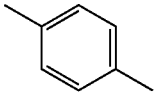 | 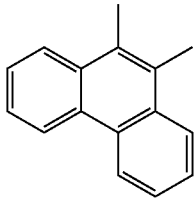 | 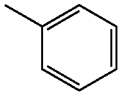 |
| 6 | 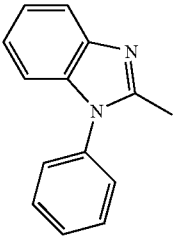 | 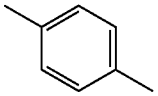 | 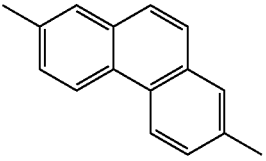 | 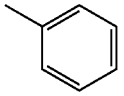 |
| 7 | 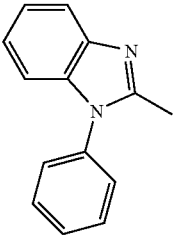 | 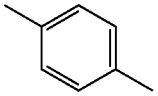 | 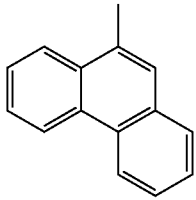 |  |
| 8 | 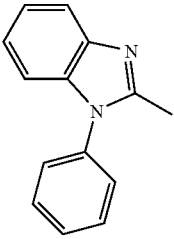 | 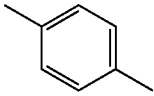 | 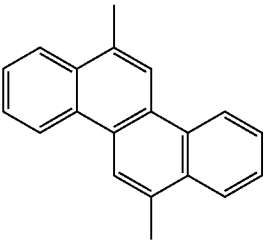 | 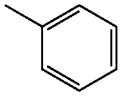 |

-continued
| | HAr | L7 | Are | Arf |
|---|---|---|---|---|
| 9 | 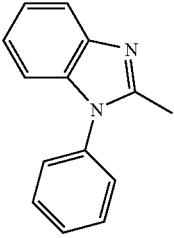 | 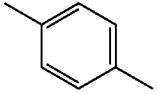 | 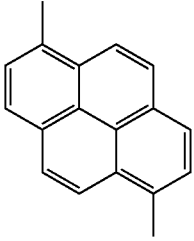 | 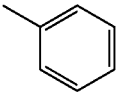 |
| 10 | 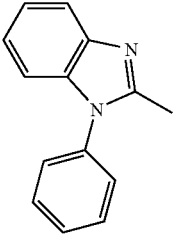 | 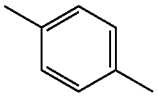 | 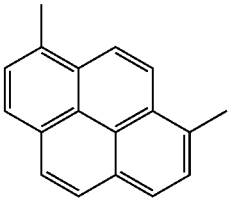 | 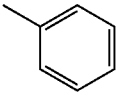 |
| 11 | 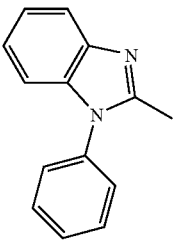 | 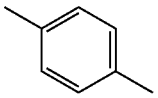 | 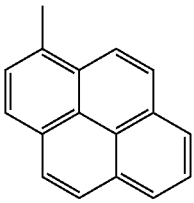 | —H |
| 12 |  | 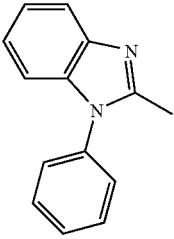 | 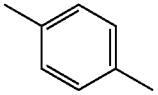 | 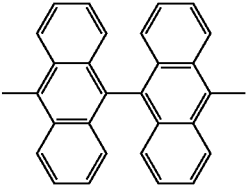 |
| 13 | 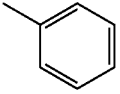 | 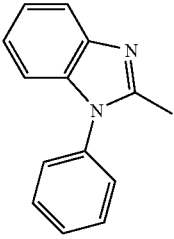 | 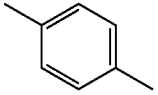 | 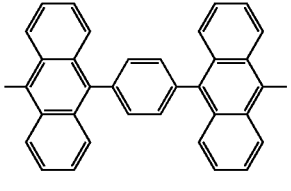 |
| 9-1 | 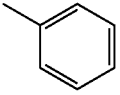 | 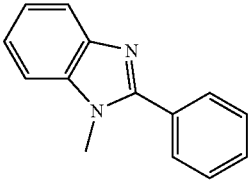 | 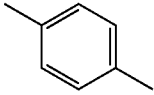 | 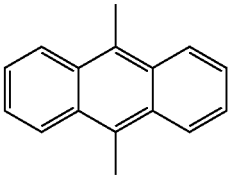 |

-continued
| | HAr | L⁷ | Arᵉ | Arᶠ |
|---|---|---|---|---|
| 2 | 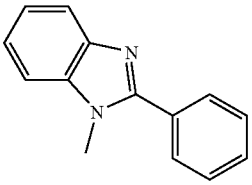 | 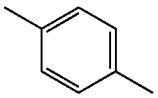 | 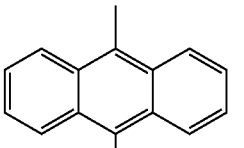 | 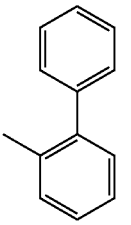 |
| 3 | 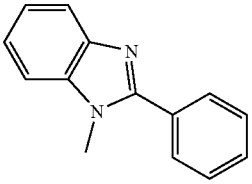 | 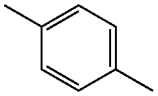 | 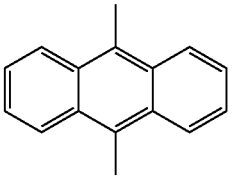 | 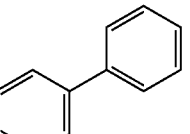 |
| 4 | 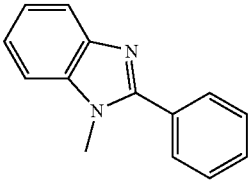 | 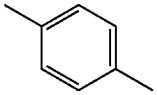 | 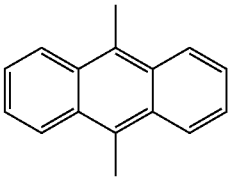 | 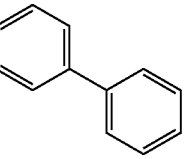 |
| 5 | 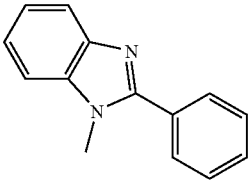 | 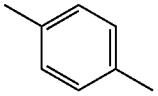 | 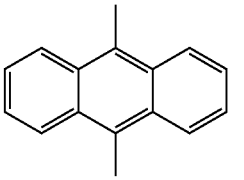 | 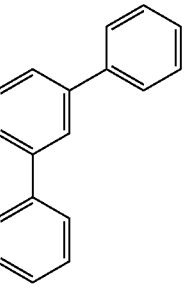 |
| 6 | 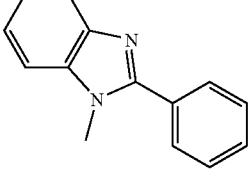 | 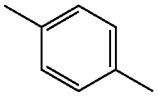 | 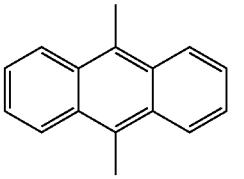 | 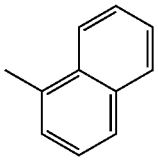 |
| 7 | 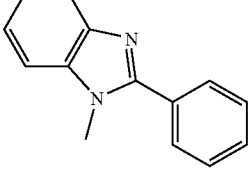 | 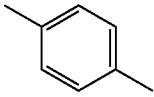 | 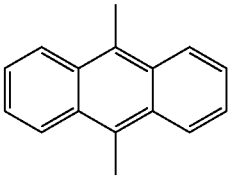 | 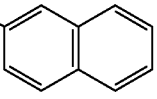 |
| 8 | 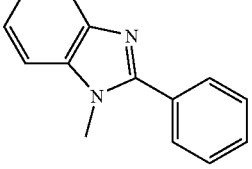 | 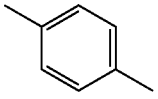 | 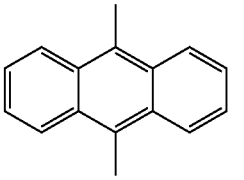 | 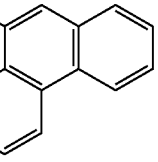 |

-continued
| | HAr | L⁷ | Arᵉ | Arᶠ |
|---|---|---|---|---|
| 9 | 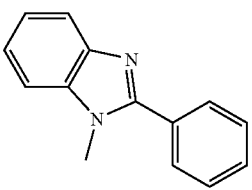 | 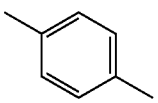 | 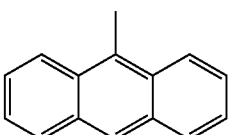 | 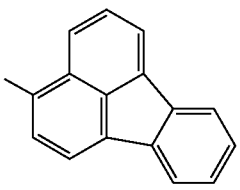 |
| 10 | 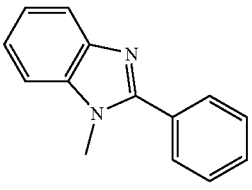 | 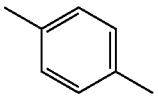 | 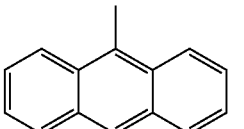 | 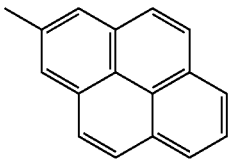 |
| 11 | 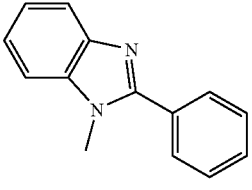 | 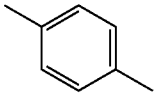 | 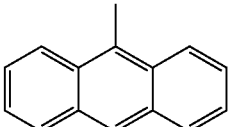 | 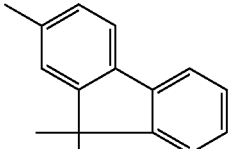 |
| 12 | 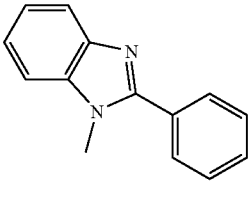 | 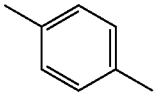 | 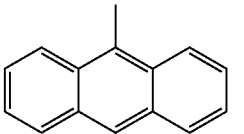 | 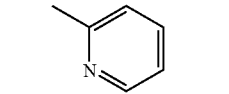 |
| 13 | 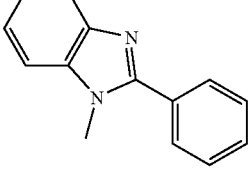 | 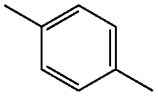 | 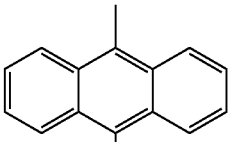 | 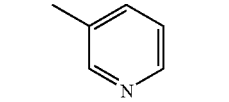 |
| 14 | 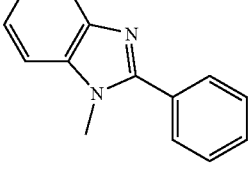 | 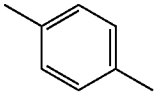 | 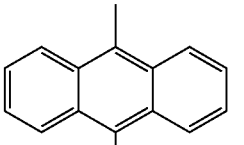 | 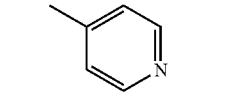 |
| 10-1 | 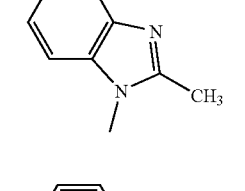 | 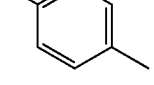 | 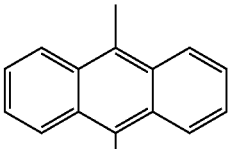 | 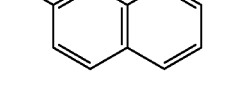 |
| 2 | 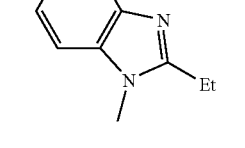 | 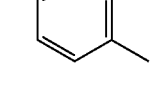 | 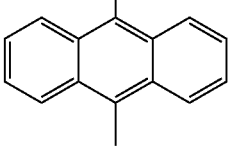 | 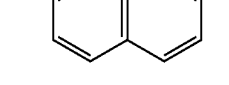 |

-continued

| | HAr | L⁷ | Arᵉ | Arᶠ |
|---|---|---|---|---|

(Structures for entries 3–8 shown as images only.)

-continued
| | HAr—L⁷—Arᵉ—Arᶠ | | |
|---|---|---|---|
| HAr | L⁷ | Arᵉ | Arᶠ |
9 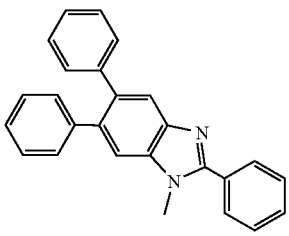
11-1 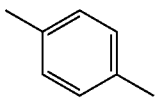
2 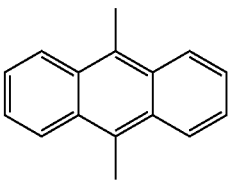
3 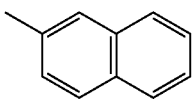
4 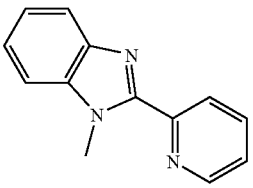
5 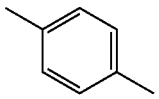
6 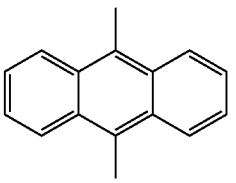

-continued
| | HAr—L⁷—Arᵉ—Arᶠ | | |
|---|---|---|---|
| HAr | L⁷ | Arᵉ | Arᶠ |
| | HAr | L⁷ | Arᵉ | Arᶠ |
|---|---|---|---|---|
| 12-1 | 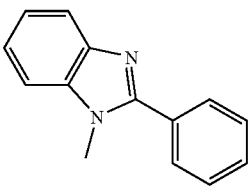 |  | 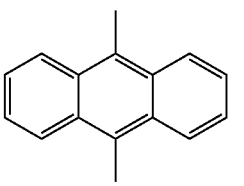 | 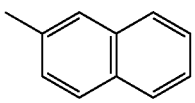 |
| 2 | 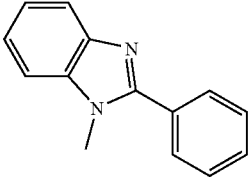 | 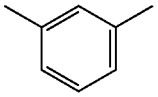 | 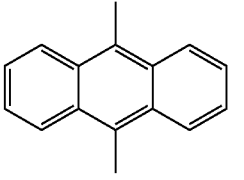 | 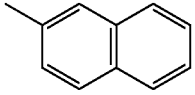 |
| 3 | 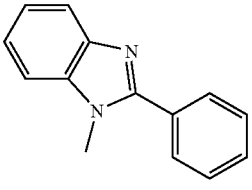 | 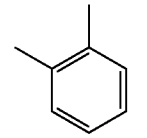 | 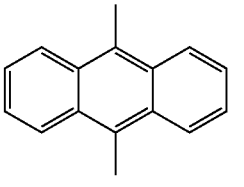 | 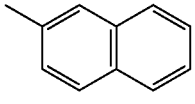 |
| 4 | 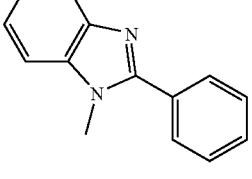 | 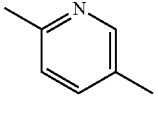 | 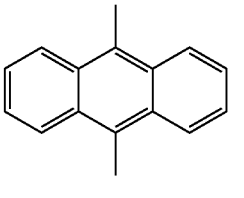 | 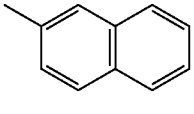 |
| 5 | 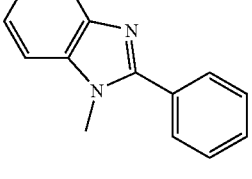 | 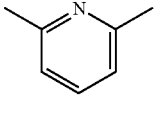 | 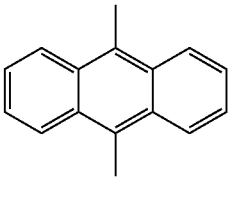 | 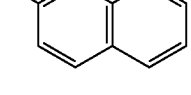 |
| 6 | 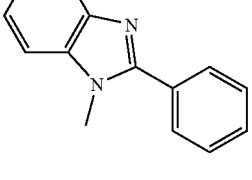 | 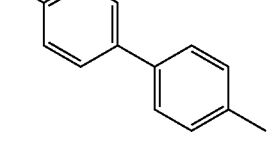 | 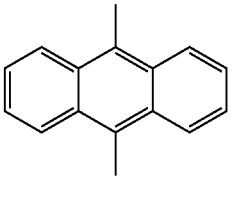 | 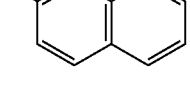 |
| 7 | 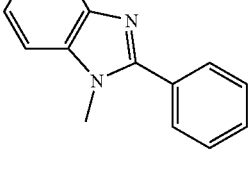 | 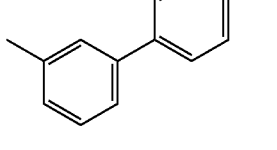 | 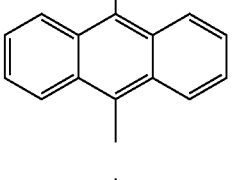 | 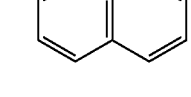 |
| 8 | 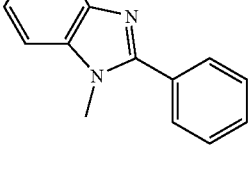 | 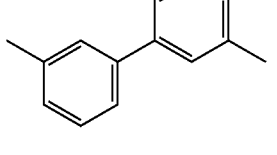 | 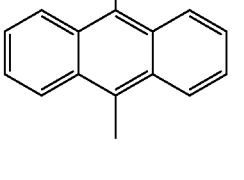 | 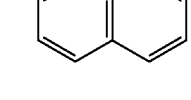 |

-continued

| | HAr | L⁷ | Arᵉ | Arᶠ |
|---|---|---|---|---|

The table contains rows 9, 10, 11, 13-1, 2, 3, 4 with chemical structures.

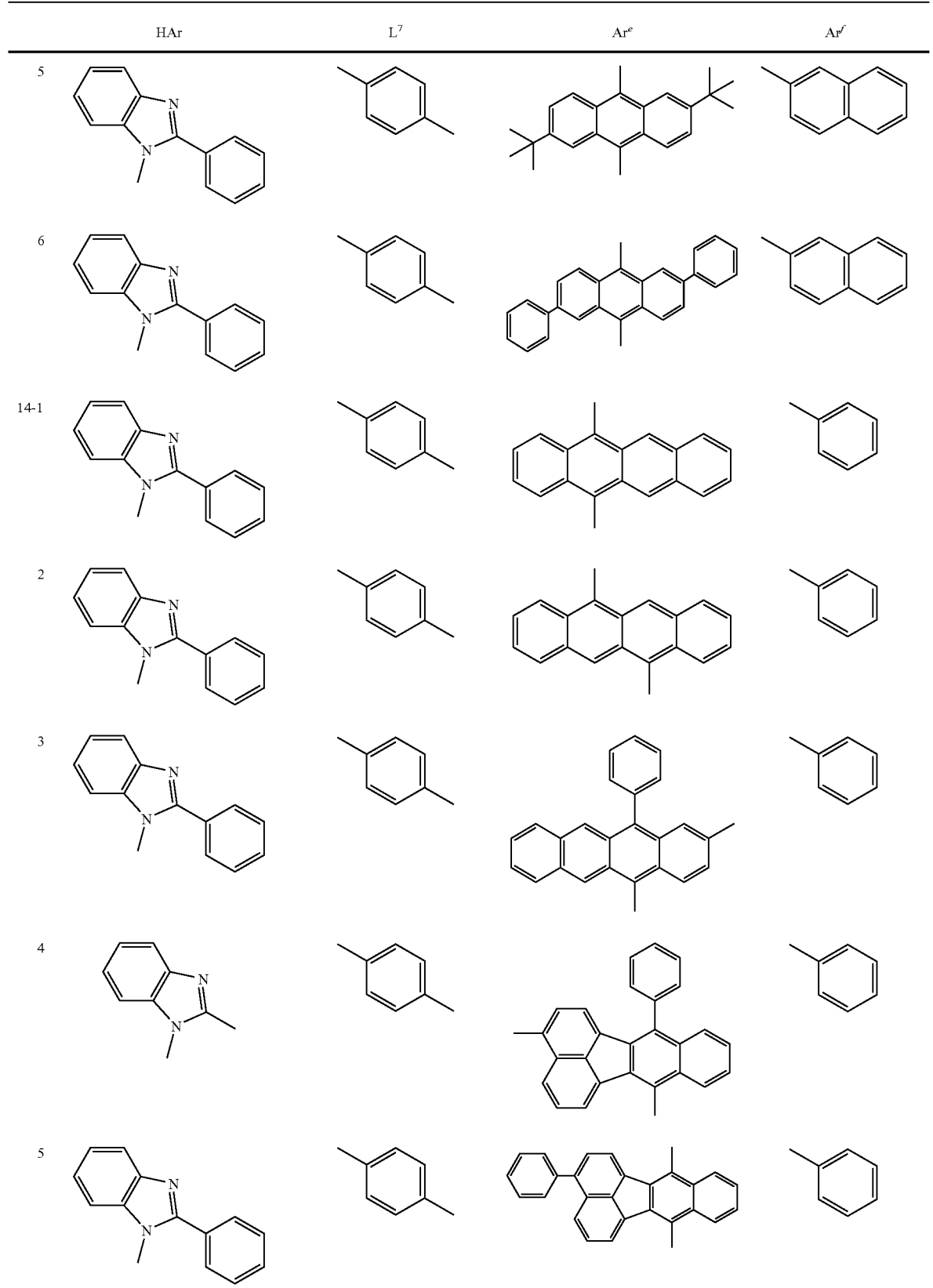

-continued
| HAr | L⁷ | Arᵉ | Arᶠ |
|---|---|---|---|
| 15-1 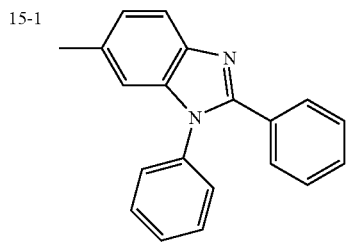 | — | 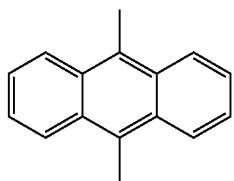 | 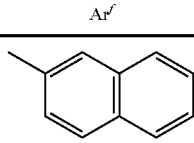 |
| 2 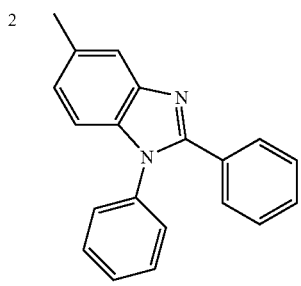 | — | 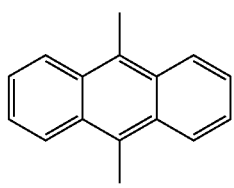 | 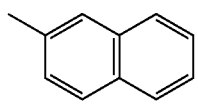 |
| 3 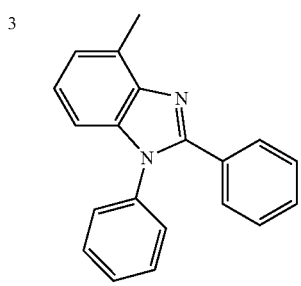 | — | 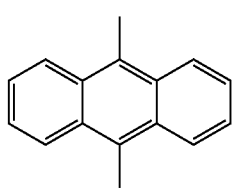 | 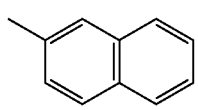 |
| 4 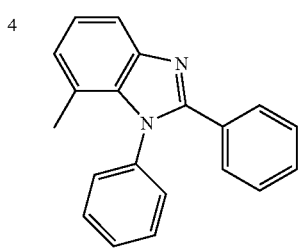 | — | 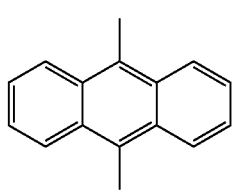 | 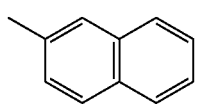 |
| 5 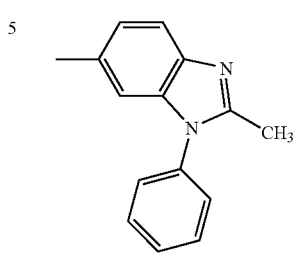 | — | 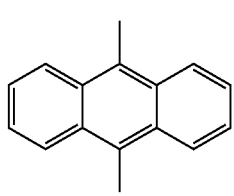 | 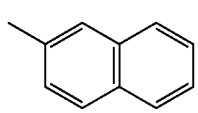 |
| 6 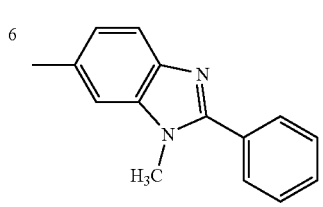 | — | 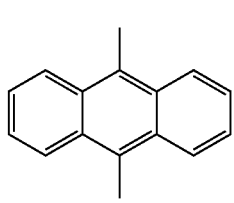 | |

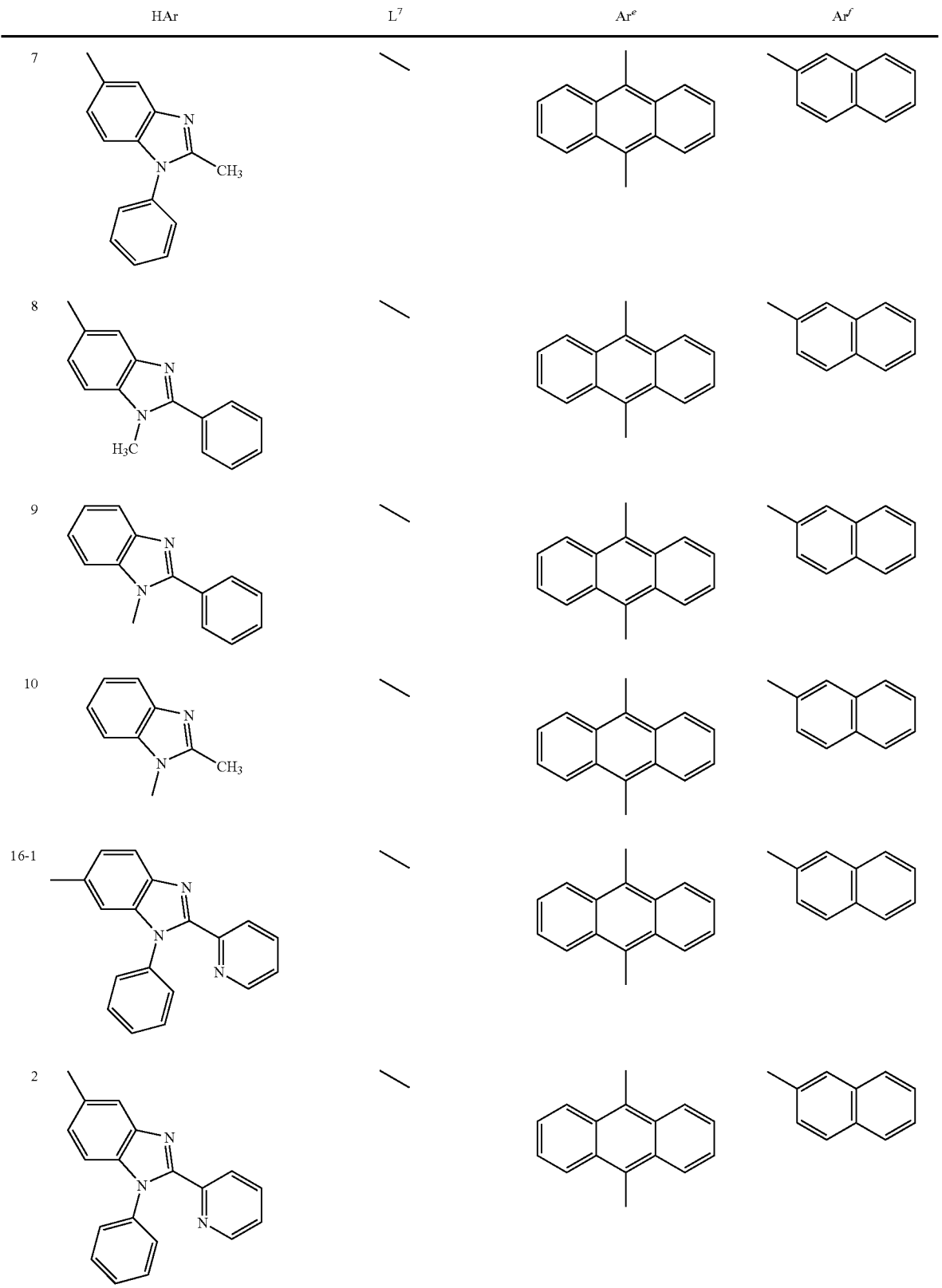

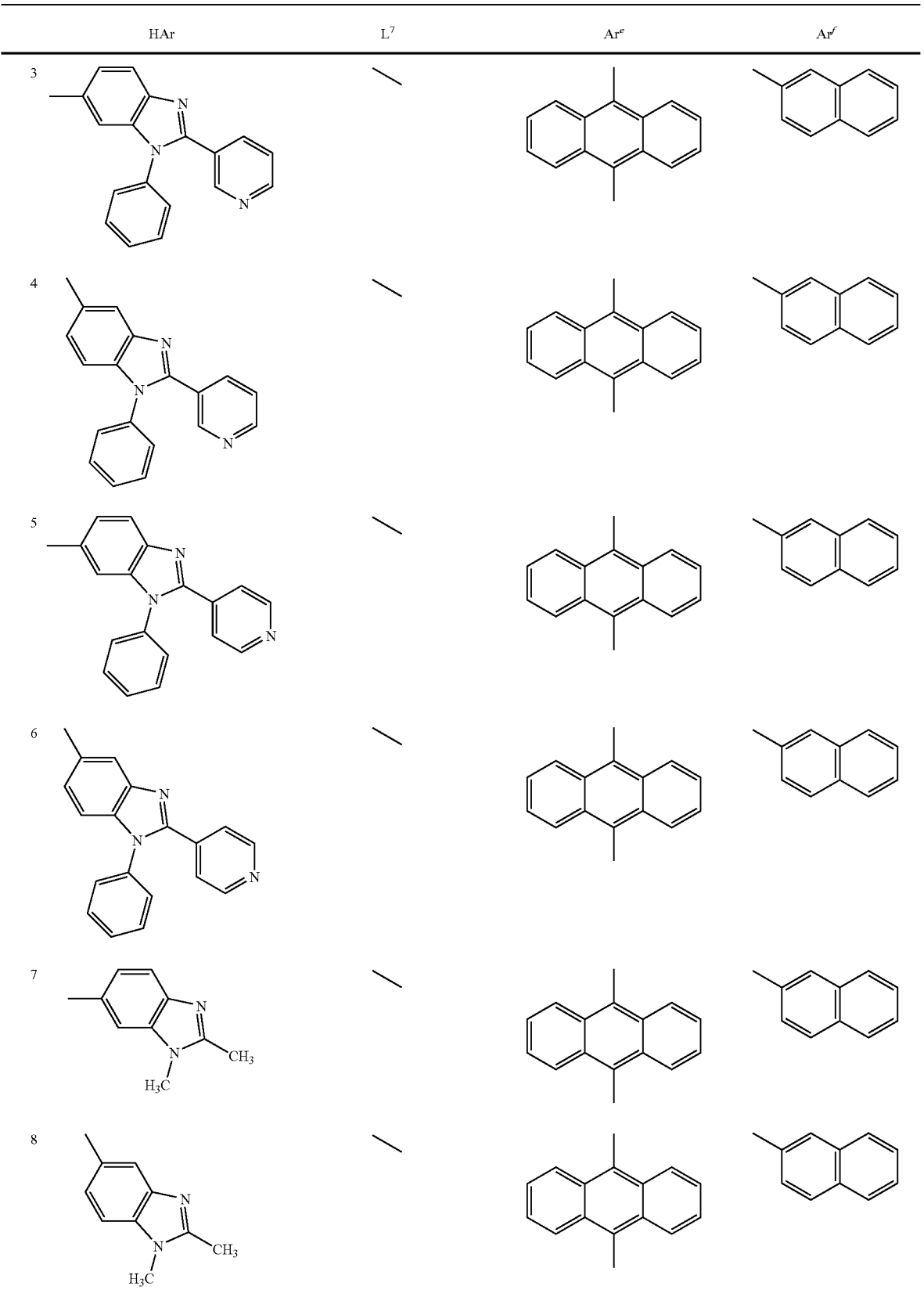

-continued
| | HAr—L⁷—Arᵉ—Arᶠ | | |
|---|---|---|---|
| HAr | L⁷ | Arᵉ | Arᶠ |
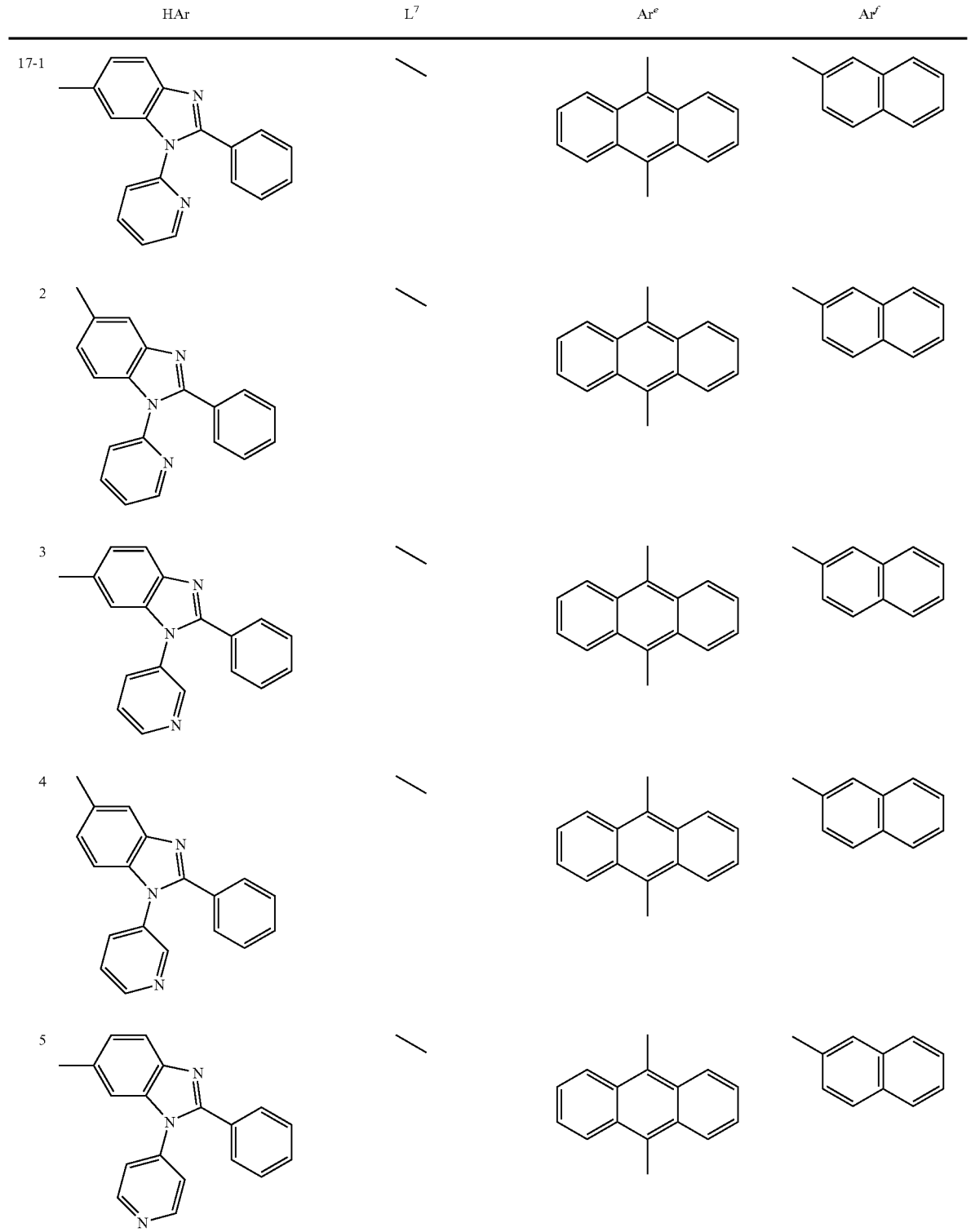

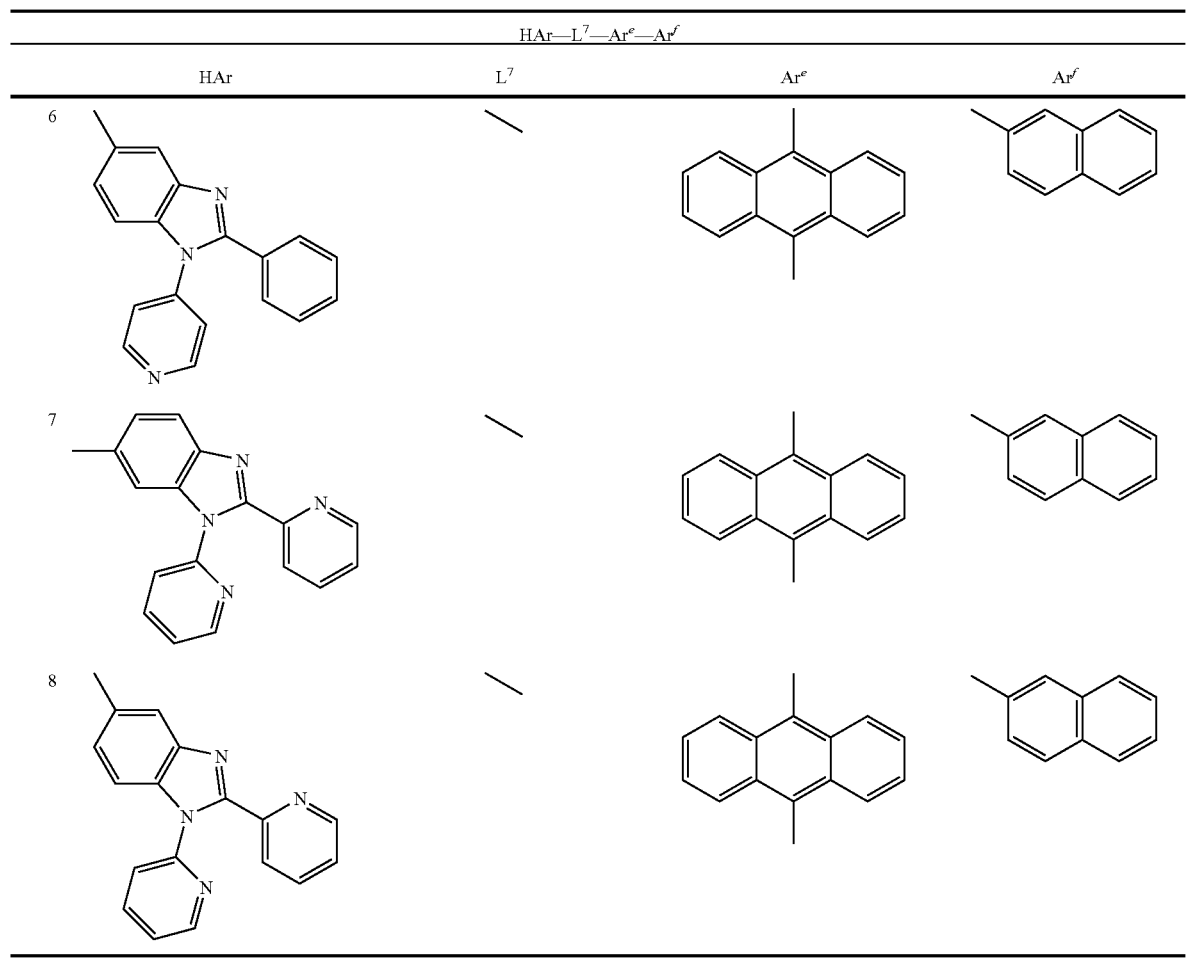

Of those specific examples, (1-1), (1-5), (1-7), (2-1), (3-1), (4-2), (4-6), (7-2), (7-7), (7-8), (7-9), (9-1), (9-7) are particularly preferred.

In addition, as the nitrogen-containing ring derivative, nitrogen-containing five-membered ring derivative are preferably exemplified. Examples of the nitrogen-containing five-membered ring include an imidazole ring, a triazole ring, a tetrazole ring, an oxadiazole ring, a thiadiazole ring, an oxatriazole ring, and a thiatriazole ring. Examples of the nitrogen-containing five-membered ring derivative include a benzoimidazole ring, a benzotriazole ring, a pyridinoimidazole ring, a pyrimidinoimidazole ring, and a pyridazinoimidazole ring. Particularly preferred is the compound represented by the following general formula (B).

$$L^B \!-\!\!\left(\!\!\begin{array}{c}N\\X^{B2}\end{array}\!\!\!\begin{array}{c}\\Z^{B2}\end{array}\!\!\right)_{\!n^{B2}} \qquad (B)$$

In the general formula (B), $L^B$ represents a divalent or more bonding group. Examples thereof include a carbon atoms, a silicon atom, a nitrogen atom, a boron atom, an oxygen atom, a sulfur atom, metal atoms (for example, a barium atom, a beryllium atom), aromatic hydrocarbon rings, aromatic heterocycles. Of those, preferred are a carbon atom, a nitrogen atom, a silicon atom, a boron atom, an oxygen atom, a sulfur atom, aromatic hydrocarbon rings, aromatic heterocyclic groups and more preferred are a carbon atom, a silicon atom, aromatic hydrocarbon rings, and aromatic heterocyclic groups.

The aromatic hydrocarbon rings and aromatic heterocyclic groups represented by $L^B$ may have a substituent. Examples of the substituent include alkyl groups, alkenyl groups, aryl groups, amino groups, alkoxy groups, aryloxy groups, acyl groups, alkoxycarbonyl groups, aryloxycarbonyl groups, acyloxy groups, acyloxyamino groups, alkoxycarbonylamino groups, aryloxycarbonylamino groups, sulfonylamino groups, sulfamoyl groups, carbamoyl groups, alkylthio groups, arylthio groups, sulfonyl groups, halogen atoms, cyano groups, and aromatic heterocyclic groups. Preferred are alkyl groups, aryl groups, alkoxy groups, aryloxy groups, halogen atoms, cyano groups, and aromatic heterocyclic groups, more preferred are alkyl groups, aryl groups, alkoxy groups, aryloxy groups, and aromatic heterocyclic groups, and particularly preferred are alkyl groups, aryl groups, alkoxy groups, and aromatic heterocyclic groups.

Specific examples of $L^B$ include compounds represented below.

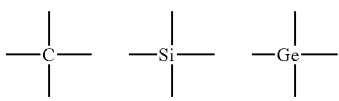

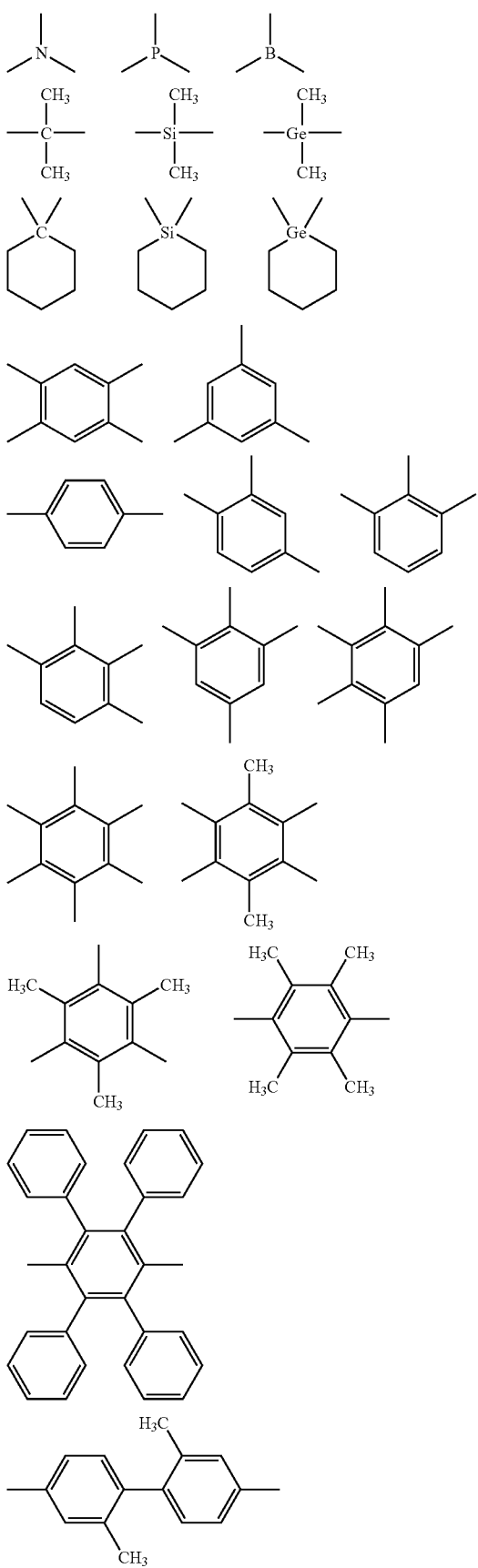

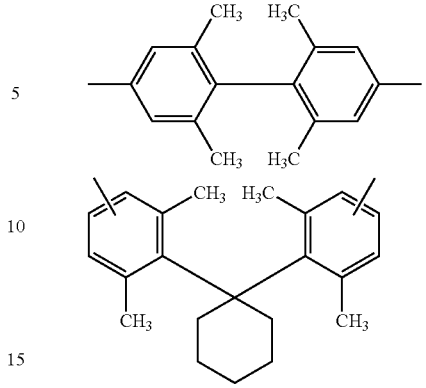

$X^{B2}$ in the general formula (B) represents —O—, —S—, or —N($R^{B2}$)—. $R^{B2}$ represents a hydrogen atom, an aliphatic hydrocarbon group, an aryl group, or a heterocyclic group.

The aliphatic hydrocarbon group represented by $R^{B2}$ is a linear or branched alkyl group (having preferably 1 to 20, more preferably to 12, or particularly preferably 1 to 8 carbon atoms such as a methyl group, an ethyl group, an isopropyl group, a t-butyl group, an n-octyl group, an n-decyl group, or an n-hexadecyl group), a cycloalkyl group (having a ring formed of preferably 3 to 10 carbon atoms such as a cyclopropyl group, a cyclopentyl group, or a cyclohexyl group), an alkenyl group (having preferably 2 to 20, more preferably 2 to 12, or particularly preferably 2 to 8 carbon atoms such as a vinyl group, an aryl group, a 2-butenyl group, or a 3-pentenyl group), or an alkynyl group (having preferably 2 to 20, more preferably 2 to 12, or particularly preferably 2 to 8 carbon atoms such as a propargyl group or a 3-pentynyl group), or is preferably an alkyl group.

The aryl group represented by $R^{B2}$ is a monocycle or a fused ring, and is an aryl group having a ring formed of preferably 6 to 30, more preferably 6 to 20, or still more preferably 6 to 12 carbon atoms. Examples of such group include a phenyl group, a 2-methylphenyl group, a 3-methylphenyl group, a 4-methylphenyl group, a 2-methoxyphenyl group, a 3-trifluoromethylphenyl group, a pentafluorophenyl group, a 1-naphthyl group, and a 2-naphthyl group. Of those, a phenyl group or a 2-methylphenyl group is preferable.

The heterocyclic group represented by $R^{B2}$ is a monocycle or a fused ring, and is a heterocyclic group having a ring formed of preferably 1 to 20, more preferably 1 to 12, or still more preferably 2 to 10 carbon atoms. The heterocyclic group is an aromatic heterocyclic group containing at least one heteroatom selected from a nitrogen atom, an oxygen atom, a sulfur atom, and a selenium atom. Examples of the heterocyclic group include groups derived from pyrrolidine, piperidine, piperazine, morpholine, thiophene, selenophene, furan, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phanazine, tetrazole, benzoimidazole, benzoxazole, benzothiazole, benzotriazole, tetrazaindene, carbazole, azepine, and the like. Preferred are groups derived from furan, thiophene, pyridine, pyrazine, pyrimidine, pyridazine, triazine, quinoline, phthalazine, naphthyridine, quinoxaline, and quinazoline, more preferred are groups derived from furan, thiophene, pyridine, and quinoline, and still more preferred is a quinolinyl group.

The aliphatic hydrocarbon group, the aryl group, and the heterocyclic group each represented by $R^{B2}$ may each have a substituent, and the substituent is preferably an alkyl group, an alkenyl group, an alkynyl group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group, or an aromatic heterocyclic group, more preferably an alkyl group, an aryl group, an alkoxy group, an aryloxy group, a halogen atom, a cyano group, or an aromatic heterocyclic group, still more preferably an alkyl group, an aryl group, an alkoxy group, an aryloxy group, or an aromatic heterocyclic group, or particularly preferably an alkyl group, an aryl group, an alkoxy group, or an aromatic heterocyclic group.

$R^{B2}$ preferably represents an aliphatic hydrocarbon group, an aryl group, or a heterocyclic group, more preferably represents an aliphatic hydrocarbon group (having preferably 6 to 30, more preferably 6 to 20, or still more preferably 6 to 12 carbon atoms) or an aryl group, or still more preferably represents an aliphatic hydrocarbon group (having preferably 1 to 20, more preferably 1 to 12, or still more preferably 2 to 10 carbon atoms).

$X^{B2}$ preferably represents —O— or —N($R^{B2}$)—, or more preferably represents —N($R^{B2}$)—.

$Z^{B2}$ represents atoms necessary for forming an aromatic ring. The aromatic ring formed of $Z^{B2}$ is any one of aromatic hydrocarbon rings and aromatic heterocyclic rings. Specific examples thereof include a benzene ring, a pyridine ring, a pyrazine ring, a pyrimidine ring, a pyridazine ring, a triazine ring, a pyrrole ring, a furan ring, a thiophene ring, a selenophene ring, a tellurophene ring, an imidazole ring, a thiazole ring, a selenazole ring, a tellulazole ring, a thiadiazole ring, an oxadiazole ring, and a pyrazole ring. Preferred are a benzene ring, a pyridine ring, a pyrazine ring, a pyrimidine ring, and a pyridazine ring, more preferred are a benzene ring, a pyridine ring, and a pyrazine ring, still more preferred are a benzene ring and pyridine ring, and particularly preferred is a pyridine ring.

The aromatic ring formed of $Z^{B2}$ may further form a fused ring with any other ring, or may have a substituent. Examples of the substituent include the same examples as those described for the substituent of the group represented by LB, and the substituent is preferably an alkyl group, an alkenyl group, an alkynyl group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group, or a heterocyclic group, more preferably an alkyl group, an aryl group, an alkoxy group, an aryloxy group, a halogen atom, a cyano group, or a heterocyclic group, still more preferably an alkyl group, an aryl group, an alkoxy group, an aryloxy group, or an aromatic heterocyclic group, or particularly preferably an alkyl group, an aryl group, an alkoxy group, or an aromatic heterocyclic group.

$n^{B2}$ represents an integer of 1 to 4, or preferably 2 or 3.

Of the nitrogen-containing five-membered ring derivatives each represented by the general formula (B), a derivative represented by the following general formula (B') is more preferable.

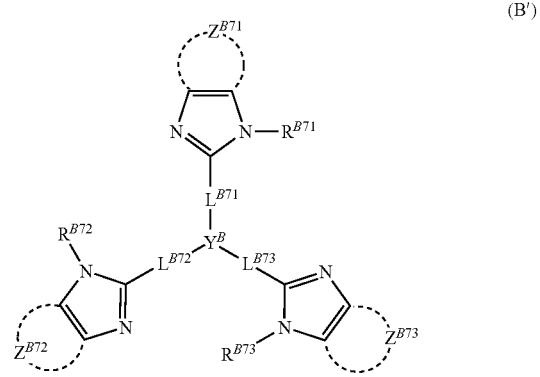

(B')

In the general formula (B'), $R^{B71}$, $R^{B72}$, and $R^{B73}$ each have the same meaning as that of $R^{B2}$ in the general formula (B), and preferable examples of $R^{B71}$, $R^{B72}$, and $R^{B73}$ are also the same as those of $R^{B2}$.

In the formula, $Z^{B71}$, $Z^{B72}$ and $Z^{B73}$ each have the same meaning as that of $Z^{B2}$ in the general formula (B), and preferable examples of $Z^{B71}$, $Z^{B72}$, and $Z^{B73}$ are also the same as those of $Z^{B2}$.

In the formula, $L^{B71}$, $L^{B72}$, and $L^{B73}$ each represent a linking group, and examples of the linking group include examples obtained by making the examples of $L^B$ in the general formula (B) divalent. The linking group is preferably a single bond, a divalent aromatic hydrocarbon ring group, a divalent aromatic heterocyclic group, or a linking group composed of a combination of two or more of them, or is more preferably a single bond. $L^{B7}$, $L^{B72}$, and $L^{B73}$ may each have a substituent. Examples of the substituent include the same examples as those described for the substituent of the group represented by $L^B$ in the general formula (B), and preferable examples of the substituent also include the same preferable examples as those described for the substituent of the group represented by $L^B$ in the general formula (B).

In the formula, $Y^B$ represents a nitrogen atom, a 1,3,5-benzenetriyl group, or a 2,4,6-triazinetriyl group. The 1,3,5-benzenetriyl group may have a substituent at any one of its 2-, 4-, and 6-positions, and examples of the substituent include an alkyl group, an aromatic hydrocarbon ring group, and a halogen atom.

Specific examples of the nitrogen-containing five-membered ring derivative represented by the general formula (B) or (B') are shown below. However, the present invention is not limited to these exemplified compounds.

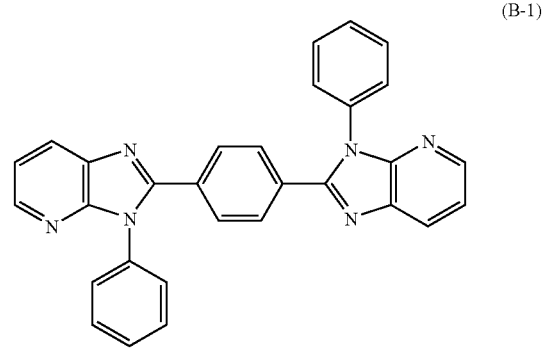

(B-1)

(B-2) 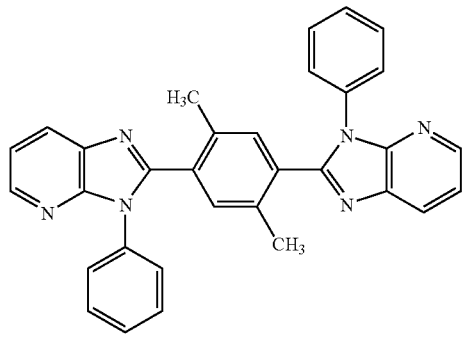
(B-6) 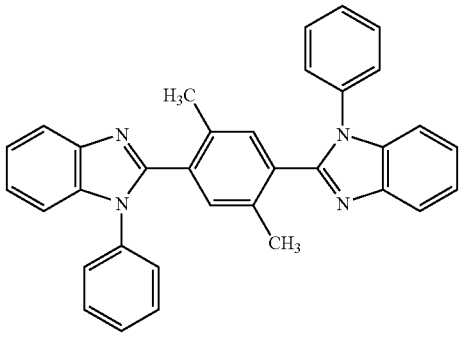
(B-3) 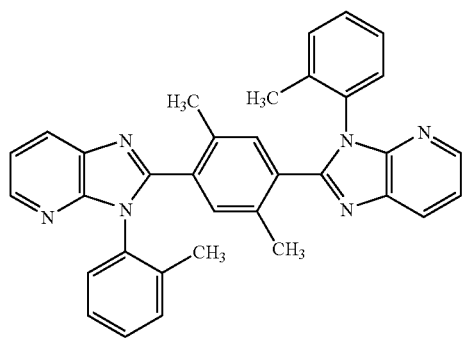
(B-7) 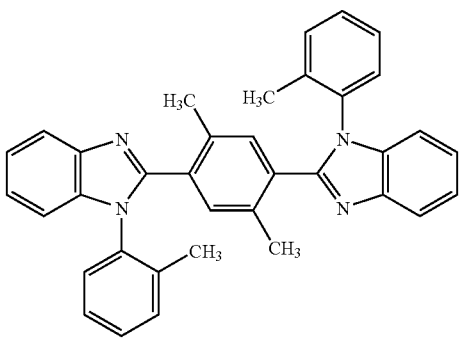
(B-4) 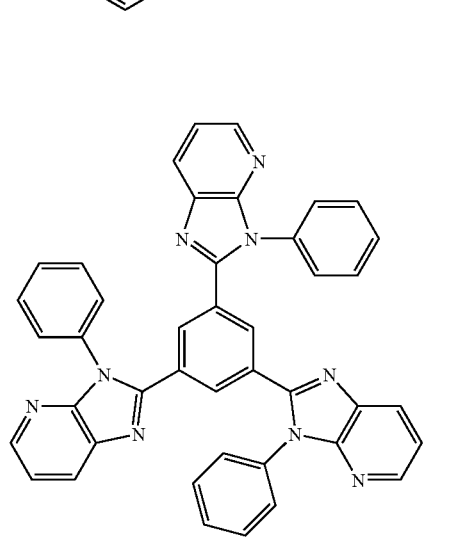
(B-8) 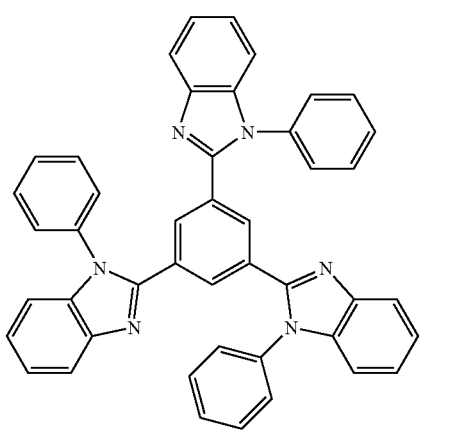
(B-5) 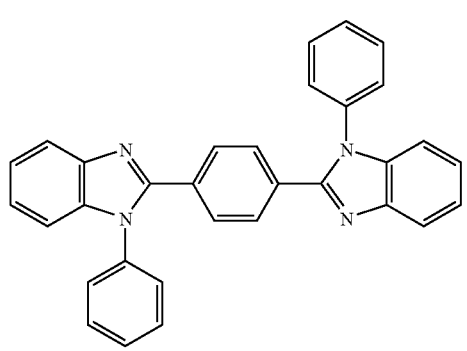
(B-9) 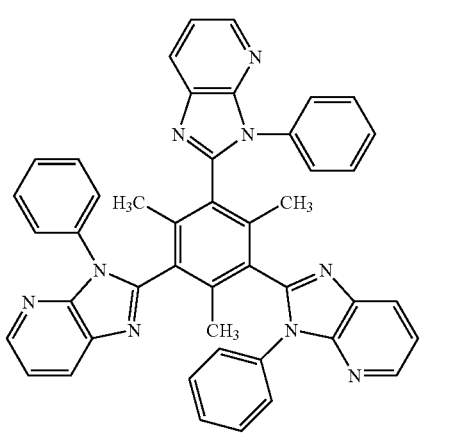

-continued
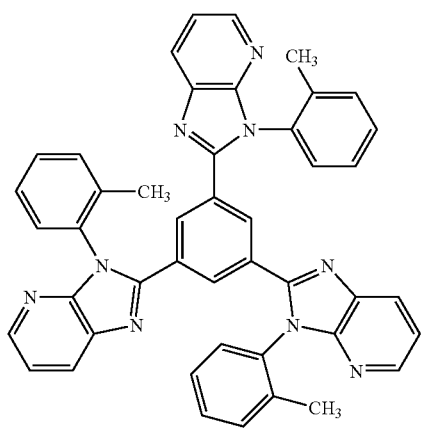
(B-10)
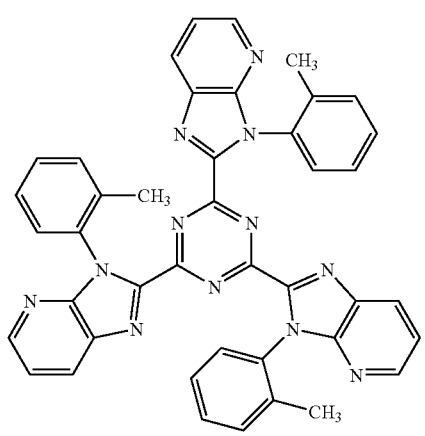
(B-11)
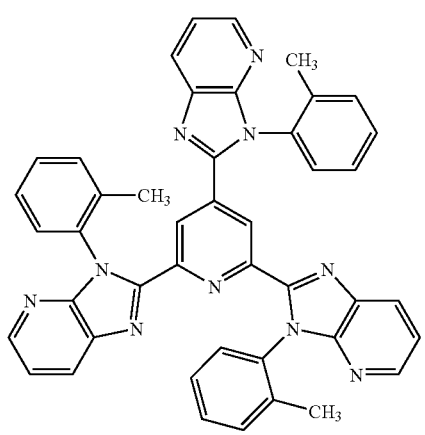
(B-12)
-continued
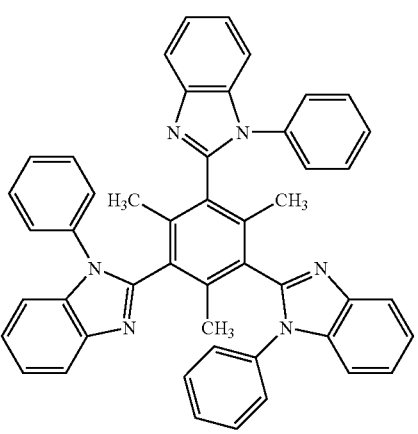
(B-13)
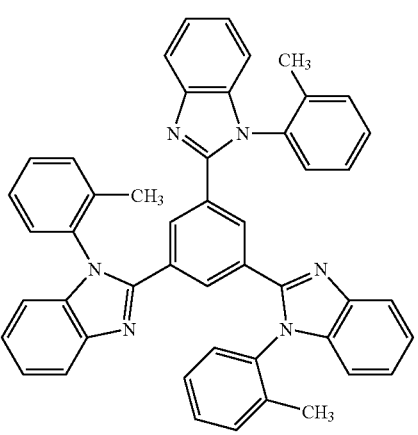
(B-14)
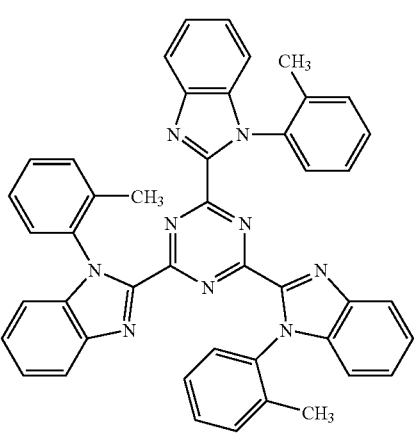
(B-15)

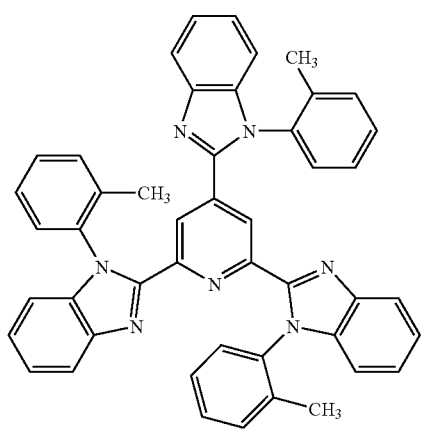

(B-16)

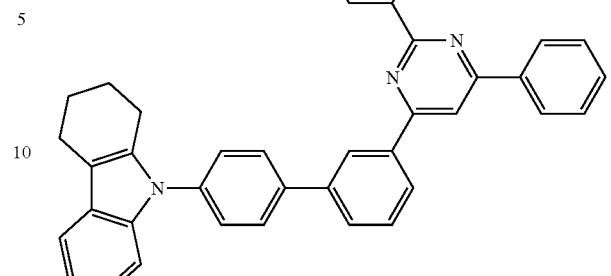

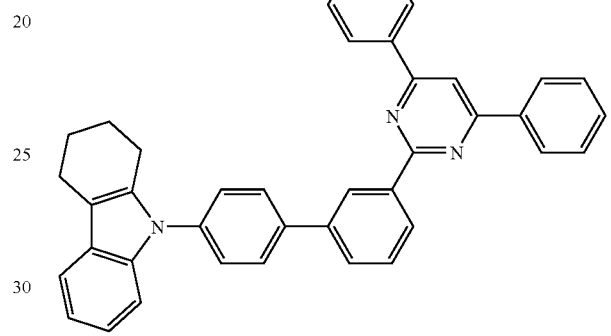

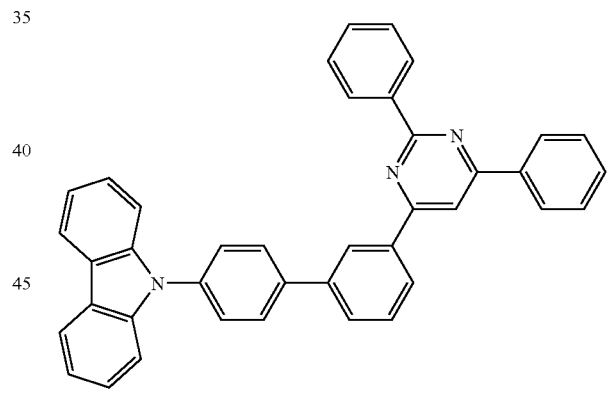

A compound of which each of the electron injecting layer and the electron transporting layer is constituted is, for example, a compound having a structure obtained by combining an electron-deficient, nitrogen-containing five-membered ring skeleton or electron-deficient, nitrogen-containing six-membered ring skeleton and a substituted or unsubstituted indole skeleton, substituted or unsubstituted carbazole skeleton, or substituted or unsubstituted azacarbazole skeleton as well as the material for an organic EL device of the present invention. In addition, a suitable electron-deficient, nitrogen-containing five-membered ring skeleton or electron-deficient, nitrogen-containing six-membered ring skeleton is a molecular skeleton such as a pyridine, pyrimidine, pyrazine, triazine, triazole, oxadiazole, pyrazole, imidazole, quinoxaline, or pyrrole skeleton, or benzimidazole or imidazopyridine obtained when two or more of them fuse with each other. Of those combinations, a preferable combination is, for example, a combination of a pyridine, pyrimidine, pyrazine, or triazine skeleton and a carbazole, indole, azacarbazole, or quinoxaline skeleton. The above-mentioned skeleton may be substituted or unsubstituted.

Specific examples of an electron transportable compound are shown below. However, the present invention is not particularly limited to these examples.

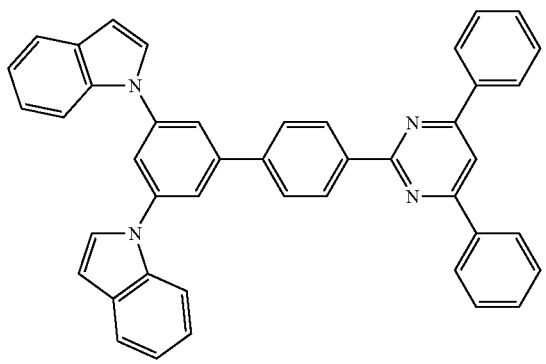

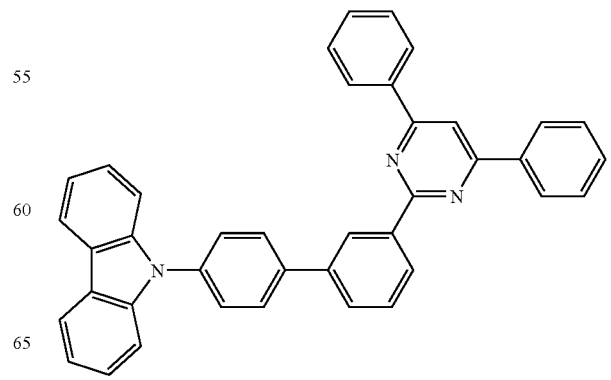

281
-continued
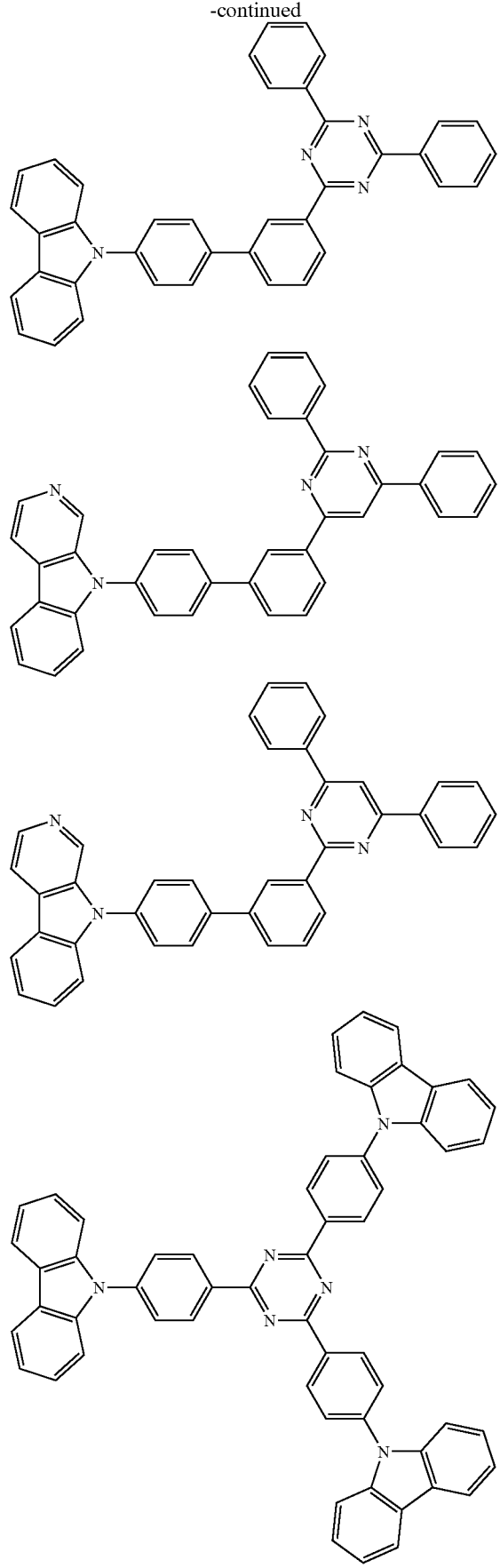
282
-continued
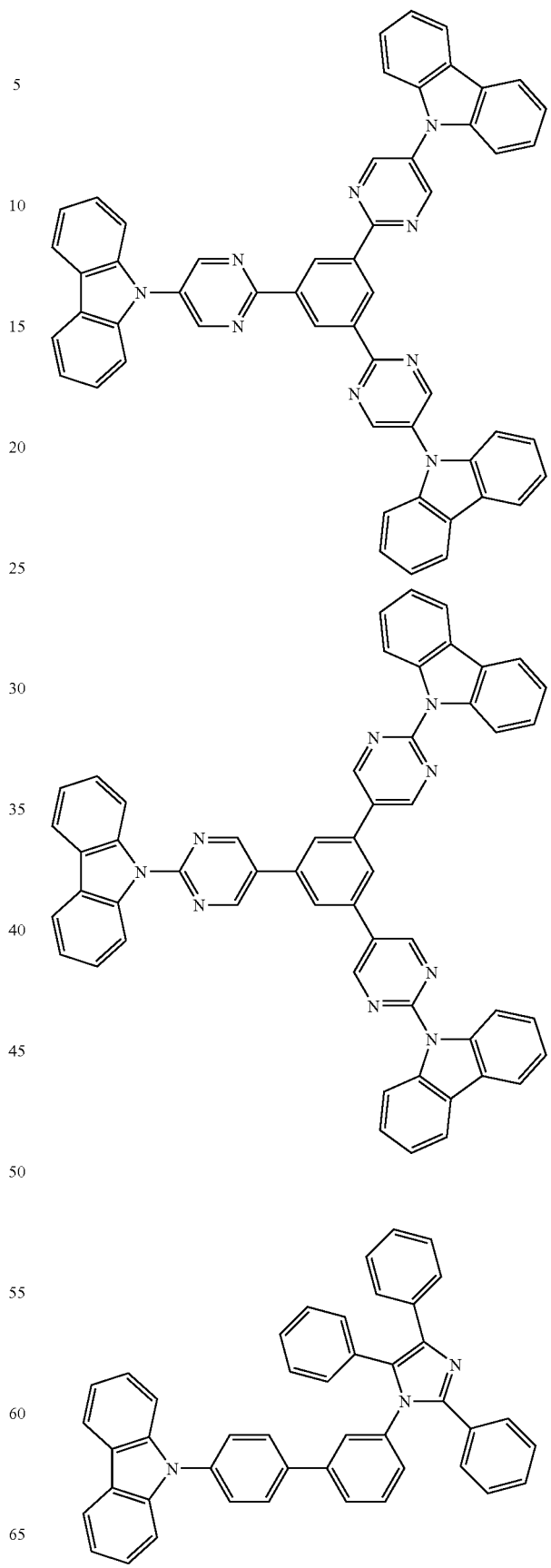

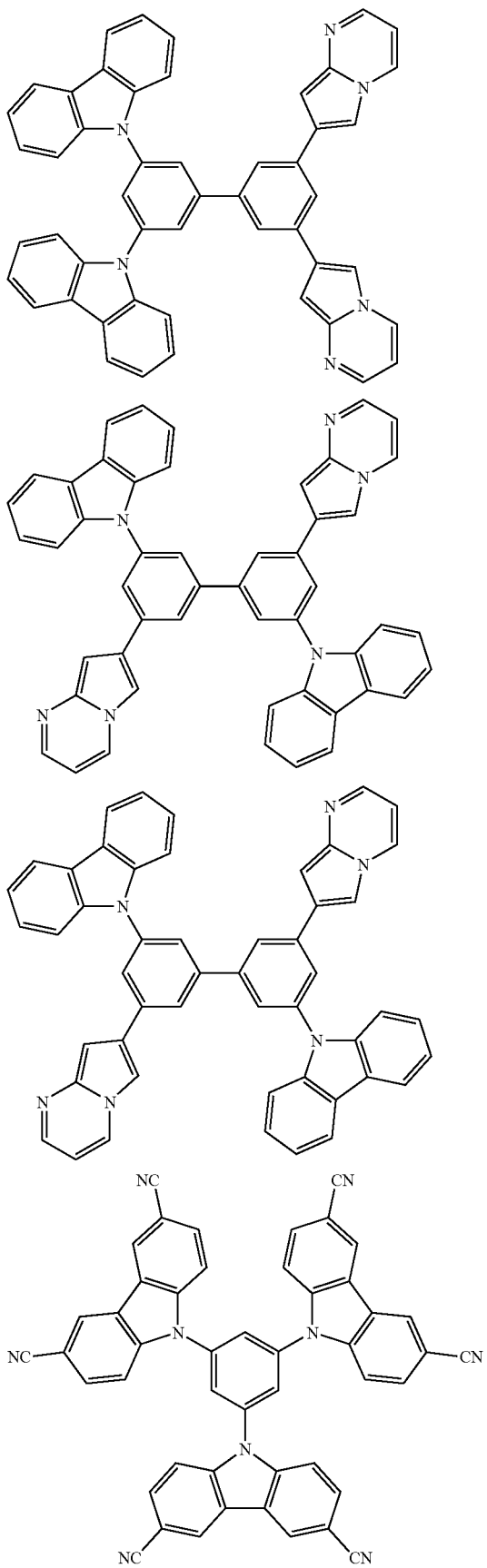

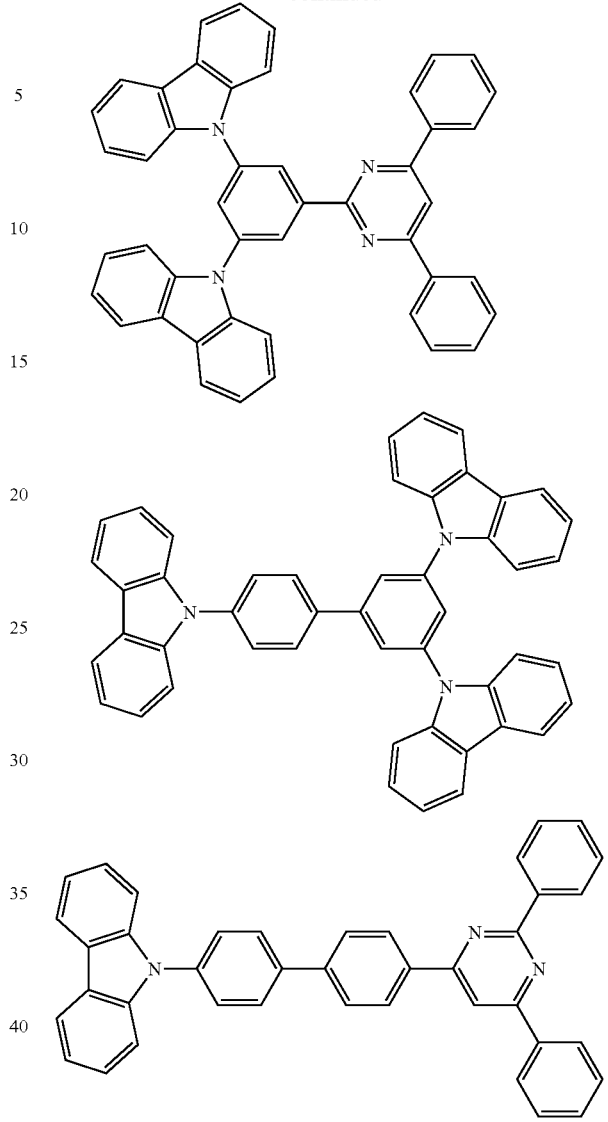

Each of the electron injecting layer and the electron transporting layer may be of a monolayer structure composed of one or two or more kinds of the above materials, or may be of a multi-layered structure composed of multiple layers identical to or different from each other in composition. Materials for those layers each preferably have a n-electron-deficient, nitrogen-containing heterocyclic group.

In addition, an insulator or semiconductor serving as an inorganic compound as well as the nitrogen-containing ring derivative is preferably used as a component of the electron injecting layer. When the electron injecting layer is constituted of an insulator or semiconductor, current leakage can be effectively prevented, and the electron injecting property of the layer can be improved.

As the insulator, at least one metal compound selected from the group consisting of alkali metal chalcogenides, alkaline earth metal chalcogenides, alkali metal halides, and alkaline earth metal halides is preferably used. It is preferable that the electron injecting layer be composed of the above-mentioned substance such as the alkali metal chalcogenide since the electron injecting property can be further improved. To be specific, preferable examples of the alkali metal chalcogenide include $Li_2O$, $K_2O$, $Na_2S$, $Na_2Se$, and $Na_2O$, and preferable examples of the alkaline earth metal chalcogenide include CaO, BaO, SrO, BeO, BaS, and CaSe. Preferable examples of the alkali metal halide include LiF, NaF, KF, LiCl, KCl, and NaCl. Preferable examples of the alkaline earth metal halide include fluorides such as $CaF_2$, $BaF_2$, $SrF_2$, $MgF_2$, and $BeF_2$ and halides other than the fluorides.

In addition, examples of the semiconductor include oxides, nitrides, and oxide nitrides containing at least one element selected from the group consisting of Ba, Ca, Sr, Yb, Al, Ga, In, Li, Na, Cd, Mg, Si, Ta, Sb, and Zn used alone or in combination of two or more. It is preferable that the inorganic compound composing the electron injecting layer form a crystallite or amorphous insulating thin film. When the electron injecting layer is composed of the insulating thin film described above, a more uniform thin film can be formed, and defects of pixels such as dark spots can be decreased. Examples of the inorganic compound include alkali metal chalcogenides, alkaline earth metal chalcogenides, alkali metal halides, and alkaline earth metal halides which are described above.

In addition, the above-mentioned reducing dopant can be preferably incorporated into the electron injecting layer in the present invention.

It should be noted that the thickness of each of the electron injecting layer and the electron transporting layer, which is not particularly limited, is preferably 1 to 100 nm.

An aromatic amine compound such as an aromatic amine derivative represented by a general formula (I) is suitably used in the hole injecting layer or hole transporting layer (a hole injecting/transporting layer is also included in this category).

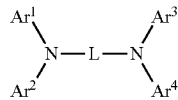

In the general formula (I), $Ar^1$ to $Ar^4$ each represent a substituted or unsubstituted aryl group having a ring formed of 6 to 50 carbon atoms, or a substituted or unsubstituted heteroaryl group having a ring formed of 5 to 50 atoms.

Examples of the substituted or unsubstituted aryl group having 6 to 50 ring hydrocarbon atoms include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, a fluoranthenyl group, and a fluorenyl group.

Examples of the substituted or unsubstituted heteroaryl group having a ring formed of 5 to 50 atoms include a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl1-indolyl group, a 4-t-butyl1-indolyl group, a 2-t-butyl3-indolyl group, and a 4-t-butyl3-indolyl group. Preferred are a phenyl group, a naphthyl group, a biphenyl group, an anthranyl group, a phenanthryl group, a pyrenyl group, a chrycenyl group, a fluoranthenyl group, and a fluorenyl group.

L represents a linking group, and specifically, a substituted or unsubstituted arylene group having a ring formed of 6 to 50 carbon atoms, a substituted or unsubstituted heteroarylene group having a ring formed of 5 to 50 carbon atoms, or a divalent group in which two or more arylene groups or heteroarylene groups are bonded by a single bond, an ether bond, a thioether bond, with an alkylene group having 1 to 20 carbon atoms, an alkenylene group having 2 to 20 carbon atoms, and an amino group. Examples of the arylene group having a ring formed of 6 to 50 carbon atoms include a 1,4-phenylene group, a 1,2-phenylene group, a 1,3-phenylene group, a 1,4-naphthylene group, a 2,6-naphthylene group, a 1,5-naphthylene group, a 9,10-anthranylene group, a 9,10-phenanthrenylene group, a 3,6-phenanthrenylene group, 1,6-pyrenylene group, a 2,7-pyrenylene group, a 6,12-chrycenylene group, a 4,4'-biphenylene group, a 3,3'-biphenylene group, a 2,2'-biphenylene group, and a 2,7-fluorenylene group. Examples of the arylene group having a ring formed of 5 to 50 atoms include a 2,5-thiophenylene group, a 2,5-silolylene group, and a 2,5-oxadiazolylene group. Preferred are a 1,4-phenylene group, a 1,2-phenylene group, a 1,3-phenylene group, a 1,4-naphthylene group, a 9,10-anthranylene group, a 6,12-chrysenylene group, a 4,4'-biphenylene group, a 3,3'-biphenlene group, a 2,2'-biphenylene group, and a 2,7-fluorenylene group. Examples of the arylene group having a ring formed of 5 to 50 atoms include a 2,5-thiphenylene group, a 2,5-silolylene group, and a 2,5-oxadiazolylene group. Preferred are a 1,4-phenylene group, a 1,2-phenylene group, a 1,3-phenylene group, a 1,4-naphthylene group, a 9,10-anthranylene group, a 6,12-chrysenylene group, a 4,4'-biphenylene group, a 3,3'-biphenylene group, a 2,2'-biphenylene group, and a 2,7-fluorenylene group.

In the case where L represents a linking group formed of two or more arylene groups or heteroarylene groups, adjacent arylene groups or heteroarylene groups may be bonded to each other through a divalent group to form a ring. Examples of the divalent group forming a ring include a tetra methylene group, a penta methylene group, a hexa methylene group, a diphenylmethane-2,2'-diyl group, a diphenyl ethane-3,3'-diyl group, and a diphenylpropane-4,4'-diyl group.

The substituent of each of $Ar^1$ to $Ar^4$ and L is, for example, a substituted or unsubstituted aryl group having a ring formed of 6 to 50 carbon atoms, a substituted or unsubstituted heteroaryl group having a ring formed of 5 to 50 atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having a ring formed of 6 to 50 carbon atoms, a substituted or unsubstituted heteroaryloxy group having a ring formed of 5 to 50 atoms, a substituted or unsubstituted arylthio group having a ring formed of 6 to 50 carbon atoms, a substituted or unsubstituted heteroarylthio group having a ring formed of 5 to 50 atoms, a substituted or unsubstituted alkoxycarbonyl group having 2 to 50 carbon atoms, an amino group substituted by a substituted or unsubstituted aryl group having a ring formed of 6 to 50 carbon atoms or by a substituted or unsubstituted heteroaryl group having a ring formed of 5 to 50 atoms, a halogen group, a cyano group, a nitro group, or a hydroxyl group.

Examples of the substituted or unsubstituted aryl group having 6 to 50 ring hydrocarbon atoms include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, a fluoranthenyl group, and a fluorenyl group.

Examples of the substituted or unsubstituted heteroaryl group having a ring formed of 5 to 50 atoms include a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin- 5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl1-indolyl group, a 4-t-butyl1-indolyl group, a 2-t-butyl3-indolyl group, and a 4-t-butyl3-indolyl group.

Examples of the substituted or unsubstituted alkyl group having 1 to 50 carbon atoms include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroispropyl group, a 2,3-dinitro-t-butyl group, and 1,2,3-trinitropropyl group.

Examples of the substituted or unsubstituted cycloalkyl group having 3 to 50 carbon atoms include a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group.

The substituted or unsubstituted alkoxy group having 1 to 50 carbon atoms is a group represented by —OY. Examples of Y include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroispropyl group, a 2,3-dinitro-t-butyl group, and 1,2,3-trinitropropyl group.

Examples of the substituted or unsubstituted aralkyl group having 7 to 50 carbon atoms include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrolylmethyl group, a 2-(1-pyrrolyl)ethyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, a no-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenylisopropyl group, and a 1-chloro-2-phenylisopropyl group.

Examples of the substituted or unsubstituted aryloxy group having a ring formed of 6 to 50 carbon atoms is represented by —OY'. Examples of Y' include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1- naphthyl group, a 4-methyl-1-anthryl group, a 4'-methylbiphenylyl group, and a 4"-t-butyl-p-terphenyl-4-yl group.

Examples of the substituted or unsubstituted heteroaryloxy group having a ring formed of 5 to 50 atoms is represented by —OZ'. Examples of Z' include a 2-pyrrolyl group, a 3-pyrrolyl group, a pyrazinyl group, a 2-pyridinyl group, a 3-pyridinyl group, a 4-pyridinyl group, a 2-indolyl group, a 3-indolyl group, a 4-indolyl group, a 5-indolyl group, a 6-indolyl group, a 7-indolyl group, a 1-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 1-phenoxadinyl group, a 2-phenoxadinyl group, a 3-phenoxadinyl group, a 4-phenoxadinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl1-indolyl group, a 4-t-butyl1-indolyl group, a 2-t-butyl3-indolyl group, and a 4-t-butyl3-indolyl group.

The substituted or unsubstituted arylthio group having a ring formed of 6 to 50 carbon atoms is represented by —SY". Examples of Y" include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenylyl group, and a 4"-t-butyl-p-terphenyl-4-yl group.

The substituted or unsubstituted heteroarylthio group having a ring formed of 5 to 50 atoms is represented by —SZ". Examples of Z" include a 2-pyrrolyl group, a 3-pyrrolyl group, a pyrazinyl group, a 2-pyridinyl group, a 3-pyridinyl group, a 4-pyridinyl group, a 2-indolyl group, a 3-indolyl group, a 4-indolyl group, a 5-indolyl group, a 6-indolyl group, a 7-indolyl group, a 1-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9- phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 1-phenoxazinyl group, a 2-phenoxazinyl group, a 3-phenoxazinyl group, a 4-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl1-indolyl group, a 4-t-butyl1-indolyl group, a 2-t-butyl3-indolyl group, and a 4-t-butyl3-indolyl group.

The substituted or unsubstituted alkoxycarbonyl group having 2 to 50 carbon atoms is represented by —COOZ. Examples of Z include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and 1,2,3-trinitropropyl group.

The substituted or unsubstituted aryl group having a ring formed of 6 to 50 carbon atoms or an amino group substituted with a substituted or unsubstituted heteroaryl group having a ring formed of 5 to 50 atoms is represented by —NPQ. Examples of P and Q include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, a an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenylyl group, and a 4"-t-butyl-p-terphenyl-4-yl group, a 2-pyrrolyl group, a 3-pyrrolyl group, pyrazinyl group, a 2-pyridinyl group, a 3-pyridinyl group, a 4-pyridinyl group, a 2-indolyl group, a 3-indolyl group, a 4-indolyl group, a 5-indolyl group, a 6-indolyl group, a 7-indolyl group, a 1-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 1-phenoxazinyl group, a 2-phenoxazinyl group, a 3-phenoxazinyl group, a 4-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl1-indolyl group, a 4-t-butyl1-indolyl group, a 2-t-butyl3-indolyl group, and a 4-t-butyl3-indolyl group.

Specific examples of the compound represented by the general formula (I) are shown below. However, the present invention is not limited to these examples.

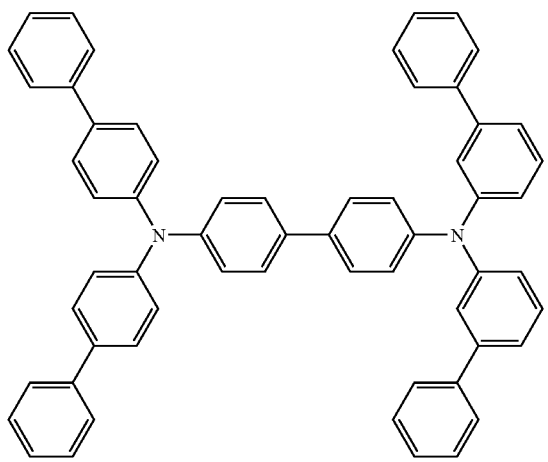

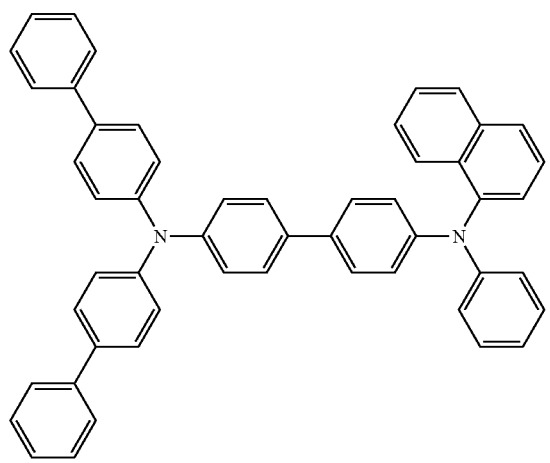

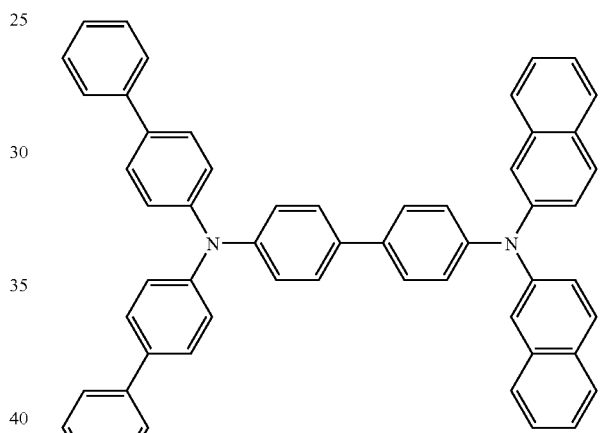

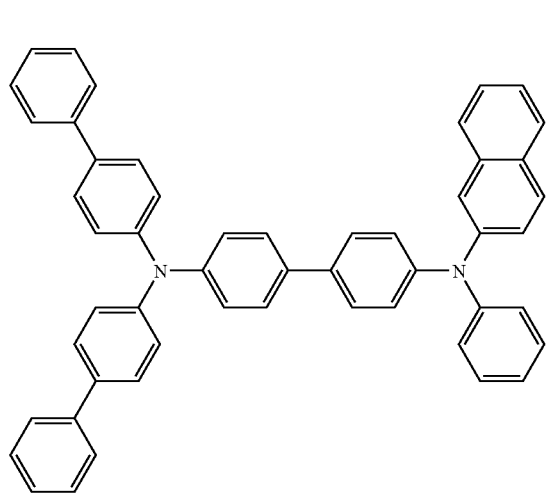

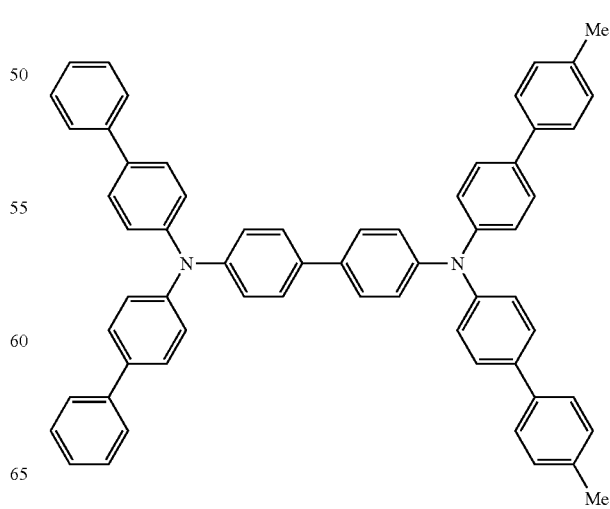

297
-continued
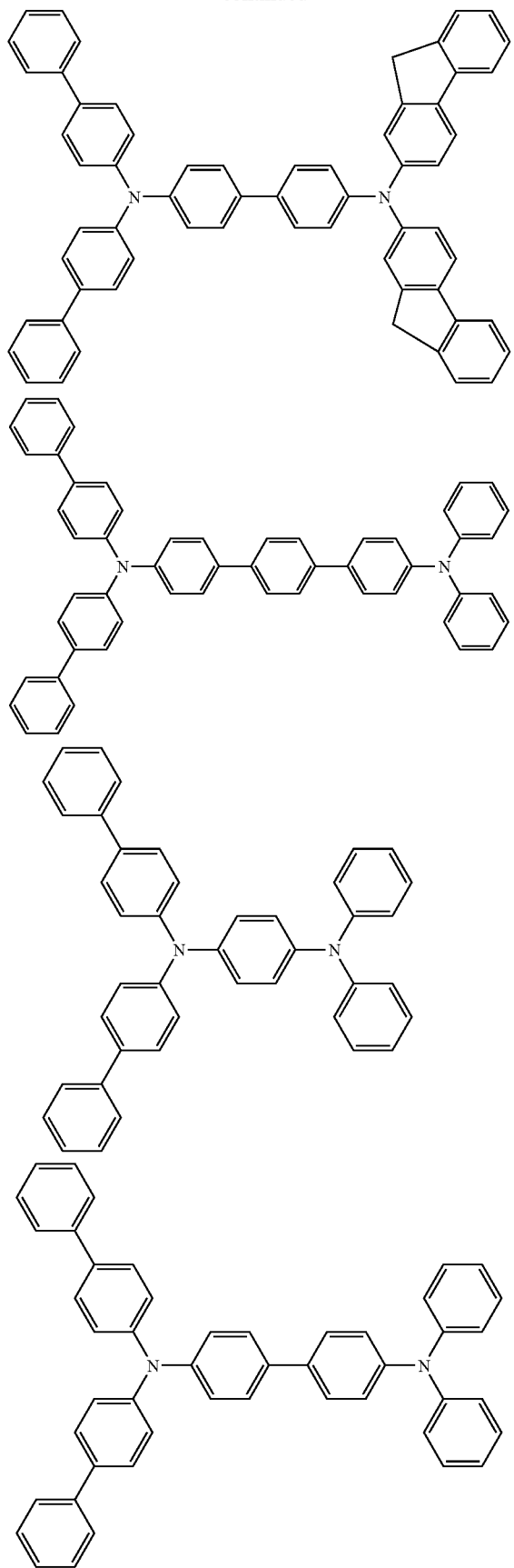
298
-continued
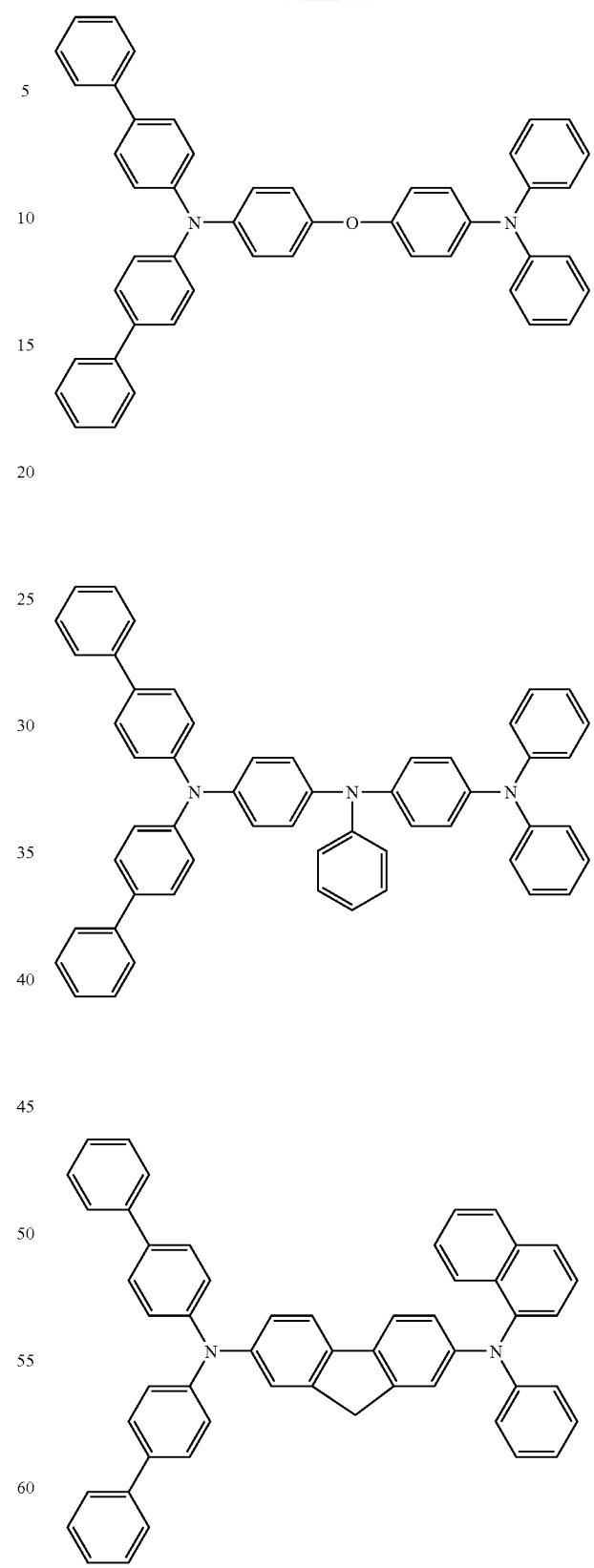

299
-continued
300
-continued
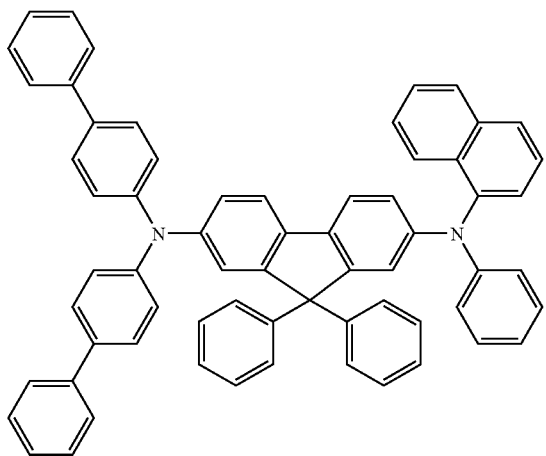
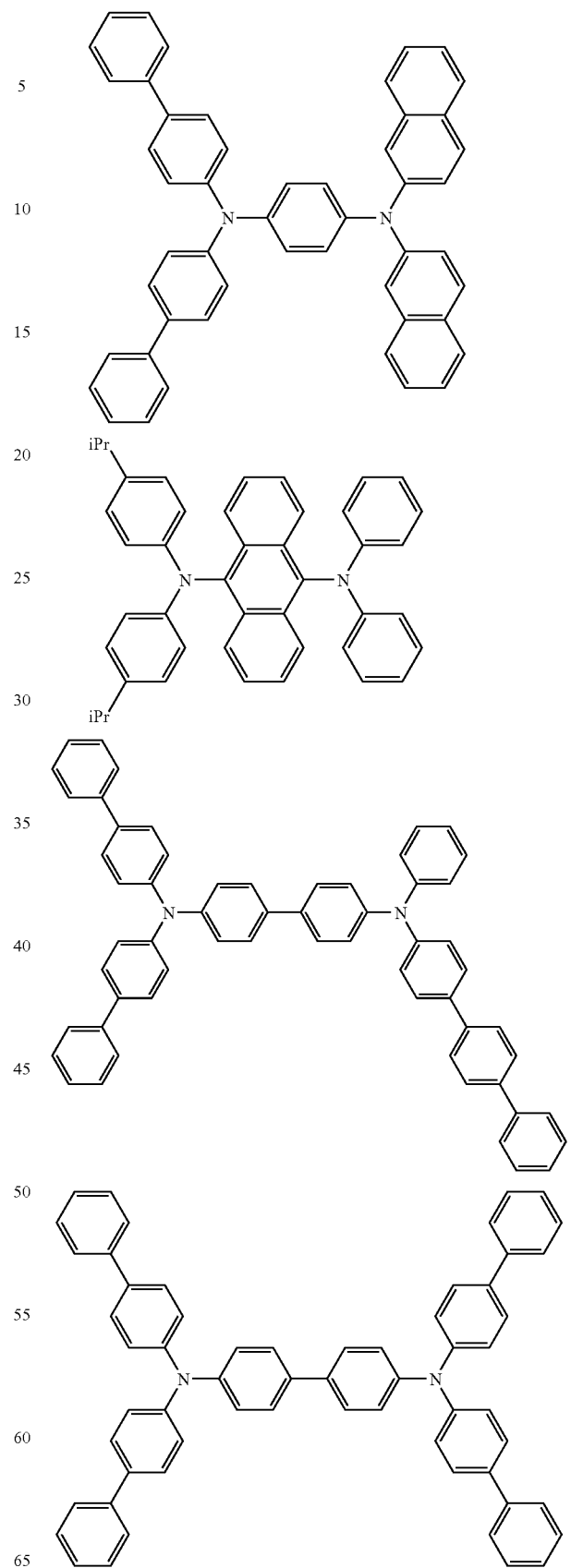

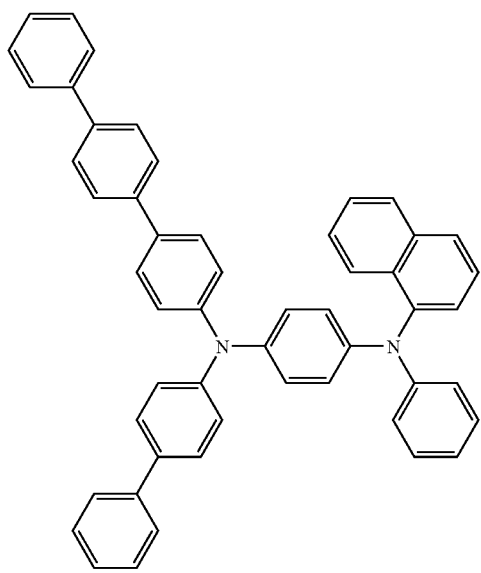

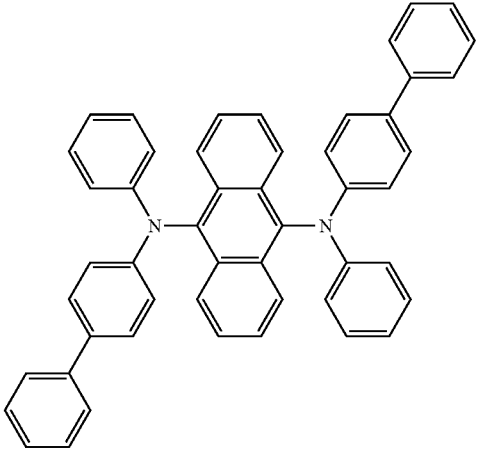

In addition, an aromatic amine represented by the following general formula (II) is also suitably used in the formation of the hole injecting layer or hole transporting layer.

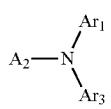
(II)

In the general formula (II), the definition of $Ar^1$ to is the same as that of $Ar^1$ to $Ar^4$ in the general formula (I). Specific examples of the compound represented by the general formula (II) are shown below. However, the present invention is not limited to these examples.

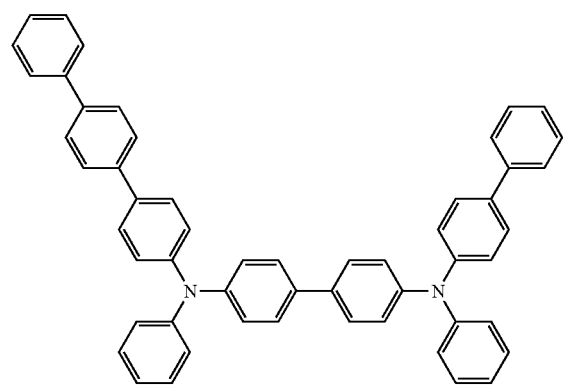

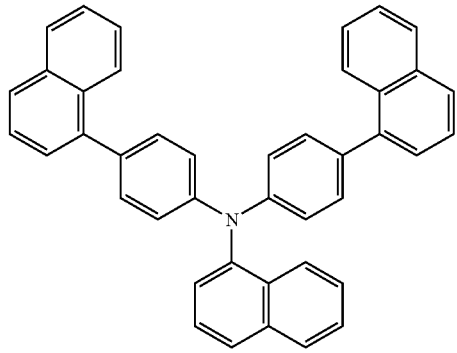

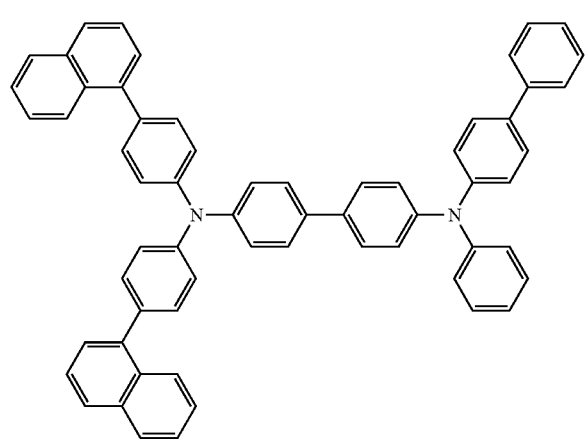

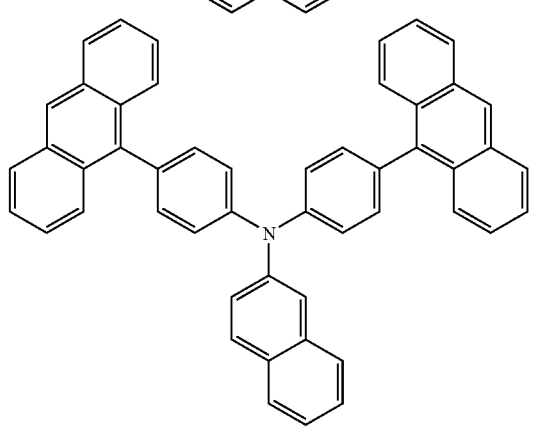

303
-continued
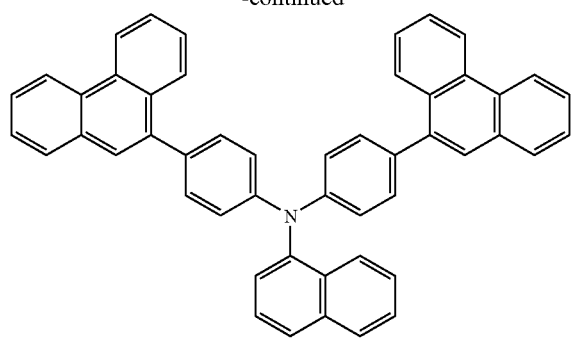
304
-continued
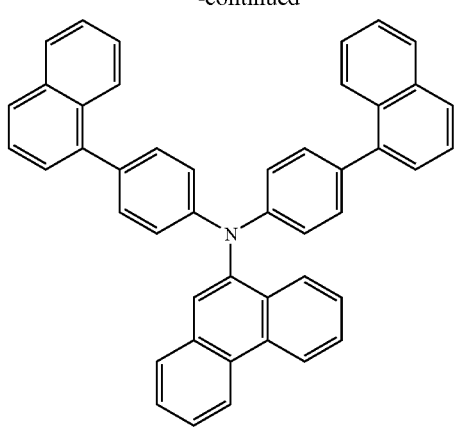
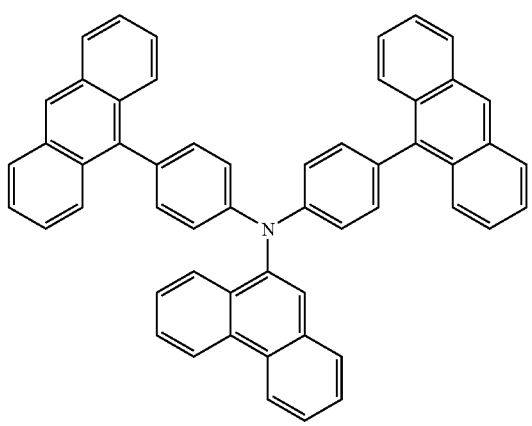
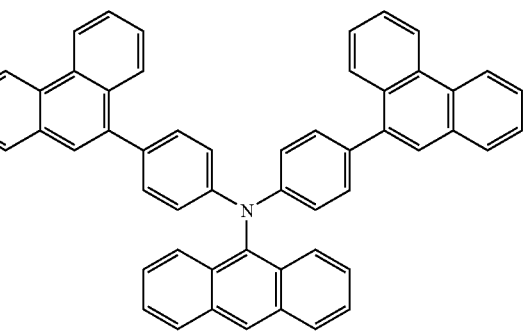
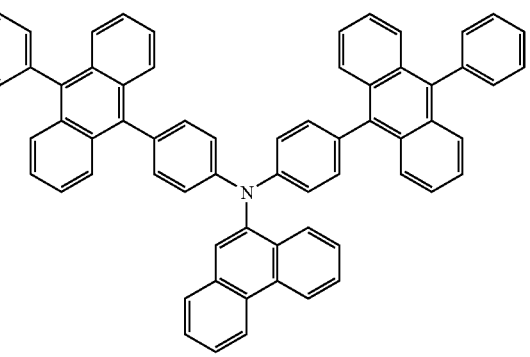

305
-continued

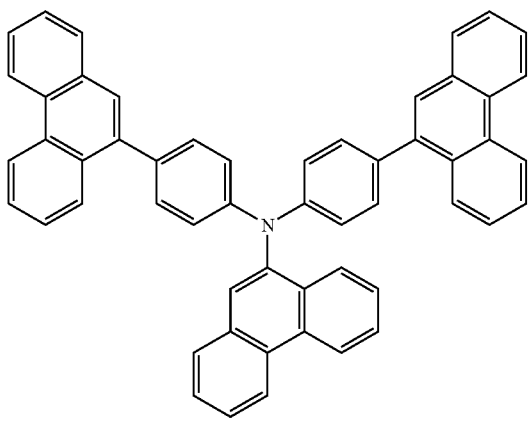

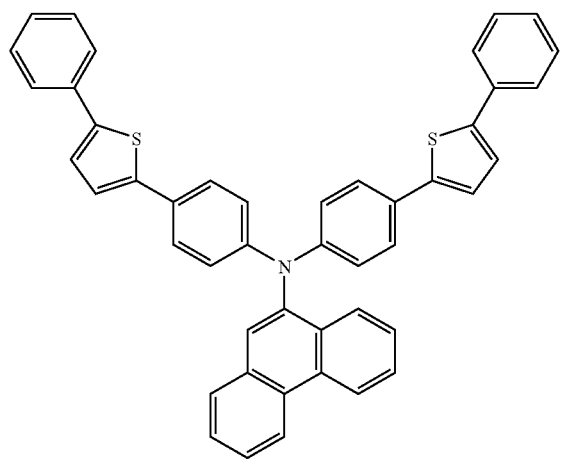

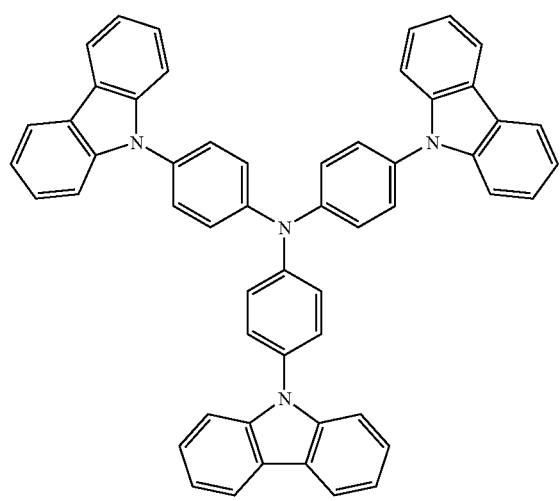

306
-continued

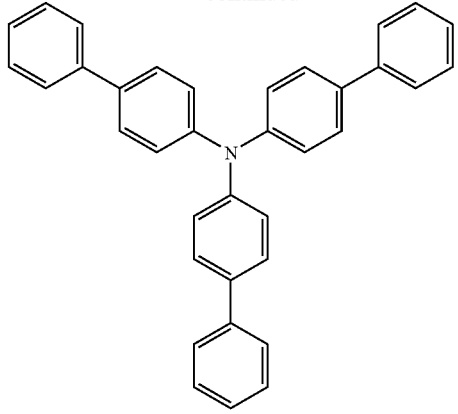

The compound of the present invention can be used in each of the hole injecting layer, the hole transporting layer, the electron injecting layer, and the electron transporting layer because the compound can transport both a hole and an electron.

In the present invention, the anode in the organic EL device has the function of injecting holes into the hole transporting layer or the light emitting layer. It is effective that the anode has a work function of 4.5 eV or greater. Specific examples of the material for the anode used in the present invention include indium tin oxide alloys (ITO), tin oxide (NESA), gold, silver, platinum, and copper. In addition, as the cathode, a material having a small work function is preferred in view to inject an electron into an electron-injecting layer or a light-emitting layer. Examples of the cathode material are not particularly limited, and specifically indium, aluminum, magnesium, an magnesium-indium alloy, a magnesium-aluminum alloy, an aluminum-lithium alloy, an aluminum-scandium-lithium alloy, and a magnesium-silver alloy may be used.

The method of forming the layers in the organic EL device of the present invention is not particularly limited. A conventionally known process such as the vacuum vapor deposition process or the spin coating process can be used. The organic thin film layer which is used in the organic EL device of the present invention and includes the compound represented by general formula (1) described above can be formed in accordance with a known process such as the vacuum vapor deposition process or the molecular beam epitaxy process (MBE process) or, using a solution prepared by dissolving the compounds into a solvent, in accordance with a coating process such as the dipping process, the spin coating process, the casting process, the bar coating process, or the roll coating process.

The thickness of each layer in the organic thin film layer in the organic EL device of the present invention is not particularly limited. In general, an excessively thin layer tends to have defects such as pin holes, whereas an excessively thick layer requires a high applied voltage to decrease the efficiency. Therefore, a thickness in the range of several nanometers to 1 μm is preferable.

EXAMPLES

Next, the present invention is described in detail by way of examples, but the present invention is not limited to the following examples. Note that, in the synthetic examples below, DMF refers to dimethylformamide, THF refers to tetrahydrofuran, DMF refers to dimethoxyethane, NBS refers to N-bromosuccine imide, Ph refers to a phenyl group, AcOEt refers to ethyl acetate, and NMP refers to N-methylpyrrolidone.

Synthesis Example 1

Synthesis of Compound No. 1

(1) Synthesis of Compound 1

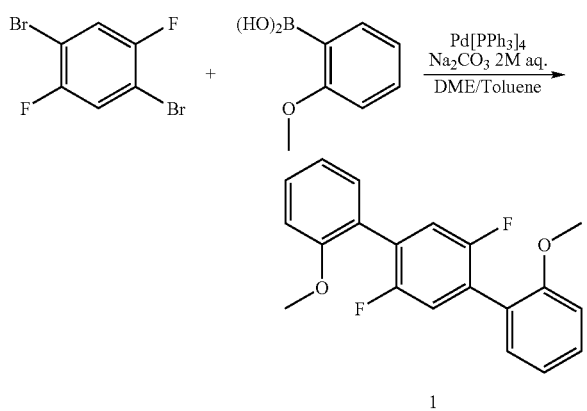

1,4-dibromo-2,5-difluorobenzene (49.3 g, 181.5 mmol), 2-methoxyphenylboronic acid (66.2 g, 435.6 mmol), and a 2 M aqueous solution of $Na_2CO_3$ (363 mL, 726 mmol), DME (360 mL), toluene (360 mL), and $Pd[PPh_3]_4$ (20.8 g, 18.0 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (500 mL) was charged into the funnel. Then, the mixture was extracted with $CH_2Cl_2$. The extract was dried with $MgSO_4$, and was then filtrated and concentrated. The resultant sample was purified by silica gel column chromatography, whereby a white solid was obtained in an amount of 38.5 g in 65% yield. FD-MS $C_{20}H_{16}F_2O_2$: theoretical value 326, observed value 326

(2) Synthesis of Compound 2

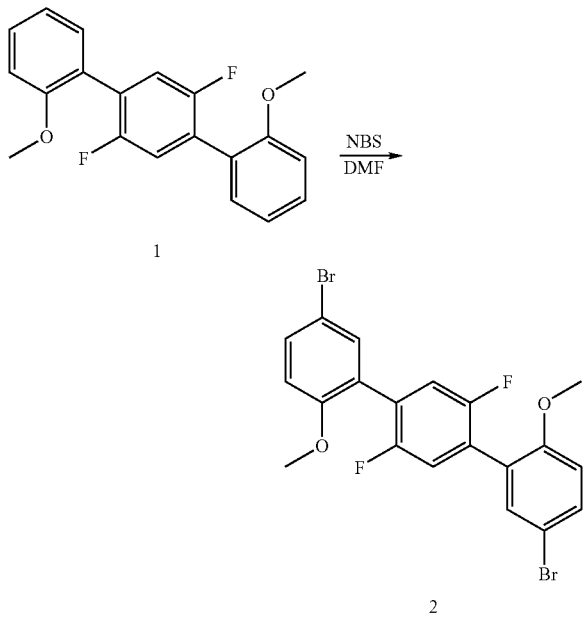

Compound 1 (36.6 g, 112.2 mmol), NBS (39.9 g, 224 mmol), and DMF (1,000 mL) were loaded into a three-necked flask, and the mixture was stirred under an Ar atmosphere at room temperature for 8 hours. After the completion of the reaction, the resultant sample was transferred to a separating funnel, and water (1,000 mL) was charged into the funnel. Then, the mixture was extracted with AcOEt. The resultant sample was purified by column chromatography, whereby a white solid was obtained in an amount of 38 g in 70% yield. FD-MS $C_{20}H_{14}Br_2F_2O_2$: theoretical value 484, observed value 484

(3) Synthesis of Compound 3

Compound 2 (37.2 g, 76.8 mmol), a 1 M solution of $BBr_3$ in $CH_2Cl_2$ (180 mL, 180 mmol), and $CH_2Cl_2$ (500 mL) were loaded into a three-necked flask, and the mixture was stirred under an Ar atmosphere at 0° C. for 8 hours. After that, the mixture was left to stand at room temperature overnight. After the completion of the reaction, the resultant was neutralized with a saturated aqueous solution of $NaHCO_3$. The resultant sample was transferred to a separating funnel, and was extracted with $CH_2Cl_2$. The resultant sample was purified by column chromatography, whereby a white solid was obtained in an amount of 28 g in 80% yield.

FD-MS $C_{18}H_{10}Br_2F_2O_2$: theoretical value 456, observed value 456

(4) Synthesis of Compound 4

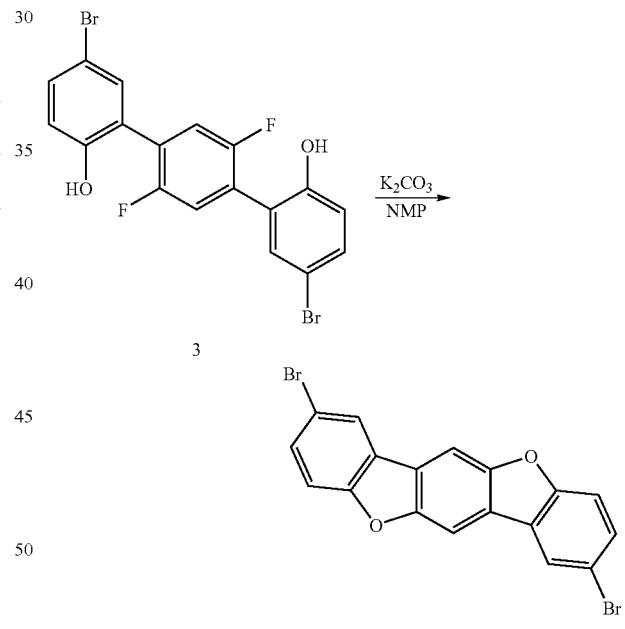

Compound 3 (27.4 g, 60.1 mmol), $K_2CO_3$ (18.2 g, 132 mmol), and NMP (250 mL) were loaded into a three-necked flask, and the mixture was stirred under an Ar atmosphere at 150° C. for 8 hours. After the completion of the reaction, the resultant was cooled to room temperature. The resultant sample was transferred to a separating funnel, and water (500 mL) was charged into the funnel. Then, the mixture was extracted with AcOEt. The resultant sample was purified by column chromatography, whereby a white solid was obtained in an amount of 20 g in 80% yield.

FD-MS $C_{18}H_8Br_2O_2$: theoretical value 416, observed value 416

(5) Synthesis of Compound No. 1

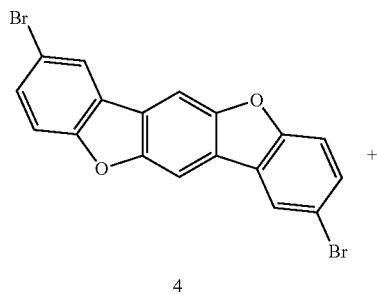

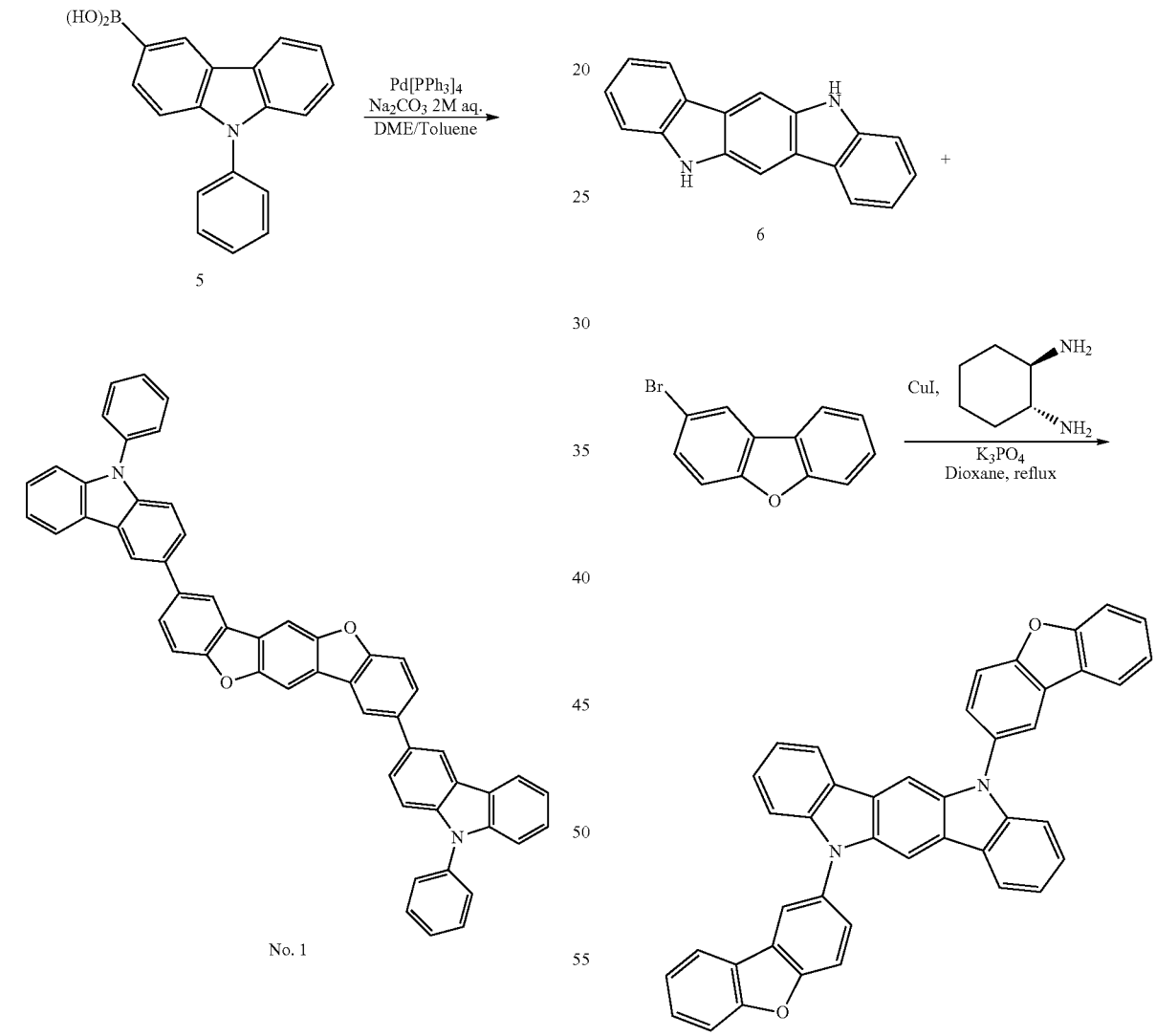

Compound 4 (2.5 g, 6.0 mmol), Compound 5 (3.8 g, 13.2 mmol), a 2 M aqueous solution of Na$_2$CO$_3$ (12 mL, 24 mmol), DME (12 mL), toluene (12 mL), and Pd[PPh$_3$]$_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The extract was dried with MgSO$_4$, and was then filtrated and concentrated. The resultant sample was purified by silica gel column chromatography. The purified product was concentrated and exsiccated, and was then recrystallized twice, whereby a white powder (Compound No. 1) was obtained. The powder was purified by sublimation, whereby a white solid was obtained in an amount of 2.0 g in 45% yield.

FD-MS C$_{54}$H$_{32}$N$_2$O$_2$: theoretical value 740, observed value 740

Synthesis Example 2

Synthesis of Compound No. 11

Compound 6 (2.6 g, 10 mmol), 2-bromodibenzofuran (5.0 g, 20 mmol), CuI (1.9 g, 10 mmol), trans-cyclohexane-1,2-diamine (3.4 g, 30 mmol), K$_3$PO$_4$ (8.5 g, 40 mmol), and 1,4-dioxane (10 mL) were loaded into a three-necked flask, and the mixture was refluxed under an argon atmosphere for 10 hours.

After the completion of the reaction, the resultant was cooled to room temperature. The resultant sample was transferred to a separating funnel, and water (50 mL) was charged into the funnel. Then, the mixture was extracted with $CH_2Cl_2$. The resultant sample was purified by column chromatography. The purified product was concentrated and exsiccated, and was then recrystallized twice, whereby a white powder (Compound No. 11) was obtained. The powder was purified by sublimation, whereby a white solid was obtained in an amount of 2.1 g in 35% yield.

FD-MS $C_{42}H_{24}N_2O_2$: theoretical value 588, observed value 588

Synthesis Example 3

Synthesis of Compound No. 22

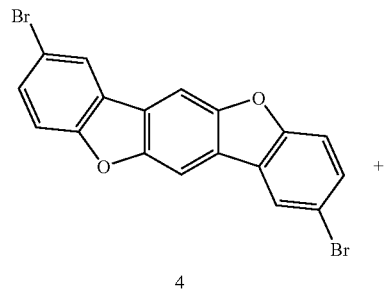

4

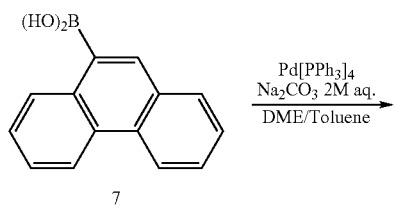

7

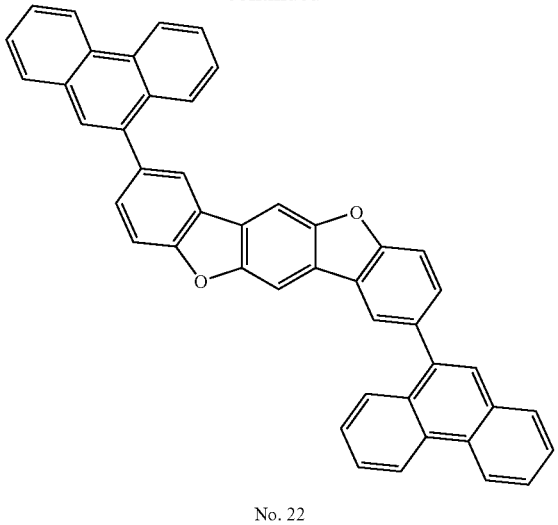

No. 22

Compound 4 (2.5 g, 6.0 mmol), Compound 7 (2.9 g, 13.2 mmol), a 2 M aqueous solution of $Na_2CO_3$ (12 mL, 24 mmol), DME (12 mL), toluene (12 mL), and $Pd[PPh_3]_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated and exsiccated, and was then recrystallized twice, whereby a white powder (Compound No. 22) was obtained. The powder was purified by sublimation, whereby a white solid was obtained in an amount of 1.3 g in 35% yield.

FD-MS $C_{46}H_{26}O_2$: theoretical value 610, observed value 610

Synthesis Example 4

Synthesis of Compound No. 28

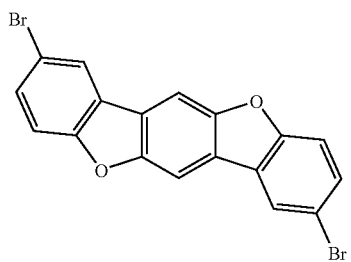

4

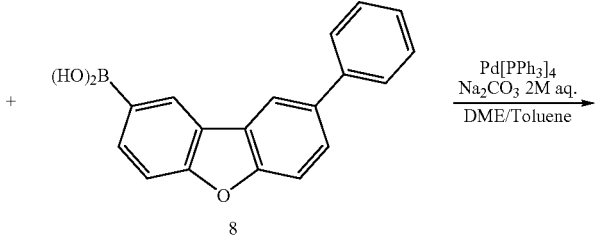

8

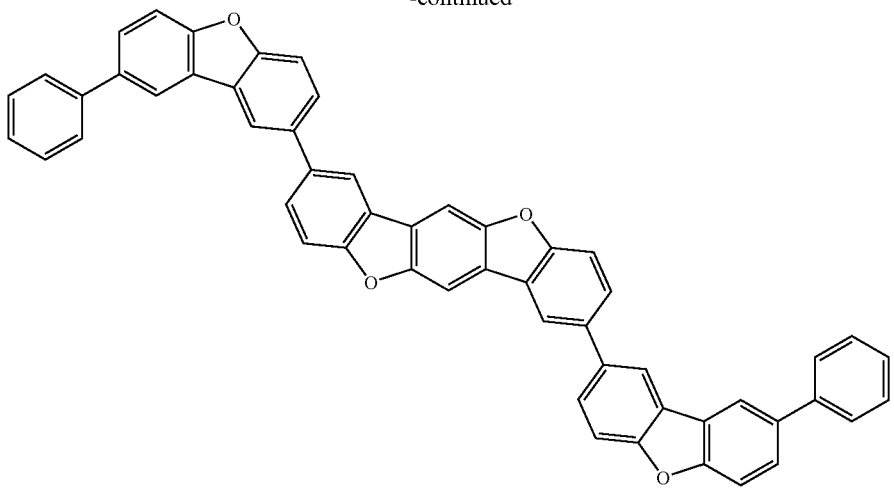

No. 28

Compound 4 (2.5 g, 6.0 mmol), Compound 8 (3.8 g, 13.2 mmol), a 2 M aqueous solution of $Na_2CO_3$ (12 mL, 24 mmol), DME (12 mL), toluene (12 mL), and $Pd[PPh_3]_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated and exsiccated, and was then recrystallized twice, whereby a white powder (Compound No. 28) was obtained. The powder was purified by sublimation, whereby a white solid was obtained in an amount of 2.1 g in 47% yield.

FD-MS $C_{54}H_{30}O_4$: theoretical value 742, observed value 742

Synthesis Example 5

Synthesis of Compound No. 39

(1) Synthesis of Compound 9

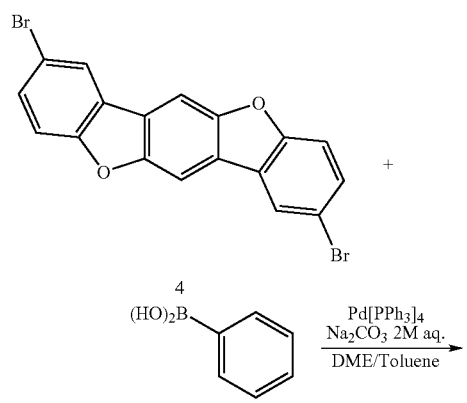

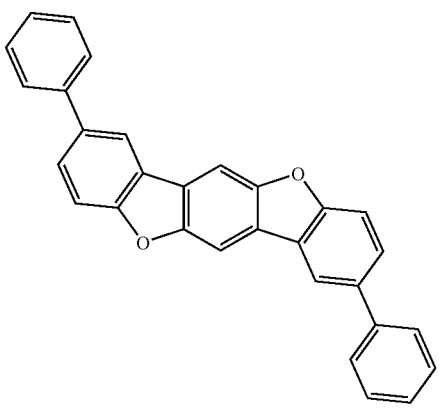

9

Compound 4 (10.0 g, 24.0 mmol), phenylboronic acid (6.4 g, 52.8 mmol), a 2 M aqueous solution of $Na_2CO_3$ (48 mL, 96 mmol), DME (48 mL), toluene (48 mL), and $Pd[PPh_3]_4$ (1.4 g, 1.2 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (300 mL) was charged into the funnel. Then, the mixture was extracted with $CH_2Cl_2$. The extract was dried with $MgSO_4$, and was then filtrated and concentrated. The resultant sample was purified by silica gel column chromatography, whereby a white solid was obtained in an amount of 7.5 g in 76% yield.

FD-MS $C_{30}H_{18}O_2$: theoretical value 410, observed value 410

(2) Synthesis of Compound 10

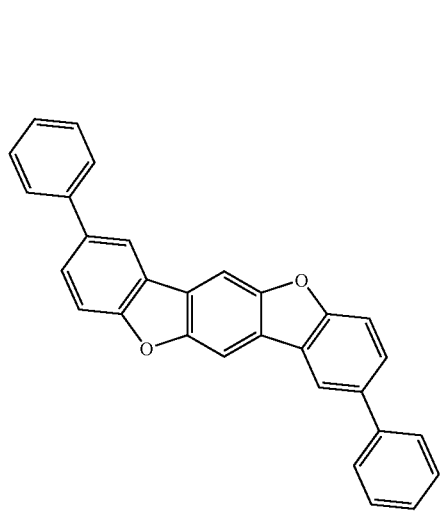

Compound 9 (7.5 g, 18.3 mmol) and CH$_2$Cl$_2$ (100 mL) were loaded into a three-necked flask, and bromine (2.9 g, 18.3 mmol) was dropped to the flask under an Ar atmosphere at 0° C. After that, the mixture was stirred at room temperature for 8 hours. After the completion of the reaction, the resultant sample was transferred to a separating funnel, and water (50 mL) was charged into the funnel. Then, the mixture was extracted with CH$_2$Cl$_2$. The organic layer was washed with a saturated aqueous solution of NaNO$_2$ (50 mL) and dried with MgSO$_4$, and was then filtrated and concentrated. The resultant sample was purified by column chromatography, whereby a white solid was obtained in an amount of 5.4 g in 60% yield.

FD-MS C$_{30}$H$_{17}$BrO$_2$: theoretical value 489, observed value 489

(3) Synthesis of Compound No. 39

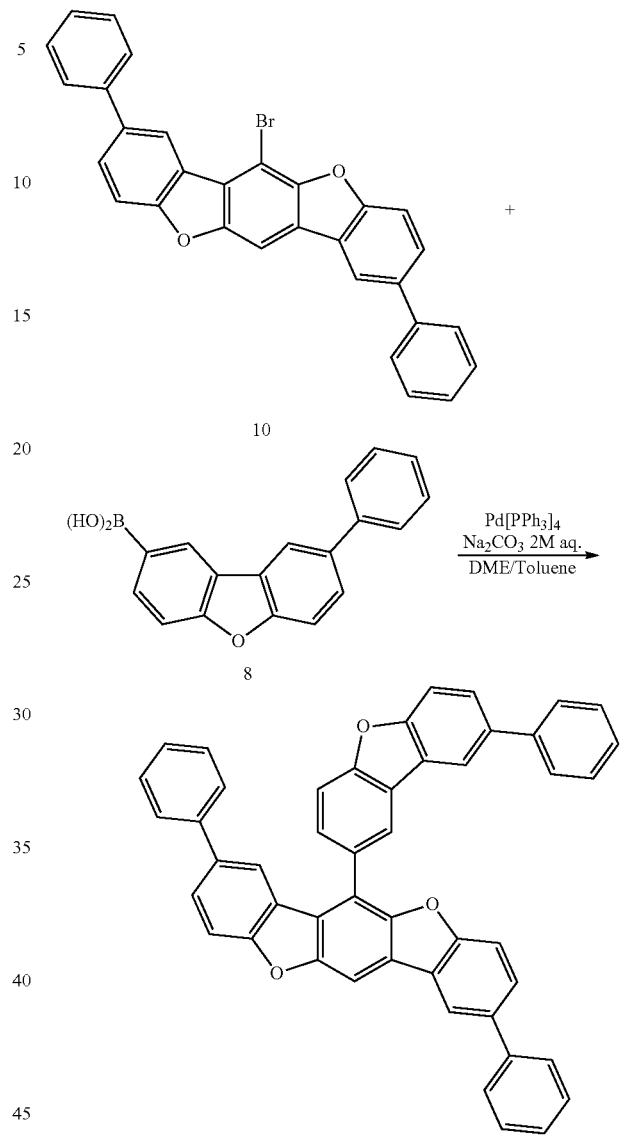

Compound 10 (4.9 g, 10.0 mmol), Compound 8 (3.2 g, 11.0 mmol), a 2 M aqueous solution of Na$_2$CO$_3$ (10 mL, 20 mmol), DME (20 mL), toluene (20 mL), and Pd[PPh$_3$]$_4$ (0.58 g, 0.5 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (100 mL) was charged into the funnel. Then, the mixture was extracted with CH$_2$Cl$_2$. The extract was dried with MgSO$_4$, and was then filtrated and concentrated. The resultant sample was purified by silica gel column chromatography. The purified product was concentrated and exsiccated, and was then recrystallized twice, whereby a white powder (Compound No. 39) was obtained. The powder was purified by sublimation, whereby a white solid was obtained in an amount of 1.8 g in 28% yield.

FD-MS C$_{48}$H$_{28}$O$_3$: theoretical value 652, observed value 652

Synthesis Example 6

Synthesis of Compound No. 57

(1) Synthesis of Compound 11

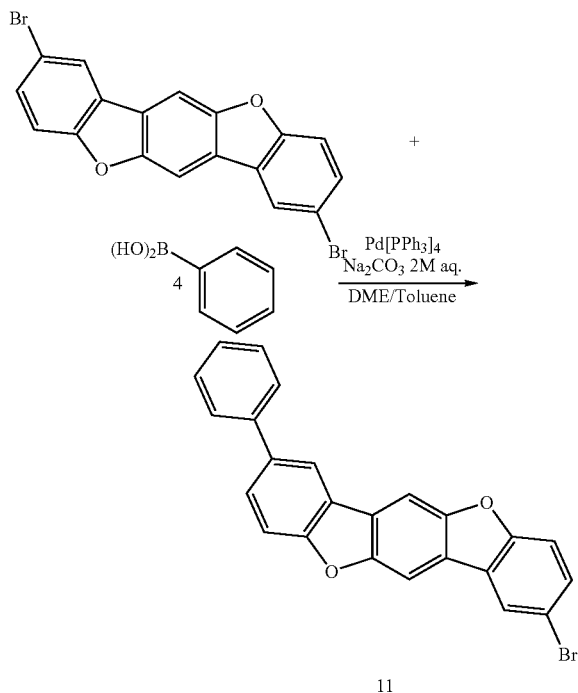

Compound 4 (16.6 g, 40.0 mmol), phenylboronic acid (4.9 g, 40 mmol), a 2 M aqueous solution of $Na_2CO_3$ (40 mL, 80 mmol), DME (80 mL), toluene (80 mL), and $Pd[PPh_3]_4$ (2.3 g, 2.0 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (300 mL) was charged into the funnel. Then, the mixture was extracted with $CH_2Cl_2$. The extract was dried with $MgSO_4$, and was then filtrated and concentrated. The resultant sample was purified by silica gel column chromatography, whereby a white solid was obtained in an amount of 10.7 g in 65% yield.

FD-MS $C_{24}H_{13}BrO_2$: theoretical value 413, observed value 413

(2) Synthesis of Compound 12

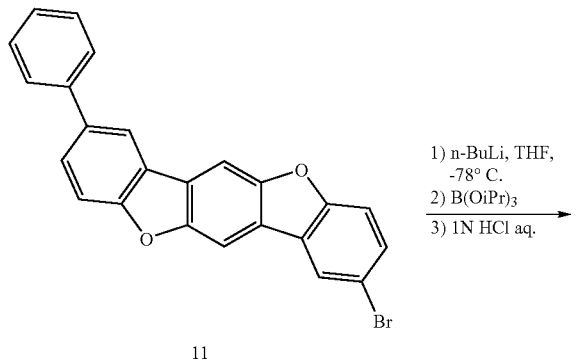

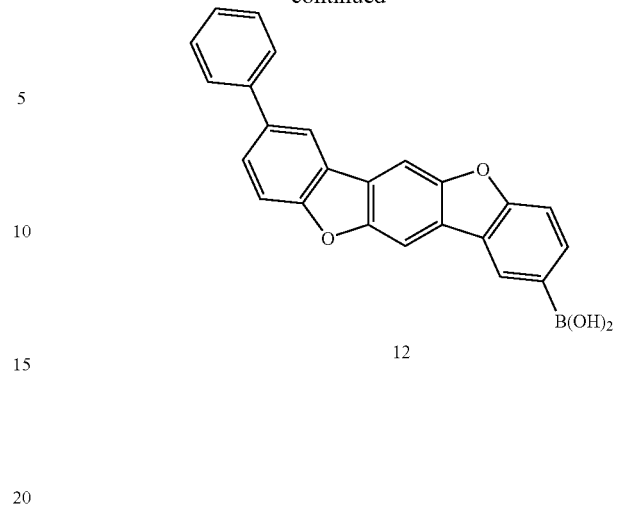

Compound 11 (10 g, 24.2 mmol) and THF (240 mL) were loaded into a three-necked flask, and the mixture was cooled to −78° C. Then, n-BuLi (1.65 M solution in n-hexane, 16.1 mL, 26.6 mmol) was added dropwise to the flask, and the resultant mixture was stirred at −78° C. for 20 minutes. Triisopropyl borate (13.7 g, 72.6 mmol) was added to the resultant, and the mixture was stirred at −78° C. for 1 hour. After that, the resultant was left to stand overnight at room temperature. Then, 1 N HCl (100 mL) was charged into the resultant, and the mixture was stirred at room temperature for 1 hour. The resultant sample was concentrated, and was then transferred to a separating funnel. Water (100 mL) was charged into the funnel, and the mixture was extracted with $CH_2Cl_2$. The extract was dried with $MgSO_4$, and was then filtrated and concentrated. The resultant sample was purified by recrystallization (toluene-hexane), whereby a white solid was obtained in an amount of 5.5 g in 60% yield.

(3) Synthesis of Compound No. 57

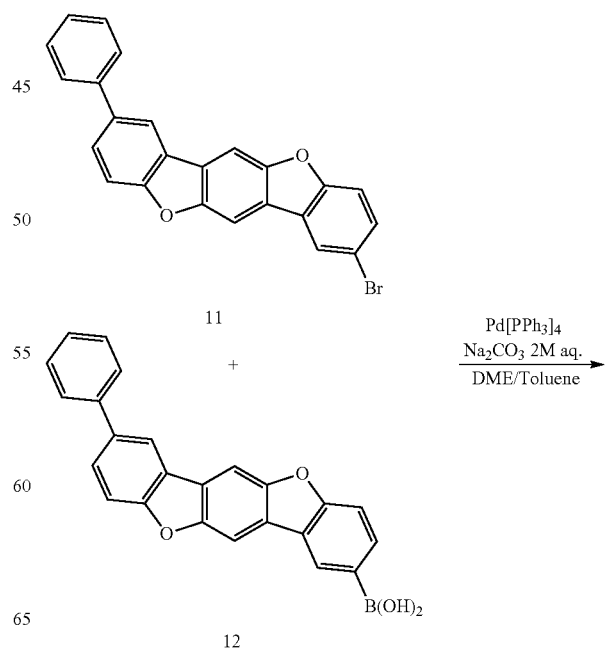

-continued

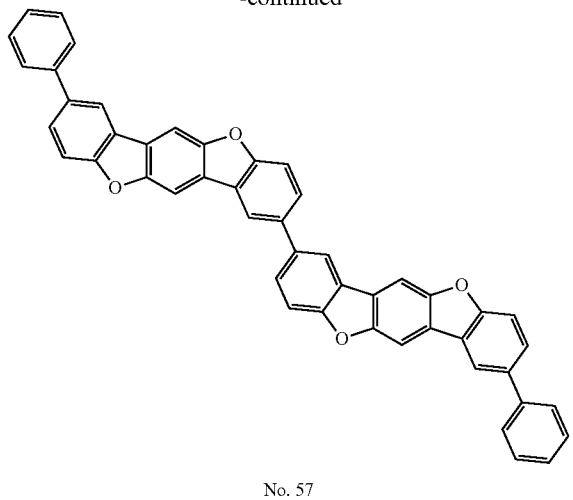

No. 57

Compound 11 (2.5 g, 6.0 mmol), Compound 12 (2.5 g, 6.6 mmol), a 2 M aqueous solution of Na$_2$CO$_3$ (6 mL, 12 mmol), DME (12 mL), toluene (12 mL), and Pd[PPh$_3$]$_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (100 mL) was charged into the funnel. Then, the mixture was extracted with CH$_2$Cl$_2$. The extract was dried with MgSO$_4$, and was then filtrated and concentrated. The resultant sample was purified by silica gel column chromatography. The purified product was concentrated and exsiccated, and was then recrystallized twice, whereby a white powder (Compound No. 57) was obtained. The powder was purified by sublimation, whereby a white solid was obtained in an amount of 1.6 g in 40% yield.

FD-MS C$_{48}$H$_{26}$O$_4$: theoretical value 666, observed value 666

Synthesis Example 7

Synthesis of Compound No. 58

(1) Synthesis of Compound 14

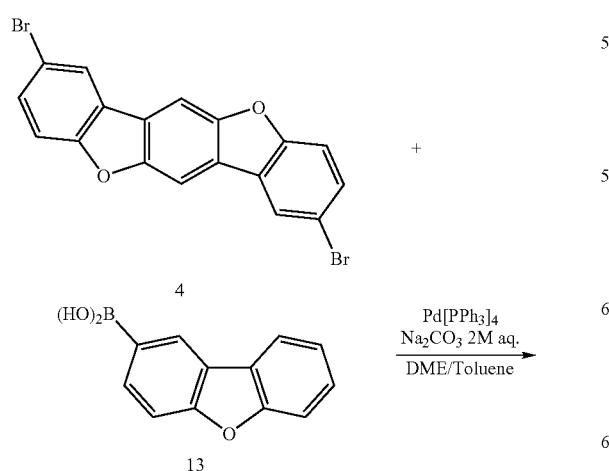

-continued

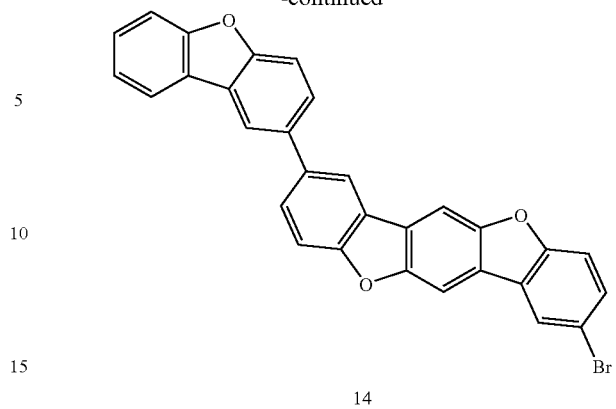

14

Compound 4 (16.6 g, 40 mmol), Compound 13 (8.5 g, 40 mmol), a 2 M aqueous solution of Na$_2$CO$_3$ (40 mL, 80 mmol), DME (80 mL), toluene (80 mL), and Pd[PPh$_3$]$_4$ (2.3 g, 2.0 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (300 mL) was charged into the funnel. Then, the mixture was extracted with CH$_2$Cl$_2$. The extract was dried with MgSO$_4$, and was then filtrated and concentrated. The resultant sample was purified by silica gel column chromatography, whereby a white solid was obtained in an amount of 11.1 g in 55% yield.

FD-MS C$_{30}$H$_{15}$BrO$_3$: theoretical value 503, observed value 503

(2) Synthesis of Compound 15

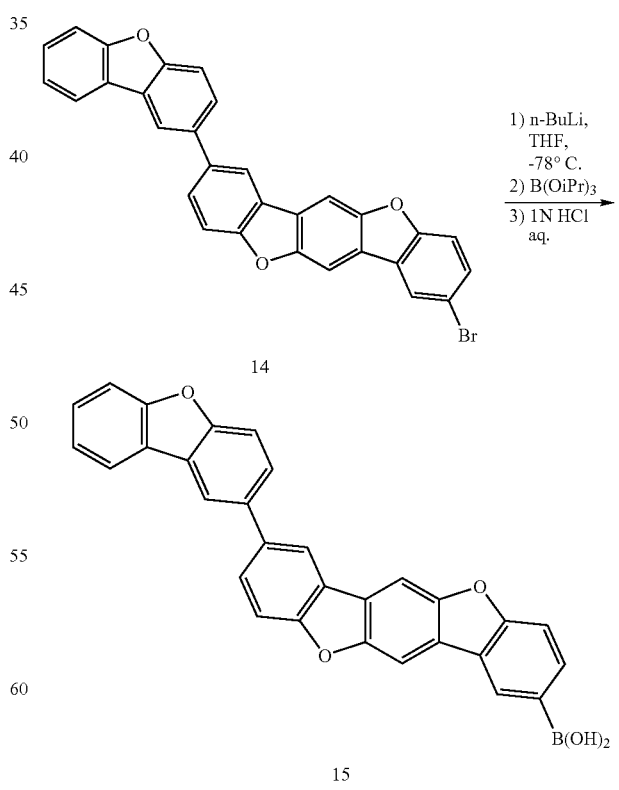

Compound 14 (11 g, 21.9 mmol) and THF (220 mL) were loaded into a three-necked flask, and the mixture was cooled to −78° C. Then, n-BuLi (1.65 M solution in n-hexane, 14.5 mL, 24.0 mmol) was added dropwise to the flask, and the resultant mixture was stirred at −78° C. for 20 minutes. Triisopropyl borate (12.4 g, 65.6 mmol) was added to the resultant, and the mixture was stirred at −78° C. for 1 hour. After that, the resultant was left to stand overnight at room temperature. Then, 1 N HCl (100 mL) was charged into the resultant, and the mixture was stirred at room temperature for 1 hour. The resultant sample was concentrated, and was then transferred to a separating funnel. Water (100 mL) was charged into the funnel, and the mixture was extracted with CH$_2$Cl$_2$. The extract was dried with MgSO$_4$, and was then filtrated and concentrated. The resultant sample was purified by recrystallization (toluene-hexane), whereby a white solid was obtained in an amount of 6.4 g in 62% yield.

(3) Synthesis of Compound No. 58

Compound 14 (3.0 g, 6.0 mmol), Compound 15 (3.1 g, 6.6 mmol), a 2 M aqueous solution of Na$_2$CO$_3$ (6 mL, 12 mmol), DME (12 mL), toluene (12 mL), and Pd[PPh$_3$]$_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (100 mL) was charged into the funnel. Then, the mixture was extracted with CH$_2$Cl$_2$. The extract was dried with MgSO$_4$, and was then filtrated and concentrated. The resultant sample was purified by silica gel column chromatography. The purified product was concentrated and exsiccated, and was then recrystallized twice, whereby a white powder (Compound No. 58) was obtained. The powder was purified by sublimation, whereby a white solid was obtained in an amount of 1.3 g in 26% yield.

FD-MS C$_{60}$H$_{30}$O$_6$: theoretical value 846, observed value 846

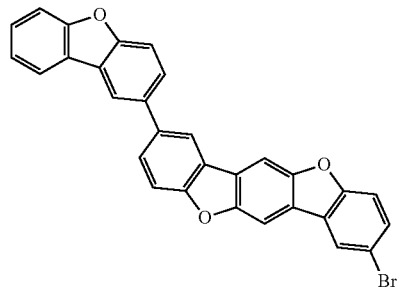

14

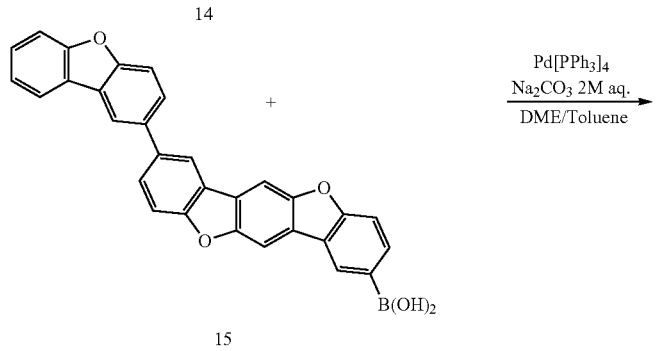

15

Pd[PPh$_3$]$_4$
Na$_2$CO$_3$ 2M aq.
DME/Toluene

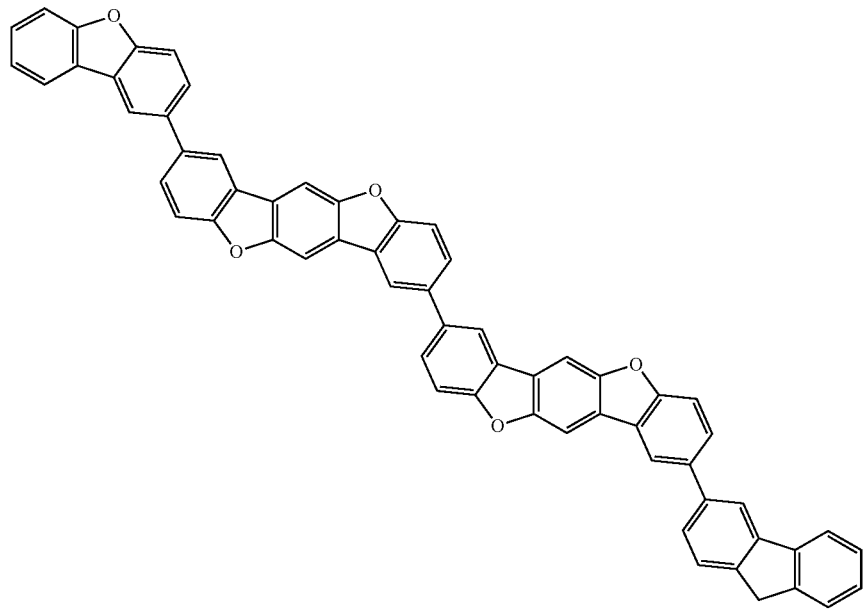

No. 58

Synthesis Example 8

Synthesis of Compound No. 60

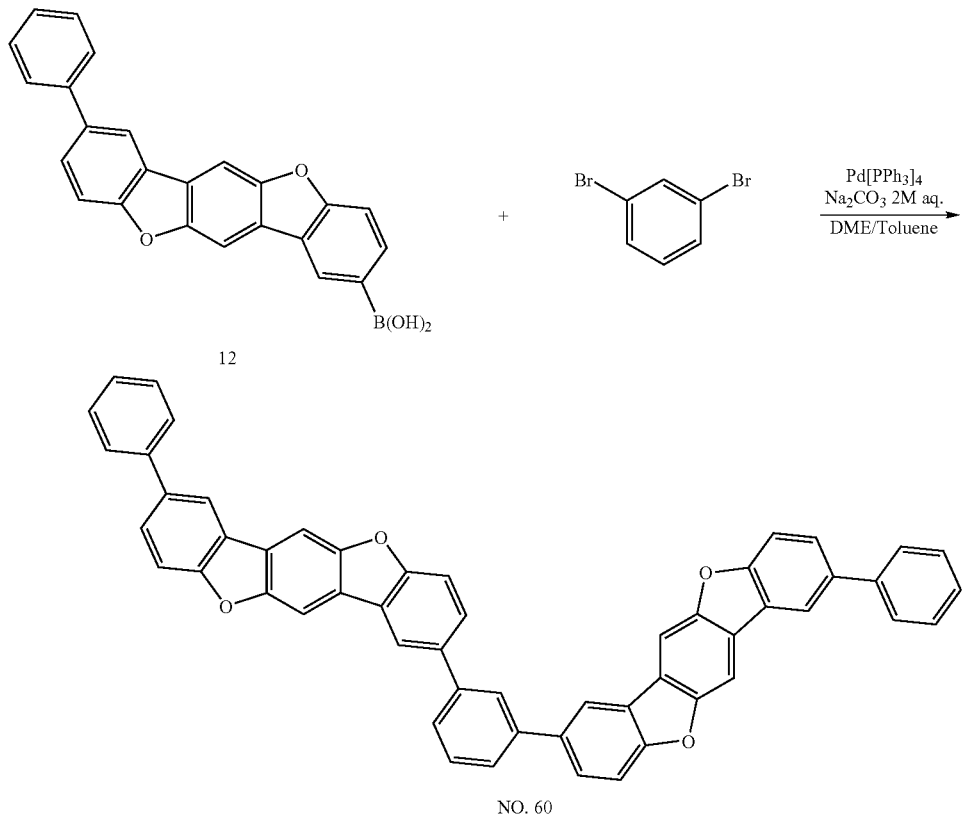

Compound 12 (5.5 g, 14.5 mmol), 1,3-dibromobenzene (1.7 g, 7.3 mmol), a 2 M aqueous solution of $Na_2CO_3$ (15 mL, 30 mmol), DME (15 mL), toluene (15 mL), and $Pd[PPh_3]_4$ (0.42 g, 0.37 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated and exsiccated, and was then recrystallized twice, whereby a white powder (Compound No. 60) was obtained. The powder was purified by sublimation, whereby a white solid was obtained in an amount of 1.6 g in 29% yield.

FD-MS $C_{54}H_{30}O_4$: theoretical value 742, observed value 742

Synthesis Example 9

Synthesis of Compound No. 62

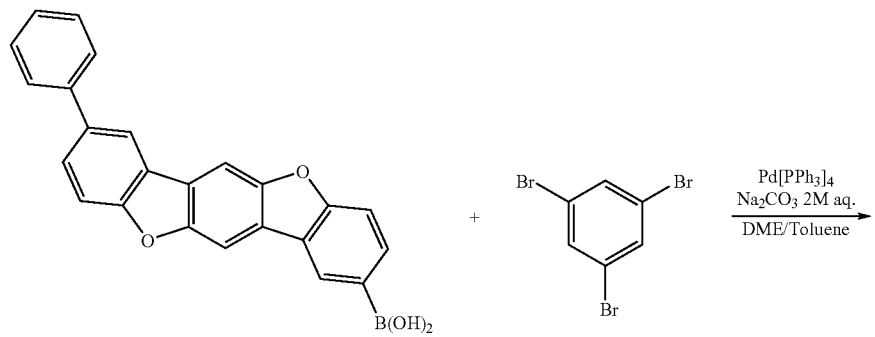

-continued

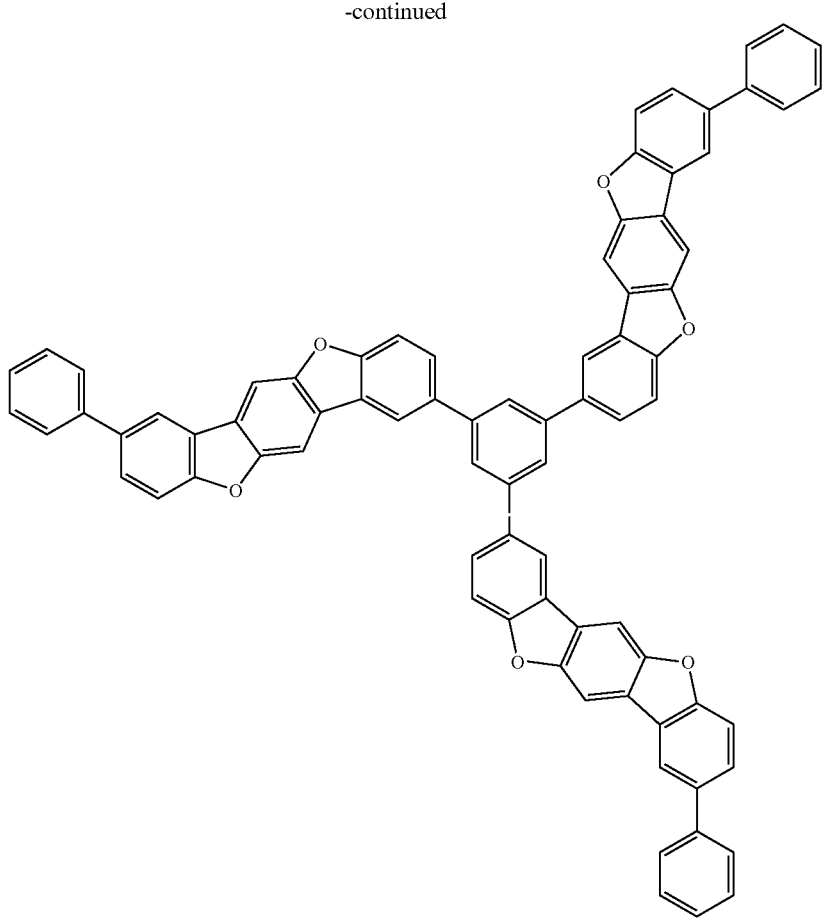

No. 62

Compound 12 (8.3 g, 21.9 mmol), 1,3,5-tribromobenzene (2.3 g, 7.3 mmol), a 2 M aqueous solution of $Na_2CO_3$ (22.5 mL, 45 mmol), DME (15 mL), toluene (15 mL), and $Pd[PPh_3]_4$ (0.63 g, 0.56 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (150 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated and exsiccated, and was then recrystallized twice, whereby a white powder (Compound No. 62) was obtained. The powder was purified by sublimation, whereby a white solid was obtained in an amount of 1.1 g in 14% yield.

FD-MS $C_{78}H_{42}O_6$: theoretical value 1075, observed value 1075

Synthesis Example 10

Synthesis of Compound No. 20

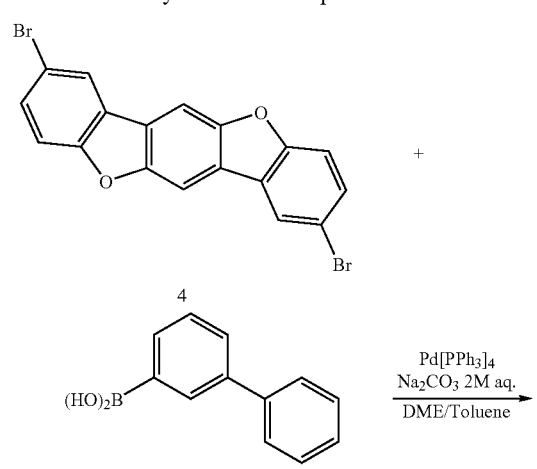

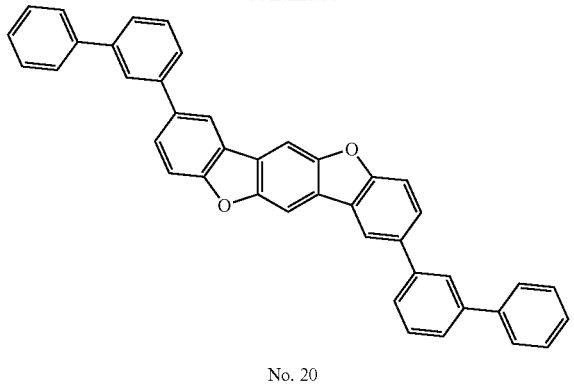

No. 20

Compound 4 (2.5 g, 6.0 mmol), 3-biphenylboronic acid (2.6 g, 13.2 mmol), a 2 M aqueous solution of $Na_2CO_3$ (12 mL, 24 mmol), DME (12 mL), toluene (12 mL), and $Pd[PPh_3]_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated and exsiccated, and was then recrystallized twice, whereby a white powder (Compound No. 20) was obtained. The powder was purified by sublimation, whereby a white solid was obtained in an amount of 1.3 g in 39% yield.

FD-MS $C_{42}H_{26}O_2$: theoretical value 562, observed value 562

Synthesis Example 11

Synthesis of Compound No. 67

(1) Synthesis of Compound 17

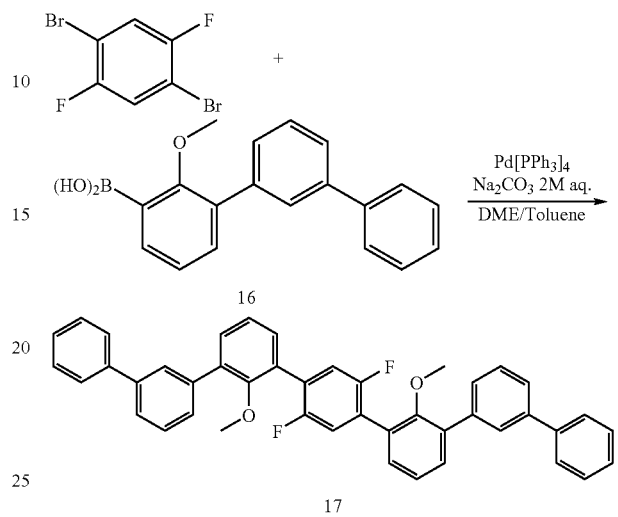

1,4-dibromo-2,5-difluorobenzene (5.4 g, 20.0 mmol), Compound 16 (12.8 g, 42.0 mmol), a 2 M aqueous solution of $Na_2CO_3$ (40 mL, 80.0 mmol), DME (40 mL), toluene (40 mL), and $Pd[PPh_3]_4$ (1.2 g, 1.0 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (100 mL) was charged into the funnel. Then, the mixture was extracted with $CH_2Cl_2$. The extract was dried with $MgSO_4$, and was then filtrated and concentrated. The resultant sample was purified by silica gel column chromatography, whereby a white solid was obtained in an amount of 8.8 g in 70% yield. FD-MS $C_{44}H_{32}F_2O_2$: theoretical value 630, observed value 630

(2) Synthesis of Compound 18

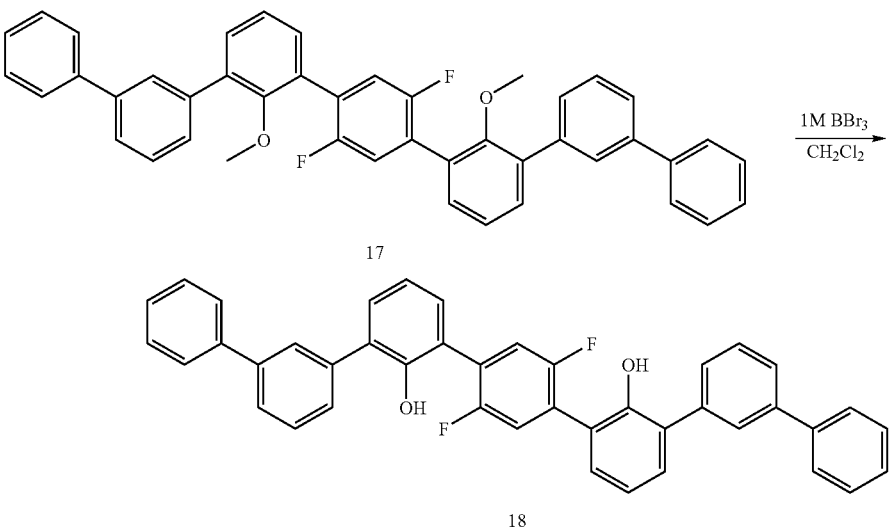

Compound 17 (8.8 g, 14.0 mmol), a 1 M solution of BBr$_3$ in CH$_2$Cl$_2$ (34 mL, 34.0 mmol), and CH$_2$Cl$_2$ (140 mL) were loaded into a three-necked flask, and the mixture was stirred under an Ar atmosphere at 0° C. for 8 hours. After that, the mixture was left to stand at room temperature overnight. After the completion of the reaction, the resultant was neutralized with a saturated aqueous solution of NaHCO$_3$. The resultant sample was transferred to a separating funnel, and was extracted with CH$_2$Cl$_2$. The resultant sample was purified by silica gel column chromatography, whereby a white solid was obtained in an amount of 7.8 g in 93% yield. FD-MS C$_{42}$H$_{28}$F$_2$O$_2$: theoretical value 602, observed value 602

(3) Synthesis of Compound No. 67

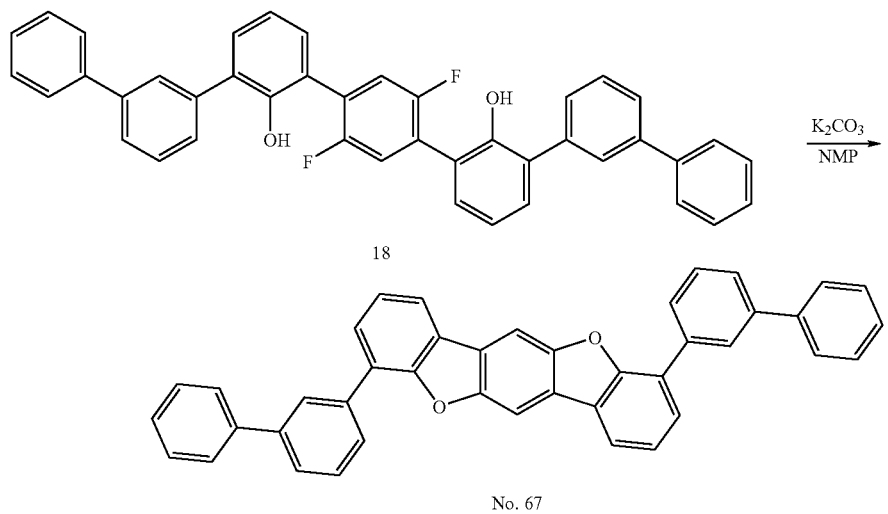

Compound 18 (7.8 g, 12.9 mmol), K$_2$CO$_3$ (7.2 g, 51.8 mmol), and NMP (50 mL) were loaded into a three-necked flask, and the mixture was stirred under an Ar atmosphere at 200° C. for 3 hours. After the completion of the reaction, the resultant was cooled to room temperature. Toluene (500 mL) was charged into the resultant sample. The mixture was transferred to a separating funnel, and was washed with water. The washed product was dried with MgSO$_4$, and was then filtrated and concentrated. The resultant sample was purified by silica gel column chromatography. The purified product was concentrated and exsiccated, and was then recrystallized twice, whereby a white powder (Compound No. 67) was obtained. The powder was purified by sublimation, whereby a white solid was obtained in an amount of 2.5 g in 35% yield.

FD-MS C$_{42}$H$_{26}$O$_2$: theoretical value 562, observed value 562

An apparatus and measurement conditions adopted for field desorption mass spectrometry (FD-MS) in each of Synthesis Examples 1 to 11 are shown below.

Apparatus: HX110 (manufactured by JEOL Ltd.)
Conditions: accelerating voltage 8 kV
scan range m/z=50 to 1,500
emitter kind: carbon
emitter current: 0 mA→2 mA/min→40 mA (held for 10 minutes)

Example 1

Production of Organic EL Device

A glass substrate provided with an ITO transparent electrode measuring 25 mm by 75 mm by 1.1 mm (manufactured by GEOMATEC Co., Ltd.) was subjected to ultrasonic cleaning in isopropyl alcohol for 5 minutes. Further, the substrate was subjected to ultraviolet (UV)-ozone cleaning for 30 minutes.

The glass substrate provided with a transparent electrode thus cleaned was mounted on a substrate holder of a vacuum deposition apparatus. First, Compound A was deposited from the vapor onto the surface of the glass substrate on the side where a transparent electrode line was formed so as to cover the transparent electrode, whereby a hole transporting layer having a thickness of 30 nm was obtained.

Compound No. 1 as a host for phosphorescence and Ir(Ph-ppy)$_3$ as a dopant for phosphorescence were co-deposited from the vapor onto the hole transporting layer, whereby a phosphorescent layer having a thickness of 30 nm was obtained. The concentration of Ir(Ph-ppy)$_3$ was 5 mass %.

Subsequently, Compound B having a thickness of 10 nm, Compound C having a thickness of 20 nm, LiF having a thickness of 1 nm, and metal Al having a thickness of 80 nm were sequentially laminated on the phosphorescent layer, whereby a cathode was obtained. It should be noted that LiF as an electron injectable electrode was formed at a rate of 1 Å/min.

Compound A

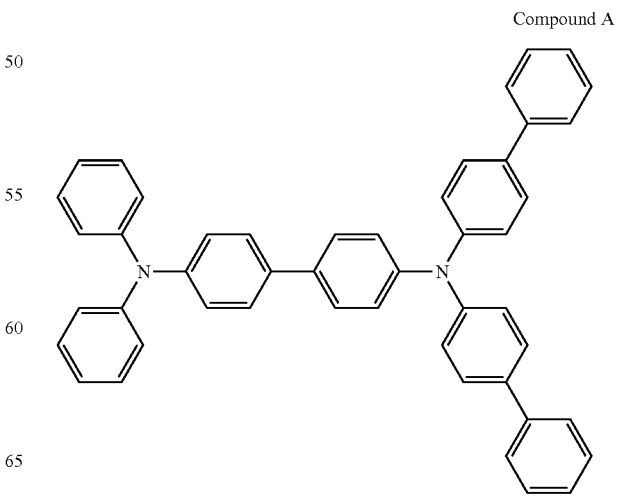

-continued

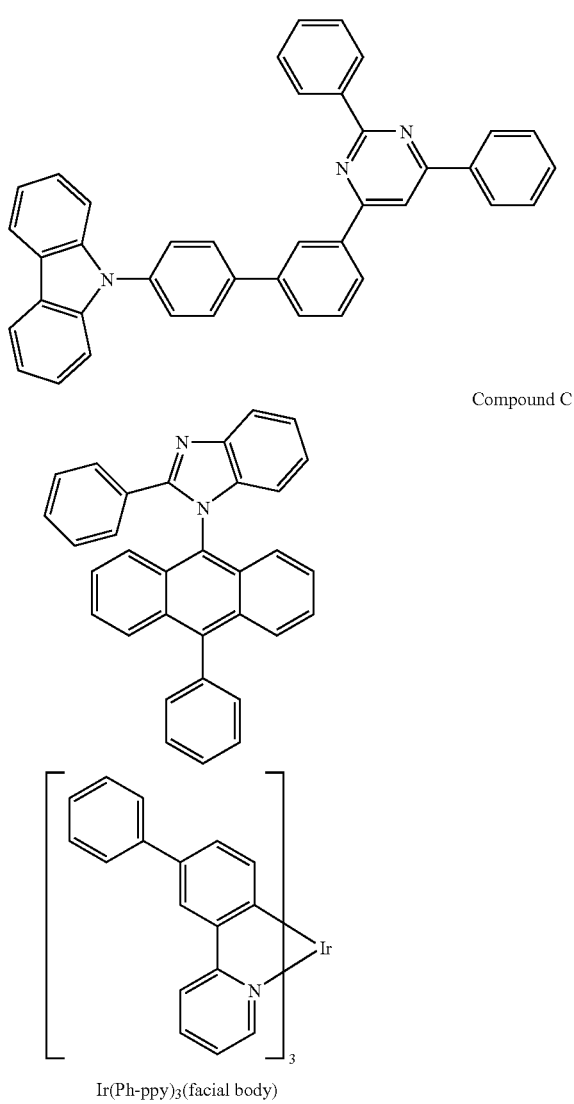

Compound B

Compound C

Ir(Ph-ppy)₃(facial body)

(Evaluation of Organic EL Device for Light Emitting Performance)

The organic EL device thus produced was caused to emit light by being driven with a direct current. The luminance (L) of the emitted light and the current density at which the device started to emit the light were measured. Then, the current efficiency (L/J) of the device at a luminance of 1,000 cd/m² was determined. Further, the lifetime of the device at a luminance of 20,000 cd/m² was determined. Table 1 shows the results.

Examples 2 to 9

Organic EL devices were each produced in the same manner as in Example 1 except that a host material listed in Table 1 was used instead of Host Compound No. 1 in Example 1, and the devices were each evaluated in the same manner as in Example 1. Table 1 shows the results of the evaluation for light emitting performance.

Comparative Examples 1 and 2

Organic EL devices were each produced in the same manner as in Example 1 except that the following compound (a) or (b) described in EP 0908787 A was used as a host material instead of Host Compound No. 1 in Example 1, and the devices were each evaluated in the same manner as in Example 1. Table 1 shows the results of the evaluation for light emitting performance.

Comparative Examples 3 and 4

Organic EL devices were each produced in the same manner as in Example 1 except that the following compound (c) or (d) described in WO 2006-122630 was used as a host material instead of Host Compound No. 1 in Example 1, and the devices were each evaluated in the same manner as in Example 1. Table 1 shows the results of the evaluation for light emitting performance.

Comparative Example 5

An organic EL device was produced in the same manner as in Example 1 except that the following compound (e) described in WO 2007-063754 was used as a host material instead of Host Compound No. 1 in Example 1, and the device was evaluated in the same manner as in Example 1. Table 1 shows the results of the evaluation for light emitting performance.

Comparative Example 6

An organic EL device was produced in the same manner as in Example 1 except that the following compound (f) described in JP 2008-81494 A was used as a host material instead of Host Compound No. 1 in Example 1, and the device was evaluated in the same manner as in Example 1. Table 1 shows the results of the evaluation for light emitting performance.

Comparative Example 7

An organic EL device was produced in the same manner as in Example 1 except that the following compound (g) described in US 2002-0132134 A and US 2003-0044646 A was used as a host material instead of Host Compound No. 1 in Example 1, and the device was evaluated in the same manner as in Example 1. Table 1 shows the results of the evaluation for light emitting performance.

TABLE 1

| | Host Compound | Voltage (V) @ 20 mA/cm² | Efficiency (cd/A) @ 1,000 cd/m² | Lifetime (hr) @ 20,000 cd/m² |
|---|---|---|---|---|
| Example 1 | (1) | 5.8 | 52.3 | 350 |
| Example 2 | (11) | 4.5 | 45.8 | 110 |
| Example 3 | (22) | 6.0 | 50.8 | 320 |
| Example 4 | (28) | 5.2 | 57.6 | 400 |
| Example 5 | (39) | 5.3 | 57.5 | 300 |
| Example 6 | (57) | 5.2 | 56.8 | 410 |
| Example 7 | (58) | 5.0 | 50.5 | 350 |
| Example 8 | (60) | 5.4 | 57.8 | 370 |
| Example 9 | (62) | 5.3 | 54.3 | 500 |
| Comparative Example 1 | (a) | 4.6 | 26.5 | 50 |
| Comparative Example 2 | (b) | 4.2 | 17.6 | 30 |
| Comparative Example 3 | (c) | 4.9 | 37.5 | 50 |
| Comparative Example 4 | (d) | 4.7 | 35.9 | 60 |

TABLE 1-continued

| Comparative Example 5 | (e) | 4.3 | 17.3 | 30 |
| Comparative Example 6 | (f) | 5.5 | 38.2 | 50 |
| Comparative Example 7 | (g) | 5.4 | 28.7 | 60 |

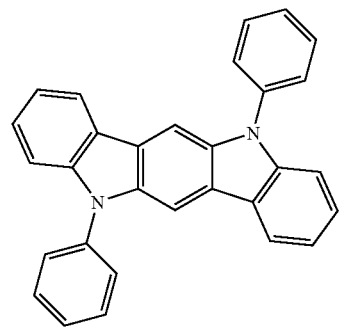

(a)

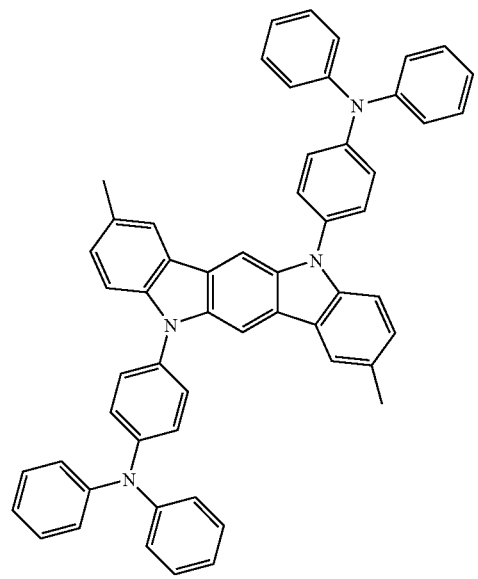

(b)

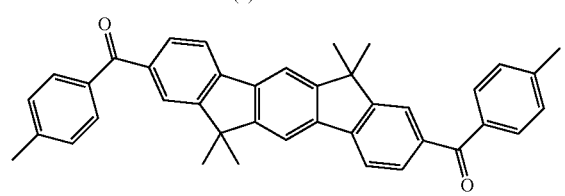

(c)

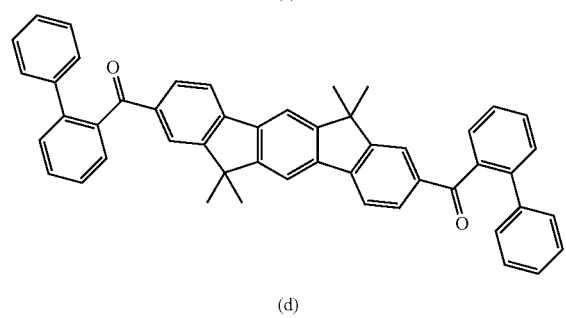

(d)

TABLE 1-continued (e)

(f)

(g)

Example 10

Production of Organic EL Device

The glass substrate provided with a transparent electrode cleaned in the same manner as described above was mounted on a substrate holder of a vacuum deposition apparatus. First, Compound A was deposited from the vapor onto the surface of the glass substrate on the side where a transparent electrode line was formed so as to cover the transparent electrode, whereby a hole transporting layer having a thickness of 30 nm was obtained.

Compound No. 198 as a host for phosphorescence and Ir(Ph-ppy)3 as a dopant for phosphorescence were co-deposited from the vapor onto the hole transporting layer, whereby a phosphorescent layer having a thickness of 30 nm was obtained. The concentration of Ir(Ph-ppy)$_3$ was 10 mass %.

Subsequently, Compound No. 20 having a thickness of 10 nm, Compound C having a thickness of 20 nm, LiF having a thickness of 1 nm, and metal Al having a thickness of 80 nm were sequentially laminated on the phosphorescent layer, whereby a cathode was obtained. It should be noted that LiF as an electron injectable electrode was formed at a rate of 1 Å/min.

(Evaluation of Organic EL Device for Light Emitting Performance)

The organic EL device thus produced was caused to emit light by being driven with a direct current. The luminance (L) of the emitted light and the current density at which the device started to emit the light were measured. Then, the current efficiency (L/J) of the device at a luminance of 1,000 cd/m$^2$ was determined. Further, the lifetime of the device at a luminance of 20,000 cd/m$^2$ was determined. Table 2 shows the results.

Examples 11 to 16

Organic EL devices were each produced in the same manner as in Example 10 except that a host compound and an electron transportable compound listed in Table 2 were used instead of Host Compound No. 198 and Electron Transportable Compound No. 20 in Example 10, and the devices were each evaluated in the same manner as in Example 10. Table 2 shows the results of the evaluation for light emitting performance.

Comparative Example 8

An organic EL device was produced in the same manner as in Example 10 except that: CBP was used instead of Host Compound No. 198 in Example 10; and BAlq was used instead of Electron Transportable Compound No. 20 in Example 10. Then, the device was evaluated in the same manner as in Example 10. Table 2 shows the results of the evaluation for light emitting performance.

TABLE 2

| | Host Compound | Electron Transportable Compound | Voltage (V) @ 20 mA/cm$^2$ | Efficiency (cd/A) @ 1,000 cd/m$^2$ | Lifetime (hr) @ 20,000 cd/m$^2$ |
|---|---|---|---|---|---|
| Example 10 | (198) | (20) | 4.7 | 65.1 | 500 |
| Example 11 | (198) | (67) | 4.5 | 63.9 | 550 |
| Example 12 | (137) | (67) | 4.5 | 57.1 | 350 |
| Example 13 | (193) | (67) | 5.2 | 61.8 | 400 |
| Example 14 | (209) | (67) | 5.3 | 63.8 | 380 |
| Example 15 | CBP | (20) | 5.3 | 47.2 | 100 |
| Example 16 | CBP | (67) | 5.1 | 48.5 | 100 |
| Comparative Example 8 | CBP | BAlq | 6.5 | 45.1 | 30 |

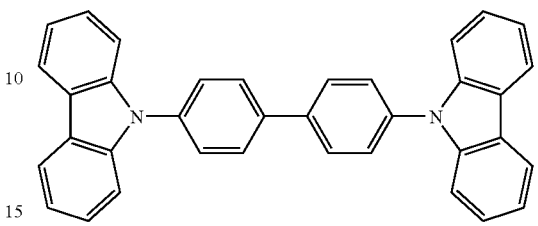

CBP

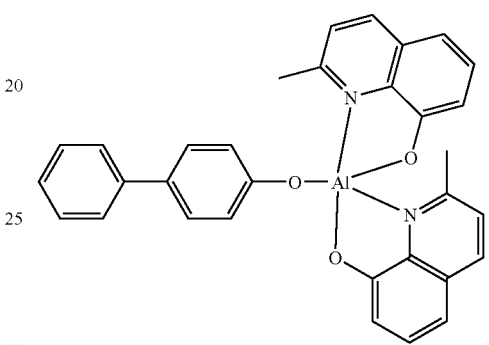

BAlq

Each of the organic EL devices of the comparative examples showed a lower current efficiency, was driven at a higher voltage, and had a shorter lifetime than those of each of the organic EL devices of the examples.

INDUSTRIAL APPLICABILITY

As described above in detail, the utilization of the material for an organic EL device of the present invention can provide an organic EL device which: shows high luminous efficiency; is free of any pixel defect; and has a long lifetime. Accordingly, the organic EL device of the present invention is extremely useful as, for example, a light source for various electronic instruments. In addition, the material can be effectively used also as a material for an organic electron device, and is extremely useful in an organic solar cell, organic semiconductor laser, a sensor using organic matter, or an organic TFT.

The invention claimed is:

1. A material for an organic electroluminescence device represented by one of formulae (11) and (12):

(11)

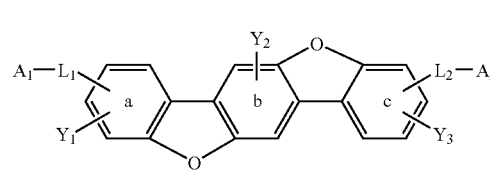

-continued

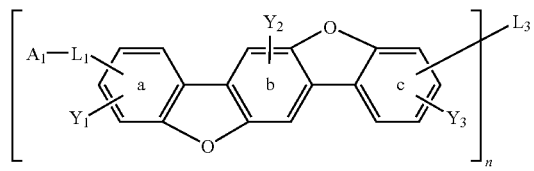

(12)

wherein:
n represents 2, 3, or 4, and the material represented by the formula (12) comprises a dimer using $L_3$ as a linking group for n=2, a trimer using $L_3$ as a linking group for n=3, or a tetramer using $L_3$ as a linking group for n=4;

$L_1$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with the benzene ring a through a carbon-carbon bond;

$L_2$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with the benzene ring c through a carbon-carbon bond;

when n represents 2, $L_3$ represents a single bond, an alkylene group having 1 to 20 carbon atoms, a substituted or unsubstituted cycloalkylene group having a ring formed of 3 to 20 carbon atoms, a divalent silyl group having 2 to 20 carbon atoms, a substituted or unsubstituted, divalent aromatic hydrocarbon group having a ring formed of 6 to 24 carbon atoms, or a substituted or unsubstituted, divalent aromatic heterocyclic group which has a ring formed of 3 to 24 atoms and which is linked with the benzene ring c through a carbon-carbon bond, when n represents 3, $L_3$ represents a trivalent alkane having 1 to 20 carbon atoms, a substituted or unsubstituted, trivalent cycloalkane having a ring formed of 3 to 20 carbon atoms, a trivalent silyl group having 1 to 20 carbon atoms, a substituted or unsubstituted, trivalent aromatic hydrocarbon group having a ring formed of 6 to 24 carbon atoms, or a substituted or unsubstituted, trivalent aromatic heterocyclic group which has 3 to 24 atoms and which is linked with the benzene ring c through a carbon-carbon bond, or when n represents 4, $L_3$ represents a tetravalent alkane having 1 to 20 carbon atoms, a substituted or unsubstituted, tetravalent cycloalkane having a ring formed of 3 to 20 carbon atoms, a silicon atom, a substituted or unsubstituted, tetravalent aromatic hydrocarbon group having a ring formed of 6 to 24 carbon atoms, or a substituted or unsubstituted, tetravalent aromatic heterocyclic group which has a ring formed of 3 to 24 atoms and which is linked with the benzene ring c through a carbon-carbon bond;

$A_1$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_1$ through a carbon-carbon bond, provided that, when $L_1$ represents an alkyl or alkylene group having 1 to 20 carbon atoms, a case where $A_1$ represents a hydrogen atom is excluded;

$A_2$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_2$ through a carbon-carbon bond, provided that, when $L_2$ represents an alkyl or alkylene group having 1 to 20 carbon atoms, a case where $A_2$ represents a hydrogen atom is excluded, and, when both $L_1$ and $L_2$ represent single bonds, a case where $A_1$ and $A_2$ simultaneously represent hydrogen atoms is excluded;

$Y_1$, $Y_2$, and $Y_3$ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with the benzene ring a, b, or c through a carbon-carbon bond, a number of each of $Y_1$ and $Y_3$ is 0, 1, 2, or 3, and a number of $Y_2$ is 0, 1, or 2; and $A_1$, $A_2$, $L_1$, $L_2$, and $L_3$ are each free of any carbonyl group.

2. The material for an organic electroluminescence device according to claim 1, wherein $A_1$ in each of formulae (11) and (12) represents a silyl group having 3 to 20 carbon atoms, or an aromatic heterocyclic group which has a ring formed of 3 to 24 atoms and which is linked with $L_1$ through a carbon-carbon bond.

3. The material for an organic electroluminescence device according to claim 1, wherein $A_1$ in each of formulae (11) and (12) represents an aromatic heterocyclic group which is linked with $L_1$ through a carbon-carbon bond and which is selected from pyridazine, pyrimidine, pyrazine, 1,3,5-triazine, carbazole, dibenzofuran, dibenzothiophene, phenoxazine, phenothiazine, and dihydroacridine.

4. The material for an organic electroluminescence device according to claim 1, wherein the material is represented by one of formulae (13) and (14):

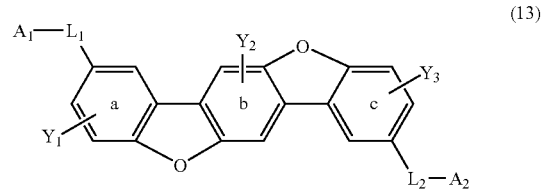

(13)

-continued (14)

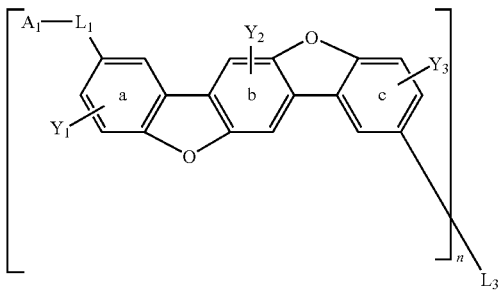

wherein n, $L_1$, $L_2$, $L_3$, $A_1$, $A_2$, $Y_1$, $Y_2$, and $Y_3$ are as defined in claim 1.

5. The material for an organic electroluminescence device according to claim 4, wherein $A_1$ in each of formulae (13) and (14) represents a silyl group having 3 to 20 carbon atoms, or an aromatic heterocyclic group which has a ring formed of 3 to 24 atoms and which is linked with $L_1$ through a carbon-carbon bond.

6. The material for an organic electroluminescence device according to claim 4, wherein $A_1$ in each of formulae (13) and (14) represents an aromatic heterocyclic group which is linked with $L_1$ through a carbon-carbon bond and which is selected from pyridazine, pyrimidine, pyrazine, 1,3,5-triazine, carbazole, dibenzofuran, dibenzothiophene, phenoxazine, phenothiazine, and dihydroacridine.

7. An organic electroluminescence device comprising one or more organic thin film layers including a light emitting layer between a cathode and an anode and further comprising an electron transporting layer between the light emitting layer and the cathode, wherein the electron transporting layer comprises the material for an organic electroluminescence device represented by one of formulae (1) and (2):

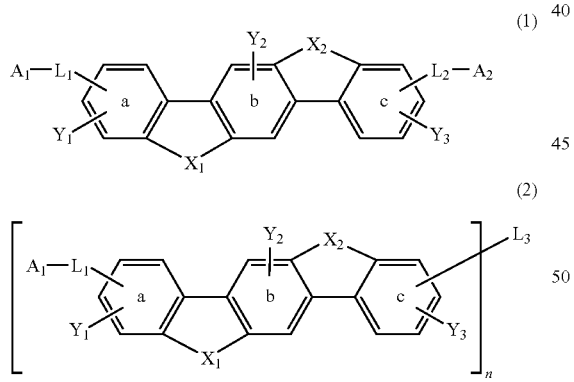

wherein:
$X_1$ and $X_2$ each independently represent O, N—$R_1$, or $CR_2R_3$, provided that a case where both $X_1$ and $X_2$ represent $CR_2R_3$ is excluded;
$R_1$, $R_2$, and $R_3$ each independently represent an alkyl group having 1 to 20 carbon atoms, a substituted or unsubstituted cycloalkyl group having a ring formed of 3 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group having a ring formed of 3 to 24 atoms, provided that, when both $X_1$ and $X_2$ represent N—$R_1$, at least one $R_1$ represents a substituted or unsubstituted residue of dibenzofuran, dibenzothiophene, phenoxazine, phenothiazine, dihydroacridine or N-methylbenzimidazole;
n represents 2, 3, or 4, and the material represented by the formula (2) comprises a dimer using $L_3$ as a linking group for n=2, a trimer using $L_3$ as a linking group for n=3, or a tetramer using $L_3$ as a linking group for n=4;
$L_1$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring a through a carbon-carbon bond;
$L_2$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring c through a carbon-carbon bond;
when n represents 2, $L_3$ represents a single bond, an alkylene group having 1 to 20 carbon atoms, a substituted or unsubstituted cycloalkylene group having a ring formed of 3 to 20 carbon atoms, a divalent silyl group having 2 to 20 carbon atoms, a substituted or unsubstituted, divalent aromatic hydrocarbon group having a ring formed of 6 to 24 carbon atoms, or a substituted or unsubstituted, divalent aromatic heterocyclic group which has a ring formed of 3 to 24 atoms and which is linked with the benzene ring c through a carbon-carbon bond, when n represents 3, $L_3$ represents a trivalent alkane having 1 to 20 carbon atoms, a substituted or unsubstituted, trivalent cycloalkane having a ring formed of 3 to 20 carbon atoms, a trivalent silyl group having 1 to 20 carbon atoms, a substituted or unsubstituted, trivalent aromatic hydrocarbon group having a ring formed of 6 to 24 carbon atoms, or a substituted or unsubstituted, trivalent aromatic heterocyclic group which has 3 to 24 atoms and which is linked with the benzene ring c through a carbon-carbon bond, or when n represents 4, $L_3$ represents a tetravalent alkane having 1 to 20 carbon atoms, a substituted or unsubstituted, tetravalent cycloalkane having a ring formed of 3 to 20 carbon atoms, a silicon atom, a substituted or unsubstituted, tetravalent aromatic hydrocarbon group having a ring formed of 6 to 24 carbon atoms, or a substituted or unsubstituted, tetravalent aromatic heterocyclic group which has a ring formed of 3 to 24 atoms and which is linked with the benzene ring c through a carbon-carbon bond;
$A_1$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_1$ through a carbon-carbon bond, provided that, when L₁ represents an alkyl or alkylene group having 1 to 20 carbon atoms, a case where A₁ represents a hydrogen atom is excluded;

A₂ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with L₂ through a carbon-carbon bond, provided that, when L₂ represents an alkyl or alkylene group having 1 to 20 carbon atoms, a case where A₂ represents a hydrogen atom is excluded, and, when X₁ and X₂ each represent O or CR₂R₃ and both L₁ and L₂ represent single bonds, a case where A₁ and A₂ simultaneously represent hydrogen atoms is excluded;

the substituent of A₁ and A₂ is selected from the group consisting of an alkyl group having 1 to 10 carbon atoms, a cycloalkyl group having a ring formed of 3 to 40 carbon atoms, an alkoxy group having 1 to 6 carbon atoms, a cycloalkoxy group having a ring formed of 3 to 10 carbon atoms, an aromatic hydrocarbon group having a ring formed of 6 to 40 carbon atoms, an aromatic heterocyclic group having a ring formed of 3 to 40 atoms, an amino group substituted with an aromatic hydrocarbon group having a ring formed of 6 to 40 carbon atoms, an ester group having an aromatic hydrocarbon group having a ring formed of 6 to 40 carbon atoms, an ester group having an alkyl group having 1 to 6 carbon atoms, cyano group, nitro group, and halogen atom;

Y₁, Y₂ and Y₃ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with the benzene ring a, b, or c through a carbon-carbon bond, a number of each of Y₁ and Y₃ is 0, 1, 2, or 3, and a number of Y₂ is 0, 1, or 2; and A₁, A₂, L₁, L₂, and L₃ are each free of any carbonyl group.

8. The organic electroluminescence device according to claim 7, wherein the light emitting layer comprises, as a host material, a material for an organic electroluminescence device serving as a compound having a π-conjugated heteroacene skeleton crosslinked with a carbon atom, nitrogen atom, oxygen atom, or sulfur atom.

9. The organic electroluminescence device according to claim 7, wherein the light emitting layer comprises a material for an organic electroluminescence device represented by any one of formulae (15) to (18) as a host material:

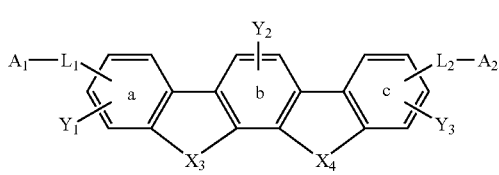

(15)

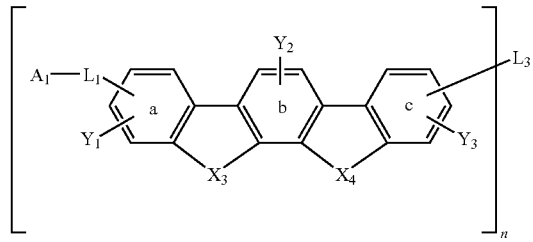

(16)

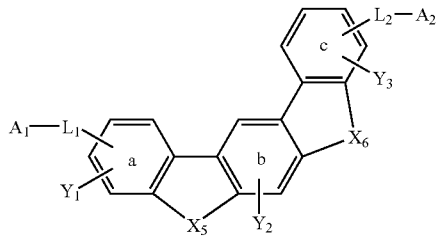

(17)

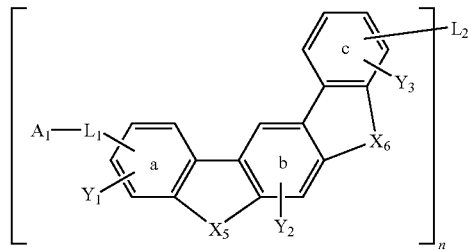

(18)

wherein:

X₃, X₄, X₅, and X₆ each independently represent O, S, N—R₁, or CR₂R₃;

R₁, R₂, and R₃ each independently represent an alkyl group having 1 to 20 carbon atoms, a substituted or unsubstituted cycloalkyl group having a ring formed of 3 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group having a ring formed of 3 to 24 atoms, provided that, when both X₃ and X₄, or both X₅ and X₆, represent N—R₁, at least one R₁ represents a substituted or unsubstituted fused aromatic heterocyclic group having a ring formed of 8 to 24 atoms;

n represents 2, 3, or 4, and the material represented by one of the formulae (16) and (18) comprises a dimer using L₃ as a linking group for n=2, a trimer using L₃ as a linking group for n=3, or a tetramer using L₃ as a linking group for n=4;

L₁ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring a through a carbon-carbon bond;

L₂ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms: or a substituted or unsubstituted, monovalent or divalent aromatic heterocyclic group which has a ring formed of 3 to 24 atoms and which is linked with a benzene ring c through a carbon-carbon bond, provided that, when both $X_7$ and $X_8$, both $X_9$ and $X_{10}$, or both $X_{11}$ and $X_{12}$, represent $CR_2R_3$ and both $L_1$ and $L_2$ represent substituted or unsubstituted, monovalent or divalent aromatic hydrocarbon groups having a ring formed of 6 to 24 carbon atoms, a case where $L_1$ and $L_2$ are simultaneously linked at para positions with respect to a benzene ring b is excluded;

when n represents 2, $L_3$ represents a single bond, an alkylene group having 1 to 20 carbon atoms, a substituted or unsubstituted cycloalkylene group having a ring formed of 3 to 20 carbon atoms, a divalent silyl group having 2 to 20 carbon atoms, a substituted or unsubstituted, divalent aromatic hydrocarbon group having a ring formed of 6 to 24 carbon atoms, or a substituted or unsubstituted, divalent aromatic heterocyclic group which has a ring formed of 3 to 24 atoms and which is linked with the benzene ring c through a carbon-carbon bond, when n represents 3, $L_3$ represents a trivalent alkane having 1 to 20 carbon atoms, a substituted or unsubstituted, trivalent cycloalkane having a ring formed of 3 to 20 carbon atoms, a trivalent silyl group having 1 to 20 carbon atoms, a substituted or unsubstituted, trivalent aromatic hydrocarbon group having a ring formed of 6 to 24 carbon atoms, or a substituted or unsubstituted, trivalent aromatic heterocyclic group which has 3 to 24 atoms and which is linked with the benzene ring c through a carbon-carbon bond, or when n represents 4, $L_3$ represents a tetravalent alkane having 1 to 20 carbon atoms, a substituted or unsubstituted, tetravalent cycloalkane having a ring formed of 3 to 20 carbon atoms, a silicon atom, a substituted or unsubstituted, tetravalent aromatic hydrocarbon group having a ring formed of 6 to 24 carbon atoms, or a substituted or unsubstituted, tetravalent aromatic heterocyclic group which has a ring formed of 3 to 24 atoms and which is linked with the benzene ring c through a carbon-carbon bond, provided that, when both $X_7$ and $X_8$, both $X_9$ and $X_{10}$, or both $X_{11}$ and $X_{12}$, represent $CR_2R_3$ and both $L_1$ and $L_3$ represent a substituted or unsubstituted, monovalent, divalent, trivalent, or tetravalent aromatic hydrocarbon group having a ring formed of 6 to 24 carbon atoms, a case where $L_1$ and $L_3$ are simultaneously linked at para positions with respect to the benzene ring b is excluded;

$A_1$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_1$ through a carbon-carbon bond, provided that, when $L_1$ represents an alkyl or alkylene group having 1 to 20 carbon atoms, a case where $A_1$ represents a hydrogen atom is excluded;

$A_2$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_2$ through a carbon-carbon bond, provided that, when $L_2$ represents an alkyl or alkylene group having 1 to 20 carbon atoms, a case where $A_2$ represents a hydrogen atom is excluded, and, when $X_7$ and $X_8$, $X_9$ and $X_{10}$, or $X_{11}$ and $X_{12}$, each represent O, S, or $CR_2R_3$ and both $L_1$ and $L_2$ represent single bonds, a case where $A_1$ and $A_2$ simultaneously represent hydrogen atoms is excluded;

$Y_1, Y_2$, and $Y_3$ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with the benzene ring a, b, or c through a carbon-carbon bond, a number of each of $Y_1$ and $Y_3$ is 0, 1, 2, or 3, and a number of $Y_2$ is 0, 1, or 2; and $A_1, A_2, L_1, L_2$, and $L_3$ are each free of any carbonyl group.

10. The organic electroluminescence device according to claim 9, wherein the material for an organic electroluminescence device in the light emitting layer is represented by any one of formulae (19) to (22) as a host material:

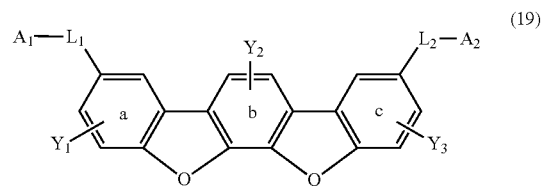
(19)

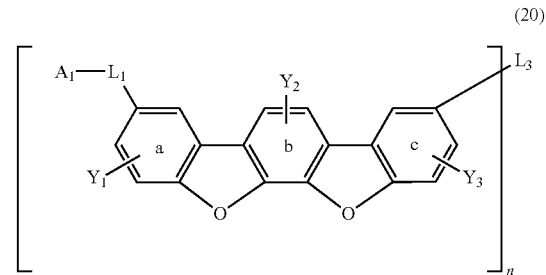
(20)

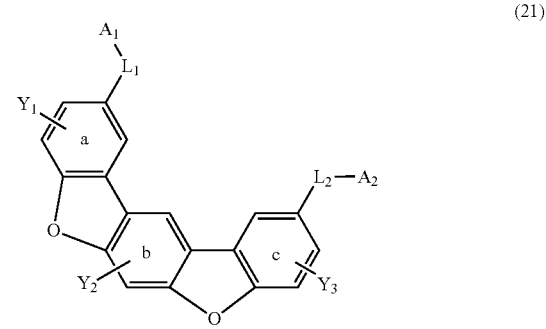
(21)

-continued

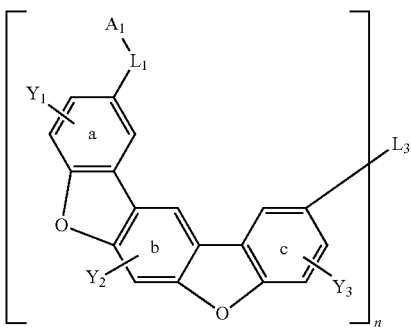

(22)

wherein n, $L_1$, $L_2$, $L_3$, $A_1$, $A_2$, $Y_1$, $Y_2$, and $Y_3$ are as defined in claim 9.

11. The organic electroluminescence device according to claim 7, further comprising a hole transporting layer between the light emitting layer and the anode, wherein the hole transporting layer contains the material for an organic electroluminescence device.

12. The organic electroluminescence device according to claim 7, further comprising a reducing dopant at an interfacial region between the cathode and the organic thin film layers.

13. The organic electroluminescence device according to claim 7, wherein the light emitting layer further contains a phosphorescent material.

14. The organic electroluminescence device according to claim 7, wherein the light emitting layer contains a host material and a phosphorescent material, and the phosphorescent material comprises an orthometalated complex of an iridium (Ir), osmium (Os), or platinum (Pt) metal.

15. The organic electroluminescence device according to claim 7, further comprising an electron injecting layer between the light emitting layer and the cathode, wherein the electron injecting layer contains a nitrogen-containing ring derivative.

* * * * *